United States Patent
Averback et al.

(10) Patent No.: US 7,241,738 B2
(45) Date of Patent: Jul. 10, 2007

(54) PEPTIDES EFFECTIVE IN THE TREATMENT OF TUMORS AND OTHER CONDITIONS REQUIRING THE REMOVAL OR DESTRUCTION OF CELLS

(75) Inventors: Paul Averback, Quebec (CA); Jack Gemmell, Mississauga (CA)

(73) Assignee: Nymox Pharmaceutical Corporation, Quebec (CA)

( * ) Notice: Subject to any disclaimer, the term of this patent is extended or adjusted under 35 U.S.C. 154(b) by 169 days.

(21) Appl. No.: 10/198,070

(22) Filed: Jul. 19, 2002

(65) Prior Publication Data

US 2003/0109437 A1    Jun. 12, 2003

Related U.S. Application Data

(60) Provisional application No. 60/331,477, filed on Nov. 16, 2001, provisional application No. 60/306,161, filed on Jul. 19, 2001, provisional application No. 60/306,150, filed on Jul. 19, 2001.

(51) Int. Cl.
*C07K 4/00* (2006.01)
*A61K 38/00* (2006.01)

(52) U.S. Cl. .................. 514/12; 530/300; 530/324; 530/326; 530/327

(58) Field of Classification Search .............. 514/2, 514/12; 530/300, 324, 325, 326, 327
See application file for complete search history.

(56) References Cited

U.S. PATENT DOCUMENTS

| 5,830,670 A | 11/1998 | de la Monte et al. |
| 5,948,634 A | 9/1999 | de la Monte et al. |
| 5,948,888 A | 9/1999 | de la Monte et al. |
| 6,071,705 A | 6/2000 | Wands et al. |

FOREIGN PATENT DOCUMENTS

| WO | WO 0200718 A2 * | 1/2002 |
| WO | WO 02070539 A2 * | 1/2002 |
| WO | WO 02 097030 A | 12/2002 |

OTHER PUBLICATIONS

Burgess et al. (J. Cell Biol. 111:2129-2138, 1990).*
Lazar et al. ( Mol. Cell Biol. 8:1247-1252, 1998).*
Wen et al. (Proc. Natl. Acad. Sci. U.S.A. 98: 4622-4627, 2001).*
Brady et al. (Nature 1994; 368, 692-693).*
Bork (2000) "Powers and Pitfalls in Sequence Analysis: The 70% Hurdle." Genome Research 10:398-400.*
Skolnick and Fetrow (2000) "From gene to protein structure and function: novel applications of computational approaches in the genomic era." Trends in Biotech. 18(1): 34-39.*
Doerks et al., (Jun. 1998) "Protein annotation: detective work for function prediction." Trends in Genetics 14(6): 248-250.*
Smith and Zhang (Nov. 1997) "The challenges of genome sequence annotation or 'The devil is in the details'." Nature Biotechnology 15:1222-1223.*
Bork and Bairoch (Oct. 1996) "Go hunting in sequence databases but watch out for the traps." Trends in Genetics 12(10): 425-427.*
Nair et al. (J. Immunol. 2003; 170: 1362-73).*
Okada et al. (J. Biol. Chem. 1999; 274: 27359-27370).*
Sijts et al.: "*Immunodominant Mink Cell Focus-Inducing Murine Leukemia Virus (MuLV)-Encoded CTL Epitope, Identified by its MHC Class I-Binding Motif, Explains MuLV-Type Specificity of MCF-Directed Cytotoxic T. Lymphocytes*" Journal of Immunology, vol. 152, 1994, pp. 106-116.
Feltkamp et al.: "Efficient MHC Class I-Peptide Binding Is Required Bu Does Not Ensure MHC Class I-Restricted Immunogenicity" *Molecular Immunology*, vol. 31, No. 18, Dec. 1994, pp. 1391-1401.
International Search Report issued in PCT/CA02/01106 dated of mailing Sep. 11, 2003.
Nair et al. "Mimicry of native peptide antigens by the corresponding retro-inverso analogs is dependent on their intrinsic structure and interaction propensities" *J Immunol*. Feb. 1, 2003;170(3):1362-73.

* cited by examiner

*Primary Examiner*—Shanon Foley
*Assistant Examiner*—Brandon Fetterolf
(74) *Attorney, Agent, or Firm*—Hunton & Williams LLP

(57) ABSTRACT

The present invention relates to peptides, compositions, and methods of treating conditions requiring removal or destruction of harmful or unwanted cells in a patient, such as benign and malignant tumors, using proteins (and peptides derived from the amino acid sequences of such proteins), the amino acid sequence of which includes at least one amino acid sequence derived from neural thread proteins and other related molecules.

8 Claims, 9 Drawing Sheets

Figure 1

AD7C-NTP [SEQ ID NO. 1]

```
   1  tttttttttttgag ATG GAG TTT TCG CTC TTG TTG CCC AGG CTG GAG TGC AAT GGC GCA ATC   62
   1                  M   E   F   S   L   L   L   P   R   L   E   C   N   G   A   I   16

63  TCA GCT CAC CGC AAC CTC CGC CTC CCG GGT TCA AGC GAT TCT CCT GCC TCA GCC TCC CCA  122
  17   S   A   H   R   N   L   R   L   P   G   S   S   D   S   P   A   S   A   S   P   36

123  GTA GCT GGG ATT ACA GGC ATG TGC ACC CAC GCT CGG CTA ATT TTG TAT TTT TTT TTA GTA  182
  37   V   A   G   I   T   G   M   C   T   H   A   R   L   I   L   Y   F   F   L   V   56

183  GAG ATG GAG TTT CTC CAT GTT GGT CAG GCT GGT CTC GAA CTC CCG ACC TCA GAT GAT CCC  242
  57   E   M   E   F   L   H   V   G   Q   A   G   L   E   L   P   T   S   D   D   P   76

243  TCC GTC TCG GCC TCC CAA AGT GCT AGA TAC AGG ACT GGC CAC CAT GCC CGG CTC TGC CTG  302
  77   S   V   S   A   S   Q   S   A   R   Y   R   T   G   H   H   A   R   L   C   L   96

303  GCT AAT TTT TGT GGT AGA AAC AGG GTT TCA CTG ATG TGC CCA AGC TGG TCT CCT GAG CTC  362
  97   A   N   F   C   G   R   N   R   V   S   L   M   C   P   S   W   S   P   E   L  116

363  AAG CAG TCC ACC TGC CTC AGC CTC CCA AAG TGC TGG GAT TAC AGG CGT GCA GCC GTG CCT  422
 117   K   Q   S   T   C   L   S   L   P   K   C   W   D   Y   R   R   A   A   V   P  136

423  GGC CTT TTT ATT TTA TTT TTT TTA AGA CAC AGG TGT CCC ACT CTT ACC CAG GAT GAA GTG  482
 137   G   L   F   I   L   F   F   L   R   H   R   C   P   T   L   T   Q   D   E   V  156

483  CAG TGG TGT GAT CAC AGC TCA CTG CAG CCT TCA ACT CCT GAG ATC AAG CAT CCT CCT GCC  542
 157   Q   W   C   D   H   S   S   L   Q   P   S   T   P   E   I   K   H   P   P   A  176

543  TCA GCC TCC CAA GTA GCT GGG ACC AAA GAC ATG CAC CAC TAC ACC TGG CTA ATT TTT ATT  602
 177   S   A   S   Q   V   A   G   T   K   D   M   H   H   Y   T   W   L   I   F   I  196

603  TTT ATT TTT AAT TTT TTG AGA CAG AGT CTC AAC TCT GTC ACC CAG GCT GGA GTG CAG TGG  662
 197   F   I   F   N   F   L   R   Q   S   L   N   S   V   T   Q   A   G   V   Q   W  216

663  CGC AAT CTT GGC TCA CTG CAA CCT CTG CCT CCC GGG TTC AAG TTA TTC TCC TGC CCC AGC  722
 217   R   N   L   G   S   L   Q   P   L   P   P   G   F   K   L   F   S   C   P   S  236

723  CTC CTG AGT AGC TGG GAC TAC AGG CGC CCA CCA CGC CTA GCT AAT TTT TTT GTA TTT TTA  782
 237   L   L   S   S   W   D   Y   R   R   P   P   R   L   A   N   F   F   V   F   L  256

783  GTA GAG ATG GGG TTC ACC ATG TTC GCC AGG TTG ATC TTG ATC TCT GGA CCT TGT GAT CTG  842
 257   V   E   M   G   F   T   M   F   A   R   L   I   L   I   S   G   P   C   D   L  276

843  CCT GCC TCG GCC TCC CAA AGT GCT GGG ATT ACA GGC GTG AGC CAC CAC GCC CGG CTT ATT  902
 277   P   A   S   A   S   Q   S   A   G   I   T   G   V   S   H   H   A   R   L   I  296

903  TTT AAT TTT TGT TTG TTT GAA ATG GAA TCT CAC TCT GTT ACC CAG GCT GGA GTG CAA TGG  962
 297   F   N   F   C   L   F   E   M   E   S   H   S   V   T   Q   A   G   V   Q   W  316

963  CCA AAT CTC GGC TCA CTG CAA CCT CTG CCT CCC GGG CTC AAG CGA TTC TCC TGT CTC AGC 1022
 317   P   N   L   G   S   L   Q   P   L   P   P   G   L   K   R   F   S   C   L   S  336

1023  CTC CCA AGC AGC TGG GAT TAC GGG CAC CTG CCA CCA CAC CCC GCT AAT TTT TGT ATT TTC 1082
 337   L   P   S   S   W   D   Y   G   H   L   P   P   H   P   A   N   F   C   I   F  356

1083  ATT AGA GGC GGG GTT TCA CCA TAT TTG TCA GGC TGG TCT CAA ACT CCT GAC CTC AGG tgac 1143
 357   I   R   G   G   V   S   P   Y   L   S   G   W   S   Q   T   P   D   L   R       375

1144  ccacctgcctcagccttccaaagtgctgggattacaggcgtgagccacctcacccagccggctaatttagataaaaaaat 1223

1224  atgtagcaatggggggtcttgctatgttgcccaggctggtctcaaacttctggcttcatgcaatccttccaaatgagcca 1303

1304  caacacccagccagtcacattttttaaacagttacatctttatttagtatactagaaagtaatacaataaacatgtcaa 1383

1384  acctgcaaattcagtagtaacagagttcttttataaacttttaaacaaagctttagagca                      1442
```

Figure 2

NTP[122] [SEQ ID NO. 2]

| | | |
|---|---|---|
| 1 | Met-Met-Val-Cys-Trp-Asn-Arg-Phe-Gly-Lys-<br>M   M   V   C   W   N   R   F   G   K | |
| 11 | Trp-Val-Tyr-Phe-Ile-Ser-Ala-Ile-Phe-Asn-<br>W   V   Y   F   I   S   A   I   F   N | |
| 21 | Phe-Gly-Pro-Arg-Tyr-Leu-Tyr-His-Gly-Val-<br>F   G   P   R   Y   L   Y   H   G   V | |
| 31 | Pro-Phe-Tyr-Phe-Leu-Ile-Leu-Val-Arg-Ile-<br>P   F   Y   F   L   I   L   V   R   I | |
| 41 | Ile-Ser-Phe-Leu-Ile-Gly-Asp-Met-Glu-Asp-<br>I   S   F   L   I   G   D   M   E   D | |
| 51 | Val-Leu-Leu-Asn-Cys-Thr-Leu-Leu-Lys-Arg-<br>V   L   L   N   C   T   L   L   K   R | |
| 61 | Ser-Ser-Arg-Phe-Arg-Phe-Trp-Gly-Ala-Leu-<br>S   S   R   F   R   F   W   G   A   L | |
| 71 | Val-Cys-Ser-Met-Asp-Ser-Cys-Arg-Phe-Ser<br>V   C   S   M   D   S   C   R   F   S | |
| 81 | Arg-Val-Ala-Val-Thr-Tyr-Arg-Phe-Ile-Thr-<br>R   V   A   V   T   Y   R   F   I   T | |
| 91 | Leu-Leu-Asn-Ile-Pro-Ser-Pro-Ala-Val-Trp-<br>L   L   N   I   P   S   P   A   V   W | |
| 101 | Met-Ala-Arg-Asn-Thr-Ile-Asp-Gln-Gln-Val-<br>M   A   R   N   T   I   D   Q   Q   V | |
| 111 | Leu-Ser-Arg-Ile-Lys-Leu-Glu-Ile-Lys-Arg-<br>L   S   R   I   K   L   E   I   K   R | |
| 121 | Cys-Leu<br>C   L | |

Figure 3

NTP[112] [SEQ ID NO. 3]

| | | | | | | | | | | |
|---|---|---|---|---|---|---|---|---|---|---|
| 1 | Met-Ala-Gln-Ser-Arg-Leu-Thr-Ala-The-Ser- | | | | | | | | | |
| | M | A | Q | S | R | L | T | A | T | S |
| 11 | Ala-Ser-Arg-Val-Gln-Ala-Ile-Leu-Leu-Ser- | | | | | | | | | |
| | A | S | R | V | Q | A | I | L | L | S |
| 21 | Gln-Pro-Pro-Lys-Gln-Leu-Gly-Leu-Arg-Ala- | | | | | | | | | |
| | Q | P | P | K | Q | L | G | L | R | A |
| 31 | Pro-Ala-Asn-Thr-Pro-Leu-Ile-Phe-Val-Phe- | | | | | | | | | |
| | P | A | N | T | P | L | I | F | V | F |
| 41 | Ser-Leu-Glu-Ala-Gly-Phe-His-His-Ile-Cys- | | | | | | | | | |
| | S | L | E | A | G | F | H | H | I | C |
| 51 | Gln-Ala-Gly-Leu-Lys-Leu-Leu-Thr-Ser-Gly- | | | | | | | | | |
| | Q | A | G | L | K | L | L | T | S | G |
| 61 | Asp-Pro-Pro-Ala-Ser-Ala-Phe-Gln-Ser-Ala- | | | | | | | | | |
| | D | P | P | A | S | A | F | Q | S | A |
| 71 | Gly-Ile-Thr-Gly-Val-Ser-His-Leu-Thr-Gln- | | | | | | | | | |
| | G | I | T | G | V | S | H | L | T | Q |
| 81 | Pro-Ala-Asn-Leu-Asp-Lys-Lys-Ile-Cys-Ser- | | | | | | | | | |
| | P | A | N | L | D | K | K | I | C | S |
| 91 | Asn-Gly-Gly-Ser-Cys-Tyr-Val-Ala-Gln-Ala- | | | | | | | | | |
| | N | G | G | S | C | Y | V | A | Q | A |
| 101 | Gly-Leu-Lys-Leu-Leu-Ala-Ser-Cys-Asn-Pro- | | | | | | | | | |
| | G | L | K | L | L | A | S | C | N | P |
| 111 | Ser-Lys | | | | | | | | | |
| | S | K | | | | | | | | |

Figure 4

NTP[106] [SEQ ID NO. 4]

| | | | | | | | | | | |
|---|---|---|---|---|---|---|---|---|---|---|
| 1 | Met- | Trp- | Thr- | Leu- | Lys- | Ser- | Ser- | Leu- | Val- | Leu- |
| | M | W | T | L | K | S | S | L | V | L |
| 11 | Leu- | Leu- | Cys- | Leu- | Thr- | Cys- | Ser- | Tyr- | Ala- | Phe- |
| | L | L | C | L | T | C | S | Y | A | F |
| 21 | Met- | Phe- | Ser- | Ser- | Leu- | Arg- | Gln- | Lys- | Thr- | Ser- |
| | M | F | S | S | L | R | Q | K | T | S |
| 31 | Glu- | Pro- | Gln- | Gly- | Lys- | Val- | Pro- | Cys- | Gly- | Glu- |
| | E | P | Q | G | K | V | P | C | G | E |
| 41 | His- | Phe- | Arg- | Ile- | Arg- | Gln- | Asn- | Leu- | Pro- | Glu- |
| | H | F | R | I | R | Q | N | L | P | E |
| 51 | His- | Thr- | Gln- | Gly- | Trp- | Leu- | Gly- | Ser- | Lys- | Trp- |
| | H | T | Q | G | W | L | G | S | K | W |
| 61 | Leu- | Trp- | Leu- | Leu- | Phe- | Ala- | Val- | Val- | Pro- | Phe- |
| | L | W | L | L | F | A | V | V | P | F |
| 71 | Val- | Ile- | Leu- | Lys- | Cys- | Gln- | Arg- | Asp- | Ser- | Glu- |
| | V | I | L | K | C | Q | R | D | S | E |
| 81 | Lys- | Asn- | Lys- | Val- | Arg- | Met- | Ala- | Pro- | Phe- | Phe- |
| | K | N | K | V | R | M | A | P | F | F |
| 91 | Leu- | His- | His- | Ile- | Asp- | Ser- | Ile- | Ser- | Gly- | Val- |
| | L | H | H | I | D | S | I | S | G | V |
| 101 | Ser- | Gly- | Lys- | Arg- | Met- | Phe | | | | |
| | S | G | K | R | M | F | | | | |

Figure 5

NTP [106] [SEQ ID NO. 5]

```
1    Met-Phe-Phe-Val-Leu-Tyr-Arg-Phe-Cys-Phe-
     M   F   F   V   L   Y   R   F   C   F

11   Cys-Phe-Phe-Glu-Thr-Glu-Ser-His-Ser-Leu-
     C   F   F   E   T   E   S   H   S   L

21   Thr-Gln-Ala-Gly-Val-Gln-Trp-Cys-Glu-Leu-
     T   Q   A   G   V   Q   W   C   E   L

31   Gly-Ser-Pro-Gln-Pro-Leu-Pro-Ser-Gly-Phe-
     G   S   P   Q   P   L   P   S   G   F

41   Lys-Arg-Phe-Ser-Cys-Leu-Ser-Leu-Leu-Ser-
     K   R   F   S   C   L   S   L   L   S

51   Ser-Trp-Asp-Tyr-Ser-His-Glu-Pro-Pro-His-
     S   W   D   Y   S   H   E   P   P   H

61   Pro-Val-Ile-Cys-Ser-Phe-Leu-Met-Glu-Lys-
     P   V   I   C   S   F   L   M   E   K

71   Cys-Leu-Ile-Leu-Tyr-Lys-Pro-Asn-Gly-Asp-
     C   L   I   L   Y   K   P   N   G   D

81   Thr-Ile-Gly-Pro-Ile-Leu-Val-Gln-Gln-Gly-
     T   I   G   P   I   L   V   Q   Q   G

91   Lys-Arg-Gln-Lys-Leu-Tyr-Ile-Ser-Ala-Asp-
     K   R   Q   K   L   Y   I   S   A   D

100  Leu-Val-His-Leu-Ile-Ala
     L   V   H   L   I   A
```

Figure 6

NTP[98] [SEQ ID NO. 6]

| | | | | | | | | | | |
|---|---|---|---|---|---|---|---|---|---|---|
| 1 | Glu- | Ala- | Tyr- | Tyr- | Thr- | Met- | Leu- | His- | Leu- | Pro- |
| | E | A | Y | Y | T | M | L | H | L | P |
| 11 | Thr- | Thr- | Asn- | Arg- | Pro- | Lys- | Ile- | Ala- | His- | Cys |
| | T | T | N | R | P | K | I | A | H | C |
| 21 | Ile- | Leu- | Phe- | Asn- | Gln- | Pro- | His- | Ser- | Pro- | Arg- |
| | I | L | F | N | Q | P | H | S | P | R |
| 31 | Ser- | Asn- | Ser- | His- | Ser- | His- | Pro- | Asn- | Pro- | Leu- |
| | S | N | S | H | S | H | P | N | P | L |
| 41 | Lys- | Leu- | His- | Arg- | Arg- | Ser- | His- | Ser- | His- | Asn- |
| | K | L | H | R | R | S | H | S | H | N |
| 51 | Arg- | Pro- | Arg- | Ala- | Tyr- | Ile- | Leu- | Ile- | Thr- | Ile- |
| | R | P | R | A | Y | I | L | I | T | I |
| 61 | Leu- | Pro- | Ser- | Lys- | Leu- | Lys- | Leu- | Arg- | Thr- | His- |
| | L | P | S | K | L | K | L | R | T | H |
| 71 | Ser- | Gln- | Ser- | His- | His- | Asn- | Pro- | Leu- | Ser- | Arg- |
| | S | Q | S | H | H | N | P | L | S | R |
| 81 | Thr- | Ser- | Asn- | Ser- | Thr- | Pro- | Thr- | Asn- | Ser- | Phe- |
| | T | S | N | S | T | P | T | N | S | F |
| 91 | Leu- | Met- | Thr- | Ser- | Ser- | Lys- | Pro- | Arg | | |
| | L | M | T | S | S | K | P | R | | |

Figure 7

NTP[75] [SEQ ID NO. 7]

```
1    Ser-Ser-Ser-Leu-Gly-Leu-Pro-Lys-Cys-Trp-
     S   S   S   L   G   L   P   K   C   W

11   Asp-Tyr-Arg-His-Glu-Leu-Leu-Ser-Leu-Ala-
     D   Y   R   H   E   L   L   S   L   A

21   Leu-Met-Ile-Asn-Phe-Arg-Val-Met-Ala-Cys
     L   M   I   N   F   R   V   M   A   C

31   Thr-Phe-Lys-Gln-His-Ile-Glu-Leu-Arg-Gln-
     T   F   K   Q   H   I   E   L   R   Q

41   Lys-Ile-Ser-Ile-Val-Pro-Arg-Lys-Leu-Cys-
     K   I   S   I   V   P   R   K   L   C

51   Cys-Met-Gly-Pro-Val-Cys-Pro-Val-Lys-Ile-
     C   M   G   P   V   C   P   V   K   I

61   Ala-Leu-Leu-Thr-Ile-Asn-Gly-His-Cys-Thr-
     A   L   L   T   I   N   G   H   C   T

71   Trp-Leu-Pro-Ala-Ser
     W   L   P   A   S
```

Figure 8

NTP[68] [SEQ ID NO. 8]

| | | | | | | | | | | |
|---|---|---|---|---|---|---|---|---|---|---|
| 1 | Met- | Phe- | Val- | Phe- | Cys- | Leu- | Ile- | Leu- | Asn- | Arg- |
| | M | F | V | F | C | L | I | L | N | R |
| 11 | Glu- | Lys- | Ile- | Lys- | Gly- | Gly- | Asn- | Ser- | Ser- | Phe- |
| | E | K | I | K | G | G | N | S | S | F |
| 21 | Phe- | Leu- | Leu- | Ser- | Phe- | Phe- | Phe- | Ser- | Phe- | Gln- |
| | F | L | L | S | F | F | F | S | F | Q |
| 31 | Asn- | Cys- | Cys- | Gln- | Cys- | Phe- | Gln- | Cys- | Arg- | Thr- |
| | N | C | C | Q | C | F | Q | C | R | T |
| 41 | Thr- | Glu- | Gly- | Tyr- | Ala- | Val- | Glu- | Cys- | Phe- | Tyr- |
| | T | E | G | Y | A | V | E | C | F | Y |
| 51 | Cys- | Leu- | Val- | Asp- | Lys- | Ala- | Ala- | Phe- | Glu- | Cys- |
| | C | L | V | D | K | A | A | F | E | C |
| 61 | Trp- | Trp- | Phe- | Tyr- | Ser- | Phe- | Asp- | Thr | | |
| | W | W | F | Y | S | F | D | T | | |

Figure 9

NTP[61] [SEQ ID NO. 9]

```
1    Met-Glu-Pro-His-Thr-Val-Ala-Gln-Ala-Gly-
     M    E    P   H   T   V   A   Q   A   G

11   Val-Pro-Gln-His-Asp-Leu-Gly-Ser-Leu-Gln-
     V   P   Q   H   D   L   G   S   L   Q

21   Ser-Leu-Leu-Pro-Arg-Phe-Lys-Arg-Phe-Ser-
     S   L   L   P   R   F   K   R   F   S

31   Cys-Leu-Ile-Leu-Pro-Lys-Ile-Trp-Asp-Tyr-
     C   L   I   L   P   K   I   W   D   Y

41   Arg-Asn-Met-Asn-Thr-Ala-Leu-Ile-Lys-Arg-
     R   N   M   N   T   A   L   I   K   R

51   Asn-Arg-Tyr-Thr-Pro-Glu-Thr-Gly-Arg-Lys-
     N   R   Y   T   P   E   T   G   R   K

61   Ser
     S
```

PEPTIDES EFFECTIVE IN THE TREATMENT OF TUMORS AND OTHER CONDITIONS REQUIRING THE REMOVAL OR DESTRUCTION OF CELLS

This application claims priority to provisional application Ser. No. 60/306,161, entitled: "Proteins and peptides effective in the treatment of tumors and other conditions requiring the removal or destruction of cells," filed on Jul. 19, 2001, provisional patent application Ser. No. 60/306,150, entitled: "Peptides effective in the treatment of tumors and other conditions requiring the removal or destruction of cells," filed Jul. 19, 2001, and provisional patent application Ser. No. 60/331,477, entitled: "Peptides effective in the treatment of tumors and other conditions requiring the removal or destruction of cells," filed on Nov. 16, 2001, the disclosure of each of which is incorporated by reference herein in its entirety.

FIELD OF THE INVENTION

The present invention is directed to methods of treating conditions requiring removal or destruction of cellular elements, such as benign or malignant tumors in humans, using proteins and peptides containing amino acid sequences corresponding to, similar to or homologous to part of the amino acid sequence of neural thread proteins. The method includes, but is not limited to, administering the compounds intramuscularly, orally, intravenously, intrathecally, intratumorally, intranasally, topically, transdermally, etc., either alone or conjugated to a carrier.

BACKGROUND OF THE INVENTION

The essence of many medical treatments and procedures involves the removal or destruction of harmful or unwanted tissue. Examples of such important treatments include the surgical removal of cancerous growths, the destruction of metatastic tumors through chemotherapy, and the reduction of glandular (e.g. prostate) hyperplasia. Other examples include the removal of unwanted facial hair, warts, subcutaneous tissue, lymphoid tissue or fatty tissue.

There is a need for an effective agent that will destroy and hence either facilitate the removal of or inhibit the further growth of harmful or unwanted cells and tissue, but that will have mainly local effects and minimal or absent systemic toxicity. Neural thread proteins and their related molecules are one class of such agents as disclosed in pending U.S. patent application Ser. No. 10/092,934, entitled: Methods of Treating Tumors and Related Conditions Using Neural Thread Proteins, filed on Mar. 8, 2002, the disclosure of which is incorporated be reference herein in its entirety. Peptides containing amino acid sequences corresponding to part of the amino acid sequence of a neural thread protein, AD7c-NTP also are such agents. These peptides are disclosed in pending U.S. application Ser. No. 10/153,334, entitled: Peptides Effective in the Treatment of Tumors and Other Conditions Requiring the Removal or Destruction of Cells, filed May 24, 2002, the disclosure of which is incorporated by reference herein in its entirety.

Cancer is an abnormality in a cell's internal regulatory mechanisms that results in uncontrolled growth and reproduction of the cell. Normal cells make up tissues, and when these cells lose their ability to behave as a specified, controlled, and coordinated unit (dedifferentiation) the defect leads to disarray amongst the cell population. When this occurs, a tumor is formed.

Benign overgrowths of tissue are abnormalities in which it is desirable to remove cells from an organism. Benign tumors are cellular proliferations that do not metastasize throughout the body but do, however, cause disease symptoms. Such tumors can be lethal if they are located in inaccessible areas in organs such as the brain. There are benign tumors of organs including lung, brain, skin, pituitary, thyroid, adrenal cortex and medulla, ovary, uterus, testis, connective tissue, muscle, intestines, ear, nose, throat, tonsils, mouth, liver, gall bladder, pancreas, prostate, heart, and other organs.

Surgery often is the first step in the treatment of cancer. The objective of surgery varies. Sometimes it is used to remove as much of the evident tumor as possible, or at least to debulk it (remove the major bulk(s) of tumor so that there is less that needs to be treated by other means). Depending on the cancer type and location, surgery also may provide some symptomatic relief to the patient. For instance, if a surgeon can remove a large portion of an expanding brain tumor, the pressure inside the skull will decrease, leading to improvement in the patient's symptoms.

Not all tumors are amenable to surgery. Some may be located in parts of the body that make them impossible to completely remove. Examples of these would be tumors in the brainstem (a part of the brain that controls breathing) or a tumor which has grown in and around a major blood vessel. In these cases, the role of surgery is limited due to the high risk associated with tumor removal.

In some cases, surgery is not used to debulk tumor because it is not necessary. An example is Hodgkin's lymphoma, a cancer of the lymph nodes that responds very well to combinations of chemotherapy and radiation therapy. In Hodgkin's lymphoma, surgery is rarely needed to achieve cure, but almost always used to establish a diagnosis.

Chemotherapy is a common form of cancer treatment that involves the use of medications (usually given by mouth or injection) which specifically attack rapidly dividing cells (such as those found in a tumor) throughout the body. This makes chemotherapy useful in treating cancers that have already metastasized, as well as tumors that have a high chance of spreading through the blood and lymphatic systems but are not evident beyond the primary tumor. Chemotherapy may also be used to enhance the response of localized tumors to surgery and radiation therapy. This is the case, for example, for some cancers of the head and neck.

Unfortunately, other cells in the human body that also normally divide rapidly (such as the lining of the stomach and hair) also are affected by chemotherapy. For this reason, many chemotherapy agents induce undesirable side effects such as nausea, vomiting, anemia, hair loss or other symptoms. These side effects are temporary, and there exist medications that can help alleviate many of these side effects. As our knowledge has continued to grow, researchers have devised newer chemotherapeutic agents that are not only better at killing cancer cells, but that also have fewer side effects for the patient.

Chemotherapy is administered to patients in a variety of ways. Some are pills and some are administered by an intravenous or other injection. For injectable chemotherapy, a patient goes to the doctor's office or hospital for treatment. Other chemotherapeutic agents require continuous infusion into the bloodstream, 24 hours a day. For these types of chemotherapy, a minor surgical procedure may be performed to implant a small pump worn by the patient. The pump then slowly administers the medication. In many cases, a permanent port is placed in a patient's vein to eliminate the requirement of repeated needle sticks.

Radiation therapy is another commonly used weapon in the fight against cancer. Radiation kills cancer by damaging the DNA within the tumor cells. The radiation is delivered in different ways, the most common of which involves pointing a beam of radiation at the patient in a highly precise manner, and focusing on the tumor. To do this, a patient lies on a table and the beam moves around him/her. The procedure lasts minutes, but may be done daily for several weeks (depending on the type of tumor), to achieve a particular total prescribed dose.

Another radiation method sometimes employed, called brachytherapy, involves taking radioactive pellets (seeds) or wires and implanting them in the body in the area of the tumor. The implants can be temporary or permanent. For permanent implants, the radiation in the seeds decays over a period of days or weeks so that the patient is not radioactive. For temporary implants, the entire dose of radiation is usually delivered in a few days, and the patient must remain in the hospital during that time. For both types of brachytherapy, radiation generally is delivered to a very targeted area to gain local control over a cancer (as opposed to treating the whole body, as chemotherapy does.)

Some highly selected patients may be referred for bone marrow transplants. This procedure is usually performed either because a patient has a cancer that is particularly aggressive or because they have a cancer that has relapsed after being treated with conventional therapy. Bone marrow transplantation is a complicated procedure. There are many types, and they vary in their potential for causing side effects and cure. Most transplants are performed at special centers, and in many cases their use is considered investigational.

There are a number of other therapies, though most of them are still being explored in clinical trials and have not yet become standard care. Examples include the use of immunotherapy, monoclonal antibodies, anti-angiogenesis factors, and gene therapy.

Immunotherapy: There are various techniques designed to help the patient's own immune system fight the cancer, quite separately from radiation or chemotherapy. Oftentimes, to achieve the goal researchers inject the patient with a specially derived vaccine. Monoclonal Antibodies: These are antibodies designed to attach to cancerous cells (and not normal cells) by taking advantage of differences between cancerous and non-cancerous cells in their anitgenic and/or other characteristics. The antibodies can be administered to the patient alone or conjugated to various cytotoxic compounds or in radioactive form, such that the antibody preferentially targets the cancerous cells, thereby delivering the toxic agent or radioactivity to the desired cells.

Anti-Angiogenesis Factors: As cancer cells rapidly divide and tumors grow, they can soon outgrow their blood supply. To compensate for this, some tumors secrete a substance believed to help induce the growth of blood vessels in their vicinity, thus providing the cancer cells with a vascular source of nutrients. Experimental therapies have been designed to arrest the growth of blood vessels to tumors.

Gene Therapy: Cancer is the product of a series of mutations that ultimately lead to the production of a cancer cell and its excessive proliferation. Cancers can be treated by introducing genes to the cancer cells that will act either to check or stop the cancer's proliferation, turn on the cell's programmed cell mechanisms to destroy the cell, enhance immune recognition of the cell, or express a pro-drug that converts to a toxic metabolite or a cytokine that inhibits tumor growth.

Benign tumors and malformations also can be treated by a variety of methods including surgery, radiotherapy, drug therapy, thermal or electric ablation, cryotherapy, and others. Although benign tumors do not metastasize, they can grow large and they can recur. Surgical extirpation of benign tumors has all the difficulties and side effects of surgery in general and oftentimes must be repeatedly performed for some benign tumors, such as for pituitary adenomas, meningeomas of the brain, prostatic hyperplasia, and others.

There still other are conditions involving unwanted cellular elements where selective cellular removal is desirable. For example, heart disease and strokes are commonly caused by atherosclerosis, which is a proliferative lesion of fibrofatty and modified smooth muscle elements which distort the blood vessel wall, narrow the lumen, constrict blood flow, predispose to focal blood clots, and ultimately lead to blockage and infarction. Various treatments for atherosclerosis include bypass grafts; artificial grafts; angioplasty with recanalization, curettage, radiation, laser, or other removal; pharmacotherapy to inhibit atherosclerosis through lipid reduction; anti-clotting therapies; and general measures of diet, exercise, and lifestyle. A method for removing atherosclerotic lesions without the risk and side effects of surgical procedures is needed.

Other examples of unwanted cellular elements where selective cellular removal is desirable include viral induced growths, such as warts. Another example is hypertrophic inflammatory masses found in inflammatory conditions, and hypertrophic scars or keloids. Still other examples are found in cosmetic contexts such as the removal of unwanted hair, e.g., facial hair, or for shrinkage of unwanted tissue areas for cosmetic purposes, such as in the facial dermis and connective tissues or in the dermas and connective tissue of the extremities.

Still other examples will be obvious to those of ordinary skill in the art. In all or most of these examples there is a need for treatments that can remove or destroy the unwanted cellular elements without the risks and side effects of conventional therapies and to remove the unwanted cellular elements with more precision.

Neural thread proteins (NTP) are a family of recently characterized brain proteins. One member of this family, AD7c-NTP, is a ~41 kD membrane associated phosphoprotein with functions associated with neuritic sprouting (de la Monte et al., *J. Clin. Invest.*, 100:3093-3104 (1997); de la Monte et al., *Alz. Rep.*, 2:327-332 (1999); de la Monte S M and Wands J R, *Journal of Alzheimer's Disease*, 3:345-353 (2001)). The gene that encodes AD7c-NTP and predicted protein sequence for AD7c-NTP has been identified and described (de la Monte et al., *J. Clin. Invest.*, 100:3093-3104 (1997)). In addition to the ~41 kD species, other species of neural thread protein (~26 kD, ~21 kD, ~17 kD, and ~15 kD) have been identified and associated with neuroectodermal tumors, astrocytomas, and glioblastomas and with injury due to hypoxia, schema, or cerebral infarction (Xu et al., *Cancer Research*, 53:3823-3829 (1993); de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2): 118-25 (1996); de la Monte et al., *J. Clin. Invest.*, 100:3093-3104 (1997); and de la Monte et al., *Alz. Rep.*, 2:327-332 (1999)).

Species of neural thread protein have been described and claimed in U.S. Pat. Nos. 5,948,634; 5,948,888; and 5,830,670, all for "Neural Thread Protein Gene Expression and Detection of Alzheimer's Disease" and in U.S. Pat. No. 6,071,705 for "Method of Detecting Neurological Disease or Dysfunction." The disclosures of these patents are specifically incorporated herein by reference in their entirety. As described therein, NTP is upregulated and produced during cell death. Thus, dead and dying nerve cells are described as overproducing NTP, and accordingly, its presence indicates the death of nerve cells and the onset of Alzheimer's disease (AD).

Other species of neural thread protein have been identified as other products of the AD7c-NTP gene (e.g. a 112 amino acid protein described in NCBI Entrez-Protein database Accession #XP_032307 PID g15928971) or as being similar to neural thread proteins (e.g. a 106 amino acid protein described in NCBI Entrez-Protein database Accession #AAH14951 PID g15928971, another 106 amino acid protein described in NCBI Entrez-Protein database Accession #XP_039102 PID g18599339 and a 61 amino acid protein described in NCBI Entrez-Protein database Accession #AAH02534 PID g12803421).

Neural thread protein is associated with AD and NTP is upregulated in association with cell death in AD. AD7c-NTP mRNA is upregulated in AD brain compared to controls; AD7c-NTP protein levels in brain and in CSF are higher in AD than controls; and AD7c-NTP immunoreactivity is found in senile plaques, in neurofibrillary tangles (NFT), in degenerating neurons, neuropil threads, and dystrophic neurotic sprouts in AD and Down syndrome brains (Ozturk et al., *Proc. Natl. Acad. Sci. USA*, 86:419-423 (1989); de la Monte et al., *J. Clin. Invest.*, 86(3):1004-13 (1990); de la Monte et al., *J. Neurol. Sci.*, 113(2):152-64 (1992); de la Monte et al., *Ann. Neurol.*, 32(6):733-42 (1992); de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2):118-25 (1996); de la Monte et al., *J. Clin. Invest.*, 100:3093-3104 (1997); and de la Monte et al., *Alz. Rep.*, 2:327-332 (1999)). NTP is localized within cells, within fine processes within the neuropil, or is extracellular in both AD and Down's Syndrome brains. de la Monte et al., *Ann. Neurol.*, 32(6):733-42 (1992).

Elevated levels of AD7c-NTP protein have been found in both CSF and urine of AD patients (de la Monte and Wands, *Front Biosci* 7: 989-96 (2002); de la Monte and Wands, *Journal of Alzheimer's Disease* 3: 345-353 (2001); Munzar et al, *Alzheimer's Reports* 4: 61-65 (2001); Kahle et al, *Neurology* 54: 1498-1504 (2000); Munzar et al, *Alzheimer Reports* 3: 155-159 (2000); de la Monte et al, *Alzheimer's Reports* 2: 327-332 (1999); and de la Monte et al, *J Clin Invest* 100: 3093-3104 (1997).

Over-expression of NTP also has been linked to the process of cell death in Alzheimer's disease (de la Monte and Wands, *J. Neuropathol. Exp. Neurol.*, 60:195-207 (2001); de la Monte and Wands, *Cell Mol Life Sci* 58: 844-49 (2001). AD7c-NTP has also been identified in Down's Syndrome brain tissue (Wands et al., International Patent Publication No. WO 90/06993; de la Monte et al, *J Neurol Sci* 135: 118-25 (1996); de la Monte et al., *Alz. Rep.*, 2:327-332 (1999)). There is some evidence that over-expression of NTP also may be associated with normal tension glaucoma (Golubnitschaja-Labudova et al, *Curr Eye Res* 21: 867-76 (2000)).

NTP has proven to be an effective agent for causing cell death both in vitro in glioma and neuroblastoma cell cultures and in vivo in normal rodent muscle tissue, subcutaneous connective tissue, and dermis, and in a variety of different human and non-human origin tumors, including mammary carcinoma, skin carcinoma and papilloma, colon carcinoma, glioma of brain, and others in rodent models. See the pending U.S. patent application Ser. No. 10/092,934, entitled: Methods of Treating Tumors and Related Conditions Using Neural Thread Proteins, filed on Mar. 8, 2002.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to the present invention.

There remains a need in the art for new, less toxic treatments for treating unwanted cellular elements. The present invention satisfies these needs.

SUMMARY OF THE INVENTION

The present invention involves in part the discovery that peptide sequences contained in AD7c-NTP that the inventors have found to be effective agents for the destruction or removal of harmful or unwanted cells, and variants and homologs thereof, also are found in other proteins in other organisms, including humans and other mammals. Once the peptide sequences have been discovered, these proteins can be found by a person ordinarily skilled in the art through the use of widely available public and commercial protein databases such as the National Center Biotechnology Information's Protein database and search programs such as BLAST® (Basic Local Alignment Search Tool). See Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402.

A person having ordinary skill in the art then can screen these proteins by using the assay method described herein to determine their effectiveness as agents for the destruction or removal of unwanted or harmful cells. A person ordinarily skilled in the art, having found one or more such effective agents, then can determine which portions of those agents contain sequences homologous with or similar to the AD7c-NTP peptide sequences described herein, or described in pending U.S. application Ser. No. 10/153,334, entitled: Peptides Effective in the Treatment of Tumors and Other Conditions Requiring the Removal or Destruction of Cells, filed May 24, 2002, have those portions of those agents synthesized using methods known to those skilled in the art, and test the synthesized agents for their effectiveness as agents for the destruction or removal of unwanted or harmful cells. Furthermore, a person ordinarily skilled in the art could also use the amino acid sequences of any such proteins found to determine other peptide sequences not similar to or homologous with homologous with or similar to the AD7c-NTP peptide sequences described herein, and described in pending U.S. application Ser. No. 10/153,334, entitled: Peptides Effective in the Treatment of Tumors and Other Conditions Requiring the Removal or Destruction of Cells, filed May 24, 2002. These new synthesized sequences could then be tested for their effectiveness as agents for the destruction or removal of unwanted or harmful cells.

The present invention is directed to peptides, compositions, and methods of treating unwanted cellular proliferations, such as benign and malignant tumors, glandular (e.g. prostate) hyperplasia, unwanted facial hair, warts, and unwanted fatty tissue. Such a method comprises administering to a mammal in need, a therapeutically effective amount of a Related Protein, a Related Peptide, or an NTP Peptide known to be an effective agent for causing cell death. The terms "Related Protein," "Related Peptide," and "NTP Peptide" are defined below.

The peptides of the present invention have at least one amino acid sequence corresponding to part of the amino acid sequence of a species of neural thread protein. The compositions of the invention include the peptides and a pharmaceutically acceptable carrier. The inventive peptides or proteins ("cell death peptide") can be administered alone, or they can be conjugated to a carrier or an antibody and formulated into a composition. The cell death peptides can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc., either alone or conjugated to a carrier. Alternatively, the cell death peptide can be expressed in vivo by administering a gene that expresses the peptide, by administering a vaccine that induces such production or by introducing cells, bacteria or viruses that express the peptide in vivo, either because of genetic modification or otherwise.

In addition, the cell death peptide may be used in conjunction with other therapies for treating benign and malignant tumors and other unwanted or harmful cellular growths. Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows the complete amino acid sequence [SEQ ID NO: 1] and nucleic acid sequence [SEQ ID NO: 125] of the AD7c-NTP gene and the AD7c-NTP protein product of that gene (Sequences 120 and 121 from U.S. Pat. Nos. 5,830,670, 5,948,634, and 5,948,888; de la Monte et al., *J. Gun. Invest.*, 100:3093-3104 (1997); NCBI Entrez-Protein Accession # AAC08737; PID g3002527) [SEQ ID NO. 1].

FIG. 2: Shows the complete amino acid sequences of the 122 amino acid neural thread protein (Sequence 40 from U.S. Pat. Nos. 5,830,670, 5,948,634, and 5,948,888; NCBI Entrez-Protein Accession #AAE25447 PID g10048540) [SEQ ID NO. 2] ("NTP-122").

FIG. 3: Shows the complete amino acid sequences of the 112 amino acid neural thread protein (NCBI Entrez-Protein Accession #XP_032307 PID g15928971) [SEQ ID NO. 3] ("NTP-112").

FIG. 4: Shows the complete amino acid sequences of a 106 amino acid neural thread protein-like protein (NCBI Entrez-Protein Accession #AAH14951 PID g15928971) [SEQ ID NO. 4] ("NTP-106A").

FIG. 5: Shows the complete amino acid sequences of a 106 amino acid neural thread protein-like protein (NCBI Entrez-Protein Accession #XP_039102 PID g18599339) [SEQ ID NO. 5] ("NTP-106B").

FIG. 6: Shows the complete amino acid sequences of the 98 amino acid neural thread protein (Sequence 30 from U.S. Pat. Nos. 5,830,670, 5,948,634, and 5,948,888; NCBI Entrez-Protein Accession # AAE25445, PID g10048538) [SEQ ID NO. 6] ("NTP-98").

FIG. 7: Shows the complete amino acid sequences of the 75 amino acid neural thread protein (Sequence 48 from U.S. Pat. Nos. 5,830,670, 5,948,634, and 5,948,888; NCBI Entrez-Protein Accession #AAE25448, PID g10048541) [SEQ ID NO. 7] ("NTP-75").

FIG. 8: Shows the complete amino acid sequences of the 68 amino acid neural thread protein (Sequence 36 from U.S. Pat. Nos. 5,830,670, 5,948,634, and 5,948,888; NCBI Entrez-Protein Accession #AAE25446, PID g10048539) [SEQ ID NO. 8] ("NTP-66").

FIG. 9: Shows the complete amino acid sequences of the 61 amino acid neural thread protein-like protein (NCBI Entrez-Protein Accession #AAH02534, PID g12803421) [SEQ ID NO. 9] ("NTP-61").

DETAILED DESCRIPTION OF THE PREFERRED EMBODIMENTS

Terms and phrases used herein are defined as set forth below unless otherwise specified.

The expression "AD7c-NTP" refers to the ~41 kD protein and the gene and the nucleic acid sequences coding for it described in de la Monte et al., *J. Clin. Invest.*, 100:3093-104 (1997), in Sequences 120 and 121 of U.S. Pat. Nos. 5,948, 634, 5,948,888, and 5,830,670 and in GenBank #AF010144, the nucleic acid and amino acid sequences for which are illustrated in FIG. 1. The term "AD7c-NTP" also includes biologically active fragments, variants, derivatives, homologues and mimetics of AD7c-NTP.

The term "NTP" or "neural thread protein" refers to neural thread proteins and related molecules (including pancreatic thread protein) and the nucleic acid sequences coding for those proteins, and includes (but is not limited to) the following proteins and the nucleic acid sequences encoding the amino acid sequences for these proteins:

(a) AD7c-NTP;
(b) the ~42, ~26, ~21, ~17, ~14, and ~8 kD species of neural thread protein as described in U.S. Pat. Nos. 5,948,634, 5,948,888, 5,830,670, and 6,071,705 and in de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2):118-25 (1996), de la Monte et al., *J. Clin. Invest.*, 100:3093-3104 (1997) and de la Monte et al., *Alz. Rep.*, 2:327-332 (1999);
(c) proteins specifically recognized by monoclonal antibody #2 on deposit with the American Type Culture Collection, Manassas, Va., under accession number HB-12546 or monoclonal antibody #5 on deposit with the American Type Culture Collection, Manassas, Va., under accession number HB-12545;
(d) proteins coded by the AD7c-NTP gene;
(e) the 122 amino acid neural thread protein described in Sequence 40 from U.S. Pat. Nos. 5,830,670, 5,948,634, and 5,948,888 and listed in NCBI Entrez-Protein Accession #AAE25447, PID g10048540, the amino acid sequences for which is illustrated in FIG. 2 ("NTP-122");
(f) the 112 amino acid neural thread protein listed in NCBI Entrez-Protein Accession #XP_032307, PID g14725132, the amino acid sequences for which is illustrated in FIG. 3 ("NTP-112");
(g) a 106 amino acid neural thread protein-like protein listed in NCBI Entrez-Protein Accession #AAH14951 PID g15928971, the amino acid sequences for which is illustrated in FIG. 4 ("NTP-106A");
(h) a 106 amino acid neural thread protein-like protein listed in NCBI Entrez-Protein Accession #XP_039102, PID g18599339, the amino acid sequence for which is illustrated in FIG. 5 ("NTP-106B");

(i) the 98 amino acid neural thread protein described in Sequence 30 from U.S. Pat. Nos. 5,830,670, 5,948,634, and 5,948,888 and listed in NCBI Entrez-Protein Accession # AAE25445, PID g10048538, the amino acid sequences for which is illustrated in FIG. 6 ("NTP-98");

(j) the 75 amino acid neural thread protein described in Sequence 48 from U.S. Pat. Nos. 5,830,670, 5,948,634, and 5,948,888 and listed in NCBI Entrez-Protein Accession #AAE25448, PID g10048541, the amino acid sequences for which is illustrated in FIG. 7 ("NTP-75");

(k) the 68 amino acid neural thread protein described in Sequence 36 from U.S. Pat. Nos. 5,830,670, 5,948,634, and 5,948,888 and listed in NCBI Entrez-Protein Accession #AAE25446, PID g10048539, the amino acid sequences for which is illustrated in FIG. 8 ("NTP-68");

(l) the 61 amino acid neural thread protein-like protein listed in NCBI Entrez-Protein Accession #AAH02534, PID g12803421, the amino acid sequences for which is illustrated in FIG. 9 ("NTP-61");

(m) pancreatic thread protein;

(n) the neural pancreatic thread protein (nPTP) described in U.S. Pat. No. 6,071,705; and (o) proteins specifically recognized by the antibodies produced by a hybridoma from the group consisting of HB 9934, HB 9935, and HB 9936 deposited at the American Type Culture Collection.

The expression "NTP peptide" refers to peptides comprising amino acid sequences corresponding to at least a part of the amino acid sequence of NTP or to fragments of NTP and includes homologues, derivatives, variants, fusion proteins, and peptide mimetics of such peptides unless the context indicates otherwise. The expression "NTP peptide" also includes (but is not limited to) the peptides specifically listed in U.S. patent applications Ser. Nos. 10/092,934, and 10/153334. The expression "NTP peptide" also perferably includes (but is not limited to) the following amino acid sequences of NTP:

```
                                           [SEQ ID NO 10]
(a)  NTP peptide #1: AD7c-NTP p239-243
     SSWDY
     Ser-Ser-Trp-Asp-Tyr

[SEQ ID NO.11]
(b)  NTP peptide #2, AD7c-NTP p31-39
     PASASPVAG
     Pro-Ala-Ser-Ala-Ser-Pro-Val-Ala-Gly

[SEQ ID NO.12]
(c)  NTP peptide #3, AD7c-NTP p14-24
     GAISAHRNLRL
     Gly-Ala-Ile-Ser-Ala-His-Arg-Asn-Leu-Arg-Leu

[SEQ ID NO.13]
(d)  NTP peptide #4, AD7c-NTP p53-58
     FFLVEM
     Phe-Phe-Leu-Val-Glu-Met

[SEQ ID NO.14]
(e)  NTP peptide #5, AD7c-NTP p208-216
     SVTQAGVQW
     Ser-Val-Thr-Gln-Ala-Gly-Val-Gln-Trp

[SEQ ID NO.15]
(f)  NTP peptide #6, NTP-122 p106-122
     IDQQVLSRIKLEIKRCL
     Ile-Asp-Gln-Gln-Val-Leu-Ser-Arg-Ile-Lys-Leu-
     Glu-Ile-Lys-Arg-Cys-Leu

[SEQ ID NO.16]
(g)  NTP peptide #7, NTP-122 p111-119
     LSRIKLEIK
     Leu-Ser-Arg-Ile-Lys-Leu-Glu-Ile-Lys
``` and includes homologues, derivatives, variants, fragments, fusion proteins, and peptide mimetics of these specifically listed NTP peptides.

The phrase "Related Protein" refers to proteins containing one or more amino acid sequences identical, closely similar to, or homologous to one or more NTP peptides.

The expression "Related Peptide" refers to peptides consisting of amino acid sequences corresponding to at least a part of the amino acid sequence of a Related Protein and includes homologs, variants, fusion proteins, reverse-D peptides and peptide mimetics of such peptides. The expression "Related Peptide" also preferably includes (but is not limited to) the following amino acid sequences of Related Proteins:

```
                                           [SEQ ID NO.17]
(a) Related Peptide #1 transient receptor potential
    channel 6, variant delta (NCBI Accession
    CAC01686, PID g9716913), p356-377
    GDHGRPNLSRLKLAIKYEVKKM
    Gly-Asp-His-Gly-Arg-Pro-Asn-Leu-Ser-Arg-Leu-
    Lys-Leu-Ala-Ile-Lys-Tyr-Glu-Val-Lys-Lys-Met

[SEQ ID NO.18]
(b) Related Peptide #2 putative capacitative
    calcium channel (NCBI Accession NP_065122,
    PID g9966865), p345-360
    QQSIAVKFLAVFGVSI
    Gln-Gln-Ser-Ile-Ala-Val-Lys-Phe-Leu-Ala-Val-
    Phe-Gly-Val-Ser-Ile

[SEQ ID NO.19]
(c) Related Peptide #3 trp-related protein 4
    truncated variant gamma, (NCBI Accession
    AF063825_1, PID g6665596), p337-357
    GLLFPVFSVCYLIAPKSPLGL
    Gly-Leu-Leu-Phe-Pro-Val-Phe-Ser-Val-Cys-Tyr-
    Leu-Ile-Ala-Pro-Lys-Ser-Pro-Leu-Gly-Leu
``` and includes homologues, derivatives, variants, fusion proteins, and peptide mimetics of these specifically listed Related Peptides.

The phrase "cell death peptide" refers to a Related Protein or Related Peptide that has been proven to be an effective agent for causing cell death.

The term "fragment" refers to a protein or polypeptide that consists of a continuous subsequence of the amino acid sequence of an NTP protein, NTP peptide, Related Protein or Related Peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same NTP protein or NTP peptide, or Related Protein or Related Peptide, with a contiguous amino acid sequence in common or not, joined together, either directly or through a linker.

The term "variant" refers to a protein or polypeptide in which one or more amino acid substitutions, deletions, and/or insertions are present as compared to the amino acid sequence of an NTP protein, NTP peptide, Related Protein, or Related Peptide and includes naturally occurring allelic variants or alternative splice variants of an NTP protein, NTP peptide, Related Protein or Related Peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

Table 3 sets out another scheme of amino acid substitution:

TABLE 3

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include NTP proteins, NTP peptides, Related Proteins and Related Peptides with additional amino acid residues before or after the NTP protein, NTP peptide, Related Protein or Related Peptide amino acid sequence on linker peptides. For example, a cysteine residue may be added at both the amino and carboxy terminals of a Related Peptide in order to allow the cyclisation of the Related Peptide by the formation of a di-sulphide bond. The term "variant" also encompasses polypeptides that have the amino acid sequence of a Related Protein or Related Peptide with at least one and up to 25 or more additional amino acids flanking either the 3' or 5' end of the Related Protein or Related Peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type Related Proteins or Related Peptides. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *Proteins—Structure And Molecular Properties*, 2nd Ed., T. E. Creighton, W. H. Freeman and Company, New York (1993) and Wold, F., "Posttranslational Protein Modifications: Perspectives and Prospects," pgs. 1-12 in *Posttranslational Covalent Modification Of Proteins*, B. C. Johnson, Ed., Academic Press, New York (1983); Seifter et al., *Meth. Enzymol.* 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of an NTP protein, NTP peptide, Related Protein, or Related Peptide, as the case may be, as determined by standard methods that are commonly used to compare the similarity in position of the amino acids of two polypeptides. The degree of similarity or identity between two proteins can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carillo H. and Lipman, D., SIAM, *J. Applied Math.*, 48: 1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research*, 12(1): 387 (1984)), BLASTP, BLASTN, and FASTA, Atschul, S. F. et al., *J. Molec. Biol.*, 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.*, 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3× (times) the average diagonal; the "average diagonal" is the average of the diagonal of the comparison matrix being used; the "diagonal" is the score or number assigned to each perfect amino acid by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure*, vol. 5, supp. 3 [1978] for the PAM250 comparison matrix; see Henikoff et al., *Proc. Natl. Acad. Sci USA*, 89:10915-10919 [1992] for the BLOSUM 62 comparison matrix) also may be used by the algorithm. The percent identity then is calculated by the algorithm. Homologues will typically have one or more amino acid substitutions, deletions, and/or insertions as compared with the comparison NTP protein, NTP peptide, Related Protein or Related Peptide, as the case may be.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the NTP peptide, Related Protein or Related Peptide on which the peptide mimetic is based. As a result of this similar active-site geometry, the peptide mimetic has effects on biological systems that are similar to the biological activity of the NTP peptide, Related Protein, or Related Peptide.

The peptide mimetics of this invention preferably are substantially similar in both three-dimensional shape and biological activity to the NTP peptides, Related Proteins, or Related Peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala$^1$-Peptide T Binding", Smith C. S. et al., *Drug Development Res.*, 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the Related Protein or Related Peptide by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.*, 41:561-566, incorporated herein by reference). According to this modification, the amino acid sequences of the peptides may be identical to the sequences of an NTP peptide, Related Protein, or Related Peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.*, 41:181-184, incorporated herein by reference in its entirety).

Thus, the amino acid sequences of these peptides may be identical to the sequences of an NTP peptide, Related Protein, or Related Peptide, except that one or more of the peptide bonds are replaced by an isostere pseudopeptide bond. The expression "amino acid sequence(s)" preferably is used herein to denote a sequence of at least two amino acids, preferably at least four, and more preferably at least five. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of NTP peptides, Related Proteins, and Related Peptides represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the NTP peptides, Related Protein, or Related Peptide may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of an NTP peptide, Related Protein, or Related Peptide. Thus, the carboxy terminal residue of an L-amino acid NTP peptide, Related Protein, or Related Peptide becomes the amino terminal for the D-amino acid peptide and so forth. For example, the NTP peptide, SSWDY [SEQ ID NO: 10], becomes $Y_d D_d W_d S_d S_d$, where $D_d$, $S_d$, $W_d$, and $Y_d$ are the D-amino acids corresponding to the L-amino acids, D, S, W, and Y respectively.

The term "enantiomer" refers to a biologically active protein or peptide where one or more the L-amino acid residues in the amino acid sequence of an NTP peptide, Related Protein, or Related Peptide is replaced with the corresponding D-amino acid residue(s).

Amino acids and amino acid residues described herein may be referred to according to the accepted one or three-letter code provided in the table below.

TABLE 1

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |

TABLE 1-continued

| Amino Acid | One-Letter Symbol | Three-Letter Symbol |
|---|---|---|
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The present invention is directed to a composition comprising cell death peptides as defined above in this invention. A preferred cell death peptide is similar or homologous to an NTP peptide. However, the use of other cell death peptides based on portions or fragments of Related Proteins also is encompassed by the invention. For example, the AD7c-NTP peptide sequences and similar variants and homologs also are found in a wide variety of human and non-human proteins ("Related Proteins"). In particular, the AD7c-NTP gene contains Alu-type sequences that are closely similar to those also found in other genes in the human and other primate genomes.

It therefore is reasonable to expect that some, if not all, of the Related Proteins also will prove to be effective agents for causing cell death because they contain peptide sequences homologous or closely similar to the AD7c-NTP peptides ("Related Peptides"). Similarly a person ordinarily skilled in the art could synthesize specific Related Peptides based on the amino acid sequence for any Related Protein found to be an effective agent for causing cell death and test them for efficacy as agents for causing cell death.

Other peptide sequences derived from a Related Protein found to be an effective agent for causing cell death also may be effective agents for causing cell death. A person ordinarily skilled in the art can synthesize without undue experimentation fragments of an effective Related Protein spanning the entire amino acid sequence of that protein in order to identify other effective peptide sequences.

Some Related Proteins include the following proteins known to contain amino acids identical, closely similar to, or homologous to NTP peptide sequences:

| Protein Identification Number (PID) | SEQ. ID NO. | Amino Acid Sequences of Protein |
|---|---|---|
| g10121865 | 20 | MEVSPLQPVN ENMQVNKIKK NEDAKKRLSV ERIYQKKTQL EHILLRPDTY IGSVELVTQQ MWVYDEDVGI NYREVTFVPG LYKIFDEILV NAADNKQRDP KMSCIRVTID PENNLISIWN NGKGIPVVEH KVEKMYVPAL IFGQLLTSSN YDDDEKKVTG GRNGYGAKLC NIFSTKFTVE TASREYKKMF KQTWMDNMGR AGEMELKPFN GEDYTCITFQ PDLSKFKMQS LDKDIVALMV RRAYDIAGST KDVKVFLNGN KLPVKGFRSY VDMYLKDKLD ETGNSLKVIH EQVNHRWEVC LTMSEKGFQQ ISFVNSIATS KGGRHVDYVA DQIVTKLVDV VKKKNKGGVA VKAHQRELCN GAILAHCNLR LMGSSDSPAS ASRVAGIAGG CHHTQLIFVF LVETGFHHVG QAGLERLTSG DPPASASQSS GITDVKVKNH MWIFVNALIE NPTFDSQTKE NMTLQPKSFG STCQLSEKFI KAAIGCGIVE SILNWVKFKA QVQLNKKCSA |

-continued

| Protein Identification Number (PID) | SEQ. ID NO. | Amino Acid Sequences of Protein |
|---|---|---|
| | | VKHNRIKGIP KLDDANDAGG RNSTECTLIL TEGDSAKTLA VSGLGVVGRD KYGVFPLRGK ILNVREASHK Q |
| g10257409 | 21 | MTGDKGPQRL SGSSYGSISS PTSPTSPGPQ QAPPRETYLS EKIPIPDTKP GTFSLRKLWA FTGPGFLMSI AFLDPGNIES DLQAGAVAGF KLLWVLLWAT VLGLLCQRLA ARLGVVTGKD LGEVCHLYYP KSESRSVAQS GVQWCDVSSL QPLPPRCPAP SSG |
| g10433567 | 22 | MMLSVQENVH RCICKHYAPP TAPHLFFETE SHSVTQAGVQ WCDLGSLQPS PPGFKQFSCL SLSRSWDYRR VPLCLANFIV FLVETGFCRV GQAGLKLLTS SDLPASACQS AGDYRHEPLR LALTLCHFIS RTCTSVDFYI CRDLERIPHG H |
| g10434441 | 23 | MISAHRNLHL PGSSNSPASA FLSSWDYRHV PPCPANVVFL VEMGFLHVGQ AGLELPTSDD PPTLASQSAG ITGVSHRTWQ EFASLTVSQA VLRMLVWGPQ FENHCSKLLM ASEGDSSLVF FLYPLSNLN |
| g10436387 | 24 | MQGSHSAVQA GVWWCHHDSL QPWPPGLRRS SCLSLQSLWD YRSLALSLRL ACNGTTSAHC DLCLLSSSDS PASASQVAGI TGEKTAEPHK AHAAQGERHL SSHMSPDENM TEKFCPGPRA SFHLRILAAS RHLVKRLLNE YTVTVLRDKS YLRNN |
| g10437485 | 25 | MKNYYYFLGQ GLTLSPRLEC SSTISAHCNL HLLGSSNSPV AASPVAGTTG TCHHDWLIFV FLVETGFHHI GQTGLEFLTS GDPPTLASKS AGITGVSHCA WPTFLLNDMR HSFNKNLVII FYVPAIS |
| g10441986 | 26 | MRRELLAGIL LRITFNFFLF FFLPFPLVVF FIYFYFYFFL EMESHYVAQA GLELLGSSNP PASASLVAGT LSVHHCACFE SFTKRKKKLK KAFRFIQCLL LGLLKVRPLQ HQGVNSCDCE RGYFQGIFMQ AAPWEGT |
| g10945428 | 27 | MSKTLKKKKH WLSKVQECAV SWAGPPGDFG AEIRGGAERG EFPYLGRLRE EPGGGTCCIV SGKAPNPSDV LLEVNGTPVS GLTNRDTLAV IRHFREPIRL KTVKPGKVIN KDLRHYLSLQ FQKGSIDHKL QQVIRDNLYL RTIPCTTRAP RDGEVPGVDY NFISVEQFKA LEESGALLES GTYDGNFYGT PKPPAEPSPF QPDPVDQVLF DNEFDAESQR KRTTSVSKME RMDSSLPEEE EDEDKGAING SGNAENRERH SESSDWMKTV PSYNQTNSSM DFRNYMMRDE TLEPLPKNWE MAYTDTGMIY FIDHNTKTTT WLDPRLCKKA KAPEDCEDGE LPYGWEKIED PQYGTYYVDF TLVAQAGVQW HDLGSLQPPP PGFNHLNQKT QFENPVEEAK RKKQLGQVEI GSSKPDMEKS HFTRDPSQLK GVLVRASLKK STMGFGFTII GGDRPDEFLQ VKNVLKDGPA AQDGKIAPGD VIVDINGNCV FGHTHADVVQ MFQLVPVNQY VNLTLCRGYP LPDDSEDPVV DIVAATPVIN GQSLTKGETC MNPQDFKPGA MVLEQNGKSG HTSTGDGLNG PSDASEQRVS MASSGSSQPE LVTIPLIKGP KGFGFAIADS PTGQKVKMIL DSQWCQGLQK EDIIKEIYHQ NVQNLTHLQV VEVLKQFPVG ADVPLLILRG GPPSTKTAK MKTDKKENAG SLEAINEPIP QPMPFPPSII RSGSPKLDPS EVYLKSKTLY EDKPPNTKDL DVFLRKQESG FGFRVLGGDG PDQSIYIGAI IPLGAAEKDG RLRAADELMC IDGIPVKGKS HKQVLDLMTT AARNGHVLLT VRRKIFYGEK QPEDDSSQAF ISTQNGSPRL NRAEVPARPA PQEPYDVVLQ RKENEGFGFV ILTSKNKPPP |
| | | GVIPHKIGRV IEGSPADRCG KLKVGDHISA VNGQSIVELS HANIVQLIKD AGVTVTLTVI AEEEHHGPPS GTNSARQSPA LQHRPMGQSQ ANHIPGDRSA LEGEIGKDVS TSYRHSWSDH KHLAQPDTAV ISVVGSRHNQ NLGCYPVELE RGPRGFGFSL RGGKEYNMGL FILRLAEDGP AIKDGRIHVG DQIVEINGEP TQGITHTRAI ELIQAGGNKV LLLLRPGTGL IPDHGLAPSG LCSYVKPEQH |
| g1117849 | 28 | MADDQGCIEE QGVEDSANED SVDAKPDRSS FVPSLFSKKK KNVTMRSIKT TRDRVPTYQY NMNFEKLGKC IIINNKNFDK VTGMGVRNGT DKDAEALFKC FRSLGFDVIV YNDCSCAKMQ DLLKKASEED HTNAACFACI LLSHGEENME SCSVTQAGVQ RRDLGRLQPP PPRLAEGPSL MMASRPTRGP SMTQMLILDT RSQWKLTSSS PIPRFQAITR GGAQEEAPGL CKPSAPSWRS TEKTWKSCRS SPG |
| g11493409 | 29 | MGLSIASHFG LLIKKVERNI LFFFRRSLAL CQAGVQWRYL SQLTAASASW VQAILCLSLP SSWDYRHMPP RPANFCILSR DGISPCWPGW SRSLDLVIRP PRPPKVLRLQ A |
| g11493483 | 30 | MQIIFFFLFL RWSFTLVAQA GVQWRDLSSP QPPPPRFKRF SCLSPPSSWD YRHAPPHPAN FVFLVETGFL RVGQAGLELL TSGDPPASAS QSAGITGVSH HTQPDANNFL RKLFQKLF |
| g12654881 | 31 | MGHPRAIQPS VFFSPYDVHF LLYPIRCPYL KIGRFHIKLK GLHFLFSFLF FFFETQSHSV TRLECSGTIS AHCNLCLPGS SNSPASASQV AGTTGTCHHA QLIFVFLAEM GFHHIGQDGL DLNLVIHPPR SPKALGLQA |
| g12803929 | 32 | MPNHYSFCFC FCFCFRRSLA LSPRLECSGA ILAHGKLHLP GSRHSPASAS PVAGTKGARH HARLIFLYF |
| g13359183 | 33 | LFTNSPFSLL SPAQWLCFGT HLGHVQSVSH LQWEGSVQES LRSVRNSRCA LPMLSAPCSL SLHFLLFSLS PFFFFEIRVL LYRQAGVQWC YLGSLQPLPP GFKQFSCLSY PSSWDYRRPP PRQANFCIFS TDGVSPCWPR WSLSLDLMIR PPQPPEVLGL QV |
| g13375624 | 34 | MGRLVLLWGA AVFLLGGWMA LGQGGAEGVQ IQIIYFNLET VQVTWNASKY SRTNLTFHYR FNGDEAYDQC TNYLLQEGHT SGCLLDAEQR DDILYFSIRN GTHPVFTASR WMVYYLKPSS PKHVRFSWHQ DAVTVTCSDL SYGDLLYEVQ YRSPFDTEWQ TQSRSVTQAG VQWCDLCLLQ PSPPPRFKRFS CLSLPSSWDY RHPPPRLANF CIISRDGVSP CWPGWSRTCD LR |
| g13375628 | 35 | MEFLKVARRN KREQLEQIQK ELSVLEEDIK RVEEMSGLYS PVSEDSTVPQ FEAPSPSHSS IIDSTEYSQP PGFSGSSQAG VQWRYLGSLQ PPPPRYKRFS CLTLPSSWDY RRLPPHLTKK QPWYNSTLAS RRKRLTAHFE DLEQCYFSTR MSRISDDSRT ASQLDEFQEC LSKFTRYNSV RPLATLSYAS DLYNGSSIVS SIEFDRDCDY FAIAGVTKKI KVYEYDTVIQ DAVDIHYPEN EMTCNSKISC ISWSSYHKNL LASSDYEGTV ILWDGFTGQR SKVYQEHEKR CWSVDFNLMD PKLLASGSDD AKVKLWSTNL DNSVASIEAK ANVCCVKFSP SSRYHLAFGC ADHCVHYYDL RNTKQPIMVF KGHRKAVSYA KFVSGEEIVS ASTDSQKLW NVGKPYCLRS FKGHINEKNF VGLASNGDYI ACGSENNSLY LYYKGLSKTL LTFKFDTVKS VLDKDRKEDD TNEFVSAVCW RALPDGESNV LIAANSQGTI KVLELV |

| Protein Identification Number (PID) | SEQ. ID NO. | Amino Acid Sequences of Protein |
|---|---|---|
| g13376550 | 36 | MGSYFVARAG CKLLGLKGTS HFSLPKCRNC RREPLPGLFF LFFVFFFLRR SLALSPRLEC SGAIVAHCKL GLPGSLHSPA SASQVAGTIG TCHNTRIIFC ILVETGFHRV SQDGVDLLTL |
| g13430856 | 37 | MDCGSVGGQR TQRLPGRQRL LFLPVGLSGR PGGSETSARR CPSALSDGLG ALRPRAPAAR GGVSRASPLL LLLLVPSPRL AAAAPRRQLG DWERSRLGYA APPAGRSGAW RCSPGVAAAA GALPQYHGPA PALVSCRREL SLSAGSLQLE RKRRDFTSSG SRKLYFDTHA LVCLLEDNES HSFIQAGVQW HSLGLLQPPP PGFKRSSHLI LLSSWDYRHA PPHLDNFSVF LLETGFHHVG QAGLKLLTSS DPPTLAS |
| g13431835 | 38 | MSPATTGTFL LTVYSIFSKV HSDRNVYPSA GVLFVHVLER EYFKGEFPPY PKPGEISNDP ITFNTNLMGY PDRPGWLRYI QRTPYSDGVL YGSPTAENVG KPTIIEITAY NRRTFETARH NLIINIMSAE DFPLPYQAEF FIKNMNVEEM LASEVLGDFL GAVKNVWQPE RLNAINITSA LDRGGRVPLP INDLKEGVYV MVGADVPFSS CLREVENPQN QLRCSQEMEP VITCDKKFRT QFYIDWCKIS LVDKTKQVST YQEVIRGEGI LPDGGEYKPP SDSLKSRDYY TDFLITLAVP SAVALVLFLI LAYIMCCRRE GVEKRNMQTP DIQLVHHSAI QKSTKELRDM SKNREIAWPL STLPVFHPVT GEIIPPLHTD NYDSTNMPLM QTQQWSFAPV AQAGVQWRDL GSLQPPPPRN LPHQTQIPQQ QTTGKWYP |
| g13435153 | 39 | MLGLRKAAAI SLLLRNVGLQ LATLLLMSQKK LGFCGNFLFL NLAIIQTKIS SSFFFFLRQS LTLSPRLECN GAISAHCHLR LPDSSNSPAS ASQVTGITGS HHHAWLIFVF LVETGFCHVG QDGLELLTSG DPPASASQSA GITGMSHHTW PTDLFFKTVL PARLGLWDSS V |
| g13489079 | 40 | MHAVPRGFGK KVRVGVQSCP SPFSGQACPQ PSSVFWSLLK NLPFLEHLEL IGSNFSSAMP RNEPAIRNSL PPCSRAQSVG DSEVAAIGQL AFLRHLTLAQ LPSVLTGSGL VNIGPQCQQL RSLSLANLGM MGKVVYMPAL SDMLKHCKRL RDLRLEQPYF SANAQFFQAL SQCPSLQRLC LVSRSGTLQP DAVLAFMARC LQVVMCHLFT GESLATCKSL QQSLLRRWGE VTGRRPQLFT ELREEPSART SRATGRRQPC LPDSGVVCCP CGRPLAVSGI ILVGVSPSLV VKTTCVYRVL FKNLDYASIF FLVCLFETES HSVVQAGVQW RDLSSLQPLL SGLQPQPPEQ LENELEIGFS YCFVI |
| g13489081 | 41 | MEEDEFIGEK TFQRYCAEFI KHSQQIGDSW EWRPSKDCSD GYMCKIHFQI KNGSVMSHLG ASTHGQTCLP MEVKSCSVTQ AGVQLRDLSS LQPPPSGFKQ FSCLSLPSNW DYRGSPLHLA NFLYF |
| g13540498 | 42 | MTTCEFEFIF LKEQVTRICN IAPLKAYFSV HKMGKILKKL SNFSFLTHRQ SLTLSPRLEC SGAISAHCNL HLLGSSNSAA SASRVAGTTG ACHHAQLIFV FLVETGFHHV GQDGLGLLTS |
| g13543287 | 43 | MSCNPSFGGI GKGHLMREVD ALDGLCSRIC DQSGVHYKVL NRRKGPAVWG LRAQIDRKLY KQNMQKEILN TPLLTVQEGA VEDLILTEPE PEHTGKCRVS GVVLVDGSTV YAESVILTTG TFLRGMIVIG LETHPAGRLG DQPSIGLAQT LEKLGFVVGR LKTGTPPRIA KESINFSILN KHIPDNPSIP FSFTNETVWI KPEDQLPCYL THTNPRVDEI VLKNLHLNSH VKETTRGPRY CPSIESKVLR FPNRLHQVWL EPEGMDSDLI |
| | | YPQGLSMTLP AELQEKMITC IRGLEKAKVI QPDGVLLLLP RMECNGAISA HHNLPLPGYG VQYDYLDPRQ ITPSLETHLV QRLFFAGQIN GTTGYEEAAA QGVIAGINAS LRVSRKPPFV VSRTEGYIGV LIDDLTTLGT SEPYRMFTSR VEFRLSLRPD NADSRLTLRG YKDAGCVSQQ RYERACWMKS SLEEGISVLK SIEFLSSKWK KLIPEASIST SRSLPVRALD VLKYEEVDMD SLAKAVPEPL KKYTKCRELA ERLKIEATYE SVLFHQLQEI KGVQQDEALQ LPKDLDYLTI RDVSLSHEVR EKLHFSRPQT IGAASRIPGV TPAAIINLLR FVKTTQRRQS AMNESSKTDQ YLCDADRLQE REL |
| g13569856 | 44 | MPFLYDISSC WTSFCFLFFS PLDGVLLCFP GWNAVARSQL TATSASQVQA ILLVSASGVA GIIGTCHHAQ PIFVFLVEMG FHHVGQACLK LLNSGDPPAS ASQSAGITGM SHHARPFFFF FSF |
| g13591868 | 45 | MSEAENEFIN WVATAAIEAN CSQCWLCVEL PEAAGNGLPW RIVPANISEW ICQYQWEWDN TWFCFDFLSQ SVSLSPRLEC SGTILAQCNL CLLGSSDSPA SASQVAGIIG ACRHAWLIFC IFSRDGVSPY CPG |
| g13591870 | 46 | MALFLDKMGS LQKGNYSSQS GMIPGSWQHK MKLQLILKSS KAYYVLSDAA MSLQKYGRAL RYIKLALQSH DTYCCLCTNM LSEVLLFLSQ YLTLCGDIQL MLAQNANNRA AHLEEFHYQT KEDQEILHSL HRESSCQGVP QAWTTWFTVG LCSLAHAYLS IQKRGRNIRV LIFALYLFIY FLRRSFALVA QAGVQWCNLG SLKPPPPGFK QFSCLSLPSS WNYRHAPPCP ASPPWPPKVL GLQV |
| g1362993 | 47 | RSLTLWPSLE YSGTISAHCN LRLPGSSDSR ASASRAAGIT GVSHCARPCM LFDPEFDLLA GVQLLPFEPP TGKALSRKD |
| g13631907 | 48 | MEFRKLRGME TRPPANTARL QPPRDLRSSS PRKQLSESSD DDYDDVDIPT PAEDTPPPLP PKPKFRSPSD EGPGSMGDDG QLSPGVLVRC ASGPPPNSPR PGPPPSTSSP HLTAHSEPSL WNPPSRELDK PPLLPPKKEK MKRKGCALLV KLFNGCPLRI HSTAAWTHPS TKDQHLLLGA EEGIFILNRN DQEATLEMLF PSRTTWVYSI NNVLMSLSGK TPHLYSHSIL GLLERKETRA GNPIAHSPH RLLARKNMVS TKIQDTKGCR ACCVAEGASS GGPFLCGALE TSVVLLQWYQ PMNKFLLVRQ VLFPLPTPLS VFALLTGPGS ELPAVCIGVS PGRPGKSVLF HTVRFGALSC WLGEMSTEHR GPVQVTQVEE DMVMVLMDGS VKLVTPEGSP VRGLRTPEIP MTEAVEAVAM VGGQLQAFWK HGVQVWALGS DQLLQELRDP TLTFRLLGSP RLECSGTISP HCNLLLPGSS NSPASASRVA GITGL |
| g13644612 | 49 | MSMVLGGPFS KGHTASDEYF QIFHNISFFE TESCSVAQAG VQWCNLGSLQ ALPPRFTPFS CLSLPSSWDY RHPPPCPDNV FVFSVETGLH CVSQDGLNLL TL |
| g13646055 | 50 | MDCGSVGGQR TQRLPGRQRL LFLPVGLSGR PGGSETSARR CLSALSDGLG ALRPRAPAAR GGVSRASPLL LLLLVPSPRL AAAAPRRQLG DWERSRLGYA APPAGRSSAW RCSPGVAAAA GALPQYHGPA PALVSCRREL SLSAGSLQLE RKRRDFTSSG SRKLYFDTHA LVCLLEDNES HSFIQAGVQW HSLGLLQPPP PGFKRSSHLI LLSSWDYRHA PPHLDNFSVF LLETGFHHVG QAGLKLLTSS DPPTLAS |

| Protein Identification Number (PID) | SEQ. ID NO. | Amino Acid Sequences of Protein |
|---|---|---|
| g13646423 | 51 | MNFFFKTEFL SVTQAGMQWH NFSSLQPLPP GFKQFSCLSL LSSWDYRHTP PCPANFCIFS RGGVSPCWSG WSRTPDFMIH PPRPPKVLRL QK |
| g13648611 | 52 | MPLAAYCYLR VVGKGSYGEV TLVKHRRDGK QYVIKKLNLR NASSRERRAA EQEAQLLSQL KHPNIVTYKE SWEGGDGLLY IVMGFCEGGD LYRKLKEQKG QLLPENQVVE WFVQIAMALQ YLHEKHILHR DLKTQNVFLT RTNIIKVGDL GIARVLENHC DMASTLIGTP YYMSPELFSN KPYNYKSDVW ALGCCVYEMA TLKHAFNAKD MNSLVYRIIE GKLPPMPRDY SPELAELIRT MLSKRPEERP SVRSILRQPY IKRQISFFLE ATKIKTSKNN IKNGDSQSKP FATVVSGEAE SNHEVIHPQP LSSEGSQTYI MGEGKCLSQE KPRASGLLKS PASLKAHTCK QDLSNTTELA TISSVNIDIL PAKGRDSVSD GFVQENQPRY LDASNELGGI CSISQVEEEM LQDNTKSSAQ PENLIPMWSS DIVTGEKNEP VKPLQPLIKE QKPKDQSLAL SPKLECSGTI LAHSNLRLLG SSDSPASASR VAGITGVCHH AQDQVAGECI IEKQGRIHPD LQPHNSGSEP SLSRQRRQKR REQTEHRGEK RQVRRDLFAF QESPPRFLPS HPIVGKVDVT STQKEAENQR RVVTGSVSSS RSSEMSSSKD RPLSARERRR LKQSQEEMSS SGPSVRKASL SVAGPGKPGE EDQPLPARRL SSDCSVTQER KQIHCLSEDE LSSSTSSDK SDGDYGEGKG QTNEINALVQ LMTQTLKLDS KESCEDVPVA NPVSEFKLHR KYRDTLILHG KVAEEAEEIH FKELPSAIMP GSEKIRRLVE VLRTDVIRGL GVQLLEQVYD LLEEEDEFDR EVRLREHMGE KYTTYSVKAR QLKFFEENMN F |
| g13651342 | 53 | MFISFGRLIF SFFLTWSLSL SPRLECSGTI LAHCNPTSQV QAILPASASR VAGITGMHHH TCLIFVLLVK MGFCHVGHAG LELVT |
| g13652010 | 54 | MESGQPSLSF YFLFIYFFEI GSHFVTQAGV QWHNLDSLQL SLASAPQVAG TTGACHHARL IFGVFCRDWV LPC |
| g13653409 | 55 | MLLVDADQPE PMRSGARELA LFLTPEPGAE AKEVEETIEG MLLRLEEFCS LADLIRSDTS QILEENIPVL KAKLTEMRGI YAKVDRLEAF VKMVGHHVAF LEADVLQAER DHGAFPQALR RWLGSAGLPS FRNVECSGTI PARCNLRLPG SSDSPASASQ VAGIPEVTCT GARDVRAAHT V |
| g13699916 | 56 | MSRGNENRLT HRRQTVLREK GRRLANRGPA YMFNDHSTSL SIEEERFLDA AEYGNIPVVR KMLEECLSLN VNCVDYMGQN ALQLAVANEH LEITELLLKK ENLSRVGDAL LLAISKGYVR IVEAILNIPA FAEGKRLATS PSQSELQQDD FYAYDEDGTR FSHDVTPIIL AAHCQEYEIV HTLLRKGARI ERPHDYFCKC TECSQKQKHD SFSHSRSRIN AYKGLASPAY LSLSSEDPVM TALELSNELA VLANIEKEFK NDYRKLSMQC KDFVVGLLDL CRNTEEVEAI LNGDAETRQP GDLARPNLSR LKLAIKYEVK KFVAHPNCQQ QLLSIWYENL SGLRQQTMAV KFLVVLAVAI GLPFLALIYW CAPCSKMGKI LRGPFMKFVA HAASFTIFLG LLVMNAADRF EGTKLLPNET STDNARQLFR MKTSCFSWME MLIISWVIGM IWAECKEIWT QGPKEYLFEL WNMLDFGMLA IFAASFIARF MAFWHASKAQ SIIDANDTLK DLTKVTLGDN VKYYNLARIK WDPTDPQIIS EGLYAIAVVL SFSRIAYILP ANESFGPLQI SLGRTVKDIF KFMVIFIMVF VAFMIGMFNL YSYYIGAKQN EAFTTVEESF KTLFWAIFGL SEVKSVVINY NHKFIENIGY VLYGVYNVTM VIVLLNMLIA MLNSSFQEIE DDADVEWKFA RAKLWFSYFE EGRTLPVPFN LVPSPKSLLY LLLKFKKWMS ELIQGHKKGF QEDAEMNKRN EEKKFGILGS HEDLSKFSLD RNQLAHNKQS STRSSEDFHL NSFSNPPRQY QKIMKRLIKR YVLQAQIDKE SDEVNEGELK EIKQDISSLR YELLEEKSQN TEDLAELIRK LGERLSLESK QEESRR |
| g13702149 | 57 | MSRGNENRLT HRRQTVLREK GRRLANRGPA YMFNDHSTSL SIEEERFLDA AEYGNIPVVR KMLEECLSLN VNCVDYMGQN ALQLAVANEH LEITELLLKK ENLSRVGDAL LLAISKGYVR IVEAILNIPA FAEGKRLATS PSQSELQQDD FYAYDEDGTR FSHDVTPIIL AAHCQEYEIV HTLLRKGARI ERPHDYFCKC TECSQKQKHD SFSHSRSRIN AYKGLASPAY LSLSSEDPVM TALELSNELA VLANIEKEFK NDYRKLSMQC KDFVVGLLDL CRNTEEVEAI LNGDAETRQP GDLARPNLSR LKLAIKYEVK KFVAHPNCQQ QLLSIWYENL SGLRQQTMAV KFLVVLAVAI GLPFLALIYW CAPCSKMGKI LRGPFMKFVA HAASFTIFLG LLVMNAADRF EGTKLLPNET STDNARQLFR MKTSCFSWME MLIISWVIGM IWAECKEIWT QGPKEYLFEL WNMLDFGMLA IFAASFIARF MAFWHASKAQ SIIDANDTLK DLTKVTLGDN VKYYNLARIK WDPTDPQIIS EGLYAIAVVL SFSRIAYILP ANESFGPLQI SLGRTVKDIF KFMVIFIMVF VAFMIGMFNL YSYYIGAKQN EAFTTVEESF KTLFWAIFGL SEVRSVVINY NHKFIENIGY VLYGVYNVTM VIVLLNMLIA MINSSFQEIE RNEEKKFGIL GSHEDLSKFS LDRNQLAHNK QSSTRSSEDF HLNSFSNPPR QYQKIMKRLI KRYVLQAQID KESDEVNEGE LKEIKQDISS LRYELLEEKS QNTEDLAELI RRLGERLSLE SKQEESRR |
| g14043238 | 58 | MESRSVAQAG VQWPDLGSLQ PLPPRFKRFF CLSLQSSWDY RHAPPRPANF VFLVETGFCH VSQAGLELLT SSDPPPRPPK VLR |
| g14192931 | 59 | MISVHCNLCL PGSSDPPASA SQVAGITGVR HCMASGAVLN KVRRHQCSGD LEVRGSHGSL GEAPWGKSVP GRGTASRKGP GAGVIGNSKE ASTGRAQWSA PVIPATQEAK AGGLLEPRSL ISAWATYQDL ISINKLKEKR G |
| g14198309 | 60 | MTRSLFKGNF WSADILSTIG YDNIIQHLNN GRKNCKEFED FLKERAAIEE RYGKDLLNLS RKKPCGQSEI NTLKRALEVF KQQVDNVAQC HIQLAQSLRE EARKMEEFRE KQKLQRKKME SHSVTQAGAQ WHDLGSLQAL PPGFMPFSCL SLPSSWNYRL PPPPRLAEPR NQDHGVA |
| g14249973 | 61 | MESHSVTQAG VQWRDLGSLQ PLPPGFKQFS HLSLPSSWDY RRVPPYLGNF CIFSGEGVSP CWPGWS |
| g16226025 | 62 | MGSLSTANVE FCLDVFKELN SNNIGDNIFF SSLSLLYALS MVLLGARGET AEQLEKVLHF SHTVDSLKPG FKDSPKCSQA GRIHSEFGVE FSQINQPDSN CTLSIANRLY GTKTMAFHQQ YLSCSEKWYQ ARLQTVDFEQ STEETRKTIN AWVENKTNGK VANLFGKSTI DPSSVMVLVN TIYFKGQRQN KEQVRETVKS PFQLSEGKNV TVEMMYQIGT FKLAFVKEPQ MQVLELPYVN NKLSMIILLP VGIANLKQIE KQLNSGTFHE WTSSSNMMER EVEVHLPRFK LEIKYELNSL LKPLGVTDLF NQVKADLSGM SPTKGLYLSK AIHKSYLDVS EEGTEAAAAT GDSIAVKSLP MRAQFKANHP FLFFIRHTHT NTILFCGKLA SP |

| Protein Identification Number (PID) | SEQ. ID NO. | Amino Acid Sequences of Protein |
|---|---|---|
| g16517174 | 63 | MAQFYYKRNV NAPYRDRIPL RIVRAESELS PSEKAYLNAV EKGDYASVKK SLEEAEIYFK ININCIDPLG RTALLIAIEN ENLELIELLL SFNVYVGDAL LHAIRKEVVG AVELLLNHKK PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK LAIKYRQKEF VAQPNCQQLL ASRWYDEFPG WRRRHWAVKM VTCFIIGLLF PVFSVCYLIA PKSPLGLFIR KPFIKFICHT ASYLTFLFLL LLASQHIDRS DLNRQGPPPT IVEWMILPWV LGFIWGEIKQ MWDGGLQDYI HDWWNLMDFV MNSLYLATIS LKIVAFVKYS ALNPRESWDM WHPTLVAEAL FAIANIFSSL RLISLFTANS HLGPLQISLG RMLLDILKFL FIYCLVLLAF ANGLNQLYFY YEETKGLTCK GIRCEKQNNA FSTLFETLQS LFWSIFGLIN LYVTNVKAQH EFTEFVGATM FGTYNVISLV VLLNMLIAMM NNSYQLIADH ADIEWKFART KLWMSYFEEG GTLPTPFNVI PSPKSLWYLI KWIWTHLCKK KMRRKPESFG TIGVRTQHRR AADNLRHHQ YQEVMRNLVK RYVAAMIRDA KTEEGLTEEN FKELKQDISS FRFEVLGLLR GSKLSTIQSA NASKESSNSA DSDEKSDSEG NSKDKKKNFS LFDLTTLIHP RSAAIASERH NISNGSALVV QEPPREKQRK VNFVTDIKNF GLFHRRSKQN AAEQNANQIF SVSEEVARQQ AAGPLERNIQ LESRGLASRG DLSIPGLSEQ CVLVDHRERN TDTLGLQVGK RVCPFKSEKV VVEDTVPIIP KEKHAKEEDS SIDYDLNLPD TVTHEDYVTT RL |
| g16517176 | 64 | MAQFYYKRNV NAPYRDRIPL RIVRAESELS PSEKAYLNAV EKGDYASVKK SLEEAEIYFK ININCIDPLG RTALLIAIEN ENLELIELLL SFNVYVGDAL LHAIRKEVVG AVELLLNHKK PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK LAIKYRQKEA SYGEKLNRCG MADFRTTSMI GGI |
| g16758330 | 65 | MSQSPGFVTR RGGSPKAAPG AGARRNESQD YLLMDELGDD GYPQLQQPPY GYYPSFRGNE NRLTHRRQTV LREKGRRLAN RGPAYMFNDH STSLSIEEER FLDAAEYGNI PVVRKMLEEC LSLNVNCVDY MGQNALQLAV ANEHLEITEL LLKKENLSRV GDALLLAISK QYVRIVEAIL NHPAFAEGKR LATSPSQSEL QQDDFYAYDE DGTRFSHDVT PIILAAHCQE YEIVHTLLRK GARIERPHDY FCKCTECSQK QKHDSFSHSR SRINAYKGLA SPAYLSLSSE DPVMTALELS NELAVLANIE KEFKNDYRKL SMQCKDFVVG LLDLCRNTEE VEAILNGDAE TRQPGDLARP NLSRLKLAIK YEVKKFVAHP NCQQQLLSIW YENLSGLRQQ TMAVKFLVCA AVAIGLPFLA LIYWCAPCSK MGKILRGPFM KFVAHAASFT IFLGLLVMNA ADRFEGTKLL PNETSTDNAR QLFRMKTSCF SWMEMLIISW VIGMIWAECK EIWTQGPKEY LFELWNMLDF GMLAIFAASF IARFMAFWHA SKAQSIIDAN DTLKDLTKVT LGDNVKYYNL ARIKWDPTDP QIISEGLYAI AVVLSFSRIA YILPANESFG PLQISLGRTV KDIFKFMVIF IMVFVAFMIA MFNLYSYYIG AKQNEAFTTV EESFKTLFWA IFGLSEVKSV VINYNHKFIE NIGYVLYGVY NVTMVIVLLN MLIAMINSSF QEIEDDADVE WKFARAKLWF SYFEEGRTLP VPFNLVPSPK SLLYLLLKFK KWMSELIQGH KKGFQEDAEM NKRNEEKKFG |

ILGSHEDLSK FSLDRNQLAH NKQSSTRSSE DFHLNSFSNP PRQYQKIMKR LIKRYVLQAQ IDKESDEVNE GELKEIKQDI SSLRYELLEE KSQNTEDLAE LIRKLGERLS LESKQEESRR

| g1710216 | 66 | MGHPRAIQPS VFFSPYDVHF LLYPIRCPYL KIGRFHIKLK GLHFLFSFLF FFFETQSHSV TRLECSGTIS AHCNLCLPGS SNSPASASRV AGTAGTCRRA QLIFVFLAEM GFHHVGRDGL DLNLVIHPPR SPKALGLQA |
| g17978303 | 67 | MGSLSTANVE FCLDVFKELN SNNIGDNIFF SSLSLLYALS MVLLGARGET AEQLEKVLHF SHTVDSLKPG FKDSPKCSQA GRIHSEFGVE FSQINQPDSN CTLSIANRLY GTKTMAFHQQ YLSCSEKWYQ ARLQTVDFEQ STEETRKMIN AWVENKTNGK VANLFGKSTI DPSSVMLVNT TIYFKGQRQN KFQVRETVKS PFQLSEGKNV TVEMMYQIGT FKLAFVKEPQ MQVLELPYVN NKLSMIILLP VGIANLKQIE KQLNSGTFHE WTSSSNMMER EVEVHLPRFK LEIKYELNSL LKPLGVTDLF NQVKADLSGM SPTKGLYLSK AIHKSYLDVS EEGTEAAAAT GDSIAVKSLP MRAQFKANHP FLFFIRHTHT NTILFCGKLA SP |
| g18376629 | 68 | MLRNSTFKNM QRRHTTLREK GRRQAIRGPA YMFNEKGTSL TPEEERFLDS AEYGNIPVVR KMLEESKTLN FNCVDYMGQN ALQLAVGNEH LEVTELLLKK ENLARVGDAL PLAISKGYVR IVEAILNHPA FAQGQRLTLS PLEQELRDDD FYAYDEDGTR FSHDITPIIL AAHCQEYEIV HILLLKGARI ERPHDYFCKC NECTEKQRKD SFSHSRSRMN AYKGLASAAY LSLSSEDPVL TALELSNELA RLANIETEFK NDYRKLSMQC KDFVVGVLDL CRDTEEVEAI LNGDVNFQVW SDHHRPSLSR IKLAIKYEVK KFVAHPNCQQ QLLTMWYENL SGLRQQSIAV KFLAVFGVSI GLPFLAIAYW IAPCSKLGRT LRSPFMKFVA HAVSFTIFLG LLVVNASDRF EGVKTLPNET FTDYPKQIFR VKTTQFSWTE MLIMKWVLGM IWSECKEIWE EGPREYVLHL WNLLDFGMLS IFVASFTARF MAFLKATEAQ LYVDQHVQDD TLHNVSLPPE VAYFTYARDK WWPSDPQIIS EGLYAIAVVL SFSRIAYILP ANESFGPLQI SLGRTVKDIF KFMVIFIMVF VAFMIGMFNL YSYYRGAKYN PAFTTVEESF KTLFWSIFGL SEVISVVLKY DHKFIENIGY VLYGVYNVTM VVVLLNMLIA MINNSYQEIE EDADVEWKFA RAKLWLSYFD EGRTLPAPFN LVPSPKSFYY LIMRIKMCLI KLCKSKAKSC ENDLEMGMLN SKFKKTRYQA GMRNSENLTA NNTLSKPTRY QKIMKRLIKR YVLKAQVDRE NDEVNEGELK EIKQDISSLR YELLEEKSQA TGELADLIQQ LSEKFGKNLN KDHLRVNKGK DI |
| g1843388 | 69 | MKVRLLRQLS AAAKVKAPSG LQGPPQAHQF ISLLLEEYGA LCQAARSIST FLGTLENEHL KKFQVTWELH NKHLFENLVF SEPLLQSNLP ALVSQIRLGT TTHDTCSEDT YSTLLQRYQR SEEELRRVAE EWLECQKRID AYVDEQMTMK TKQRMLTEDW ELFKQRRFIE EQLTNKKAVT GENNFTDTMR HVLSSRLSMP DCPNCNYRRR CACDDCSLSH ILTCGIMDPP VTDDIHIHQL PLQVDPAPDY LAERSPPSVS SASSGSGSSS PITIQQHPRL ILTDSGSAPT FCSDDEDVAP LSAKFADIYP LSNYDDTEVV ANMNGIHSEL NGGGENMALK DESPQISSTS SSSSEADDEE ADGESSGEPP GAPKEDGVLG SRSPRTEESK ADSPPPSYPT QQAEQAPNTC ECHVCKQEAS GLTPSAMTAG ALPPGHQFLS PEKPTHPALH LYPHIHGHVP LHTVPHLPRP LTHPTLYATP PFTHSKALPP APVQNHTNKH QVFNASLQDH |

| Protein Identification Number (PID) | SEQ. ID NO. | Amino Acid Sequences of Protein |
|---|---|---|
| | | IYPSCFGNTP EWNSSKFISL WGSEVMNDKN WNPGTFLPDT ISGSEILGPT LSETRPEALP PPSSNETPAV SDSKEKKNAA KKKCLYNFQD AFMEANKVVM ATSSATSSVS CTATTVQSSN SQFRVSSKRP PSVGDVFHGI SKEDHRHSAP AAPRNSPTGL APLPALSPAA LSPAALSPAS TPHLANLAAP SFPKTATTTP GFVDTRKSFC PAPLPPATDG SISAPPSVCS DPDCEGHRCE NGVYDPQQDD GDESADEDSC SEHSSSTSTS TNQKEGKYCD CCYCEFFGHG GPPAAPTSRN YAEMREKLRL RLTKRKEEQP KKMDQISERE SVVDHRRVED LLQFINSSET KPVSSTRAAK RARHKQRKLE EKARLEAEAR AREHLHLQEE QRRREEEEDE EEEDRFKEE FQRLQELQKL RAVKKKKKER PSKDCPKLDM LTRNFQAATE SVPNSGNIHN GSLEQTEEPE TSSHSPSRHM NHSEPRPGLG ADGDAADPVD TRDSKFLLPK EVNGKQHEPL SFFFDIMQHH KEGNGKQKLR QTSKASSEPA RRPTEPPKAT EGQSKPRAQT ESKAKVVDLM SITEQKREER KVNSNNNNKK QLNHIKDEKS NPTPMEPTSP GEHQQNSKLV LAESPQPKGK NKKNKKKKGD RVNNSIDGVS LLLPSLGYNG AILAHCNLRL PGSSDCAASA SQVVGITDDV FLPKDIDLDS VDMDETEREV EYFKRFCLDS ARQTRQRLSI NWSNFSLKKA TFAAH |
| g20140144 | 70 | MGSLSTANVE FCLDVFKELN SNNIGDNIFF SSLSLLYALS MVLLGARGET AEQLEKVLHF SHTVDSLKPG FKDSPKCSQA GRIHSEFGVE FSQINQPDSN CTLSIANRLY GTKTMAFHQQ YLSCSEKWYQ ARLQTVDFEQ STEETRKMIN AWVENKTNGK VANLFGKSTI DPSSVMVLVN IIYFKGQRQN KFQVRETVKS PFQLSEGKNV TVEMMYQIGT FKLAFVKEPQ MQVLELPYVN NKLSMIILLP VGIANLKQIE KQLNSGTFHE WTSSSNMMER EVEVHLPRFK LEIKYELNSL LKPLGVTDLF NQVKADLSGM SPTKGLYLSK AIHKSYLDVS EEGTEAAAAT GDSIAVKSLP MRAQFKANHP FLFFIRHTHT NTILFCGKLA SP |
| g20476660 | 71 | MMAALYPSTD LSGASSSSLP SSPSSSSPNE VMALKDVREV KEENTLNEKL FLLACDKGDY YMVKKILEEN SSGDLNINCV DVLGRNAVTI TIENENLDIL QLLLDYGCQS ADALLVAIDS EVVGAVDILL NHRPKRSSRP TIVKLMERIQ NPEYSTTMDV APVILAAHRN NYEILTMLLK QDVSLPKPHA VGCECTLCSA KNKKDSLRHS RFRLDIYRCL ASPALIMLTE EDPILRAFEL SADLKELSLV EVEFRNDYEE LARQCKMFAK DLLAQARNSR ELEVILNHTS SDEPLDKRGL LEERMNLSRL KLAIKYNQKE FVSQSNCQQF LNTVWFGQMS GYRRKPTCKK IMTVLTVGIF WPVLSLCYLI APKSQFGRII HTPFMKFIIH GASYFTFLLL LNLYSLVYNE DKKNTMGPAL ERIDYLLILW IIGMIWSDIK RLWYEGLEDF LEESRNQLSF VMNSLYLATF ALKVVAHNKF HDFADRKDWD AFHPTLVAEG LFAFANVLSY LRLFFMYTTS SILGPLQISM GQMLQDFGKF LGMFLLVLFS FTIGLTQLYD KGYTSKEQKD CVGIFCEQQS NDTFHSFIGT CFALFWYIFS LAHVAIFVTR FSYGEELQSF VGAVIVGTYN VVVVIVLTKL LVAMLHKSFQ LIANHEDKEW KFARAKLWLS YFDDKCTLPP PFNIIPSPKT ICYMISSLSK WICSHTSKGK VKRQNSLKEW RNLKQKRDEN YQKVMCCLVH RYLTSMRQKM QSTDQATVEN LNELRQDLSK FRNEIRDLLG FRTSKYAMFY PRN |
| g20546044 | 72 | MAQFYYKRNV NAPYRDRIPL RIVRAESELS PSEKAYLNAV EKGDYASVKK SLEEAEIYFK ININCIDPLG RTALLIAIEN ENLELIELLL SFNVYVGDAL LHAIRKEVVG AVELLLNHKK PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK LAIKYRQKEF VAQPNCQQLL ASRWYDEFPG WRRRHWAVKM VTCFIIGLLF PVFSVCYLIA PKSPLGLFIR KPFIKFICHT ASYLTFLFLL LLASQHIDRS DLNRQGPPPT IVEWMILPWV LGFIWGEIKQ MWDGGLQDYI HDWWNLMDFV MNSLYLATIS LKIVAFVKYS ALNPRESWDM WHPTLVAEAL FAIANIFSSL RLISLFTANS HLGPLQISLG RMLLDILKFL FIYCLVLLAF ANGLNQLYFY YEETKGLTCK GIRCEKQNNA FSTLFETLQS LFWSIFGLIN LYVTNVKAQH EFTEFVGATM FGTYNVISLV VLLNMLIAMM NNSYQLIADH ADIEWKFART KLWMSYFEEG GTLPTPFNVI PSPKSLWYLI KWIWTHLCKK KMRRKPESFG TIGVRTQHRR AADNLRRHHQ YQVIMRNLVK RYVAAMIRDA KTEEGLTEEN FKELKQDISS FRFEVLGLLR GSKLSTIQSA NASKESSNSA DSDEKSDSEG NSKDKKKNFS LFDLTTLIHP RSAAIASERH NISNGSALVV QEPPREKQRK VNFVTDIKNF GLFHRRSKQN AAEQNANQIF SVSEEVARQQ AAGPLERNIQ LESRGLASRG DLSIPGLSEQ CVLVDHRERN TDTLGLQVGK RVCPFKSEKV VVEDTVPIIP KEKHAKEEDS SIDYDLNLPD TVTHEDYVTT RL |
| g20881287 | 73 | MSQSPRFVTR RGGSLKAAPG AGTRRNESQD YLLMDELGDD GYPQLPLPPY GYYPSFRGNE NRLTHRRQTI LREKGRRLAN RGPAYMFNDH STSLSIEEER FLDAAEYGNI PVVRKMLEEC HSLNVNCVDY MGQNALQLAV ANEHLEITEL LLKKENLSRV GDALLLAISK GYVRIVEAIL NHPAFAEGKR LATSPSQSEL QQDDFYAYDE DGTRFSHDVT PIILAAHCQE YEIVHTLLRK GARIERPHDY FCKCTECSQK QKHDSFSHSR SRINAYKGLA SPAYLSLSSE DPVMTALELS NELAVLANIE KEFKNDYRKL SMQCKDFVVG LLDLCRNTEE VEAILNGDAE TRQPGDFGRP NLSRLKLAIK YEVKKFVAHP NCQQQLLSIW YENLSGLRQQ TMAVKFLVVL AVAIGLPFLA LIYWCAPCSK MGKILRGPFM KFVAHAASFT IFLGLLVMNA ADRFEGTKLL PNETSTDNAR QLFRMKTSCF SWMEMLIISW VIGMIWAECK EIWTQGPKEY LFELWNMLDF GMLAIFAASF IARFMAFWHA SKAQSIIDAN DTLKDLTKVT LGDNVKYYNL ARIKWDPTDP QIISEGLYAI AVVLSFSRIA YILPANESFG PLQISLGRTV KDIFKFMVIF IMVFVAFMIG MFNLYSYYIG AKQNEAFTTV EESFKTLFWA IFGLSEVKSV VINYNHKFIE NIGYVLYGVY NVTMVIVLLN MLIAMINSSF QEIEDDADVE WKFARAKLWF SYFEEGRTLP VPFNLVPSPK SLLYLLLKFK KWMCELIQGQ KQGFQEDAEM NKRNEEKKFG ISGSHEDLSK FSLDKNQLAH NKQSSTRSSE DYHLNSFSNP PRQYQKIMKR LIKRYLQAQ IDKESDEVNE GELKEIKQDI SSLRYELLEE KSQNTEDLAE LIRKLGERLS LEPKLEESRR |
| g2105420 | 74 | PSGLPLLPVL FALGGLLLLS NASCVGGVLW QRRLRRLAEA LNFPPHLHPG RSEEDRVRNE YEESQWTGER DTQSSTVSTT EAEPYYRSLR DFSPQLPPTQ EEVSYSRGFT GEDEDMAFPG HLYDEVERTY PPSGAWGFPL DEVQMGPWDL HWPEDTYQDP RGIYDQVAGD LDTLEPDSLP FELRGHLVWG FNHVSQAGLK LLASSDPPAS ASQSAEITES HSVVQVGVQW RYFGSLHPLP PGSRDSLASA SRIAGITAPW EAEVSRSPQG TQDSPVTRSG PPSRGWQSLS FDGGAFHLKG |

| Protein Identification Number (PID) | SEQ. ID NO. | Amino Acid Sequences of Protein |
|---|---|---|
| | | TGELTRALLV LRLCAWPPLV THGLLLQAWS RRLLGSRLSG AFLRASVYGQ FVAGETAEEV KGCVQQLRTL SLRPLLAVPT EEEPDSAAKR MRLHHVGQAG LELLLTPAASG SVAQAGVQWR QSSDRGGGNQ AAAASRSSLLQ EAAFSPPCGR LQLPAQPASR HGARGRGSMK AKSLTSRHLL ASQGQETIIK TKVRIPALWK AEPGQHSKTP SQQNKSQYVT TLWEADVGRS LENLQVSCLN AEQNQHLRAS LSRLHRVTPP AGTSTSGPPS AACIGWHSRL HRVAQYARAQ HVRLLVDAEY TSLNPALSLL VAALAVRWNS PGEGGPWVWN TYQACLKDTF ERLGRDAEAA HRAGLAFGVK LVRGAYLDKE RAVAQLHGME DPTQPDYEAT SELNRASPFS YSRCLELMLT HVARHGPMCH LMVASHNEES VRQATKRMWE LGIPLDGTVC FGQLLGMCDH VSLALGQAGY VVYKSIPYGS LEEVIPYLIR RAQENRSVLQ GARREQELLS QELWRRLLPG CRRIPH |
| g2119643 | 75 | SCSVTLAGVQ WRDLGLLQPL PPKFKRFSCL SFPSSWDYR |
| g2119644 | 76 | EMEFNCESCS VTLAGVQWRD LGLLQPLPPK FKRFSCLSFP SSWDYR |
| g2136328 | 77 | MCPGIPGPRA EAAVGTTHPF SSPGAWLGSG SGSGPVGAPP PSPGLPPSWA AMMAALYPST DLSGASSSSL PSSPSSSSPN EVMALKDVRE VKEENTLNEK LFLLACDKGD YYMVKKILEE NSSGDLNINC VDVLGRNAVT ITIENENLDI LQLLLDYGCQ KLMERIQNPE YSTTMDVAPV ILAAHRNNYE ILTMLLKQDV SLPKPHAVGC ECTLCSAKNK KDSLRHSRFR LDIYRCLASP ALIMLTEEDP ILRAFELSAD LKELSLVEVE FRNDYEELAR QCKMFAKDLL AQARNSRELE VILNHTSSDE PLDKRGLLEE RMNLSRLKLA IKYNQKEFVS QSNCQQFLNT VWFGQMSGYR RKPTCKKIMT VLTVGIFWPV LSLCYLIAPK SQFGRIIHTP FMKFIIHGAS YFTFLLLLNL YSLVYNEDKK NTMGPALERI DYLLILWIIG MIWSDIKRLW YEGLEDFLEE SRNQLSFVMN SLYLATFALK VVAHNKFHDF ADRKDWDAFH PTLVAEGLFA FANVLSYRLF FMYTTSSIL GPLQISMGQM LQDFGKFLGM FLLVLFSFTI GLTQLYDKGY TSKEQKDCVG IFCEQQSNDT FHSFIGTCFA LFWYIFSLAH VAIFVTRFSY GEELQSFVGA VIVGTYNVVV VIVLTKLLVA MLHKSFQLIA NHEDKEWKFA RAKLWLSYFD DKCTLPPPFN IIPSPKTICY MISSLSKWIC SHTSKGKVKR QNSLKEWRNL KQKRDENYQK VMCCLVHRYL TSMRQKMQST DQATVENLNE LRQDLSKFRN EIRDLLGFRT SKYAMFYPRN |
| g3766191 | 78 | MSRGNENRLT HRRQTILREK GRRLANRGPA YMFNDHSTSL SIEEERFLDA AEYGNIPVVR KMLEECHSLN VNCVDYMGQD ALQLAVANEH LEITELLLKK ENLSRVGDAL LLAISKGYVR IVEAILNHPA FAEGKRLATS PSQSELQQDD FYAYDEDGTR FSHDVTPIIL AAHCQEYEIV HTLLRKGARI ERPHDYFCKC TECSQKQKHD SFSHSRSRIN AYKGLASPAY LSLSSEDPVM TALELSNELA VLANIEKEFK NDYRKLSMQC KDFVVGLLDL CRNTEEVEAI LNGDAETRQP GDFGRPNLSR LKLAIKYEVK KFVAHPNCQQ QLLSIWYENL SGLRQQTMAV KFLVVLAVAI GLPFLALIYW CAPCSKMGKI LRGPFMKFVA HAASFTIFLG LLVMNAADRF EGTKLLPNET STDNARQLFR MKTSCFSWME MLIISWVIGM IWAECKEIWT QGPKEYLFEL WNMLDFGMLA IFAASFIARF MAFWHASKAQ SIIDANDTLK DLTKVTLGDN VKYYNLARIK WDPTDPQIIS EGLYAIAVVL SFSRIAYILP ANESFGPLQI SLGRTVKDIF KFMVIFIMVF VAFMIGMFNL |
| | | YSYYIGAKQN EAFTTVEESF KTLFWAIFGL SEVKSVVINY NHKFIENIGY VLYGVYNVTM VIVLLNMLIA MINSSFQEIE DDADVEWKFA RAKLWFSYFE EGRTLPVPFN LVPSPKSLLY LLLKFKKWMC ELIQGQKQGF QEDAEMNKRN EEKKFGISGS HEDLSKFSLD KNQLAHNKQS STRSSEDYHL NSFSNPPRQY QKIMKRLIKR YVLQAQIDKE SDEVNEGELK EIKQDISSLR YELLEEKSQN TEDLAELIRK LGERLSLEPK LEESRR |
| g403460 | 79 | DRLSLLSPRL ECNGMILAHC KLRLPGFKRF SCLSLPSSWD YRHVPPRQVH FVFSVETGFH RAGQAGLELL TSSVPPTSAF PKCWDYRRDD QAWPTLSSFR GLNKFAFLPK FFAHPISQFQ RVECNVGCPI LLAMKYLAYS SLPGADTMLY FYFYEQEASL AVCNICRQKF HWVLYQISHL YRGVIVDNFL LHPDGRFTWT IFFLSWVKQN SLVDFFFGTE SRSVALLPRL ECSGAMSTLH TVLRPAYSHI YHPDVKEKTH FLGNVFNKRK LQKKILKTPN PLCALHSAPS PSLPPFLRCT GRLPFYLGLD DFLFVAGALM FLPVSFLNPH TLTWPPQCCT RSDCNPLRGQ REISALSHSL PTGLSMPL |
| g4200234 | 80 | MAALYACTKC HQRFPFEALS QGQQLCKECR IAHPVVKCTY CRTEYQQERL ECNGTISAHC NLHLPGSSDS PASSSRVAGI TGIKTNTICK KCAQNVQLYG TPKPCQYCNI IAAFIGNKCQ RCTNSEKKYG PPYSCEQCKQ QCAFDRKDDR KKVDGKLLCW LCTLSYKRVL QKTKEQRKHL SSSSRAGHQE KEQYSRLSGG GHYNSQKTLS TSSIQNEIPK KKSKFESITT NGDSFSPDLA LDSPGTDHFV IIAQLKEEVA TLKKMLHQKD QMILEKEKI TELKADFQYQ ESQMRAKMNQ MEKTHKEVTE QLQAKNRELL KQAAALSKSK KSEKSGAITS P |
| g4200238 | 81 | MAALYACTKC HQRFPFEALS QGQQLCKECR IAHPVVKCTY CRTEYQQERL ECNGTISAHC NLHLPGSSDS PASSSRVAGI TGIKTNTICK KCAQNVQLYG TPKPCQYCNI IAAFIGNKCQ RCTNSEKKYG PPYSCEQCKQ QCAFDRKDDR KKVDGKLLCW LCTLSYKRVL QKTKEQRKHL SSSSRAGHQE KEQYSRLSGG GHYNSFSPDL ALDSPGTDHF VIIAQLKEEV ATLKKMLHQK DQMILEKEKK ITELKADFQY QESQMRAKMN QMEKTHKEVT EQLQAKNREL LKQAAALSKS KKSEKSGAIT SP |
| g423149 | 82 | FFFFFFETES CSVAEAGVQW CDLGSLKSPP PGSSDSPASA SRVAGITGMH HHTQLIFVFL VETGSHMQLS DSTLVITTAQ NAKITARAPR DLFFFFFFFF |
| g4336401 | 83 | LPLLPRMECR GMISAHCNLC RSGSSDSPAS ASRVAGITGT CHHAQLSFPF FLFMRW |
| g4336402 | 84 | LPLLPRMECR GMISAHCNLC RSGSSDSPAS ASRVAGITGT CHHAQL |
| g4379098 | 85 | MDIEDEENMS SSTDVKENR NLDNVSPKDG STPGPGEGSQ LSNGGGGGPG RKRPLEEGSN GHSKYRLKKR RKTPGPVLPK NALMQLNEIK PGLQYTLLSQ TGPVHAPLFV MSVEVNGQVF EGSGPTKKKA KLHAAEKALR SFVQFPNASE AHLAMGRTLS VNTDFTSDQA DFPDTLFNGF ETPDKAEPPF YVGSNGDDSF SSSGDLSLSA SPVPASLAQP PLPVLPPFPP PSGKNPVMIL NELRPGLKYD FLSESGESHA KSFVMSVVVD GQFFEGSGRN KKLAKARAAQ SALAAIFNLH LDQTPSRQPI PSEGLQHLP QVLADAVSRL VLGKFGDLTD NFSSPHARRK VLAGVVMTTG |

| Protein Identification Number (PID) | SEQ. ID NO. | Amino Acid Sequences of Protein |
|---|---|---|
| | | TDVKDAKVIS VSTGTKCING EYMSDRGLAL NDCHAEIISR RSLLRFLYTQ LELYLNNKDD QKRSIFQKSE RGGFRLKENV QFHLYISTSP CGDARIFSPH EPILEGSRSY TQAGVQWCNH GSLQPRPPGL LSDPSTSTFQ GAGTTEPADR HPNRKARGQL RTKIESGEGT IPVRSNASIQ TWDGVLQGER LLTMSCSDKI ARWNVVGIQG SLLSIFVEPI YFSSIILGSL YHGDHLSRAM YQRISNIEDL PPLYTLNKPL LSGISNAEAR QPGKAPNFSV NWTVGDSAIE VINATTGKDE LGRASRLCKH ALYCRWXACA RQGSLPLTTL QDYQAQRVP |
| g4504601 | 86 | MLLSQNAFIV RSLNLVLMVY ISLVFGISYD SPDYTDESCT FKISLRNFRS ILSWELKNHS IVPTHYTLLY TIMSKPEDLK VVKNCANTTR SFCDLTDEWR STHEAYVTVL EGFSGNTTLF SCSHNFWLAI DMSFEPPEFE IVGFTNHINV MVKFPSIVEE ELQFDLSLVI EEQSEGIVKK HKPEIKGNMS GNFTYIIDKL IPNTNYCVSV YLEHSDEQAV IKSPLKCTLL PPGQESESAE SAKIGGIITV FLIALVLTST IVTLKWIGYI CLRNSLPKVL RQGLTKGWNA VAIHRCSHNA LQSETPELKQ SSCLSFPSSW DYKRASLCPS D |
| g4507277 | 87 | MPLAAYCYLR VVGKGSYGEV TLVKHRRDGK QYVIKKLNLR NASSRERRAA EQEAQLLSQL KHPNIVTYKE SWEGGDGLLY IVMGFCEGGD LYRKLKEQKG QLLPENQVVE WFVQIAMALQ YLHEKHILHR DLKTQNVFLT RTNIIKVGDL GIARVLENHC DMASTLIGTP YYMSPELFSN KPYNYKSDVW ALGCCVYEMA TLKHAFNAKD MNSLVYRIIE GKLPAMPRDY SPELAELIRT MLSKRPEERP SVRSILRQPY IKRQISFFLE ATKIKTSKNN IKNGDSQSKP FATVVSGEAE SNHEVIHPQM LSSEGSQTYI MGEGKCLSQE KPRASGLLKS PASLKAHTCK QDLSNTTELA TISSVNIDIL PAKGRDSVSD GFVQENQPRY LDASNELGGI CSISQVEEEM LQDNTKSSAQ PENLIPMWSS DIVTGEKNEP VKPLQPLIKE QKPKDQSLAL SPKLECSGTI LAHSNLRLLG SSDSPASASR VAGITGVCHH AQDQVAGECI IEKQGRIHPD LQPHNSGSEP SLSRQRRQKR REQTEHRGEK RQVRRDLFAF QESPPRFLPS HPIVGKVDVT STQKEAENQR RVVTGSVSSS RSSEMSSSKD RPLSARERRR LKQSQEEMSS SGPSVRKASL SVAGPGKPQE EDQPLPARRL SSDCSVTQER KQIHCLSEDE LSSSTSSSTDK SDGDYGEGKG QTNEINALVQ LMTQTLKLDS KESCEDVPVA NPVSEFKLHR KYRDTLILHG KVAEEAEEIH FKELPSAIMP GSEKIRRLVE VLRTDVIRGL GVQLLEQVYD LLEEEDEFDR EVRLREHMGE KYTTYSVKAR QLKFFEENMN F |
| g4507685 | 88 | MMAALYPSTD LSGASSSSLP SSPSSSSPNE VMALKDVREV KEENTLNEKL FLLACDKGDY YMVKKILEEN SSGDLNINCV DVLGRNAVTI TIENENLDIL QLLLDYGCQK LMERIQNPEY STTMDVAPVI LAAHRNNYEI LTMLLKQDVS LPKPHAVGCE CTLCSAKNKK DSLRHSRFRL DIYRCLASPA LIMLTEEDPI LRAFELSADL KELSLVEVEF RNDYEELARQ CKMFAKDLLA QARNSRELEV ILNHTSSDEP LDKRGLLEER MNLSRLKLAI KYNQKEFVSQ SNCQQFLNTV WFGQMSGYRR KPTCKKIMTV LTVGTFWPVL SLCYLIAPKS QFGRIIHTPF MKFIIHGASY FTFLLLLNLY SLVYNEDKKN TMGPALERID YLLILWIIGM IWSDIKRLWY EGLEDFLEES RNQLSFVMNS LYLATFALKV VAHNKFHDFA DRKDWDAFHP TLVAEGLFAF ANVLSYLRLF FMYTTSSILG PLQISMGQML QDFGKFLGMF |
| | | LLVLFSFTIG LTQLYDKGYT SKEQKDCVGI FCEQQSNDTF HSFIGTCFAL FWYIFSLAHV AIFVTRFSYG EELQSFVGAV IVGTYNVVVV IVLTKLLVAM LHKSFQLIAN HEDKEWKFAR AKLWLSYFDD KCTLPPPFNI IPSPKTICYM ISSLSKWICS HTSKGKVKRQ NSLKEWRNLK QKRDENYQKV MCCLVHRYLT SMRQKMQSTD QATVENLNEL RQDLSKFRNE IRDLLGFRTS KYAMFYPRN |
| g4507687 | 89 | MEGSPSLRRM TVMREKGRRQ AVRGPAFMFN DRGTSLTAEE ERFLDAAEYG NIPVVRKMLE ESKTLNVNCV DYMGQNALQL AVGNEHLEVT ELLLKKENLA RIGDALLLAI SKGYVRIVEA ILNHPGFAAS KRLTLSPCEQ ELQDDDFYAY DEDGTRFSPD ITPIILAAHC QKYEVVHMLL MKGARIERPH DYFCKCGDCM EKQRHDSFSH SRSRINAYKG LASPAYLSLS SEDPVLTALE LSNELAKLAN IEKEFKNDYR KLSMQCKDFV VGVLDLCRDS EEVEAILNGD LESAEPLEVH RHKASLSRVK LAIKYEVKKF VAHPNCQQQL LTIWYENLSG LREQTIAIKC LVVLVVALGL PFLAIGYWIA PCSRLGKILR SPFMKFVAHA ASFIIFLGLL VFNASDRFEG ITTLPNITVT DYPKQIFRVK TTQFWTEML IMVWVLGMMW SECKELWLEG PREYILQLWN VLDFGMLSIF IAAFTARFLA FLQATKAQQY VDSYVQESDL SEVTLPPEIQ YFTYARDKWL PSDPQIISEG LYAIAVVLSF SRIAYILPAN ESFGPLQISL GRTVKDIFKF MVLFIMVFFA FMIGMFILYS YYLGAKVNAA FTTVEESFKT LFWSIFGLSE VTSVVLKYDH KFIENIGYVL YGIYNVTMVV VLLNMLIAMI NSSYQEIEDD SDVEWKFARS KLWLSYFDDG KTLPPPFSLV PSPKSFVYFI MRIVNFPKCR RRRLQKDIEM GMGNSKSRLN LFTQSNSRVF ESHSFNSILN QPTRYQQIMK RLIKRYVLKA QVDKENDEVN EGELKEIKQD ISSLRYELLE DKSQATEELA ILIHKLSEKL NPSMLRCE |
| g4885373 | 90 | MSETVPPAPA ASAAPEKPLA GKKAKKPAKA AAASKKKPAG PSVSELIVQA ASSSKERGGV SLAALKKALA AAGYDVEKNN SRIKLGIKSL VSKGTLVQTK GTGASGSFKL NKKASSVETK PGASKVATKT KATGASKKLK KATGASKKSV KTPKKAKKPA ATRKSSKNPK KPKTVKPKKV AKSPAKAKAV KPKAAKARVT KPKTAKPKKA APKKK |
| g5730102 | 91 | MSQSPAFGPR RGSSPRGAAG AAAARRNESQD YLLMDSELGE DGCPQAPLPC YGYYPCFRGS DNRLAHRRQT VLREKGRRLA NRGPAYMFSD RSTSLSIEEE RFLDAAEYGN IPVVRKMLEE CHSLNVNCVD YMGQNALQLA VANEHLEITE LLLKKENLSR VGDALLLAIS KGYVRIVEAI LSHPAFAEGK RLATSPSQSE LQQDDFYAYD EDGTRFSHDV TPIILAAHCQ EYEIVHTLLR KGARIERPHD YFCKCNDCNQ KQKHDSFSHS RSRINAYKGL ASPAYLSLSS EDPVMTALEL SNELAVLANI EKEFKNDYKK LSMQCKDFVV GLLDLCRNTE EVEAILNGDV ETLQSGDHGR PNLSRLKLAI KYEVKKFVAH PNCQQQLLSI WYENLSGLRQ QTMAVKFLVV LAVAIGLPFL ALIYWFAPCS KMGKIMRGPF MKFVAHAASF TIFLGLLVMN AADRFEGTKL LPNETSTDNA KQLFRMKTSC FSWMEMLIIS WVIGMIWAEC KEIWTQGPKE YLFELWNMLD FGMLAIFAAS FIARFMAFWH ASKAQSIIDA NDTLKDLTKV TLGDNVKYYN LARIKWDPSD PQIISEGLYA IAVVLSFSRI AYILPANESF GPLQISLGRT VKDIFKFMVI FIMVFVAFMI GMFNLYSYYI GAKQNEAFTT VEESFKTLFW AIFGLSEVKS VVINYNHKFI ENIGYVLYGV YNVTMVIVLL |

| Protein Identification Number (PID) | SEQ. ID NO. | Amino Acid Sequences of Protein |
|---|---|---|
| | | NMLIAMINSS FQEIEDDADV EWKFARAKLW FSYFEEGRTL PVPFNLVPSP KSLFYLLLKL KKWISELFQG HKKGFQEDAE MNKINEEKKL GILGSHEDLS KLSLDKKQVG HNKQPSIRSS EDFHLNSFNN PPRQYQKIMK RLIKRYVLQA QIDKESDEVN EGELKEIKQD ISSLRYELLE EKSQNTEDLA ELIRELGEKL SMEPNQEETN R |
| g5802234 | 93 | SRDPPASASQ VTGIR |
| g6005868 | 94 | MASLSRALRV AAAHPRQSPT RGMGPCNLSS AAGPTAEKSV PYQRTLKEGQ GTSVVAQGPS RPLPSTANVV VIGGGSLGCQ TLYHLAKLGM SGAVLLERER LTSGTTWHTA GLLWQLRPSD VEVELLAHTR RVVSRELEEE TGLHTGWIQN GGLFIASNRQ RLDEYKRLMS LGKAYGVESH VLSPAETKTL YPLMNVDDLY GTLYVPHDGT MDPAGTCTTL ARAASARGAQ VIENCPVTGI RVWTDDFGVR RVAGVETQHG SIQTPCVVNC AGVWASAVGR MAGVKVPLVA MHHAYVVTER IEGIQSFTLL PTLEYSGTVS AHCNLRLPGS SNSRASASHV AGIKCARHHT RLIFFCILVE TEFHHVAKAG LELLSSGNPP ISDFQSARIT GVSHHA |
| g604969 | 95 | LLWVLLWATV LGLLCQRLAA RLGVVTGKDL GEVCHLYYPK SESRSVAQSG VQWCDVSSLQ PLPPRCPAPS SG |
| g6650810 | 96 | METESGSVAQ AGVQWHNLGS LQPPPSRLKQ LSYLSLPSSW DYRCTPPHPA NFLYFNRDGI SPCCPGWSPT PKLTQSTHLG LSKC |
| g6665594 | 97 | MAQFYYKRNV NAPYRDRIPL RIVRAESELS PSEKAYLNAV EKGDYASVKK SLEEAEIYFK ININCIDPLG RTALLIAIEN ENLELIELLL SFNVYVGDAL LHAIRKEVVG AVELLLNHKK PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK LAIKYRQKEF VAQPNCQQLL ASRWYDEFPG WRRRHWAVKM VTCFIIGLLF PVFSVCYLIA KPSPLGLFIR KPFIKFICHT ASYLTFLFLL LLASQHIDRS DLNRQGPPPT IVEWMILPWV LGFIWGEIKQ MWDGGLQDYI HDWWNLMDFV MNSLYLATIS LKIVAFVKYS ALNPRESWDM WHPTLVAEAL FAIANIFSSL RLISLFTANS HLGPLQISLG RMLLDILKFL FIYCLVLLAF ANGLNQLYFY YEETKGLTCK GIRCEKQNNA FSTLFETLQS LFWSIFGLIN LYVTNVKAQH EFTEFVGATM FGTYNVISLV VLLNMLIAMM NNSYQLIADH ADIEWKFART KLWMSYFEEG GTLPTPFNVI PSPKSLWYLI KWIWTHLCKK KMRRKPESFG TIGRRAADNL RRHHQYQEVM RNLVKRYVAA MIRDAKTEEV ARQQAAGPLE RNIQLESRGL ASRGDLSIPG LSEQCVLVDH RERNTDTLGL QVGKRVCPFK SEKVVVEDTV PIIPKEKHAK EEDSSIDYDL NLPDTVTHED YVTTRL |
| g6665596 | 98 | MAQFYYKRNV NAPYRDRIPL RIVRAESELS PSEKAYLNAV EKGDYASVKK SLEEAEIYFK ININCIDPLG RTALLIAIEN ENLELIELLL SFNVYVGDAL LHAIRKEVVG AVELLLNHKK 121 PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK |

| Protein Identification Number (PID) | SEQ. ID NO. | Amino Acid Sequences of Protein |
|---|---|---|
| | | LAIKYRQKEF VAQPNCQQLL ASRWYDEFPG WRRRHWAVKM VTCFIIGLLF PVFSVCYLIA PKSPLGLFIR KPFIKFICHT ASYLTFLFLL LLASQHIDRS DLNRQGPPPT IVEWMILPWV LGFIWGEIKQ MWDGGLQDYI HDWWNLMDFV MNSLYLATIS LKIVAFVKYS ALNPRESWDM WHPTLVAEAL FAIANIFSSL RLISLFTANS HLGPLQISLG RMLLDILKFL FIYCLVLLAF ANGLNQLYFY YEETKGLTCK GIRCEKQNNA FSTLFETLQS LFWSIFGLIN LYVTNVKAQH EFTEFVGATM FGTYNVISLV VLLNMLIAMM NNSYQLIARR AADNLRRHHQ YQEVMRNLVK RYVAAMIRDA KTEEGLTEEN FKELKQDISS FRFEVLGLLR GSKLSTIQSA NASKESSNSA DSDEKSDSEE EVARQQAAGP LERNIQLESR GLASRGDLSI PGLSEQCVLV DHRERNTDTL GLQVGKRVCP FKSEKVVVED TVPIIPKEKH AKEEDSSIDY DLNLPDTVTH EDYVTTRL |
| g6690167 | 99 | MRTKSEREIH LCVVLGFFXFF FETGSRSVAQ AGVQRHSHGS LQPRPPGLIQ FSHLSLPSSW DYRHAPPHLV NFL |
| g6690252 | 100 | RFFFFFFFEE SRSFAQAGVQ WRYLGSLQPP PPGFTRFSCL SLLSSWDYRR PPPRPANFLY F |
| g7243280 | 101 | ELSFPLLSLD FGAHQGLGSA DMGDMKTPDF DDLLAAFDIP DIDANEAIHS GPEENEGPGG PGKPEPGVGS ESEDTAAASA GDGPGVPAQA SDHGLPPPDI SVVSVIVKNT VCPEQSEALA GGSAGDGAQA AGVTKEGPVG PHRMQNGFGS PEPSLPGTPH SPAPPSGGTW KEKGMEGKTP LDLFAHFGPE PGDHSDPLPP SAPSPTREGA LTPPPPFPSSF ELAQENGPGM QPPVSSPPLG ALKQESCSPH HPQVLAQQGS GSSSPKATDIP ASASPPPVAG VPFFKQSPGH QSPLASPKVP VCQPLKEEDD DEGPVDKSSP GSPQSPSSGA EAADEDSNDS PASSSSRPLK VRIKTIKTSC GNITRTVTQV PSDPDPPAPL AEGAFLAEAS LLKLSPATPT SEGPKVVSVQ LGDGTRLKGT VLPVATIQNA STAMLMAASV ARKAVVLPGG TATSPKMIAK NVLGLVPQAL PKADGRAGLG TGGQKVNGAS VVMVQPSKTA TGPSTGGGTV ISRTQSSLVE AFNKILNSKN LLPAYRPNLS PPAEAGLALP PTGYRCLECG DAFSLEKSLA RHYDRRSMRI EVTCNHCARR LVFFNKCSLL LHAREHKDKG LVMQCSHLVM RPVALDQMVG QPDITPLLPV AVPPVSGPLA LPALGKGEGA ITSSAITTVA AEAPVLPLST EPPAAPATSA YTCFRCLECK EQCRDKAGMA AHFQQLGPPA PGATSNVCPT CPMMLPNRCS FSAHQRMHKN RPPHVCPECG GNFLQANFQT HLREACLHVS RRVGYRCPSC SVVFGGVNSI KSHIQTSHCE VFHKCPICPM AFKSGPSAHA HLYSQHPSFQ TQQAKLIYKC AMCDTVFTHK PLLSSHFDQH LLPQRVSVFK CPSCPLLFAQ KRTMLEHLKN THQSGRLEET AGKGAGGALL TPKTEPEELA VSQGGAAPAT EESSSSSEEE EVPSSPEPPR PAKRPRRELG SKGLKGGGGG PGGWTCGLCH SWFPERDEYV AHMKKEHGKS VKKFPCRLCE RSFCSAPSLR RHVRVNHEGI KRVYPCRYCT EGKRTFSSRL ILEKHVQVRH GLQLGAQSPG RGTTLARGSS ARAQGPGRKR RQSSDCSEE PDSTTPPAKS PRGGPGSGGH GPLRYRSSSS TEQSLMMGLR VEDGAQQCLD CGLCFASPGS LSRHRFISHK KRRGVGKASA LGLGDGEEEA PPSRSDPGGG DSPLPASGGP LTCKVCGKSC DSPLNLKTHF RTHGMAFIRA RQGAVGDN |
| g7305597 | 102 | MSQSPRFVTR RGGSLKAAPG AGTRRNESQD YLLMDELGDD GYPQLPLPPY GYYPSFRGNE NRLTHRRQTI LREKGRRLAN RGPAYMFNDH |

| Protein Identification Number (PID) | SEQ. ID NO. | Amino Acid Sequences of Protein |
|---|---|---|
| | | STSLSIEEER FLDAVEYGNI PVVWKMLEEC HSLNVNCVDY MGQNALQLAV ANEHLEITEL LLKKENLSRV GDALLLAISK GYVRIVEAIL NHPSFAEGKR LATSPSQSEL QQDDFYAYDE DGTRFSHDVT PIILAAHCQE YEIVHTLLRK GARIERPHDY FCKCTECSQK QKHDSFSHSR SRINAYKGLA SPAYLSLSSE DPVMTALELS NELAVLANIE KEFKNDYRKL SMQCKDFVVG LLDLCRNTEE VEAILNGDAE TRQPGDFGRP NLSRLKLAIK DEVKKFVAHP NCQQQLLSIW YENLSGLRQQ TMAVKFLVVL AVAIGLPFLA LIYWCAPCSK MGKILPRPFM KFVAHAASFT IFLGLLVMNA ADRFEGTKLL PNETSTDNAR QLFRMKTSCF SWMEMLIISW VIGMIWAECK EIWTQGPKEY LFELWNMLDF GMLAIFAASF IARFMAFWHA SKAQSIIDAN DTLKDLTKVT LGDNVKYYNL ARIKWDPTDP QIISEGLYAI AVVLSFSRIA YILPANESFG PLQISLGRTV KDIFKFMVIF IMVFVAFMIG MFNLYSYYIG AKQNEAFTTV EESFKTLFWA IFGLSEVKSV VINYNHKFIE NIGYVLYGVY NVTMVIVLLN MLIAMINSSF QEIEDDADVE WKFARAKLWF SYFEEGRTLP VPFNLVPSPK SLLYLLLKFK KWMCELIQGQ KQGFQEDAEM NKRNEEKKFG ISGSHEDLSK FSLDKNQLAH NKQSSTRSSE DYHLNSFSNP PRQYQKIMKR LIKRYVLQAQ IDKESDEVNE GELKEIKQDI SSLRYELLEE KSQNSEDLAE LIRKLGERLS LEPKLEESRR |
| g7512448 | 103 | GFLPATKNLL NEKNHGVLHT SVVLLTEMCE RSPDMLAHFR ENEKLVPQLV RILKNLIMSG YSPGHDVSGI SDPFLQVRIL RLLRILGRND DDSSEAMNDI LAQVATNTET SKNVGNAILY ETVLTIMDIK SESGLRVLAI NILGRFLLNN DKNIRYVALT SLLKTVQTNK NAVQRHRSTI VDCLKDLDVS IKRRAMELSF ALVNGNNIRG MMKELLYFLD SCEPEFKADC ASGIFLAAEK YAPSKRWHID TIMRVLTTAG SYVRDDAVPN LIQLITNSVE MHAYTVQRLY KAILGDYSQQ PLVQVAAWCI GEYGDLLVSG QCEEEEPIQV TEDEVLDILE SVLISNMSTS VTRGYALTAI MKLSTRFTCT VNRIKKVVSI YGSSIDVELQ RRAVEYNALF KKYDHMRSAL LERMPVMEKV TTNGPTEIVQ TNGETEPAPL ETKPPPSGPQ PTSQANDLLD LLGGNDITPV IPTAPTSKPS SAGGELLDLL GDINLTGSHS VSQAGVQWDY LGSLQPLPPA FR |
| g7522630 | 104 | MWPNGSSLGP CFRPTNITLE ERRLIASPWF AASFCVVGLA SNLLALSVLA GARQGGSHTR SSFLTFLCGL VLTDFLGLLV TGTIVVSQHA ALFEWHAVDP GCRLCRFMGV VMIFFGLSPL LLGAAMASER YLGITRPFSR PAVASQRRAW ATVGLVWAAA LALGLLPLLG VGRYTVQYPG SWCFLTLGAE SGDVAFGLLF SMLGGLSVGL SFLLNTVSVA TLCHVYHGQE AAQQRPRDSE VEMMAQLLGI MVVASVCWLP LLVFIAQTVL RNPPAMSPAG QLSRTTEKEL LIYLRVATWN QILDPWVYIL FRRAVLRRLQ PRLSTRPRRS LTLWPSLEYS GTISAHCNLR LPGSSDSRAS ASRAAGITGV SHCARPCMLF DPEFDLLAGV QLLPFEPPTG KALSRKD |
| g7669477 | 105 | MDIEDEENMS SSSTDVKENR NLDNVSPKDG STPGPGEGSQ LSNGGGGGPG RKRPLEEGSN GHSKYRLKKR RKTPGPVLPK NALMQLNEIK PGLQYTLLSQ TGPVHAPLFV MSVEVNGQVF EGSGPTKKKA KLHAAEKALR SFVQFPNASE AHLAMGRTLS VNTDFTSDQA DFPDTLFNGF ETPDKAEPPF YVGSNGDDSF SSSGDLSLSA SPVPASLAQP PLPVLPPFPP PSGKNPVMIL NELRPGLKYD FLSESGESHA KSFVMSVVVD GQFFEGSGRN KKLAKARAAQ SALAAIFNLH |

| Protein Identification Number (PID) | SEQ. ID NO. | Amino Acid Sequences of Protein |
|---|---|---|
| | | LDQTPSRQPI PSEGLQLHLP QVLADAVSRL VLGKFGDLTD NFSSPHARRK VLAGVVMTTG TDVKDAKVIS VSTGTKCING EYMSDRGLAL NDCHAEIISR SLLRFLYTQ LELYLNNKDD QKRSIFQKSE RGGFRLKENV QFHLYISTSP CGDARIFSPH EPILEGSRSY TQAGVQWCNH GSLQPRPPGL LSDPSTSTFQ GAGTTEPADR HPNRKARGQL RTKIESGEGT IPVRSNASIQ TWDGVLQGER LLTMSCSDKI ARWNVVGIQG SLLSIFVEPI YFSSIILGSL YHGDHLSRAM YQRISNIEDL PPLYTLNKPL LSGISNAEAR QPGKAPNFSV NWTVGDSAIE VINATTGKDE LGRASRLCKH ALYCRWMRVH GKVPSHLLRS KITKPNVYHE SKLAAKEYQA AKARLFTAFI KAGLGAWVEK PTEQDQFSLT P |
| g7669479 | 106 | MDIEDEENMS SSSTDVKENR NLDNVSPKDG STPGPGEGSQ LSNGGGGGPG RKRPLEEGSN GHSKYRLKKR RKTPGPVLPK NALMQLNEIK PGLQYTLLSQ TGPVHAPLFV MSVEVNGQVF EGSGPTKKKA KLHAAEKALR SFVQFPNASE AHLAMGRTLS VNTDFTSDQA DFPDTLFNGF ETPDKAEPPF YVGSNGDDSF SSSGDLSLSA SPVPASLAQP PLPVLPPFPP PSGKNPVMIL NELRPGLKYD FLSESGESHA KSFVMSVVVD GQFFEGSGRN KKLAKARAAQ SALAAIFNLH LDQTPSRQPI PSEGLQLHLP QVLADAVSRL VLGKFGDLTD NFSSPHARRK VLAGVVMTTG TDVKDAKVIS VSTGTKCING EYMSDRGLAL NDCHAEIISR SLLRFLYTQ LELYLNNKDD QKRSIFQKSE RGGFRLKENV QFHLYISTSP CGDARIFSPH EPILEGSRSY TQAGVQWCNH GSLQPRPPGL LSDPSTSTFQ GAGTTEPADR HPNRKARGQL RTKIESGEGT IPVRSNASIQ TWDGVLQGER LLTMSCSDKI ARWNVVGIQG SLLSIFVEPI YFSSIILGSL YHGDHLSRAM YQRISNIEDL PPLYTLNKPL LSGISNAEAR QPGKAPNFSV NWTVGDSAIE VINATTGKDE LGRASRLCKH ALYCRWMRVH GKVPSHLLRS KITKPNVYHE SKLAAKEYQA AKVH |
| g7770147 | 107 | MEVLLFLIF ETESCSVIRL ECSGSLQPPP PRFKQFSCLS LPSSWDYRCP PPCPINFCIF GTDRVSPCWP GWSRSR |
| g7706747 | 108 | MAQFYYKRNV NAPYRDRIPL RIVRAESELS PSEKAYLNAV EKGDYASVKK SLEEAEIYFK ININCIDPLG RTALLIAIEN ENLEIIELLL SFNVYVGDAL LHAIRKEVVG AVELLLNHKK PSGEKQVPPI LLDKQFSEFT PDITPIILAA HTNNYEIIKL LVQKGVSVPR PHEVRCNCVE CVSSSDVDSL RHSRSRLNIY KALASPSLIA LSSEDPFLTA FQLSWELQEL SKVENEFKSE YEELSRQCKQ FAKDLLDQTR SSRELEIILN YRDDNSLIEE QSGNDLARLK LAIKYRQKEF VAQPNCQQLL ASRWYDEFPG WRRRHWAVKM VTCFIIGLLF PVFSVCYLIA PKSPLGLFIR KPFIKFICHT ASYLTFLFLL LLASQHIDRS DLNRQGPPPT IVEWMILPWV LGFIWGEIKQ MWDGGLQDYI HDWWNLMDFV MNSLYLATIS LKIVAFVKYS ALNPRESWDM WHPTLVAEAL FAIANIFSSL RLISLFTANS HLGPLQISLG RMLLDILKFL FIYCLVLLAF ANGLNQLYFY YEETKGLTCK GIRCEKQNNA FSTLFETLQS LFWSIFGLIN LYVTNVKAQH EFTEFVGATM FGTYNVISLV VLLNMLIAMM NNSYQLIADH ADIEWKFART KLWMSYFEEG GTLPTPFNVI PSPKSLWYLI KWIWTHLCKK KMRRKPESFG TIGRRAADNL RRHHQYQEVM RNLVKRYVAA MIRDAKTEEG LTEENFKELK QDISSFRFEV LGLLRGSKLS TIQSANASKE SSNSADSDEK SDSEGNSDKD KKNFSLFDLT TLIHPRSAAI ASERHNISNG SALVVQEPPR EKQRKVNFVT |

| Protein Identification Number (PID) | SEQ. ID NO. | Amino Acid Sequences of Protein |
|---|---|---|
| | | DIKNFGLFHR RSKQNAAEQN ANQIFSVSEE VARQQAAGPL ERNIQLESRG LASRGDLSIP GLSEQCVLVD HRERNTDTLG LQVGKRVCPF KSEKVVVEDT VPIIPKEKHA KEEDSSIDYD LNLPDTVTHE DYVTTRL |
| g8922960 | 109 | MESYSVTQAG VQWHELCSLQ PSPPRFREMC IEQDGRVHLT VVYFGKEEIN EVKGVLENTS KAANFRNFTF IQLNGEFSRG KGLDVGARFW KGSNVLLFFC DVDIYFTSEF LNTCRLNTQP GKKVFYPVLF SQYNPGIIYG HHDAVPPLEQ QLVIKKETGF WRDFGFGMTC QYRSDFINIG GFDLDIKGWG GEDVHLYRKY LHSNLIVVRT PVRGLFHLWH EKRCMDELTP EQYKMCMQSK AMNEASHGQL GMLVFRHEIE AHLRKQKQKT SSKKT |
| g8923251 | 110 | MDITLVRKEL QELQNLYKQN STHTAQQAEL IQQLQVLNMD TQKVLRNQED VHTAESISYQ KLYNELHICF ETTKSNEAML RQSVTNLQDQ LLQKEQENAK LKEKLQESQG APLPLPQESD PDYSAQVPHR PSLSSLETLM VSQKSEIEYL QEKLKIANEK LSENISANKG FSRKSIMTSA EGKHKEPPVK RSRSLSPKSS FTDSEELQKL RKAERKIENL EKALQLKSQE NDELRDAHEK RKERLQMLQT NYRAVKEQLK QWEEGSGMTE IRKIKRADPQ QLRQEDSDAV WNELAYFKRE NQELMIQKMN LEEELDELKV HISIDKAAIQ ELNRCVAERR EEQLFRSGED DEVKRSTPEK NGKEMLEQTL QKVIELENRL KSFEKRSRKL KEGNKKLMKE NDFLKSLLKQ QQEDTETREK ELEQIIKGSK DVEKENTELQ VKISELETEV TSLRRQVAEA NALRNENEEL INPMEKSHQS ADRAKSEMAT MKVRSGRYDC KTTMTKVKFK AAKKNCSVGR HHTVLMSNVM VMSNVFENLS KDGWEDVSES SSDSEAQTSQ TLGTIIVETS QKISPTEDGK DQKESDPTED SQTQGKEIVQ TYLNIDGKTP KDYFHDKNAK KPTFQKKNCK MQKSSHTAVP TRVNREKYKN ITAQKSSSNI ILLRERIISL QQQNSVLQNA KKTAELSVKE YKEVNEKLLH QQQVSDQRFQ TSRQTIKKLN LDLAGLRKEK EDLLKKLESS SEITSLAEEN SQVTFPRIQV TSLSPSRSMD LEMKQLQYKL KNATNELTKQ SSNVKTLKFE LLAKEEHIKE MHEKISRMER DITMKRHLIE DLKFRQKVNL ESNKSFSEML QNLDKKVKTL TEECSNKKVS IDSLKQRLNV AVKEKSQYEQ MYQKSKEELE KKDLKLTLLV SRISETESAM AEIETAASKQ LQELALQSEQ VLEGAQKTLL LANEKVEEFT TFVKALAKEL QNDVHVVRRQ IRELKKMKKN RDACKTSTHK AQTLAASILN ISRSDLEEIL DTEDQVEIEK TKIDAENDKE WMLYIQKLLE GQSLTLSPRL KCNGAIMAHQ NLRLPDSSSS ASAS |
| g8923273 | 111 | MKVVPEKNAV RILWGRERGA RAMGAQRLLQ ELVEDKTRWM KWEGKRVELP DSPRSTFLLA FSPDRTLLAS THVNHNIYIT EVKTGKCVHS LIGHRRTPWC VTFHPTISGL IASGCLDGEV RIWDLHGGSE SWFTDSNNAI ASLAFHPTAQ LLLIATANEI HFWDRSRREP FAVVKTASEM ERVRLVRFDP LGHYLLTAIV NPSNQGGDDE PEIPIDGTEL SHYRQRALLQ SQPVRRTPLL HNFLHMLSSR SSGIQTEPFH PPEQASSTQQ DQGLLNRPSA FSTVQSSTAG NTLRNLSLGP TRRSLGGPLS SHPSRYHREI APGLTGSEWT RTVLSLNSRS EAESMPPPRT SASSVSLLSV LRQQEGGSQA SVYTSATEGR GFPASGLATE SDGGNGSSQN NSGSIRHELQ CDLRRFFLEY DRLQELDQSL SGEAPQTQQA QEMLNNNIES ERPGPSHQPT PHSSENNSNL SRGHLNRCRA CHNLLTFNND TLRWERTTPN YSSGEASSSW QVPSSFESVP SSGSQLPPLE RTEGQTPSSS |
| | | RLELSSSASP QEERTVGVAF NQETGHWERI YTQSSRSGTV SQEALHQDMP EESSEEDSLR RRSLALSPRL EYSGAILAHC KLRLPGSCHS PASASQVAGT TGAHHHARLI FAFLVEMEFH HVSQAGLELL TSGDLPTSAS QVLGLQA |
| g8923360 | 112 | MVHSPRSLVA NPSQVLFFLS FLFFFFLRQS FALVAQAGVQ WRNLGSLQPP PPGFKQFSCL SLLSSWDYRH APPCPAYFVF LVDMGFPHVG QTGLELLTSG DPPASASQSA GITGGSHRAQ PTSSNPYGIV FFFLPVKTFS GMSQEAGDCR ET |
| g8923452 | 113 | MPTATGLTLL TSASSAISDP GGEVSAPWGG LRTWTQPLRC WERLLPPPGD PRTVAENTQQ DECGLPGSCP ARPLSRKPEC GREGILPCCS SSAWPEGSFR PFQMNLFSFL SFFFLFFFFL RWSLTLSPRL ECSSAISAHC NLRLPGSSNS PALASQVAGI TGICHHARQI FVFLVETGFC HVGQAGLELL ISGDSPASAF QSAGIIGVSH RARPGSVFLA RSEESLYLRP GQQSQEVKV |
| g8923454 | 114 | MLLVDADQPE PMRSGARELA LFLTPEPGAE AKEVEETIEG MLLRLEEFCS LADLIRSDTS QILEENIPVL KAKLTEMRGI YAKVDRLEAF VKMVGHHVAF LEADVLQAER DHGAFPQALR RWLGSAGLPS FRNVECSGTI PARCNLRLPG SSDSPASASQ VAGITEVTCT GARDVRAAHT V |
| g8923691 | 115 | MSVYSGKVLL QTTPPHVGIQ LDKLIREVST LDGVLEVRNE HFWTLGFGSL AGSVHVRIRR DANEQMVLAH VTNRLYTLVS TLTVQIFKDD WIRPALLSGP VAANVLNFSD HHVIPMPLLK GTDGLNPYVH FLWKINFFLF FDMESLSVAQ AGVQWHDLGS LQPHLPGSSN SACLSLPSSW DYRHAPPHLP NFCIISKDGV LPCWPCWS |
| g8924071 | 116 | MESRSVAQTG VHWHNLSSLQ PLPPRFKQFS CLSLRSSWDY THLPPCLANF FVFLVETAFR HVGQAGLKLL TSGDQPTSAS QSAGITGISH RTQPVGRFLI TDSIFLFVTD LLKFSISS |
| g8924204 | 117 | MSKVLGGPFS KGHTASDKYF QIFHNISFFE TESCSVAQAG VQWCNLGSLQ ALPPRFTPFS CLSLPSSWDY RHPPPCPDNV FVFSVETGFH CVSQDGLNLL TL |
| g8980667 | 118 | MAQGTLIRVT PEQPTHAVCV LGTLTQLDIC SSAPEDCTSF SINASPGVVV DIAHSPPAKK KSTGSSTWPL DPGVEVTLTM KAASGSTGDQ KVQISYYGPK TPPVKALLYL TAVDGVSPCH PGWSAMHDLA HCNLRLQVQA ILCFSVPSSW TTGACCHAWL IFVFLVEMEF HHVGQAGLEL LTSGDLPASG SQSARITGMN HCARPSIFLI LKYL |
| g9716913 | 119 | MSQSPAFGPR RGSSPRGAAG AAAARRNESQD YLLMDSELGE DGCPQAPLPC YGYYPCFRGS DNRLAHRRQT VLREKGRRLA NRGPAYMFSD RSTSLSIEEE RFLDAAEYGN IPVVRKMLEE CHSLNVNCVD YMGQNALQLA VANEHLEITE LLLKKENLSR VGDALLLAIS KGYVRIVEAI LSHPAFAEGK RLATSPSQSE LQQDDFYAYD EDGTRFSHDV TPIILAAHCQ EYEIVHTLLR KGARIERPHD YFCKCNDCNQ KQKHDSFSHS RSRINAYKGL ASPAYLSLSS EDPVMTALEL SNELAVLANI EKEFKNDYKK LSMQCKDFVV GLLDLRRNTE EVEAILNGDV PNLSRLKLAI KYEVKKMGKI MRGPFMKFVA HAASFTIFLG LLVMNAADRF EGTKLLPNET STDNAKQLFR MKTSCFSWME MLIISWVIGM IWAECKEIWT QGPKEYLFEL WNMLDFGMLA |

| Protein Identification Number (PID) | SEQ. ID NO. | Amino Acid Sequences of Protein |
|---|---|---|
| | | IFAASFIARF MAFWHASKAQ SIIDANDTLK DLTKVTLGDN VKYYNLARIK WDPSDPQIIS EGLYAIAVVL SFSRIAYTLP ANESFGPLQI SLGRTVKDIF KFMVIFIMVF VAFMIGMFNL YSYYIGAKQN EAFTTVEESF KTLFWAIFGL SEVKSVVINY NHKFIENIGY VLYGVYNVTM VIVLLNMLIA MINSSFQEIE DDADVEWKFA RAKLWFSYFE EGRTLPVPFN LVPSPKSLFY LLLKLKKWIS ELFQGHKKGF QEDAEMNKIN EEKKLGILGS HEDLSKLSLD KKQVGHNKQP SIRSSEDFHL NSFNNPPRQY QKIMKRLIKR YVLQAQIDKE SDEVNEGELK EIKQDISSLR YELLEEKSQN TEDLAELIRE LGEKLSMEPN QEETNR |
| g9966865 | 120 | MLRNSTFKNM QRRHTTLREK GRRQAIRGPA YMFNEKGTSL TPEEERFLDS AEYGNIPVVR KMLEESKTLN FNCVDYMGQN ALQLAVGNEH LEVTELLLKK ENLARVGDAL LLAISKGYVR IVEAILNHPA FAQGQRLTLS PLEQELRDDD FYAYDEDGTR FSHDITPIIL AAHCQEYEIV HILLLKGARI ERPHDYFCKC NECTEKQRKD SFSHSRSRMN AYKGLASAAY LSLSSEDPVL TALELSNELA RLANIETEFK NDYRKLSMQC KDFVVGVLDL CRDTEEVEAI LNGDVNFQVW SDHHRPSLSR IKLAIKYEVK KFVAHPNCQQ QLLTMWYENL SGLRQQSIAV KFLAVFGVSI GLPFLAIAYW IAPCSKLGRT LRSPFMKFVA HAVSFTIFLG LLVVNASDRF EGVKTLPNET FTDYPKQIFR VKTTQFSWTE MLIMKWVLGM IWSECKEIWE EGPREYVLHL WNLLDFGMLS IFVASFTARF MAFLKATEAQ LYVDQHVQDD TLHNVSLPPE VAYFTYARDK WWPSDPQIIS EGLYAIAVVL SFSRIAYILP ANESFGPLQI SLGRTVKDIF KFMVIFIMVF VAFMIGMFNL YSYYRGAKYN PAFTTVEESF KTLFWSIFGL SEVISVVLKY DHKFIENIGY VLYGVYNVTM VVVLLNMLIA MINNSYQEIE EDADVEWKFA RAKLWLSYFD EGRTLPVPFN LVPSPKSFYY LIMRIKMCLI KLCKSKAKSC ENDLEMGMLN SKFKKTRYQA GMRNSENLTA NNTLSKPTRY QKIMKRLIKR YVLKAQVDRE NDEVNEGELK EIKQDISSLR YELLEEKSQA TGELADLIQQ LSEKFGKNLN KDHLRVNKGK DI |
| g9967846 | 121 | MDDGCPQLPL PPHGYYPSLR GTDNRLTHRR QTVLREKGRR LANRGPAYMF NDHSTTLSIE EERFLDAAEY GNIPVVRKML EECLSLNVNC VDYMGQNALQ LAVANEHLEI TELLLKKENL SRVGDALLLA ISKGYVRIVE AILSHPAFAE GKRLATSPSQ SELQQDDFYA YDEDGTRFSH DVTPIILAAH CQEYEIVHTL LRKGARIERP HDYFCKCSEC NQKQKHDSFS HSRSRINAYK GLASPAYLSL SSEDPVMTAL ELSNELAVLA NIEKEFKNDY KKLSMQCKDF VVGLLDLCRN TEEVEAILNG DVETCQSGDQ GRPNLSRLKL AIKYEVKKFV AHPNCQQQLL SIWYENLSGL RQQTMAVKFL VVLGVAIGLP FLALIYWCAP CSKMGKIMRG PFMKFVAHAA SFTIFLGLLV MNAADRFEGT KLRPNETSTD NAKQLFRMKT SCFSWMEMLI ISWVIGMIWA ECKEIWAQGP KEYLFELWNM LDFGMLAIFA ASFIARFMAF WHASKAQSII DANDTLKDLT KVTLGEDVKY YNLARIKWDP SDPQIISEGL YAIAVVLSFS RIAYILPANE SFGPLQISLG RTVKDIFKFM VIFIMVFVAF MIGMFNLYSY YIGAKQNEAF TTVEESFKTL FWAIFGLSEV KSVVINYNHK FIENIGYVLY GVYNVTMIAM INSSFQEIED DADVEWKFAR AKLWFSYFEE GRTLPVPFNL VPSPKSLLYL LLKFKKWGFE LFQGHKKAFQ ED AEMNRNEEK KFGILGSHED LSKLSVDKKQ LGQNKQSSIR SSEDFHLNSF NNPPRQYQKI MKRLIKRYVL QAQIDKESDE |
| | | VNEGELKEIK QDISSLRYEL LEEKSQNTED LAELIRKLGE KLSSEPKQEE INR |
| g9967886 | 122 | MFNDHSTTLS IEEERFLDAA EYGNIPVVRK MLEECLSLNV NCVDYMGQNA LQLAVANEHL EITELLLKKE NLSRVGDALL LAISKGYVRI VEAILSHPAF AEGKRLATSL SQSELQQDDF YAYDEDGTRF SHDVTPIILA AHCQEYEIVH TLLRKGARIE RPHDYFCKCS ECNQKQKHDS FSHSRSRINA YKGLASPAYL SLSSSEDPVMT ALELSNELAV LANIEKEFKN DYKKLSMQCK DFVVGLLDLC RNTEEVEAIL NGDIETCQPG DQGRPNLSRL KLAIKYEVKK FVAHPNCQQQ LLSIWYENLS GLRQQTMAVK FLVVLGVAIG LPFLALIYWC APCSKMGKIM RGPFMKFVAH AASFTIFLGL LVMNAADRFE GTKLRPNETS TDNAKQLFRM KTSCFSWMEM LIISWVIGMV WAECKEIWAQ GPKEYLFELW NMLDFGMLAI FAASFIARFM AFWHASKAQS IIDANDTLKD LTKVTLGEDV KYYNLARIKW DPSDPQIISE GLYAIAVVLS FSRIAYILPA NESFGPLQIS LGRTVKDIFK FMVIFIMVFV AFMIGMFNLY SHYIGAKQNE AFTTYVISDV LTMEIAD |
| g9967888 | 123 | MDDGCPQLPL PPHGYYPSLR GTDNRLTHRR QTVLREKGRR LANRGPAYMF NDHSTTLSIE EERFLDAAEY GNIPVVRKML EECLSLNVNC VDYMGQNALQ LAVANEHLEI TELLLKKENL SRVGDALLLA ISKGYVRIVE AILSHPAFAE GKRLATSPSQ SELQQDDFYA YDEDGTRFSH DVTPIILAAH CQEYEIVHTL LRKGARIERP HDYFCECSEC NQKQKHDSFS HSRSRINAYK GLASPAYLSL SSEDPVMTAL ELSNELAVLA NIEKEFKNDY KKLSMQCKDF VVGLLDLCRN TEEVEAILNG DVETCQPGDQ GRPNLSRLKL AIKYEVKKFV AHPNCQQQLL SIWYENLSGL RQQTMAVKFL VVLGVAIGLP FLALIYWCAP CSKMGKIMRG PFMKFVAHAA SFTIFLGLLV MNAADRFEGT KLRPNETSTD NAKQLFRMKT SCFSWMEMLI ISWVIARIKW DPSDPQIISE GLYAIAVVLS FSRIAYILPA NESFGPLQIS LGRTVKDIFK FMVIFIMVFV AFMIGMFHLY SYYIGAKQNE AFTTVEESFK TLFWAIFGLS EVKSVVINYN HKFIENIGYV LYGVYNVTMV IVLLNMLIAM INSSFQEIED DADVEWKFAR AKLWFSYFEE GRTLPVPFNL VPSPKSLLYL LLKFKKWGFE LFQGHKKAFQ EDAEMNKRNE EKKFGILGSH EDLSKLSVDK KQLGQNKQSS IRSSEDFHLN SFNNPPRQYQ KIMKRLIKRY VLQAQIDKES DEVNEGELKE IKQDISSLRY ELLEEKSQNT EDLAELIRKL GEKLSSEPKQ EEINR |
| g9716913 | 124 | MSQSPAFGPR RGSSPRGAAG AAARRNESQD YLLMDSELGE DGCPQAPLPC YGYYPCFRGS DNRLAHRRQT VLREKGRRLA NRGPAYMFSD RSTSLSIEEE RFLDAAEYGN IPVVRKMLEE CHSLNVCVD YMGQNALQLA VANEHLEITE LLLKKENLSR VGDALLLAIS KGYVRIVEAI LSHPAFAEGK RLATSPSQSE LQQDDFYAYD EDGTRFSHDV TPIILAAHCQ EYEIVHTLLR KGARIERPHD YFCKCNDCNQ KQKHDSFSHS RSRINAYKGL ASPAYLSLSS EDPVMTALEL SNELAVLANI EKEFKNDYKK LSMQCKDFVV GLLDLRRNTE EVEAILNGDV ETLQSGDHGR PNLSRLKLAI KYEVKKMGKI MRGPFMKFVA HAASFTIFLG LLVMNAADRF EGTKLLPNET STDNAKQLFR MKTSCFSWME MLIISWVIGM IWAECKEIWT QGPKEYLFEL IFAASFIARF MAFWHASKAQ SIIDANDTLK DLTKVTLGDN VKYYNLARIK WDPSDPQIIS EGLYAIAVVL SFSRIAYTLP ANESFGPLQI SLGRTVKDIF KFMVIFIMVF VAFMIGMFNL |

-continued

| Protein Identification Number (PID) | SEQ. ID NO. | Amino Acid Sequences of Protein |
|---|---|---|
| | | YSYYIGAKQN EAFTTVEESF KTLFWAIFGL SEVKSVVINY NHKFIENIGY VLYGVYNVTM VIVLLNMLIA MINSSFQEIE DDADVEWKFA RAKLWFSYFE EGRTLPVPFN LVPSPKSLFY LLLKLKKWIS ELFQGHKKGF QEDAEMNKIN EEKKLGILGS HEDLSKLSLD KKQVGHNKQP SIRSSEDFHL NSFNNPPRQY QKIMKRLIKR YVLQAQIDKE SDEVNEGELK EIKQDISSLR YELLEEKSQN TEDLAELIRE LGEKLSMEPN QEETNR |

NTP peptides, Related Proteins, Related Peptides, and fragments, variants, derivatives, homologues and mimetics thereof encompassed by this invention can be prepared using methods known to those of skilled in the art, such as recombinant DNA technology, protein synthesis and isolation of naturally occurring NTP petides, Related Proteins, Related Peptides, and fragments, variants, derivatives and homologues thereof.

An NTP peptide, Related Protein, or Related Peptide can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds., *Current Protocols in Molecular Biology*, Green Publishers Inc. and Wiley and Sons, N.Y. [1994].

A gene or cDNA encoding an NTP peptide, Related Protein, or Related Peptide may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other Related Proteins. In addition, where a gene encoding an NTP peptide, Related Protein, or Related Peptide has been identified from one species, all or a portion of that gene may be used as a probe to identify homologous genes from other species. The probes or primers may be used to screen cDNA libraries from various tissue sources believed to express an NTP peptide, Related Protein, or Related Peptide gene. Typically, conditions of high stringency will be employed for screening to minimize the number of false positives obtained from the screen.

Another means to prepare a gene encoding an NTP peptide, Related Protein, or Related Peptide is to employ chemical synthesis using methods well known to the skilled artisan, such as those described by Engels et al.(Angew. Chem. Intl. Ed., 28:716-734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding an NTP peptide, Related Protein, or Related Peptide will be several hundred nucleotides in length. Nucleic acids larger than about 100 nucleotides can be synthesized as several fragments using these methods. The fragments then can be ligated together to form the full length NTP peptide, Related Protein, or Related Peptide. Usually, the DNA fragment encoding the amino terminus of the protein will have an ATG, which encodes a methionine residue. This methionine may or may not be present on the mature form of the Related Protein, Related Peptide or NTP peptide, depending on whether the protein produced in the host cell is designed to be secreted from that cell.

The gene, cDNA, or fragment thereof encoding the Related Protein, Related Peptide or NTP peptide can be inserted into an appropriate expression or amplification vector using standard ligation techniques. The vector typically is selected to be functional in the particular host cell employed (i.e., the vector is compatible with the host cell machinery such that amplification of the gene and/or expression of the gene can occur). The gene, cDNA or fragment thereof encoding the Related Protein, Related Peptide or NTP peptide may be amplified/expressed in prokaryotic, yeast, insect (baculovirus systems) and/or eukaryotic host cells. Selection of the host cell will depend in part on whether the Related Protein, Related Peptide or NTP peptide is to be glycosylated and/or phosphorylated. If so, yeast, insect, or mammalian host cells are preferable.

Typically, the vectors used in any of the host cells will contain 5' flanking sequence (also referred to as a promoter) and other regulatory elements, such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a tag sequence, i.e., an oligonucleotide molecule located at the 5' or 3' end of the Related Protein, Related Peptide or NTP peptide coding sequence; the oligonucleotide molecule encodes polyHis (such as hexaHis), or other tag such as FLAG, HA (hemaglutinin Influenza virus) or myc for which commercially available antibodies exist. This tag typically is fused to the polypeptide upon expression of the polypeptide, and can serve as a means for affinity purification of the Related Protein, Related Peptide or NTP peptide from the host cell. Affinity purification can be accomplished, for example, by column chromatography using antibodies against the tag as an affinity matrix. Optionally, the tag can subsequently be removed from the purified Related Protein, Related Peptide or NTP peptide by various means such as using certain peptidases.

The human immunoglobulin hinge and Fc region could be fused at either the N-terminus or C-terminus of the Related Protein, Related Peptide or NTP peptide by one skilled in the art. The subsequent Fc-fusion protein could be purified by use of a Protein A affinity column. Fc is known to exhibit a long pharmacokinetic half-life in vivo and proteins fused to Fc have been found to exhibit a substantially greater half-life in vivo than the unfused counterpart. Also, fusion to the Fc region allows for dimerization/multimerization of the molecule that may be useful for the bioactivity of some molecules.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native Related Protein, Related Peptide or NTP peptide gene 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the Related Protein, Related Peptide or NTP peptide gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the Related Protein, Related Peptide or NTP peptide. If the vector of choice does not contain an origin of replication site, one may be chemically synthesized based on a known sequence, and ligated into the vector. The transcription termination element is typically located 3' of the end of the Related Protein, Related Peptide or NTP peptide coding sequence and serves to terminate transcription of the Related Protein, Related Peptide or NTP peptide. Usually, the transcription termination element in prokaryotic cells is a G-C rich fragment followed by a poly T sequence. While the element may be cloned from a library or purchased commercially as part of a vector, it also can be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the Related Protein, Related Peptide or NTP peptide to be synthesized. The Shine-Dalgarno sequence is varied but is typically a polypurine (i.e., having a high A-G content). Many Shine-Dalgarno sequences have been identified, each of which can be readily synthesized by a person having ordinary skill in the art using methods set forth herein, and used in a prokaryotic vector.

In those cases where it is desirable for Related Protein, Related Peptide or NTP peptide to be secreted from the host cell, a signal sequence may be used to direct the Related Protein, Related Peptide or NTP peptide out of the host cell where it is synthesized, and the carboxy-terminal part of the protein may be deleted in order to prevent membrane anchoring. Typically, the signal sequence is positioned in the coding region of the Related Protein/Related Peptide/NTP peptide gene or cDNA, or directly at the 5' end of the Related Protein/Related Peptide/NTP peptide gene coding region. Many signal sequences have been identified, and any of them that are functional in the selected host cell may be used in conjunction with the Related Protein/Related Peptide/NTP peptide gene or cDNA. Therefore, the signal sequence may be homologous or heterologous to the Related Protein/Related Peptide/NTP peptide gene or cDNA, and may be homologous or heterologous to the Related Protein/Related Peptide/NTP peptide gene or cDNA. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the Related Protein/Related Peptide/NTP peptide gene or cDNA may be increased by the presence of one or more introns in the vector. This is particularly true where the Related Protein, Related Peptide or NTP peptide is produced in eukaryotic host cells, especially mammalian host cells. The introns used may be naturally occurring within the Related Protein/Related Peptide/NTP peptide gene, especially where the gene used is a full length genomic sequence or a fragment thereof. Where the intron is not naturally occurring within the gene (as for most cDNAs), the intron(s) may be obtained from another source. The position of the intron with respect to the flanking sequence and the Related Protein/Related Peptide/NTP peptide gene is generally important, as the intron must be transcribed to be effective. As such, where the Related Protein/Related Peptide/NTP peptide gene inserted into the expression vector is a cDNA molecule, the preferred position for the intron is 3' to the transcription start site, and 5' to the polyA transcription termination sequence. Preferably for Related Protein/Related Peptide/NTP peptide cDNA, the intron or introns will be located on one side or the other (i.e., 5' or 3') of the cDNA such that it does not interrupt this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention typically are constructed from starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to blunt the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra. Alternatively, two or more of the elements to be inserted into the vector may first be ligated together (if they are to be positioned adjacent to each other) and then ligated into the vector.

An additional method for constructing the vector is to conduct all ligations of the various elements simultaneously in one reaction mixture. Here, many nonsense or nonfunctional vectors will be generated due to improper ligation or insertion of the elements. The functional vector may be identified and selected, however, by restriction endonuclease digestion.

Preferred vectors for practicing this invention are those that are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15b (Novagen, Madison, Wis.), PGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding full length or truncated Related Protein, Related Peptide or NTP peptide has been inserted into the proper site of the vector, the completed vector may be inserted into a suitable host cell for amplification and/or polypeptide expression. Host cells may be prokaryotic host cells (such as *E. coli*) or eukaryotic host cells (such as a yeast cell, an insect cell, or a vertebrate cell). The host cell, when cultured under appropriate conditions, can synthesize Related Protein, Related Peptide or NTP peptide which can subsequently be collected from the culture medium (if the host cell secretes it into the medium) or directly from the host cell producing it (if it is not secreted).

After collection, the Related Protein, Related Peptide or NTP peptide can be purified using methods such as molecular sieve chromatography, affinity chromatography, and the like. Selection of the host cell for Related Protein, Related Peptide or NTP peptide production will depend in part on whether the Related Protein, Related Peptide or NTP peptide is to be glycosylated or phosphorylated (in which case eukaryotic host cells are preferred), and the manner in which the host cell is able to fold the protein into its native tertiary structure (e.g., proper orientation of disulfide bridges, etc.) such that the biologically active protein is prepared by the Related Protein, Related Peptide or NTP peptide that has biological activity. The Related Protein, Related Peptide or NTP peptide may be folded after synthesis using appropriate chemical conditions as discussed below. Suitable cells or cell lines useful in the invention include mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification can be accomplished by those skilled in the art, using the guidelines provided herein. Other suitable mammalian cell lines include the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5.alpha., DH10, and MC1061) are well-known as host cells in the field of biotechnology. Various strains of *B. subtilis, Pseudomonas* spp., other *Bacillus* spp., *Streptomyces* spp., and the like may also be employed in this method. Many strains of yeast cells known to those skilled in the art also are available as host cells for expression of the polypeptides of the present invention.

Additionally, where desired, insect cell systems may be utilized in the methods of the present invention. Such systems are described for example in Kitts, et al. (*Biotechniques*, 14:810-817 [1993]), Lucklow (*Curr. Opin. Biotechnol.*, 4:564-572 [1993]) and Lucklow et al. (*J. Virol.*, 67:4566-4579 [1993]). Preferred insect cells are Sf-9 and Hi5 (Invitrogen, Carlsbad, Calif.).

Insertion (also referred to as transformation or transfection) of the vector into the selected host cell may be accomplished using methods such as the calcium chloride, electroporation, microinjection, lipofection, or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary. Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of Related Protein, Related Peptide or NTP peptide produced in the host cell can be evaluated using standard methods known in the art. Such methods include, without limitation, Western blot analysis, SDS-polyacrylamide gel electrophoresis, non-denaturing gel electrophoresis, HPLC separation, mass spectroscopy, mmunoprecipitation, and/or activity assays such as DNA binding gel shift assays.

If the Related Protein, Related Peptide or NTP peptide has been designed to be secreted from the host cells, the majority of the Related Protein, Related Peptide or NTP peptide may be found in the cell culture medium. Proteins prepared in this way will typically not possess an amino terminal methionine, as it is removed during secretion from the cell. If the Related Protein, Related Peptide or NTP peptide is not secreted from the host cells, however, it will be present in the cytoplasm and/or the nucleus (for eukaryotic host cells) or in the cytosol, (for gram negative bacteria host cells), and it may have an amino terminal methionine.

For Related Protein, Related Peptide or NTP peptide situated in the host cell cytoplasm and/or nucleus, the host cells typically are first disrupted mechanically or with detergent to release the intra-cellular contents into a buffered solution. Related Protein, Related Peptide or NTP peptide then can be isolated from this solution.

Purification of Related Protein, Related Peptide or NTP peptide from solution can be accomplished using a variety of techniques. If the protein has been synthesized such that it contains a tag such as hexaHistidine (e.g. NTP peptide/hexaHis) or other small peptide such as FLAG (Sigma-Aldrich, St. Louis, Mich.) or calmodulin-binding peptide (Stratagene, La Jolla, Calif.) at either its carboxyl or amino terminus, it may essentially be purified in a one-step process by passing the solution through an affinity column where the column matrix has a high affinity for the tag or for the protein directly (i.e., a monoclonal antibody specifically recognizing the Related Protein or Related Peptide). For example, polyhistidine binds with great affinity and specificity to nickel, zinc and cobalt; thus immobilized metal ion affinity chromatography which employs a nickel-based affinity resin (as used in Qiagen's QIAexpress system or Invitrogen's Xpress System) or a cobalt-based affinity resin (as used in BD Biosciences-CLONTECH's Talon system) can be used for purification of Related Protein/polyHis. (See for example, Ausubel et al., eds., *Current Protocols in Molecular Biology,* Section 10.11.8, John Wiley & Sons, New York [1993]).

Where the Related Protein, Related Peptide or NTP peptide is prepared without a tag attached, and no antibodies are available, other well known procedures for purification can be used. Such procedures include, without limitation, ion exchange chromatography, hydroxyapatite chromatography, hydrophobic interaction chromatography, molecular sieve chromatography, HPLC, native gel electrophoresis in combination with gel elution, and preparative isoelectric focusing (Isoprime machine/technique, Hoefer Scientific). In some cases, two or more of these techniques may be combined to achieve increased purity.

If it is anticipated that the Related Protein, Related Peptide or NTP peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation. If the Related Protein, Related Peptide or NTP peptide has formed inclusion bodies in the cytosol, the inclusion bodies can often bind to the inner and/or outer cellular membranes and thus will be found primarily in the pellet material after centrifugation. The pellet material then can be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The Related Protein, Related Peptide or NTP peptide in its now soluble form then can be analyzed using gel electrophoresis, immunoprecipitation or the like. If it is desired to isolate the Related Protein, Related Peptide or NTP peptide, isolation may be accomplished using standard methods such as those set forth below and in Marston et al. (*Meth. Enz.,* 182:264-275 [1990]).

In some cases, the Related Protein, Related Peptide or NTP peptide may not be biologically active upon isolation. Various methods for refolding or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. In most cases the refolding/oxidation solution also will contain a reducing agent or the reducing agent plus its, oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol(bME)/dithio-b(ME). In many instances a cosolvent is necessary to increase the efficiency of the refolding and the more common reagents used for this purpose include glycerol, polyethylene glycol of various molecular weights, and arginine.

If Related Protein, Related Peptide or NTP peptide inclusion bodies are not formed to a significant degree in the host cell, the Related Protein, Related Peptide or NTP peptide may be found primarily in the supernatant after centrifugation of the cell homogenate, and the Related Protein, Related Peptide or NTP peptide can be isolated from the supernatant using methods such as those set forth below.

In those situations where it is preferable to partially or completely isolate the Related Protein, Related Peptide or NTP peptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying Related Proteins, Related Peptides or NTP peptides using recombinant DNA techniques, the Related Proteins, Related Peptides or NTP peptides and their fragments, variants, homologues and derivatives may be prepared by chemical synthesis methods (such as solid phase peptide synthesis) using techniques known in the art such as those set forth by Merrifield et al., (*J. Am. Chem. Soc.,* 85:2149 [1963]), Houghten et al. (*Proc Natl Acad. Sci. USA,* 82:5132 [1985]), and Stewart and Young (*Solid Phase Peptide Synthesis,* Pierce Chemical Co., Rockford, Ill. [1984]). Such polypeptides may be synthesized with or without a methionine on the amino terminus. Chemically synthesized Related Proteins, Related Peptides or NTP peptides may be oxidized using methods set forth in these references to form disulfide bridges. The Related Proteins, Related Peptides or NTP peptides are expected to have biological activity comparable to Related Proteins, Related Peptides or NTP peptides produced recombinantly or purified from natural sources, and thus may be used interchangeably with recombinant or natural Related Protein, Related Peptide or NTP peptide.

Chemically modified Related Protein, Related Peptide or NTP peptide compositions in which the Related Protein, Related Peptide or NTP peptide is linked to a polymer are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of Related Protein/Related Peptide/NTP peptide polymers is a mixture of polymers.

In some cases, it may be desirable to prepare nucleic acid and/or amino acid variants of the naturally occurring Related Proteins, Related Peptides or NTP peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, also may be used to prepare such variants. Other methods known to the skilled artisan may be used as well.

Preferred nucleic acid variants are those containing nucleotide substitutions accounting for codon preference in the host cell that is to be used to produce the Related Protein, Related Peptide or NTP peptide. Such codon optimization can be determined via computer algorithms which incorporate codon frequency tables such as Ecohigh.Cod for codon preference of highly expressed bacterial genes as provided by the University of Wisconsin Package Version 9.0, Genetics Computer Group, Madison, Wis. Other useful codon frequency tables include Celegans_high.cod, Celegans_low.cod, Drosophila_high.cod, Human_high.cod, Maize_high.cod, and Yeast_high.cod. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

Related Proteins, Related Peptides, NTP peptides, fragments, homologs, variants, derivatives and salts thereof can be made using conventional peptide synthesis techniques known to one of ordinary skill in the art. These techniques include chemical coupling methods (cf. Wunsch, E: "Methoden der organischen Chemie", Volume 15, Band 1+2, *Synthese von Peptiden, thime Verlag, Stuttgart* (1974), and Barrany, G.; Marrifield, R. B.: "The Peptides", eds. E. Gross, J. Meienhofer, Volume 2, Chapter 1, pp. 1-284, Academic Press (1980)), enzymatic coupling methods (cf. Widmer, F. Johansen, J. T., *Carlsberg Res. Commun.,* Vol. 44, pp. 37-46 (1979), and Kullmann, W.: "Enzymatic Peptide Synthesis", CRC Press Inc. Boca Raton, Fla. (1987), and Widmer, F., Johansen, J. T. in "Synthetic Peptides in Biology and Medicines:, eds. Alitalo, K., Partanen, P., Vatieri, A., pp. 79-86, Elsevier, Amsterdam (1985)), or a combination of chemical and enzymatic methods if this is advantageous for the process design and economy. Using the guidelines provided herein, those skilled in the art are capable of varying the peptide sequence of the Related Protein, Related Peptide or NTP peptide to make a homologue having the same or similar biological activity (bioactivity) as the original or native Related Protein, Related Peptide or NTP peptide.

There can be advantages for using a mimetic of a given Related Protein, Related Peptide or NTP peptide rather than the protein itself. In general, peptide mimetics are more bioavailable, have a longer duration of action and can be cheaper to produce than proteins and peptides.

Thus the Related Proteins, Related Peptides and NTP peptides described above have utility in the development of such small chemical compounds with similar biological activities and therefore with similar therapeutic utilities. Peptide mimetics of Related Proteins, Related Peptides and NTP peptides can be developed using combinatorial chemistry techniques and other techniques known in the art (see e.g. Proceedings of the 20th European Peptide Symposium, ed. G. Jung, E. Bayer, pp. 289-336, and references therein).

Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is described in the paper "Tritriated D-ala$^1$-Peptide T Binding", Smith C. S. et al., *Drug Development Res.* 15, pp. 371-379 (1988).

A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is provided in conformationally restricted thymopentin-like compounds, such as those disclosed in U.S. Pat. No. 4,457, 489 (1985), Goldstein, G. et al., the disclosure of which is incorporated by reference herein in its entirety.

A third method is to substitute peptide bonds in the Related Protein, Related Peptide or NTP peptide by pseudopeptide bonds that confer resistance to proteolysis. A number of pseudopeptide bonds have been described that in general do not affect peptide structure and biological activity. One example of this approach is to substitute retro-inverso pseudopeptide bonds ("Biologically active retroinverso analogues of thymopentin," Sisto A. et al in Rivier, J. E. and Marshall, G. R. (eds) "Peptides, Chemistry, Structure and Biology," *Escom, Leiden* (1990), pp. 722-773) and Dalpozzo, et al. (1993), *Int. J. Peptide Protein Res.,* 41:561-566, incorporated herein by reference). According to this modification, the amino acid sequences of the peptides may be identical to the sequences of the Related Proteins, Related Peptides and NTP peptides described above, except that one or more of the peptide bonds are replaced by a retro-inverso pseudopeptide bond. Preferably, the most N-terminal peptide bond is substituted, since such a substitution will confer resistance to proteolysis by exopeptidases acting on the N-terminus.

The synthesis of peptides with one or more reduced retro-inverso pseudopeptide bonds is known in the art (Sisto (1990) and Dalpozzo, et al. (1993), cited above). Thus, peptide bonds can be replaced by non-peptide bonds that allow the peptide mimetic to adopt a similar structure, and therefore biological activity, to the original peptide. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.,* 41:181-184, incorporated herein by reference in its entirety). Thus, the amino acid sequences of these peptides may be identical to the sequences of a Related Protein, Related Peptide or NTP peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of Related Proteins, Related Peptides and NTP peptides represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371 and incorporated herein by reference in its entirety). Peptoids are oligomers of N-substituted glycines. A number of N-alkyl groups have been described, each corresponding to the side chain of a natural amino acid (Simon, et al. (1992), cited above and incorporated herein by reference in its entirety). Some or all of the amino acids of the Related Protein, Related Peptide or NTP peptide are replaced with the N-substituted glycine corresponding to the replaced amino acid.

The development of peptide mimetics can be aided by determining the tertiary structure of the original Related Protein, Related Peptide or NTP peptide by NMR spectroscopy, crystallography and/or computer-aided molecular modeling. These techniques aid in the development of novel compositions of higher potency and/or greater bioavailability and/or greater stability than the original peptide (Dean (1994), *BioEssays*, 16: 683-687; Cohen and Shatzmiller (1993), *J. Mol. Graph.*, 11: 166-173; Wiley and Rich (1993), *Med. Res. Rev.*, 13: 327-384; Moore (1994), *Trends Pharmacol. Sci.*, 15: 124-129; Hruby (1993), *Biopolymers*, 33: 1073-1082; Bugg et al. (1993), *Sci. Am.*, 269: 92-98, all incorporated herein by reference in their entirety).

Once a potential peptide mimetic compound is identified, it may be synthesized and assayed using the methods outlined in the examples below to assess its activity. The peptide mimetic compounds obtained by the above methods, having the biological activity of the Related Proteins, Related Peptides or NTP Peptides and similar three-dimensional structure, are encompassed by this invention. It will be readily apparent to one skilled in the art that a peptide mimetic can be generated from any of the Related Proteins, Related Peptides or NTPeptides bearing one or more of the modifications described above. It will furthermore be apparent that the peptide mimetics of this invention can further be used for the development of even more potent non-peptidic compounds, in addition to their utility as therapeutic compounds.

A number of organizations exist today that are capable of synthesizing the Related Proteins, Related Peptides, and NTP Peptides described herein. For example, given the sequence of an NTP Peptide, the organization can synthesize the peptide and forward the synthesized peptide with accompanying documentation and proof of the identity of the peptide.

This invention also encompasses the use of Related Proteins, Related Peptides and NTP peptides and their corresponding nucleic acid molecules for assays to test, either qualitatively or quantitatively, for the presence of Related Proteins, Related Peptide, NTP peptides, Related Protein/Related Peptide/NTP peptide DNA or corresponding RNA in mammalian tissue or bodily fluid samples. Related Proteins, Related Peptides, NTP peptides and their corresponding nucleic acid molecules may have use in the preparation in such assays, whether or not the Related Protein, Related Peptide or NTP peptide or the encoded Related Protein, Related Peptide or NTP peptide show biological activity. A Related Protein, Related Peptide or NTP peptide nucleic acid sequence may be a useful source of hybridization probes to test, either qualitatively or quantitatively, for the presence of Related Protein, Related Peptide or NTP peptide DNA or corresponding RNA in mammalian tissue or bodily fluid samples.

A Related Protein, Related Peptide or NTP peptide which is not in itself biologically active may be useful for preparing antibodies that recognize and/or bind to Related Proteins, Related Peptides or NTP peptides. Such antibodies may be prepared using standard methods. Thus, antibodies that react with the Related Proteins, Related Peptides or NTP peptides, as well as short chain antibody fragments and other reactive fragments of such antibodies, also are contemplated as within the scope of the present invention. The antibodies may be polyclonal, monoclonal, recombinant, chimeric, single-chain and/or bispecific. Typically, the antibody or fragment thereof will either be of human origin, or will be humanized, i.e., prepared so as to prevent or minimize an immune reaction to the antibody when administered to a patient. Preferred antibodies are human antibodies, either polyclonal or monoclonal. The antibody fragment may be any fragment that is reactive with Related Proteins, Related Peptides or NTP peptides of the present invention, such as, $F_{ab}$, $F_{ab'}$, etc. Also provided by this invention are the hybridomas generated by presenting any Related Protein, Related Peptide or NTP peptide as an antigen to a selected mammal, followed by fusing cells (e.g., spleen cells) of the mammal with certain cancer cells to create immortalized cell lines by known techniques. The methods employed to generate such cell lines and antibodies directed against all or portions of a Related Protein, Related Peptide or NTP peptide also are encompassed by this invention.

The antibodies may further be used for in vivo and in vitro diagnostic or research purposes, such as in labeled form to detect the presence of Related Protein, Related Peptide or NTP peptide in a body fluid or cell sample.

This invention also encompasses the use of one or more Related Proteins, Related Peptides or NTP peptides as calibration standards in assays that test, either qualitatively or quantitatively, for the presence of Related Proteins, Related Peptides, NTP peptides, Related Protein/Related Peptide/NTP peptide DNA or corresponding RNA in mammalian tissue or bodily fluid samples.

The present invention is directed to novel methods of treating conditions requiring removal of cells, such as benign and malignant tumors, glandular (e.g. prostate) hyperplasia, unwanted facial hair, warts, and unwanted fatty tissue. Such a method comprises administering to a mammal in need a therapeutically effective amount of Related Protein, Related Peptide or NTP peptide.

The condition can be, for example, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

As used herein, the term "malignant tumor" is intended to encompass all forms of human carcinomas, sarcomas and melanomas which occur in the poorly differentiated, moderately differentiated, and well-differentiated forms.

This invention satisfies a need in the art for treatments that can remove benign tumors with less risk and fewer of the undesirable side effects of surgery. A method for removing benign tumors in surgically hazardous areas such as in deep locations in the body (e.g., brain, heart, lungs, and others) is particularly needed.

The method of treating conditions where cells must be removed can be used in conjunction with conventional methods of treating such conditions, such as surgical excision, chemotherapy, and radiation. Related Protein, Related Peptide or NTP peptide can be administered before, during, or after such conventional treatments.

The condition to be treated can also be a hyperplasia, hypertrophy, or overgrowth of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Other conditions that can be treated using the method of the invention are virally, bacterially, or parasitically altered tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

The condition to be treated can also be a malformation or disorder of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

In particular, the condition to be treated can be tonsillar hypertrophy, prostatic hyperplasia, psoriasis, eczema, dermatoses or hemorrhoids. The condition to be treated can be a vascular disease, such as atherosclerosis or arteriosclerosis, or a vascular disease, such as varicose veins. The condition to be treated also can be a cosmetic modification to a tissue, such as skin, eye, ear, nose, throat, mouth, muscle, connective tissue, hair, or breast tissue.

Therapeutic compositions of Related Proteins, Related Peptides and/or NTP peptides are within the scope of the present invention. Such compositions may comprise a therapeutically effective amount of a Related Protein, Related Peptide or NTP peptide in admixture with a pharmaceutically acceptable carrier. The carrier material may be water for injection, preferably supplemented with other materials common in solutions for administration to mammals. Typically, a Related Protein, Related Peptide or NTP peptide for therapeutic use will be administered in the form of a composition comprising purified Related Protein, Related Peptide or NTP peptide in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions including buffers known to those having ordinary skill in the art with an appropriate range of pH values, including Tris buffer having a pH of about 7.0-8.5, or acetate buffer having a pH of about 4.0-5.5, which may further include sorbitol or a suitable substitute therefor.

The use of Related Proteins, Related Peptides or NTP peptides conjugated or linked or bound to an antibody, antibody fragment, antibody-like molecule, or a molecule with a high affinity to a specific tumor marker, such as a cellular receptor, signal peptide or over-expressed enzyme, for targeting to the unwanted cellular elements also is encompassed by the scope of the invention. The antibody, antibody fragment, antibody-like molecule, or molecule with a high affinity to a specific tumor marker is used to target the Related Protein, Related Peptide or NTP peptide conjugate to a specific cellular or tissue target. For example, a tumor with a distinctive surface antigen or expressed antigen can be targeted by the antibody, antibody fragment, or antibody-like binding molecule and the tumor cells can be killed by the Related Protein, Related Peptide or NTP peptide. Such an approach using antibody targeting has the anticipated advantages of decreasing dosage, increasing the likelihood of binding to and uptake by the target cells, and increased usefulness for targeting and treating metastatic tumors and microscopic sized tumors.

This invention also encompasses the use of Related Proteins, Related Peptides and NTP peptides conjugated or linked or bound to a protein or other molecule to form a composition that, upon cleavage at or near the site(s) of the tumor or other unwanted cells by a tumor- or site-specific enzyme or protease or by an antibody conjugate that targets tumor or other unwanted cells, releases the Related Protein, Related Peptide or NTP peptide at or near the site(s) of the tumor or other unwanted cells This invention also encompasses the use of Related Proteins, Related Peptides and NTP peptides conjugated or linked or bound to a protein or other molecule to form a composition that releases the Related Protein, Related Peptide or NTP peptide or some biologically active fragment of the Related Protein, Related Peptide or NTP peptide upon exposure of the tissue to be treated to light (as in laser therapies or other photo-dynamic or photo-activated therapy), other forms of electromagnetic radiation such as infra-red radiation, ultraviolet radiation, x-ray or gamma ray radiation, localized heat, alpha or beta radiation, ultrasonic emissions, or other sources of localized energy.

The Related Proteins, Related Peptides or NTP peptides may be employed alone, together, or in combination with other pharmaceutical compositions, such as cytokines, growth factors, antibiotics, apoptotis-inducing agents, anti-inflammatories, and/or chemotherapeutic agents as is appropriate for the indication being treated.

This invention also encompasses therapeutic compositions of Related Proteins, Related Peptides or NTP peptides employing dendrimers, fullerenes, and other synthetic molecules, polymers and macromolecules where the Related Protein, Related Peptide or NTP peptide and/or its corresponding DNA molecule is conjugated with, attached to or enclosed in the molecule, polymer or macromolecule, either by itself or in conjunction with other species of molecule such as a tumor-specific marker. For example, U.S. Pat. No. 5,714,166, Bioactive and/or Targeted Dendimer Conjugates, provides a method of preparing and using, inter alia, dendritic polymer conjugates composed of at least one dendrimer with a target director(s) and at least one bioactive agent conjugated to it.

This invention also encompasses therapeutic compositions of Related Proteins, Related Peptides or NTP peptides and/or genes and drug delivery vehicles such as lipid emulsions, micelle polymers, polymer microspheres, electroactive polymers, hydrogels and liposomes.

The use of Related Proteins, Related Peptides or NTP peptides or related genes or gene equivalents transferred to the unwanted cells also is encompassed by the invention. Overexpression of Related Protein, Related Peptide or NTP peptide within the tumor can be used to induce the cells in the tumor to die and thus reduce the tumor cell population. The gene or gene equivalent transfer of Related Protein, Related Peptide or NTP peptide to treat the unwanted cellular elements is anticipated to have the advantage of requiring less dosage, and of being passed on to the cellular progeny of the targeted cellular elements, thus necessitating less frequent therapy, and less total therapy. This invention also encompasses the transfer of genes that code for a fusion protein containing a Related Protein, Related Peptide or NTP peptide to the unwanted cells or neighboring cells where, following the expression of the gene and the production and/or secretion of the fusion protein, the fusion protein is cleaved either by native enzymes or proteases or by a prodrug to release the Related Protein, Related Peptide or NTP peptide in, at or near the unwanted cells.

The use of cloned recombinant Related Protein-, Related Peptide- or NTP peptide-antibody conjugates; cloned recombinant Related Protein-, Related Peptide- or NTP peptide-antibody fragment conjugates; and cloned recombinant Related Protein-, Related Peptide- or NTP peptide-antibody-like protein conjugates also is encompassed by the invention. The advantages of a cloned Related Protein, Related Peptide or NTP peptide combined with targeting conjugate (such as an antibody, antibody fragment, antibody-like molecule, or a molecule with a high affinity to a cancer-specific receptor or other tumor marker) are that such a molecule combines the targeting advantages described above in addition to advantages for manufacturing and standardized production of the cloned conjugated molecule.

Solid dosage forms for oral administration include but are not limited to, capsules, tablets, pills, powders, and granules. In such solid dosage forms, the active compound preferably is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition also can include adjuvants, such as wetting agents, emulsifying and suspending agents, sweetening, flavoring, and perfuming agents.

Actual dosage levels of active ingredients in the compositions of the invention may be varied to obtain an amount of Related Protein, Related Peptide or NTP peptide that is effective to obtain a desired therapeutic response for a particular composition and method of administration. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on $mg/M^2$ of body surface) is described by E. J. Freireich et al., *Cancer Chemother. Rep.*, 50(4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of the Related Protein, Related Peptide or NTP peptide administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

A method of administering a Related Protein, Related Peptide or NTP peptide composition according to the invention includes, but is not limited to, administering the compounds intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

Another method of administering a Related Protein, Related Peptide or NTP peptide of the invention is by a transdermal or transcutaneous route. One example of such an embodiment is the use of a patch. In particular, a patch can be prepared with a fine suspension of Related Protein, Related Peptide or NTP peptide in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the Related Protein, Related Peptide or NTP peptide compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used that ensures the firm placement of the patch in contact with the skin. For instance, an adhesive bandage could be used to hold the patch in place on the skin.

Related Protein, Related Peptide or NTP peptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547-556 [1983]), poly (2-hydroxyethyl-methacrylate) (Langer et al., *J. Biomed. Mater. Res.,* 15: 167-277 [1981] and Langer, *Chem. Tech.,* 12: 98-105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., Eppstein et al., *Proc. Natl. Acad. Sci. USA,* 82: 3688-3692 [1985]; EP 36,676; EP 88,046; and EP 143,949).

Another method of administering a Related Protein, Related Peptide or NTP peptide of the invention is by direct or indirect infusion of Related Protein, Related Peptide or NTP peptide into the tumor or other tissue to be treated. One example of such an embodiment is the direct injection of Related Protein, Related Peptide or NTP peptide into the tumor or other tissue to be treated. The treatment may consist of a single injection, multiple injections on one occasion or a series of injections over a period of hours, days or months with the regression or destruction of the tumor or other tissue to be treated being monitored by means of biopsy, imaging or other methods of monitoring tissue growth. The injection into the tumor or other tissue to be treated may be by a device inserted into an orifice such as the nose, mouth, ear, vagina, rectum or urethra or through an incision in order to reach the tumor or tissue in vivo and may performed in conjunction with an imaging or optical system such as ultrasound or fibre optic scope in order to identify the appropriate site for the injection(s). Another example of such an embodiment is the use of a device that can provide a constant infusion of Related Protein, Related Peptide or NTP peptide to the tissue over time.

Another method of administering a Related Protein, Related Peptide or NTP peptide of the invention is in conjunction with a surgical or similar procedure employed to physically excise, ablate or otherwise kill or destroy tumor or other tissue or cellular elements required or desired to be removed or destroyed wherein a Related Protein, Related Peptide or NTP peptide of the invention is administered to the immediate area(s) surrounding the area(s) where the tumor or other tissue was removed in order to destroy or impede the growth of any tumor cells or other cellular elements not removed or destroyed by the procedure Another method of administering a Related Protein, Related Peptide or NTP peptide of the invention is by implantation of a device within the tumor or other tissue to be treated. One example of such an embodiment is the implantation of a wafer containing Related Protein, Related Peptide or NTP peptide in the tumor or other tissue to be treated. The wafer releases a therapeutic dose of Related Protein, Related Peptide or NTP peptide into the tissue over time. Alternatively or additionally, the composition may be administered locally via implantation into the affected area of a membrane, sponge, or other appropriate material on to which the Related Protein, Related Peptide or NTP peptide has been absorbed. Where an implantation device is used, the device may be implanted into any suitable tissue or organ, and delivery of the Related Protein, Related Peptide or NTP peptide may be directly through the device via bolus, or via continuous administration, or via catheter using continuous infusion.

An alternative method of administration is to introduce one or more copies of a Related Protein-, Related Peptide- or NTP peptide-encoding gene into the cell being targeted and, if necessary, inducing the copy(ies) of the gene to begin producing Related Protein, Related Peptide or NTP peptide intracellularly. One manner in which gene therapy can be applied is to use the Related Protein-, Related Peptide- or NTP peptide-encoding gene (either genomic DNA, cDNA, and/or synthetic DNA encoding the Related Protein, Related Peptide or NTP peptide (or a fragment, variant, homologue or derivative thereof) which may be operably linked to a constitutive or inducible promoter to form a gene therapy DNA construct. The promoter may be homologous or heterologous to an endogenous Related Protein-, Related Peptide- or NTP peptide-encoding gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (such as, for example, for cell targeting) cell-specific internalization factors, and transcription factors to enhance expression by a vector as well as factors to enable vector manufacture.

Means of gene delivery to a cell or tissue in vivo or ex vivo include (but are not limited to) direct injection of bare DNA, ballistic methods, liposome-mediated transfer, receptor-mediated transfer (ligand-DNA complex), electroporation, and calcium phosphate precipitation, as disclosed in, for example, U.S. Pat. No. 4,970,154, WO 96/40958, U.S. Pat. No. 5,679,559, U.S. Pat. No. 5,676,954, and U.S. Pat. No. 5,593,875, the disclosures of which are incorporated by reference herein in their entirety. They also include use of a viral vector such as a retrovirus, adenovirus, adeno-associated virus, pox virus, lentivirus, papilloma virus or herpes simplex virus, use of a DNA-protein conjugate and use of a liposome. The use of gene therapy vectors is described, for example, in U.S. Pat. Nos. 5,672,344, 5,399,346, 5,631,236, and 5,635,399, the disclosures of which are incorporated by reference herein in their entirety.

The Related Protein-, Related Peptide- or NTP peptide-encoding gene may be delivered through implanting into patients certain cells that have been genetically engineered ex vivo, using methods such as those described herein, to express and secrete the Related Protein, Related Peptide or NTP peptide or fragments, variants, homologues, or derivatives thereof. Such cells may be animal or human cells, and may be derived from the patient's own tissue or from another source, either human or non-human. Optionally, the cells may be immortalized or they may be stem cells. However, in order to decrease the chance of an immunological response, it is preferred that the cells be encapsulated to avoid infiltration of surrounding tissues. The encapsulation materials typically are biocompatible, semi-permeable polymeric enclosures or membranes that allow release of the protein product(s) but prevent destruction of the cells by the patient's immune system or by other detrimental factors from the surrounding tissues. Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, the disclosures of which are incorporated by reference herein in their entirety. A system for encapsulating living cells is described in PCT WO 91/10425, the disclosure of which are incorporated by reference herein in their entirety. Techniques for formulating a variety of other sustained or controlled delivery means, such as liposome carriers, bio-erodible particles or beads, are also known to those in the art, and are described, for example, in U.S. Pat. No. 5,653,975, the disclosure of which are incorporated by reference herein in their entirety. The cells, with or without encapsulation, may be implanted into suitable body tissues or organs of the patient.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

In particular, this invention expressly incorporates by reference the examples contained in pending U.S. patent application Ser. No. 10/092,934, Methods of Treating Tumors and Related Conditions Using Neural Thread Proteins, which show that the entire AD7c-NTP protein is an effective agent for causing cell death both in vitro in glioma and neuroblastoma cell cultures and in vivo in normal rodent muscle tissue, subcutaneous connective tissue, and dermis and in a variety of different human and non-human origin tumors, including mammary carcinoma, skin carcinoma and papilloma, colon carcinoma, glioma of brain, and others in rodent models. This invention also expressly incorporates by reference the examples contained in U.S. patent applications Ser. No. 10/153334, which show that NTP peptides are effective agents for causing cell death in vivo in normal rodent muscle tissue, subcutaneous connective tissue, dermis and other tissue.

EXAMPLE 1

The purpose of this example was to determine the effect of NTP peptide #6 on tissue at sites of injection.

Male Sprague-Dawley rats (300 gram weight range) were anesthetized with ether and given NTP peptide #6 by intraprostatic infusion after open surgical visualization of the prostate. The injections consisted of 300 µl of NTP peptide #6, 1 mg/mL in PBS pH 7.4. (1.0 mg/kg) (n=8), control injections of PBS alone (n=6), and controls with no injection (n=2). Rats were painlessly sacrificed after 72 hours. Prostate glands were dissected, fixed in 10% buffered formalin for 24 hours, embedded in paraffin, sectioned, and stained with H & E. For each animal the entire prostate gland was embedded and sectioned. All stained sections were examined histologically and measured. For each prostate at least 4 histological sections were examined, and for each histological section two cross-sectional diameters (D) at 90° from each other were measured (total of ≧8 measurements per prostate). The mean diameter from these measurements for each prostate was used to estimate volume according to $$V = \frac{4}{3}\left(\frac{D}{2}\right)^3.$$

Results: The reduction in prostate volume in NTP peptide #6 injected rats was estimated to be on average 45% compared to controls (there was no discernible difference between control PBS injections alone, and controls with no injections). Treated rat prostate showed extensive loss of glandular epithelium, flattening and atrophy. NTP peptide #6 in PBS pH 7.4 open infusions of 1.0 mg/kg into rat prostate produced an estimated prostate volume reduction of >40% compared to untreated or PBS treated controls, at 72 hours.

EXAMPLE 2

The purpose of this example was to determine the effect of NTP peptide #7 on tissue at sites of injection.

Four normal rats were injected in the skin and subcutaneously, each in four different foci, and in extremity skeletal muscle, each in two different foci, with NTP peptide #7 in saline in quantities of 100 to 400 mL at concentrations of 0.1-1 mg/mL delivered from plastic syringes through stainless steel 26 gauge needles.

The animals were observed for 24 hours and painlessly sacrificed at 24 hours. The individual foci of infiltration were excised, fixed in 10% formalin, embedded in paraffin, and stained and examined by standard histopathological methods.

The controls received saline alone.

Results: Injection of NTP peptide # 7 produced acute necrosis of tissue at the injection sites. The necrosis was evident in muscle tissue, subcutaneous connective tissue, and dermis at the sites where NTP peptide # 7 was injected. The necrosis correlated with the areas of injection and did not appear to spread far beyond the site of injection.

Apart from the mild areas of inflammation, controls showed no evidence of necrosis or cell loss. The controls showed minimal or absent muscle changes. Control injections had mild to minimal acute inflammation at the injection sites and focal microhemorrhages from the needles.

EXAMPLE 3

The purpose of this example was to determine the effect of Related Peptide #1 on tissue at sites of injection.

Rats were injected in the skin and subcutaneously as in Example 2 above with Related Peptide #1.

The animals were observed for 24 hours and painlessly sacrificed at 24 hours. Tissues were excised, fixed in 10% formalin, embedded in paraffin, and stained and examined by standard histopathological methods.

The controls were the same as Example 2.

Results: Injection of Related Peptide #1 produced cell death and necrosis of tissue at the injection sites. Similar to Example 2 above, the cell death was present in muscle tissue, subcutaneous connective tissue, and dermis at the sites where Related Peptide #1 was injected.

Apart from the mild areas of inflammation, controls showed minimal evidence of necrosis or cell loss. Control injections had mild to minimal acute inflammation at the injection sites and occasional focal microhemorrhages from the needles.

EXAMPLE 4

The purpose of this example was to determine the effect of Related Peptide #2 on tissue at sites of injection.

Male Sprague-Dawley rats (300 gram weight range) were anesthetized with ether and given Related Peptide #2 by intraprostatic infusion after open surgical visualization of the prostate. The injections consisted of 300 μl of Related Peptide #2, 1 mg/mL in PBS pH 7.4. (1.0 mg/kg) (n=8), control injections of PBS alone (n=6), and controls with no injection (n=2). Rats were painlessly sacrificed after 72 hours. Prostate glands were dissected, fixed in 10% buffered formalin for 24 hours, embedded in paraffin, sectioned, and stained with H & E. For each animal the entire prostate gland was embedded and sectioned. All stained sections were examined histologically and measured. For each prostate at least 4 histological sections were examined, and for each histological section two cross-sectional diameters (D) at 90° from each other were measured (total of >8 measurements per prostate). The mean diameter from these measurements for each prostate was used to estimate volume according to $$V = \frac{4}{3}\left(\frac{D}{2}\right)^3.$$

The controls were the same as Example 1.

Results: As in the above Example 1, injection of Related Protein #2 produced significant cell loss and atrophy in the prostate at 72 hours. Controls showed minimal or absent changes, consisting of mild focal inflammation from the needles.

EXAMPLE 5

The purpose of this example was to determine the effect of Related Peptide #3 on tissue at sites of injection.

Normal rats were injected in the prostate as in the above Examples 1 and 4 with Related Peptide #3. Rats were painlessly sacrificed after 72 hours and their prostate glands were examined as in the above Examples 1 and 4.

Results: Significant cell loss and atrophy of prostate were found at 72 hours compared to controls where there was minimal change.

The invention has been described with reference to particularly preferred embodiments and examples. Those skilled in the art will appreciate, however, that various modifications may be made to the invention without departing from the spirit and scope thereof.

What is claimed is:

1. An isolated peptide of SEQ ID NO: 18 with up to 25 additional amino acids flanking either the amino or carboxy end of the peptide, wherein the peptide is cytotoxic.

2. A composition comprising the peptide according to claim 1 and a carrier therefor.

3. An isolated protein comprising at least two repetitions of the peptide according to claim 1.

4. A composition comprising the protein according to claim 3 and a carrier therefor.

5. An isolated protein comprising the peptide according to claim 1 fused to an antibody or to a binding fragment of an antibody.

6. A composition comprising the protein according to claim 5 and a carrier therefor.

7. An isolated peptide consisting of the amino acid sequence of SEQ ID NO: 18.

8. A composition comprising the peptide according to claim 7 and a carrier therefor.

* * * * *

SEQUENCE LISTING

```
<160> NUMBER OF SEQ ID NOS: 125

<210> SEQ ID NO 1
<211> LENGTH: 375
<212> TYPE: PRT
<213> ORGANISM: Homo sapiens

<400> SEQUENCE: 1

Met Glu Phe Ser Leu Leu Leu Pro Arg Leu Glu Cys Asn Gly Ala Ile
  1               5                  10                  15

Ser Ala His Arg Asn Leu Arg Leu Pro Gly Ser Ser Asp Ser Pro Ala
                 20                  25                  30

Ser Ala Ser Pro Val Ala Gly Ile Thr Gly Met Cys Thr His Ala Arg
             35                  40                  45

Leu Ile Leu Tyr Phe Phe Leu Val Glu Met Glu Phe Leu His Val Gly
         50                  55                  60

Gln Ala Gly Leu Glu Leu Pro Thr Ser Asp Asp Pro Ser Val Ser Ala
 65                  70                  75                  80

Ser Gln Ser Ala Arg Tyr Arg Thr Gly His His Ala Arg Leu Cys Leu
                 85                  90                  95

Ala Asn Phe Cys Gly Arg Asn Arg Val Ser Leu Met Cys Pro Ser Trp
                100                 105                 110

Ser Pro Glu Leu Lys Gln Ser Thr Cys Leu Ser Leu Pro Lys Cys Trp
            115                 120                 125

Asp Tyr Arg Arg Ala Ala Val Pro Gly Leu Phe Ile Leu Phe Phe Leu
        130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
            180                 185                 190

Leu Ile Phe Ile Phe Ile Phe Asn Phe Leu Arg Gln Ser Leu Asn Ser
```

```
                195                 200                 205
Val Thr Gln Ala Gly Val Gln Trp Arg Asn Leu Gly Ser Leu Gln Pro
        210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Val Phe Leu
                245                 250                 255

Val Glu Met Gly Phe Thr Met Phe Ala Arg Leu Ile Leu Ile Ser Gly
                260                 265                 270

Pro Cys Asp Leu Pro Ala Ser Ala Ser Gln Ser Ala Gly Ile Thr Gly
            275                 280                 285

Val Ser His His Ala Arg Leu Ile Phe Asn Phe Cys Leu Phe Glu Met
        290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
            340                 345                 350

Phe Cys Ile Phe Ile Arg Gly Gly Val Ser Pro Tyr Leu Ser Gly Trp
        355                 360                 365

Ser Gln Thr Pro Asp Leu Arg
        370                 375

<210> SEQ ID NO 2
<211> LENGTH: 122
<212> TYPE: PRT
<213> ORGANISM: Unknown Organism
<220> FEATURE:
<223> OTHER INFORMATION: Description of Unknown Organism: Unknown NTP
      peptide

<400> SEQUENCE: 2

Met Met Val Cys Trp Asn Arg Phe Gly Lys Trp Val Tyr Phe Ile Ser
1               5                   10                  15

Ala Ile Phe Asn Phe Gly Pro Arg Tyr Leu Tyr His Gly Val Pro Phe
                20                  25                  30

Tyr Phe Leu Ile Leu Val Arg Ile Ile Ser Phe Leu Ile Gly Asp Met
            35                  40                  45

Glu Asp Val Leu Leu Asn Cys Thr Leu Leu Lys Arg Ser Ser Arg Phe
    50                  55                  60

Arg Phe Trp Gly Ala Leu Val Cys Ser Met Asp Ser Cys Arg Phe Ser
65                  70                  75                  80

Arg Val Ala Val Thr Tyr Arg Phe Ile Thr Leu Leu Asn Ile Pro Ser
                85                  90                  95

Pro Ala Val Trp Met Ala Arg Asn Thr Ile Asp Gln Gln Val Leu Ser
            100                 105                 110

Arg Ile Lys Leu Glu Ile Lys Arg Cys Leu
        115                 120

<210> SEQ ID NO 3
<211> LENGTH: 112
<212> TYPE: PRT
<213> ORGANISM: Homo sapiens

<400> SEQUENCE: 3

Met Ala Gln Ser Arg Leu Thr Ala Thr Ser Ala Ser Arg Val Gln Ala
```

```
                1               5              10              15
Ile Leu Leu Ser Gln Pro Pro Lys Gln Leu Gly Leu Arg Ala Pro Ala
                 20                  25                  30

Asn Thr Pro Leu Ile Phe Val Phe Ser Leu Glu Ala Gly Phe His His
                 35                  40                  45

Ile Cys Gln Ala Gly Leu Lys Leu Leu Thr Ser Gly Asp Pro Pro Ala
         50                  55                  60

Ser Ala Phe Gln Ser Ala Gly Ile Thr Gly Val Ser His Leu Thr Gln
 65                  70                  75                  80

Pro Ala Asn Leu Asp Lys Lys Ile Cys Ser Asn Gly Gly Ser Cys Tyr
                 85                  90                  95

Val Ala Gln Ala Gly Leu Lys Leu Leu Ala Ser Cys Asn Pro Ser Lys
                100                 105                 110
```

<210> SEQ ID NO 4
<211> LENGTH: 106
<212> TYPE: PRT
<213> ORGANISM: Homo sapiens

<400> SEQUENCE: 4

```
Met Trp Thr Leu Lys Ser Ser Leu Val Leu Leu Cys Leu Thr Cys
 1               5                  10                  15

Ser Tyr Ala Phe Met Phe Ser Ser Leu Arg Gln Lys Thr Ser Glu Pro
                 20                  25                  30

Gln Gly Lys Val Pro Cys Gly Glu His Phe Arg Ile Arg Gln Asn Leu
                 35                  40                  45

Pro Glu His Thr Gln Gly Trp Leu Gly Ser Lys Trp Leu Trp Leu Leu
         50                  55                  60

Phe Ala Val Val Pro Phe Val Ile Leu Lys Cys Gln Arg Asp Ser Glu
 65                  70                  75                  80

Lys Asn Lys Val Arg Met Ala Pro Phe Phe Leu His His Ile Asp Ser
                 85                  90                  95

Ile Ser Gly Val Ser Gly Lys Arg Met Phe
                100                 105
```

<210> SEQ ID NO 5
<211> LENGTH: 106
<212> TYPE: PRT
<213> ORGANISM: Homo sapiens

<400> SEQUENCE: 5

```
Met Phe Phe Val Leu Tyr Arg Phe Cys Phe Cys Phe Glu Thr Glu
 1               5                  10                  15

Ser His Ser Leu Thr Gln Ala Gly Val Gln Trp Cys Glu Leu Gly Ser
                 20                  25                  30

Pro Gln Pro Leu Pro Ser Gly Phe Lys Arg Phe Ser Cys Leu Ser Leu
                 35                  40                  45

Leu Ser Ser Trp Asp Tyr Ser His Glu Pro Pro His Pro Val Ile Cys
         50                  55                  60

Ser Phe Leu Met Glu Lys Cys Leu Ile Leu Tyr Lys Pro Asn Gly Asp
 65                  70                  75                  80

Thr Ile Gly Pro Ile Leu Val Gln Gln Gly Lys Arg Gln Lys Leu Tyr
                 85                  90                  95

Ile Ser Ala Asp Leu Val His Leu Ile Ala
                100                 105
```

```
<210> SEQ ID NO 6
<211> LENGTH: 98
<212> TYPE: PRT
<213> ORGANISM: Artificial Sequence
<220> FEATURE:
<223> OTHER INFORMATION: Description of Artificial Sequence: Unknown NTP
      peptide

<400> SEQUENCE: 6

Glu Ala Tyr Tyr Thr Met Leu His Leu Pro Thr Thr Asn Arg Pro Lys
  1               5                  10                  15

Ile Ala His Cys Ile Leu Phe Asn Gln Pro His Ser Pro Arg Ser Asn
             20                  25                  30

Ser His Ser His Pro Asn Pro Leu Lys Leu His Arg Arg Ser His Ser
         35                  40                  45

His Asn Arg Pro Arg Ala Tyr Ile Leu Ile Thr Ile Leu Pro Ser Lys
     50                  55                  60

Leu Lys Leu Arg Thr His Ser Gln Ser His His Asn Pro Leu Ser Arg
 65                  70                  75                  80

Thr Ser Asn Ser Thr Pro Thr Asn Ser Phe Leu Met Thr Ser Ser Lys
                 85                  90                  95

Pro Arg

<210> SEQ ID NO 7
<211> LENGTH: 75
<212> TYPE: PRT
<213> ORGANISM: Artificial Sequence
<220> FEATURE:
<223> OTHER INFORMATION: Description of Artificial Sequence: Unknown NTP
      peptide

<400> SEQUENCE: 7

Ser Ser Ser Leu Gly Leu Pro Lys Cys Trp Asp Tyr Arg His Glu Leu
  1               5                  10                  15

Leu Ser Leu Ala Leu Met Ile Asn Phe Arg Val Met Ala Cys Thr Phe
             20                  25                  30

Lys Gln His Ile Glu Leu Arg Gln Lys Ile Ser Ile Val Pro Arg Lys
         35                  40                  45

Leu Cys Cys Met Gly Pro Val Cys Pro Val Lys Ile Ala Leu Leu Thr
     50                  55                  60

Ile Asn Gly His Cys Thr Trp Leu Pro Ala Ser
 65                  70                  75

<210> SEQ ID NO 8
<211> LENGTH: 68
<212> TYPE: PRT
<213> ORGANISM: Artificial Sequence
<220> FEATURE:
<223> OTHER INFORMATION: Description of Artificial Sequence: Unknown NTP
      peptide

<400> SEQUENCE: 8

Met Phe Val Phe Cys Leu Ile Leu Asn Arg Glu Lys Ile Lys Gly Gly
  1               5                  10                  15

Asn Ser Ser Phe Phe Leu Leu Ser Phe Phe Ser Phe Gln Asn Cys
             20                  25                  30

Cys Gln Cys Phe Gln Cys Arg Thr Thr Glu Gly Tyr Ala Val Glu Cys
         35                  40                  45

Phe Tyr Cys Leu Val Asp Lys Ala Ala Phe Glu Cys Trp Trp Phe Tyr
     50                  55                  60
```

-continued

```
Ser Phe Asp Thr
 65

<210> SEQ ID NO 9
<211> LENGTH: 61
<212> TYPE: PRT
<213> ORGANISM: Homo sapiens

<400> SEQUENCE: 9

Met Glu Pro His Thr Val Ala Gln Ala Gly Val Pro Gln His Asp Leu
 1               5                  10                  15

Gly Ser Leu Gln Ser Leu Leu Pro Arg Phe Lys Arg Phe Ser Cys Leu
            20                  25                  30

Ile Leu Pro Lys Ile Trp Asp Tyr Arg Asn Met Asn Thr Ala Leu Ile
        35                  40                  45

Lys Arg Asn Arg Tyr Thr Pro Glu Thr Gly Arg Lys Ser
    50                  55                  60

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ser Trp Asp Tyr
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Ala Ser Ala Ser Pro Val Ala Gly
 1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Ile Ser Ala His Arg Asn Leu Arg Leu
 1               5                  10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Phe Leu Val Glu Met
 1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Val Thr Gln Ala Gly Val Gln Trp
  1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Asp Gln Gln Val Leu Ser Arg Ile Lys Leu Glu Ile Lys Arg Cys
  1               5                  10                  15

Leu

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ser Arg Ile Lys Leu Glu Ile Lys
  1               5

<210> SEQ ID NO 17
<211> LENGTH: 22
<212> TYPE: PRT
<213> ORGANISM: Homo sapiens

<400> SEQUENCE: 17

Gly Asp His Gly Arg Pro Asn Leu Ser Arg Leu Lys Leu Ala Ile Lys
  1               5                  10                  15

Tyr Glu Val Lys Lys Met
             20

<210> SEQ ID NO 18
<211> LENGTH: 16
<212> TYPE: PRT
<213> ORGANISM: Homo sapiens

<400> SEQUENCE: 18

Gln Gln Ser Ile Ala Val Lys Phe Leu Ala Val Phe Gly Val Ser Ile
  1               5                  10                  15

<210> SEQ ID NO 19
<211> LENGTH: 21
<212> TYPE: PRT
<213> ORGANISM: Homo sapiens

<400> SEQUENCE: 19

Gly Leu Leu Phe Pro Val Phe Ser Val Cys Tyr Leu Ile Ala Pro Lys
  1               5                  10                  15
```

```
Ser Pro Leu Gly Leu
            20

<210> SEQ ID NO 20
<211> LENGTH: 581
<212> TYPE: PRT
<213> ORGANISM: Homo sapiens

<400> SEQUENCE: 20

Met Glu Val Ser Pro Leu Gln Pro Val Asn Glu Asn Met Gln Val Asn
 1               5                  10                  15

Lys Ile Lys Lys Asn Glu Asp Ala Lys Lys Arg Leu Ser Val Glu Arg
             20                  25                  30

Ile Tyr Gln Lys Lys Thr Gln Leu Glu His Ile Leu Leu Arg Pro Asp
         35                  40                  45

Thr Tyr Ile Gly Ser Val Glu Leu Val Thr Gln Gln Met Trp Val Tyr
     50                  55                  60

Asp Glu Asp Val Gly Ile Asn Tyr Arg Glu Val Thr Phe Val Pro Gly
 65                  70                  75                  80

Leu Tyr Lys Ile Phe Asp Glu Ile Leu Val Asn Ala Ala Asp Asn Lys
                 85                  90                  95

Gln Arg Asp Pro Lys Met Ser Cys Ile Arg Val Thr Ile Asp Pro Glu
            100                 105                 110

Asn Asn Leu Ile Ser Ile Trp Asn Asn Gly Lys Gly Ile Pro Val Val
        115                 120                 125

Glu His Lys Val Glu Lys Met Tyr Val Pro Ala Leu Ile Phe Gly Gln
    130                 135                 140

Leu Leu Thr Ser Ser Asn Tyr Asp Asp Asp Glu Lys Lys Val Thr Gly
145                 150                 155                 160

Gly Arg Asn Gly Tyr Gly Ala Lys Leu Cys Asn Ile Phe Ser Thr Lys
                165                 170                 175

Phe Thr Val Glu Thr Ala Ser Arg Glu Tyr Lys Lys Met Phe Lys Gln
            180                 185                 190

Thr Trp Met Asp Asn Met Gly Arg Ala Gly Glu Met Glu Leu Lys Pro
        195                 200                 205

Phe Asn Gly Glu Asp Tyr Thr Cys Ile Thr Phe Gln Pro Asp Leu Ser
    210                 215                 220

Lys Phe Lys Met Gln Ser Leu Asp Lys Asp Ile Val Ala Leu Met Val
225                 230                 235                 240

Arg Arg Ala Tyr Asp Ile Ala Gly Ser Thr Lys Asp Val Lys Val Phe
                245                 250                 255

Leu Asn Gly Asn Lys Leu Pro Val Lys Gly Phe Arg Ser Tyr Val Asp
            260                 265                 270

Met Tyr Leu Lys Asp Lys Leu Asp Glu Thr Gly Asn Ser Leu Lys Val
        275                 280                 285

Ile His Glu Gln Val Asn His Arg Trp Glu Val Cys Leu Thr Met Ser
    290                 295                 300

Glu Lys Gly Phe Gln Gln Ile Ser Phe Val Asn Ser Ile Ala Thr Ser
305                 310                 315                 320

Lys Gly Gly Arg His Val Asp Tyr Val Ala Asp Gln Ile Val Thr Lys
                325                 330                 335

Leu Val Asp Val Val Lys Lys Asn Lys Gly Gly Val Ala Val Lys
            340                 345                 350

Ala His Gln Arg Glu Leu Cys Asn Gly Ala Ile Leu Ala His Cys Asn
```

```
                355                 360                 365
Leu Arg Leu Met Gly Ser Ser Asp Ser Pro Ala Ser Ala Ser Arg Val
370                 375                 380

Ala Gly Ile Ala Gly Gly Cys His His Thr Gln Leu Ile Phe Val Phe
385                 390                 395                 400

Leu Val Glu Thr Gly Phe His His Val Gly Gln Ala Gly Leu Glu Arg
                405                 410                 415

Leu Thr Ser Gly Asp Pro Pro Ala Ser Ala Ser Gln Ser Ser Gly Ile
                420                 425                 430

Thr Asp Val Lys Val Lys Asn His Met Trp Ile Phe Val Asn Ala Leu
                435                 440                 445

Ile Glu Asn Pro Thr Phe Asp Ser Gln Thr Lys Glu Asn Met Thr Leu
450                 455                 460

Gln Pro Lys Ser Phe Gly Ser Thr Cys Gln Leu Ser Glu Lys Phe Ile
465                 470                 475                 480

Lys Ala Ala Ile Gly Cys Gly Ile Val Glu Ser Ile Leu Asn Trp Val
                485                 490                 495

Lys Phe Lys Ala Gln Val Gln Leu Asn Lys Lys Cys Ser Ala Val Lys
                500                 505                 510

His Asn Arg Ile Lys Gly Ile Pro Lys Leu Asp Asp Ala Asn Asp Ala
                515                 520                 525

Gly Gly Arg Asn Ser Thr Glu Cys Thr Leu Ile Leu Thr Glu Gly Asp
                535                 540

Ser Ala Lys Thr Leu Ala Val Ser Gly Leu Gly Val Val Gly Arg Asp
545                 550                 555                 560

Lys Tyr Gly Val Phe Pro Leu Arg Gly Lys Ile Leu Asn Val Arg Glu
                565                 570                 575

Ala Ser His Lys Gln
                580

<210> SEQ ID NO 21
<211> LENGTH: 163
<212> TYPE: PRT
<213> ORGANISM: Homo sapiens

<400> SEQUENCE: 21

Met Thr Gly Asp Lys Gly Pro Gln Arg Leu Ser Gly Ser Ser Tyr Gly
  1               5                  10                  15

Ser Ile Ser Ser Pro Thr Ser Pro Thr Ser Pro Gly Pro Gln Gln Ala
                 20                  25                  30

Pro Pro Arg Glu Thr Tyr Leu Ser Glu Lys Ile Pro Ile Pro Asp Thr
             35                  40                  45

Lys Pro Gly Thr Phe Ser Leu Arg Lys Leu Trp Ala Phe Thr Gly Pro
    50                  55                  60

Gly Phe Leu Met Ser Ile Ala Phe Leu Asp Pro Gly Asn Ile Glu Ser
65                  70                  75                  80

Asp Leu Gln Ala Gly Ala Val Ala Gly Phe Lys Leu Leu Trp Val Leu
                85                  90                  95

Leu Trp Ala Thr Val Leu Gly Leu Leu Cys Gln Arg Leu Ala Ala Arg
                100                 105                 110

Leu Gly Val Val Thr Gly Lys Asp Leu Gly Glu Val Cys His Leu Tyr
            115                 120                 125

Tyr Pro Lys Ser Glu Ser Arg Ser Val Ala Gln Ser Gly Val Gln Trp
    130                 135                 140
```

```
Cys Asp Val Ser Ser Leu Gln Pro Leu Pro Pro Arg Cys Pro Ala Pro
145                 150                 155                 160

Ser Ser Gly

<210> SEQ ID NO 22
<211> LENGTH: 151
<212> TYPE: PRT
<213> ORGANISM: Homo sapiens

<400> SEQUENCE: 22

Met Met Leu Ser Val Gln Glu Asn Val His Arg Cys Ile Cys Lys His
1               5                   10                  15

Tyr Ala Pro Pro Thr Ala Pro His Leu Phe Phe Glu Thr Glu Ser His
                20                  25                  30

Ser Val Thr Gln Ala Gly Val Gln Trp Cys Asp Leu Gly Ser Leu Gln
            35                  40                  45

Pro Ser Pro Pro Gly Phe Lys Gln Phe Ser Cys Leu Ser Leu Ser Arg
        50                  55                  60

Ser Trp Asp Tyr Arg Arg Val Pro Leu Cys Leu Ala Asn Phe Ile Val
65                  70                  75                  80

Phe Leu Val Glu Thr Gly Phe Cys Arg Val Gly Gln Ala Gly Leu Lys
                85                  90                  95

Leu Leu Thr Ser Ser Asp Leu Pro Ala Ser Ala Cys Gln Ser Ala Gly
            100                 105                 110

Asp Tyr Arg His Glu Pro Leu Arg Leu Ala Leu Thr Leu Cys His Phe
        115                 120                 125

Ile Ser Arg Thr Cys Thr Ser Val Asp Phe Tyr Ile Cys Arg Asp Leu
    130                 135                 140

Glu Arg Ile Pro His Gly His
145                 150

<210> SEQ ID NO 23
<211> LENGTH: 129
<212> TYPE: PRT
<213> ORGANISM: Homo sapiens

<400> SEQUENCE: 23

Met Ile Ser Ala His Arg Asn Leu His Leu Pro Gly Ser Ser Asn Ser
1               5                   10                  15

Pro Ala Ser Ala Phe Leu Ser Ser Trp Asp Tyr Arg His Val Pro Pro
                20                  25                  30

Cys Pro Ala Asn Val Val Phe Leu Val Glu Met Gly Phe Leu His Val
            35                  40                  45

Gly Gln Ala Gly Leu Glu Leu Pro Thr Ser Asp Asp Pro Pro Thr Leu
        50                  55                  60

Ala Ser Gln Ser Ala Gly Ile Thr Gly Val Ser His Arg Thr Trp Gln
65                  70                  75                  80

Glu Phe Ala Ser Leu Thr Val Ser Gln Ala Val Leu Arg Met Leu Val
                85                  90                  95

Trp Gly Pro Gln Phe Glu Asn His Cys Ser Lys Leu Leu Met Ala Ser
            100                 105                 110

Glu Gly Asp Ser Ser Leu Val Phe Phe Leu Tyr Pro Leu Ser Asn Leu
        115                 120                 125

Asn

<210> SEQ ID NO 24
```

-continued

<211> LENGTH: 155
<212> TYPE: PRT
<213> ORGANISM: Homo sapiens

<400> SEQUENCE: 24

```
Met Gln Gly Ser His Ser Ala Val Gln Ala Gly Val Trp Trp Cys His
 1               5                  10                  15

His Asp Ser Leu Gln Pro Trp Pro Gly Leu Arg Arg Ser Ser Cys
             20                  25                  30

Leu Ser Leu Gln Ser Leu Trp Asp Tyr Arg Ser Leu Ala Leu Ser Leu
         35                  40                  45

Arg Leu Ala Cys Asn Gly Thr Thr Ser Ala His Cys Asp Leu Cys Leu
 50                  55                  60

Leu Ser Ser Ser Asp Ser Pro Ala Ser Ala Ser Gln Val Ala Gly Ile
 65                  70                  75                  80

Thr Gly Glu Lys Thr Ala Glu Pro His Lys Ala His Ala Ala Gln Gly
                 85                  90                  95

Glu Arg His Leu Ser Ser His Met Ser Pro Asp Glu Asn Met Thr Glu
             100                 105                 110

Lys Phe Cys Pro Gly Pro Arg Ala Ser Phe His Leu Arg Ile Leu Ala
         115                 120                 125

Ala Ser Arg His Leu Val Lys Arg Leu Leu Asn Glu Tyr Thr Val Thr
130                 135                 140

Val Leu Arg Asp Lys Ser Tyr Leu Arg Asn Asn
145                 150                 155
```

<210> SEQ ID NO 25
<211> LENGTH: 127
<212> TYPE: PRT
<213> ORGANISM: Homo sapiens

<400> SEQUENCE: 25

```
Met Lys Asn Tyr Tyr Tyr Phe Leu Gly Gln Gly Leu Thr Leu Ser Pro
 1               5                  10                  15

Arg Leu Glu Cys Ser Ser Thr Ile Ser Ala His Cys Asn Leu His Leu
             20                  25                  30

Leu Gly Ser Ser Asn Ser Pro Val Ala Ala Ser Pro Val Ala Gly Thr
         35                  40                  45

Thr Gly Thr Cys His His Asp Trp Leu Ile Phe Val Phe Leu Val Glu
 50                  55                  60

Thr Gly Phe His His Ile Gly Gln Thr Gly Leu Glu Phe Leu Thr Ser
 65                  70                  75                  80

Gly Asp Pro Pro Thr Leu Ala Ser Lys Ser Ala Gly Ile Thr Gly Val
                 85                  90                  95

Ser His Cys Ala Trp Pro Thr Phe Leu Leu Asn Asp Met Arg His Ser
             100                 105                 110

Phe Asn Lys Asn Leu Val Ile Phe Tyr Val Pro Ala Ile Ser
         115                 120                 125
```

<210> SEQ ID NO 26
<211> LENGTH: 137
<212> TYPE: PRT
<213> ORGANISM: Homo sapiens

<400> SEQUENCE: 26

```
Met Arg Arg Glu Leu Leu Ala Gly Ile Leu Leu Arg Ile Thr Phe Asn
 1               5                  10                  15
```

```
Phe Phe Leu Phe Phe Phe Leu Pro Phe Pro Leu Val Val Phe Phe Ile
            20                  25                  30

Tyr Phe Tyr Phe Tyr Phe Phe Leu Glu Met Glu Ser His Tyr Val Ala
        35                  40                  45

Gln Ala Gly Leu Glu Leu Leu Gly Ser Ser Asn Pro Pro Ala Ser Ala
    50                  55                  60

Ser Leu Val Ala Gly Thr Leu Ser Val His His Cys Ala Cys Phe Glu
65                  70                  75                  80

Ser Phe Thr Lys Arg Lys Lys Leu Lys Ala Phe Arg Phe Ile
                85                  90                  95

Gln Cys Leu Leu Leu Gly Leu Leu Lys Val Arg Pro Leu Gln His Gln
            100                 105                 110

Gly Val Asn Ser Cys Asp Cys Glu Arg Gly Tyr Phe Gln Gly Ile Phe
        115                 120                 125

Met Gln Ala Ala Pro Trp Glu Gly Thr
    130                 135

<210> SEQ ID NO 27
<211> LENGTH: 1150
<212> TYPE: PRT
<213> ORGANISM: Homo sapiens

<400> SEQUENCE: 27

Met Ser Lys Thr Leu Lys Lys Lys His Trp Leu Ser Lys Val Gln
1               5                   10                  15

Glu Cys Ala Val Ser Trp Ala Gly Pro Gly Asp Phe Gly Ala Glu
            20                  25                  30

Ile Arg Gly Gly Ala Glu Arg Gly Glu Phe Pro Tyr Leu Gly Arg Leu
        35                  40                  45

Arg Glu Glu Pro Gly Gly Gly Thr Cys Cys Ile Val Ser Gly Lys Ala
    50                  55                  60

Pro Asn Pro Ser Asp Val Leu Leu Glu Val Asn Gly Thr Pro Val Ser
65                  70                  75                  80

Gly Leu Thr Asn Arg Asp Thr Leu Ala Val Ile Arg His Phe Arg Glu
                85                  90                  95

Pro Ile Arg Leu Lys Thr Val Lys Pro Gly Lys Val Ile Asn Lys Asp
            100                 105                 110

Leu Arg His Tyr Leu Ser Leu Gln Phe Gln Lys Gly Ser Ile Asp His
        115                 120                 125

Lys Leu Gln Gln Val Ile Arg Asp Asn Leu Tyr Leu Arg Thr Ile Pro
    130                 135                 140

Cys Thr Thr Arg Ala Pro Arg Asp Gly Glu Val Pro Gly Val Asp Tyr
145                 150                 155                 160

Asn Phe Ile Ser Val Glu Gln Phe Lys Ala Leu Glu Glu Ser Gly Ala
                165                 170                 175

Leu Leu Glu Ser Gly Thr Tyr Asp Gly Asn Phe Tyr Gly Thr Pro Lys
            180                 185                 190

Pro Pro Ala Glu Pro Ser Pro Phe Gln Pro Asp Pro Val Asp Gln Val
        195                 200                 205

Leu Phe Asp Asn Glu Phe Asp Ala Glu Ser Gln Arg Lys Arg Thr Thr
    210                 215                 220

Ser Val Ser Lys Met Glu Arg Met Asp Ser Ser Leu Pro Glu Glu Glu
225                 230                 235                 240

Glu Asp Glu Asp Lys Gly Ala Ile Asn Gly Ser Gly Asn Ala Glu Asn
                245                 250                 255
```

-continued

Arg Glu Arg His Ser Glu Ser Ser Asp Trp Met Lys Thr Val Pro Ser
            260                 265                 270

Tyr Asn Gln Thr Asn Ser Ser Met Asp Phe Arg Asn Tyr Met Met Arg
        275                 280                 285

Asp Glu Thr Leu Glu Pro Leu Pro Lys Asn Trp Glu Met Ala Tyr Thr
    290                 295                 300

Asp Thr Gly Met Ile Tyr Phe Ile Asp His Asn Thr Lys Thr Thr Thr
305                 310                 315                 320

Trp Leu Asp Pro Arg Leu Cys Lys Lys Ala Lys Ala Pro Glu Asp Cys
                325                 330                 335

Glu Asp Gly Glu Leu Pro Tyr Gly Trp Glu Lys Ile Glu Asp Pro Gln
            340                 345                 350

Tyr Gly Thr Tyr Tyr Val Asp Phe Thr Leu Val Ala Gln Ala Gly Val
        355                 360                 365

Gln Trp His Asp Leu Gly Ser Leu Gln Pro Pro Pro Gly Phe Asn
    370                 375                 380

His Leu Asn Gln Lys Thr Gln Phe Glu Asn Pro Val Glu Glu Ala Lys
385                 390                 395                 400

Arg Lys Lys Gln Leu Gly Gln Val Glu Ile Gly Ser Ser Lys Pro Asp
                405                 410                 415

Met Glu Lys Ser His Phe Thr Arg Asp Pro Ser Gln Leu Lys Gly Val
            420                 425                 430

Leu Val Arg Ala Ser Leu Lys Lys Ser Thr Met Gly Phe Gly Phe Thr
        435                 440                 445

Ile Ile Gly Gly Asp Arg Pro Asp Glu Phe Leu Gln Val Lys Asn Val
    450                 455                 460

Leu Lys Asp Gly Pro Ala Ala Gln Asp Gly Lys Ile Ala Pro Gly Asp
465                 470                 475                 480

Val Ile Val Asp Ile Asn Gly Asn Cys Val Phe Gly His Thr His Ala
                485                 490                 495

Asp Val Val Gln Met Phe Gln Leu Val Pro Val Asn Gln Tyr Val Asn
            500                 505                 510

Leu Thr Leu Cys Arg Gly Tyr Pro Leu Pro Asp Asp Ser Glu Asp Pro
        515                 520                 525

Val Val Asp Ile Val Ala Ala Thr Pro Val Ile Asn Gly Gln Ser Leu
    530                 535                 540

Thr Lys Gly Glu Thr Cys Met Asn Pro Gln Asp Phe Lys Pro Gly Ala
545                 550                 555                 560

Met Val Leu Glu Gln Asn Gly Lys Ser Gly His Thr Ser Thr Gly Asp
                565                 570                 575

Gly Leu Asn Gly Pro Ser Asp Ala Ser Glu Gln Arg Val Ser Met Ala
            580                 585                 590

Ser Ser Gly Ser Ser Gln Pro Glu Leu Val Thr Ile Pro Leu Ile Lys
        595                 600                 605

Gly Pro Lys Gly Phe Gly Phe Ala Ile Ala Asp Ser Pro Thr Gly Gln
    610                 615                 620

Lys Val Lys Met Ile Leu Asp Ser Gln Trp Cys Gln Gly Leu Gln Lys
625                 630                 635                 640

Glu Asp Ile Ile Lys Glu Ile Tyr His Gln Asn Val Gln Asn Leu Thr
                645                 650                 655

His Leu Gln Val Val Glu Val Leu Lys Gln Phe Pro Val Gly Ala Asp
            660                 665                 670

-continued

```
Val Pro Leu Leu Ile Leu Arg Gly Gly Pro Pro Ser Thr Thr Lys Thr
            675                 680                 685

Ala Lys Met Lys Thr Asp Lys Lys Glu Asn Ala Gly Ser Leu Glu Ala
        690                 695                 700

Ile Asn Glu Pro Ile Pro Gln Pro Met Pro Phe Pro Pro Ser Ile Ile
705                 710                 715                 720

Arg Ser Gly Ser Pro Lys Leu Asp Pro Ser Glu Val Tyr Leu Lys Ser
                725                 730                 735

Lys Thr Leu Tyr Glu Asp Lys Pro Pro Asn Thr Lys Asp Leu Asp Val
            740                 745                 750

Phe Leu Arg Lys Gln Glu Ser Gly Phe Gly Phe Arg Val Leu Gly Gly
        755                 760                 765

Asp Gly Pro Asp Gln Ser Ile Tyr Ile Gly Ala Ile Ile Pro Leu Gly
    770                 775                 780

Ala Ala Glu Lys Asp Gly Arg Leu Arg Ala Ala Asp Glu Leu Met Cys
785                 790                 795                 800

Ile Asp Gly Ile Pro Val Lys Gly Lys Ser His Lys Gln Val Leu Asp
                805                 810                 815

Leu Met Thr Thr Ala Ala Arg Asn Gly His Val Leu Leu Thr Val Arg
            820                 825                 830

Arg Lys Ile Phe Tyr Gly Glu Lys Gln Pro Glu Asp Asp Ser Ser Gln
        835                 840                 845

Ala Phe Ile Ser Thr Gln Asn Gly Ser Pro Arg Leu Asn Arg Ala Glu
    850                 855                 860

Val Pro Ala Arg Pro Ala Pro Gln Glu Pro Tyr Asp Val Val Leu Gln
865                 870                 875                 880

Arg Lys Glu Asn Glu Gly Phe Gly Phe Val Ile Leu Thr Ser Lys Asn
                885                 890                 895

Lys Pro Pro Pro Gly Val Ile Pro His Lys Ile Gly Arg Val Ile Glu
            900                 905                 910

Gly Ser Pro Ala Asp Arg Cys Gly Lys Leu Lys Val Gly Asp His Ile
        915                 920                 925

Ser Ala Val Asn Gly Gln Ser Ile Val Glu Leu Ser His Ala Asn Ile
    930                 935                 940

Val Gln Leu Ile Lys Asp Ala Gly Val Thr Val Thr Leu Thr Val Ile
945                 950                 955                 960

Ala Glu Glu Glu His His Gly Pro Pro Ser Gly Thr Asn Ser Ala Arg
                965                 970                 975

Gln Ser Pro Ala Leu Gln His Arg Pro Met Gly Gln Ser Gln Ala Asn
            980                 985                 990

His Ile Pro Gly Asp Arg Ser Ala Leu Glu Gly Glu Ile Gly Lys Asp
        995                 1000                1005

Val Ser Thr Ser Tyr Arg His Ser Trp Ser Asp His Lys His Leu Ala
    1010                1015                1020

Gln Pro Asp Thr Ala Val Ile Ser Val Val Gly Ser Arg His Asn Gln
1025                1030                1035                1040

Asn Leu Gly Cys Tyr Pro Val Glu Leu Glu Arg Gly Pro Arg Gly Phe
                1045                1050                1055

Gly Phe Ser Leu Arg Gly Gly Lys Glu Tyr Asn Met Gly Leu Phe Ile
            1060                1065                1070

Leu Arg Leu Ala Glu Asp Gly Pro Ala Ile Lys Asp Gly Arg Ile His
        1075                1080                1085

Val Gly Asp Gln Ile Val Glu Ile Asn Gly Glu Pro Thr Gln Gly Ile
```

```
                        1090                1095                1100
Thr His Thr Arg Ala Ile Glu Leu Ile Gln Ala Gly Gly Asn Lys Val
1105                1110                1115                1120

Leu Leu Leu Leu Arg Pro Gly Thr Gly Leu Ile Pro Asp His Gly Leu
                1125                1130                1135

Ala Pro Ser Gly Leu Cys Ser Tyr Val Lys Pro Glu Gln His
                1140                1145                1150

<210> SEQ ID NO 28
<211> LENGTH: 253
<212> TYPE: PRT
<213> ORGANISM: Homo sapiens

<400> SEQUENCE: 28

Met Ala Asp Asp Gln Gly Cys Ile Glu Glu Gln Gly Val Glu Asp Ser
 1               5                  10                  15

Ala Asn Glu Asp Ser Val Asp Ala Lys Pro Asp Arg Ser Ser Phe Val
                20                  25                  30

Pro Ser Leu Phe Ser Lys Lys Lys Asn Val Thr Met Arg Ser Ile
            35                  40                  45

Lys Thr Thr Arg Asp Arg Val Pro Thr Tyr Gln Tyr Asn Met Asn Phe
 50                  55                  60

Glu Lys Leu Gly Lys Cys Ile Ile Asn Asn Lys Asn Phe Asp Lys
 65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
    130                 135                 140

Gly Glu Glu Asn Met Glu Ser Cys Ser Val Thr Gln Ala Gly Val Gln
145                 150                 155                 160

Arg Arg Asp Leu Gly Arg Leu Gln Pro Pro Pro Arg Leu Ala Glu
                165                 170                 175

Gly Pro Ser Leu Met Met Ala Ser Arg Pro Thr Arg Gly Pro Ser Met
            180                 185                 190

Thr Gln Met Leu Ile Leu Asp Thr Arg Ser Gln Trp Lys Leu Thr Ser
        195                 200                 205

Ser Ser Pro Ile Pro Arg Phe Gln Ala Ile Thr Arg Gly Gly Ala Gln
    210                 215                 220

Glu Glu Ala Pro Gly Leu Cys Lys Pro Ser Ala Pro Ser Trp Arg Ser
225                 230                 235                 240

Thr Glu Lys Thr Trp Lys Ser Cys Arg Ser Ser Pro Gly
                245                 250

<210> SEQ ID NO 29
<211> LENGTH: 111
<212> TYPE: PRT
<213> ORGANISM: Homo sapiens

<400> SEQUENCE: 29

Met Gly Leu Ser Ile Ala Ser His Phe Gly Leu Leu Ile Lys Lys Val
 1               5                  10                  15

Glu Arg Asn Ile Leu Phe Phe Phe Arg Arg Ser Leu Ala Leu Cys Gln
```

-continued

```
                20                  25                  30

Ala Gly Val Gln Trp Arg Tyr Leu Ser Gln Leu Thr Ala Ala Ser Ala
        35                  40                  45

Ser Trp Val Gln Ala Ile Leu Cys Leu Ser Leu Pro Ser Ser Trp Asp
    50                  55                  60

Tyr Arg His Met Pro Pro Arg Pro Ala Asn Phe Cys Ile Leu Ser Arg
65                  70                  75                  80

Asp Gly Ile Ser Pro Cys Trp Pro Gly Trp Ser Arg Ser Leu Asp Leu
                85                  90                  95

Val Ile Arg Pro Pro Arg Pro Pro Lys Val Leu Arg Leu Gln Ala
            100                 105                 110

<210> SEQ ID NO 30
<211> LENGTH: 118
<212> TYPE: PRT
<213> ORGANISM: Homo sapiens

<400> SEQUENCE: 30

Met Gln Ile Ile Phe Phe Phe Leu Phe Leu Arg Trp Ser Phe Thr Leu
1               5                   10                  15

Val Ala Gln Ala Gly Val Gln Trp Arg Asp Leu Ser Ser Pro Gln Pro
                20                  25                  30

Pro Pro Pro Arg Phe Lys Arg Phe Ser Cys Leu Ser Pro Pro Ser Ser
            35                  40                  45

Trp Asp Tyr Arg His Ala Pro Pro His Pro Ala Asn Phe Val Phe Leu
    50                  55                  60

Val Glu Thr Gly Phe Leu Arg Val Gly Gln Ala Gly Leu Glu Leu Leu
65                  70                  75                  80

Thr Ser Gly Asp Pro Ala Ser Ala Ser Gln Ser Ala Gly Ile Thr
                85                  90                  95

Gly Val Ser His His Thr Gln Pro Asp Ala Asn Asn Phe Leu Arg Lys
            100                 105                 110

Leu Phe Gln Lys Leu Phe
        115

<210> SEQ ID NO 31
<211> LENGTH: 139
<212> TYPE: PRT
<213> ORGANISM: Homo sapiens

<400> SEQUENCE: 31

Met Gly His Pro Arg Ala Ile Gln Pro Ser Val Phe Phe Ser Pro Tyr
1               5                   10                  15

Asp Val His Phe Leu Leu Tyr Pro Ile Arg Cys Pro Tyr Leu Lys Ile
                20                  25                  30

Gly Arg Phe His Ile Lys Leu Lys Gly Leu His Phe Leu Ser Phe
            35                  40                  45

Leu Phe Phe Phe Phe Glu Thr Gln Ser His Ser Val Thr Arg Leu Glu
    50                  55                  60

Cys Ser Gly Thr Ile Ser Ala His Cys Asn Leu Cys Leu Pro Gly Ser
65                  70                  75                  80

Ser Asn Ser Pro Ala Ser Ala Ser Gln Val Ala Gly Thr Thr Gly Thr
                85                  90                  95

Cys His His Ala Gln Leu Ile Phe Val Phe Leu Ala Glu Met Gly Phe
            100                 105                 110

His His Ile Gly Gln Asp Gly Leu Asp Leu Asn Leu Val Ile His Pro
```

```
                115                 120                 125
Pro Arg Ser Pro Lys Ala Leu Gly Leu Gln Ala
    130                 135

<210> SEQ ID NO 32
<211> LENGTH: 69
<212> TYPE: PRT
<213> ORGANISM: Homo sapiens

<400> SEQUENCE: 32

Met Pro Asn His Tyr Ser Phe Cys Phe Cys Phe Cys Phe Cys Phe Arg
  1               5                  10                  15

Arg Ser Leu Ala Leu Ser Pro Arg Leu Glu Cys Ser Gly Ala Ile Leu
             20                  25                  30

Ala His Gly Lys Leu His Leu Pro Gly Ser Arg His Ser Pro Ala Ser
         35                  40                  45

Ala Ser Pro Val Ala Gly Thr Lys Gly Ala Arg His His Ala Arg Leu
     50                  55                  60

Ile Phe Leu Tyr Phe
 65

<210> SEQ ID NO 33
<211> LENGTH: 162
<212> TYPE: PRT
<213> ORGANISM: Homo sapiens

<400> SEQUENCE: 33

Leu Phe Thr Asn Ser Pro Phe Ser Leu Leu Ser Pro Ala Gln Trp Leu
  1               5                  10                  15

Cys Phe Gly Thr His Leu Gly His Val Gln Ser Val Ser His Leu Gln
             20                  25                  30

Trp Glu Gly Ser Val Gln Glu Ser Leu Arg Ser Val Arg Asn Ser Arg
         35                  40                  45

Cys Ala Leu Pro Met Leu Ser Ala Pro Cys Ser Leu Ser Leu His Phe
     50                  55                  60

Leu Leu Phe Ser Leu Ser Pro Phe Phe Phe Glu Ile Arg Val Leu
 65                  70                  75                  80

Leu Tyr Arg Gln Ala Gly Val Gln Trp Cys Tyr Leu Gly Ser Leu Gln
             85                  90                  95

Pro Leu Pro Pro Gly Phe Lys Gln Phe Ser Cys Leu Ser Tyr Pro Ser
            100                 105                 110

Ser Trp Asp Tyr Arg Arg Pro Pro Arg Gln Ala Asn Phe Cys Ile
            115                 120                 125

Phe Ser Thr Asp Gly Val Ser Pro Cys Trp Pro Arg Trp Ser Leu Ser
    130                 135                 140

Leu Asp Leu Met Ile Arg Pro Pro Gln Pro Glu Val Leu Gly Leu
145                 150                 155                 160

Gln Val

<210> SEQ ID NO 34
<211> LENGTH: 232
<212> TYPE: PRT
<213> ORGANISM: Homo sapiens

<400> SEQUENCE: 34

Met Gly Arg Leu Val Leu Leu Trp Gly Ala Ala Val Phe Leu Leu Gly
  1               5                  10                  15
```

```
Gly Trp Met Ala Leu Gly Gln Gly Ala Glu Gly Val Gln Ile Gln
            20                  25                  30

Ile Ile Tyr Phe Asn Leu Glu Thr Val Gln Val Thr Trp Asn Ala Ser
        35                  40                  45

Lys Tyr Ser Arg Thr Asn Leu Thr Phe His Tyr Arg Phe Asn Gly Asp
 50                  55                  60

Glu Ala Tyr Asp Gln Cys Thr Asn Tyr Leu Leu Gln Glu Gly His Thr
 65                  70                  75                  80

Ser Gly Cys Leu Leu Asp Ala Glu Gln Arg Asp Asp Ile Leu Tyr Phe
             85                  90                  95

Ser Ile Arg Asn Gly Thr His Pro Val Phe Thr Ala Ser Arg Trp Met
            100                 105                 110

Val Tyr Tyr Leu Lys Pro Ser Ser Pro Lys His Val Arg Phe Ser Trp
            115                 120                 125

His Gln Asp Ala Val Thr Val Thr Cys Ser Asp Leu Ser Tyr Gly Asp
130                 135                 140

Leu Leu Tyr Glu Val Gln Tyr Arg Ser Pro Phe Asp Thr Glu Trp Gln
145                 150                 155                 160

Thr Gln Ser Arg Ser Val Thr Gln Ala Gly Val Gln Trp Cys Asp Leu
                165                 170                 175

Cys Leu Leu Gln Pro Ser Pro Arg Phe Lys Arg Phe Ser Cys Leu
            180                 185                 190

Ser Leu Pro Ser Ser Trp Asp Tyr Arg His Pro Pro Arg Leu Ala
            195                 200                 205

Asn Phe Cys Ile Ile Ser Arg Asp Gly Val Ser Pro Cys Trp Pro Gly
210                 215                 220

Trp Ser Arg Thr Cys Asp Leu Arg
225                 230

<210> SEQ ID NO 35
<211> LENGTH: 506
<212> TYPE: PRT
<213> ORGANISM: Homo sapiens

<400> SEQUENCE: 35

Met Glu Phe Leu Lys Val Ala Arg Arg Asn Lys Arg Glu Gln Leu Glu
 1               5                  10                  15

Gln Ile Gln Lys Glu Leu Ser Val Leu Glu Glu Asp Ile Lys Arg Val
                20                  25                  30

Glu Glu Met Ser Gly Leu Tyr Ser Pro Val Ser Glu Asp Ser Thr Val
            35                  40                  45

Pro Gln Phe Glu Ala Pro Ser Pro Ser His Ser Ser Ile Ile Asp Ser
 50                  55                  60

Thr Glu Tyr Ser Gln Pro Pro Gly Phe Ser Gly Ser Ser Gln Ala Gly
 65                  70                  75                  80

Val Gln Trp Arg Tyr Leu Gly Ser Leu Gln Pro Pro Pro Arg Tyr
                 85                  90                  95

Lys Arg Phe Ser Cys Leu Thr Leu Pro Ser Ser Trp Asp Tyr Arg Arg
            100                 105                 110

Leu Pro Pro His Leu Thr Lys Lys Gln Pro Trp Tyr Asn Ser Thr Leu
            115                 120                 125

Ala Ser Arg Arg Lys Arg Leu Thr Ala His Phe Glu Asp Leu Glu Gln
130                 135                 140

Cys Tyr Phe Ser Thr Arg Met Ser Arg Ile Ser Asp Asp Ser Arg Thr
145                 150                 155                 160
```

-continued

```
Ala Ser Gln Leu Asp Glu Phe Gln Cys Leu Ser Lys Phe Thr Arg
                165                 170                 175

Tyr Asn Ser Val Arg Pro Leu Ala Thr Leu Ser Tyr Ala Ser Asp Leu
            180                 185                 190

Tyr Asn Gly Ser Ser Ile Val Ser Ile Glu Phe Asp Arg Asp Cys
            195                 200                 205

Asp Tyr Phe Ala Ile Ala Gly Val Thr Lys Ile Lys Val Tyr Glu
    210                 215                 220

Tyr Asp Thr Val Ile Gln Asp Ala Val Asp Ile His Tyr Pro Glu Asn
225                 230                 235                 240

Glu Met Thr Cys Asn Ser Lys Ile Ser Cys Ile Ser Trp Ser Ser Tyr
                245                 250                 255

His Lys Asn Leu Leu Ala Ser Ser Asp Tyr Glu Gly Thr Val Ile Leu
                260                 265                 270

Trp Asp Gly Phe Thr Gly Gln Arg Ser Lys Val Tyr Gln Glu His Glu
            275                 280                 285

Lys Arg Cys Trp Ser Val Asp Phe Asn Leu Met Asp Pro Lys Leu Leu
    290                 295                 300

Ala Ser Gly Ser Asp Asp Ala Lys Val Lys Leu Trp Ser Thr Asn Leu
305                 310                 315                 320

Asp Asn Ser Val Ala Ser Ile Glu Ala Lys Ala Asn Val Cys Cys Val
                325                 330                 335

Lys Phe Ser Pro Ser Ser Arg Tyr His Leu Ala Phe Gly Cys Ala Asp
            340                 345                 350

His Cys Val His Tyr Tyr Asp Leu Arg Asn Thr Lys Gln Pro Ile Met
            355                 360                 365

Val Phe Lys Gly His Arg Lys Ala Val Ser Tyr Ala Lys Phe Val Ser
    370                 375                 380

Gly Glu Glu Ile Val Ser Ala Ser Thr Asp Ser Gln Leu Lys Leu Trp
385                 390                 395                 400

Asn Val Gly Lys Pro Tyr Cys Leu Arg Ser Phe Lys Gly His Ile Asn
                405                 410                 415

Glu Lys Asn Phe Val Gly Leu Ala Ser Asn Gly Asp Tyr Ile Ala Cys
            420                 425                 430

Gly Ser Glu Asn Asn Ser Leu Tyr Leu Tyr Tyr Lys Gly Leu Ser Lys
            435                 440                 445

Thr Leu Leu Thr Phe Lys Phe Asp Thr Val Lys Ser Val Leu Asp Lys
    450                 455                 460

Asp Arg Lys Glu Asp Asp Thr Asn Glu Phe Val Ser Ala Val Cys Trp
465                 470                 475                 480

Arg Ala Leu Pro Asp Gly Glu Ser Asn Val Leu Ile Ala Ala Asn Ser
                485                 490                 495

Gln Gly Thr Ile Lys Val Leu Glu Leu Val
            500                 505

<210> SEQ ID NO 36
<211> LENGTH: 120
<212> TYPE: PRT
<213> ORGANISM: Homo sapiens

<400> SEQUENCE: 36

Met Gly Ser Tyr Phe Val Ala Arg Ala Gly Cys Lys Leu Leu Gly Leu
  1               5                  10                  15

Lys Gly Thr Ser His Phe Ser Leu Pro Lys Cys Arg Asn Cys Arg Arg
```

```
                       20                  25                  30
Glu Pro Leu Pro Gly Leu Phe Phe Leu Phe Val Phe Phe Leu
            35                  40                  45

Arg Arg Ser Leu Ala Leu Ser Pro Arg Leu Glu Cys Ser Gly Ala Ile
        50                  55                  60

Val Ala His Cys Lys Leu Gly Leu Pro Gly Ser Leu His Ser Pro Ala
 65                  70                  75                  80

Ser Ala Ser Gln Val Ala Gly Thr Ile Gly Thr Cys His Asn Thr Arg
                85                  90                  95

Ile Ile Phe Cys Ile Leu Val Glu Thr Gly Phe His Arg Val Ser Gln
            100                 105                 110

Asp Gly Val Asp Leu Leu Thr Leu
        115                 120

<210> SEQ ID NO 37
<211> LENGTH: 257
<212> TYPE: PRT
<213> ORGANISM: Homo sapiens

<400> SEQUENCE: 37

Met Asp Cys Gly Ser Val Gly Gly Gln Arg Thr Gln Arg Leu Pro Gly
  1               5                  10                  15

Arg Gln Arg Leu Leu Phe Leu Pro Val Gly Leu Ser Gly Arg Pro Gly
             20                  25                  30

Gly Ser Glu Thr Ser Ala Arg Arg Cys Pro Ser Ala Leu Ser Asp Gly
         35                  40                  45

Leu Gly Ala Leu Arg Pro Arg Ala Pro Ala Ala Arg Gly Gly Val Ser
     50                  55                  60

Arg Ala Ser Pro Leu Leu Leu Leu Leu Val Pro Ser Pro Arg Leu
 65                  70                  75                  80

Ala Ala Ala Ala Pro Arg Arg Gln Leu Gly Asp Trp Glu Arg Ser Arg
                85                  90                  95

Leu Gly Tyr Ala Ala Pro Pro Ala Gly Arg Ser Gly Ala Trp Arg Cys
            100                 105                 110

Ser Pro Gly Val Ala Ala Ala Gly Ala Leu Pro Gln Tyr His Gly
        115                 120                 125

Pro Ala Pro Ala Leu Val Ser Cys Arg Arg Glu Leu Ser Leu Ser Ala
        130                 135                 140

Gly Ser Leu Gln Leu Glu Arg Lys Arg Arg Asp Phe Thr Ser Ser Gly
145                 150                 155                 160

Ser Arg Lys Leu Tyr Phe Asp Thr His Ala Leu Val Cys Leu Leu Glu
                165                 170                 175

Asp Asn Glu Ser His Ser Phe Ile Gln Ala Gly Val Gln Trp His Ser
            180                 185                 190

Leu Gly Leu Leu Gln Pro Pro Pro Gly Phe Lys Arg Ser Ser His
        195                 200                 205

Leu Ile Leu Leu Ser Ser Trp Asp Tyr Arg His Ala Pro Pro His Leu
    210                 215                 220

Asp Asn Phe Ser Val Phe Leu Leu Glu Thr Gly Phe His His Val Gly
225                 230                 235                 240

Gln Ala Gly Leu Lys Leu Leu Thr Ser Ser Asp Pro Pro Thr Leu Ala
                245                 250                 255

Ser
```

<210> SEQ ID NO 38
<211> LENGTH: 438
<212> TYPE: PRT
<213> ORGANISM: Homo sapiens

<400> SEQUENCE: 38

```
Met Ser Pro Ala Thr Thr Gly Thr Phe Leu Leu Thr Val Tyr Ser Ile
 1               5                  10                  15

Phe Ser Lys Val His Ser Asp Arg Asn Val Tyr Pro Ser Ala Gly Val
            20                  25                  30

Leu Phe Val His Val Leu Glu Arg Glu Tyr Phe Lys Gly Glu Phe Pro
        35                  40                  45

Pro Tyr Pro Lys Pro Gly Glu Ile Ser Asn Asp Pro Ile Thr Phe Asn
    50                  55                  60

Thr Asn Leu Met Gly Tyr Pro Asp Arg Pro Gly Trp Leu Arg Tyr Ile
65                  70                  75                  80

Gln Arg Thr Pro Tyr Ser Asp Gly Val Leu Tyr Gly Ser Pro Thr Ala
                85                  90                  95

Glu Asn Val Gly Lys Pro Thr Ile Ile Glu Ile Thr Ala Tyr Asn Arg
            100                 105                 110

Arg Thr Phe Glu Thr Ala Arg His Asn Leu Ile Ile Asn Ile Met Ser
        115                 120                 125

Ala Glu Asp Phe Pro Leu Pro Tyr Gln Ala Glu Phe Phe Ile Lys Asn
    130                 135                 140

Met Asn Val Glu Glu Met Leu Ala Ser Glu Val Leu Gly Asp Phe Leu
145                 150                 155                 160

Gly Ala Val Lys Asn Val Trp Gln Pro Glu Arg Leu Asn Ala Ile Asn
                165                 170                 175

Ile Thr Ser Ala Leu Asp Arg Gly Gly Arg Val Pro Leu Pro Ile Asn
            180                 185                 190

Asp Leu Lys Glu Gly Val Tyr Val Met Val Gly Ala Asp Val Pro Phe
        195                 200                 205

Ser Ser Cys Leu Arg Glu Val Glu Asn Pro Gln Asn Gln Leu Arg Cys
    210                 215                 220

Ser Gln Glu Met Glu Pro Val Ile Thr Cys Asp Lys Phe Arg Thr
225                 230                 235                 240

Gln Phe Tyr Ile Asp Trp Cys Lys Ile Ser Leu Val Asp Lys Thr Lys
                245                 250                 255

Gln Val Ser Thr Tyr Gln Glu Val Ile Arg Gly Glu Gly Ile Leu Pro
            260                 265                 270

Asp Gly Gly Glu Tyr Lys Pro Pro Ser Asp Ser Leu Lys Ser Arg Asp
        275                 280                 285

Tyr Tyr Thr Asp Phe Leu Ile Thr Leu Ala Val Pro Ser Ala Val Ala
    290                 295                 300

Leu Val Leu Phe Leu Ile Leu Ala Tyr Ile Met Cys Cys Arg Arg Glu
305                 310                 315                 320

Gly Val Glu Lys Arg Asn Met Gln Thr Pro Asp Ile Gln Leu Val His
                325                 330                 335

His Ser Ala Ile Gln Lys Ser Thr Lys Glu Leu Arg Asp Met Ser Lys
            340                 345                 350

Asn Arg Glu Ile Ala Trp Pro Leu Ser Thr Leu Pro Val Phe His Pro
        355                 360                 365

Val Thr Gly Glu Ile Ile Pro Pro Leu His Thr Asp Asn Tyr Asp Ser
    370                 375                 380
```

```
Thr Asn Met Pro Leu Met Gln Thr Gln Gln Trp Ser Phe Ala Pro Val
385                 390                 395                 400

Ala Gln Ala Gly Val Gln Trp Arg Asp Leu Gly Ser Leu Gln Pro Pro
            405                 410                 415

Pro Pro Arg Asn Leu Pro His Gln Thr Gln Ile Pro Gln Gln Gln Thr
            420                 425                 430

Thr Gly Lys Trp Tyr Pro
        435

<210> SEQ ID NO 39
<211> LENGTH: 171
<212> TYPE: PRT
<213> ORGANISM: Homo sapiens

<400> SEQUENCE: 39

Met Leu Gly Leu Arg Lys Ala Ala Ile Ser Leu Leu Arg Asn
1               5                   10                  15

Val Gly Leu Gln Leu Ala Thr Leu Leu Met Ser Gln Lys Lys Leu Gly
            20                  25                  30

Phe Cys Gly Asn Phe Leu Phe Leu Asn Leu Ala Ile Ile Gln Thr Lys
        35                  40                  45

Ile Ser Ser Ser Phe Phe Phe Leu Arg Gln Ser Leu Thr Leu Ser
    50                  55                  60

Pro Arg Leu Glu Cys Asn Gly Ala Ile Ser Ala His Cys His Leu Arg
65                  70                  75                  80

Leu Pro Asp Ser Ser Asn Ser Pro Ala Ser Ala Ser Gln Val Thr Gly
                85                  90                  95

Ile Thr Gly Ser His His His Ala Trp Leu Ile Phe Val Phe Leu Val
            100                 105                 110

Glu Thr Gly Phe Cys His Val Gly Gln Asp Gly Leu Glu Leu Leu Thr
        115                 120                 125

Ser Gly Asp Pro Pro Ala Ser Ala Ser Gln Ser Ala Gly Ile Thr Gly
    130                 135                 140

Met Ser His His Thr Trp Pro Thr Asp Leu Phe Phe Lys Thr Val Leu
145                 150                 155                 160

Pro Ala Arg Leu Gly Leu Trp Asp Ser Ser Val
                165                 170

<210> SEQ ID NO 40
<211> LENGTH: 365
<212> TYPE: PRT
<213> ORGANISM: Homo sapiens

<400> SEQUENCE: 40

Met His Ala Val Pro Arg Gly Phe Gly Lys Lys Val Arg Val Gly Val
1               5                   10                  15

Gln Ser Cys Pro Ser Pro Phe Ser Gly Gln Ala Cys Pro Gln Pro Ser
            20                  25                  30

Ser Val Phe Trp Ser Leu Leu Lys Asn Leu Pro Phe Leu Glu His Leu
        35                  40                  45

Glu Leu Ile Gly Ser Asn Phe Ser Ser Ala Met Pro Arg Asn Glu Pro
    50                  55                  60

Ala Ile Arg Asn Ser Leu Pro Pro Cys Ser Arg Ala Gln Ser Val Gly
65                  70                  75                  80

Asp Ser Glu Val Ala Ala Ile Gly Gln Leu Ala Phe Leu Arg His Leu
                85                  90                  95
```

-continued

```
Thr Leu Ala Gln Leu Pro Ser Val Leu Thr Gly Ser Gly Leu Val Asn
            100                 105                 110

Ile Gly Pro Gln Cys Gln Gln Leu Arg Ser Leu Ser Leu Ala Asn Leu
        115                 120                 125

Gly Met Met Gly Lys Val Val Tyr Met Pro Ala Leu Ser Asp Met Leu
    130                 135                 140

Lys His Cys Lys Arg Leu Arg Asp Leu Arg Leu Glu Gln Pro Tyr Phe
145                 150                 155                 160

Ser Ala Asn Ala Gln Phe Phe Gln Ala Leu Ser Gln Cys Pro Ser Leu
                165                 170                 175

Gln Arg Leu Cys Leu Val Ser Arg Ser Gly Thr Leu Gln Pro Asp Ala
            180                 185                 190

Val Leu Ala Phe Met Ala Arg Cys Leu Gln Val Val Met Cys His Leu
        195                 200                 205

Phe Thr Gly Glu Ser Leu Ala Thr Cys Lys Ser Leu Gln Gln Ser Leu
    210                 215                 220

Leu Arg Arg Trp Gly Glu Val Thr Gly Arg Arg Pro Gln Leu Phe Thr
225                 230                 235                 240

Glu Leu Arg Glu Glu Pro Ser Ala Arg Thr Ser Arg Ala Thr Gly Arg
                245                 250                 255

Arg Gln Pro Cys Leu Pro Asp Ser Gly Val Val Cys Cys Pro Cys Gly
            260                 265                 270

Arg Pro Leu Ala Val Ser Gly Ile Ile Leu Val Gly Val Ser Pro Ser
        275                 280                 285

Leu Val Val Lys Thr Thr Cys Val Tyr Arg Val Leu Phe Lys Asn Leu
    290                 295                 300

Asp Tyr Ala Ser Ile Phe Phe Leu Val Cys Leu Phe Glu Thr Glu Ser
305                 310                 315                 320

His Ser Val Val Gln Ala Gly Val Gln Trp Arg Asp Leu Ser Ser Leu
                325                 330                 335

Gln Pro Leu Leu Ser Gly Leu Gln Pro Gln Pro Pro Glu Gln Leu Glu
            340                 345                 350

Asn Glu Leu Glu Ile Gly Phe Ser Tyr Cys Phe Val Ile
        355                 360                 365

<210> SEQ ID NO 41
<211> LENGTH: 125
<212> TYPE: PRT
<213> ORGANISM: Homo sapiens

<400> SEQUENCE: 41

Met Glu Glu Asp Glu Phe Ile Gly Glu Lys Thr Phe Gln Arg Tyr Cys
1               5                   10                  15

Ala Glu Phe Ile Lys His Ser Gln Gln Ile Gly Asp Ser Trp Glu Trp
                20                  25                  30

Arg Pro Ser Lys Asp Cys Ser Asp Gly Tyr Met Cys Lys Ile His Phe
            35                  40                  45

Gln Ile Lys Asn Gly Ser Val Met Ser His Leu Gly Ala Ser Thr His
        50                  55                  60

Gly Gln Thr Cys Leu Pro Met Glu Val Lys Ser Cys Ser Val Thr Gln
65                  70                  75                  80

Ala Gly Val Gln Leu Arg Asp Leu Ser Ser Leu Gln Pro Pro Pro Ser
                85                  90                  95

Gly Phe Lys Gln Phe Ser Cys Leu Ser Leu Pro Ser Asn Trp Asp Tyr
            100                 105                 110
```

```
Arg Gly Ser Pro Leu His Leu Ala Asn Phe Leu Tyr Phe
        115                 120                 125

<210> SEQ ID NO 42
<211> LENGTH: 120
<212> TYPE: PRT
<213> ORGANISM: Homo sapiens

<400> SEQUENCE: 42

Met Thr Thr Cys Glu Phe Glu Phe Ile Phe Leu Lys Glu Gln Val Thr
1               5                   10                  15

Arg Ile Cys Asn Ile Ala Pro Leu Lys Ala Tyr Phe Ser Val His Lys
            20                  25                  30

Met Gly Lys Ile Leu Lys Lys Leu Ser Asn Phe Ser Phe Leu Thr His
        35                  40                  45

Arg Gln Ser Leu Thr Leu Ser Pro Arg Leu Glu Cys Ser Gly Ala Ile
    50                  55                  60

Ser Ala His Cys Asn Leu His Leu Leu Gly Ser Ser Asn Ser Ala Ala
65                  70                  75                  80

Ser Ala Ser Arg Val Ala Gly Thr Thr Gly Ala Cys His His Ala Gln
                85                  90                  95

Leu Ile Phe Val Phe Leu Val Glu Thr Gly Phe His Val Gly Gln
            100                 105                 110

Asp Gly Leu Gly Leu Leu Thr Ser
        115                 120

<210> SEQ ID NO 43
<211> LENGTH: 643
<212> TYPE: PRT
<213> ORGANISM: Homo sapiens

<400> SEQUENCE: 43

Met Ser Cys Asn Pro Ser Phe Gly Gly Ile Gly Lys Gly His Leu Met
1               5                   10                  15

Arg Glu Val Asp Ala Leu Asp Gly Leu Cys Ser Arg Ile Cys Asp Gln
            20                  25                  30

Ser Gly Val His Tyr Lys Val Leu Asn Arg Arg Lys Gly Pro Ala Val
        35                  40                  45

Trp Gly Leu Arg Ala Gln Ile Asp Arg Lys Leu Tyr Lys Gln Asn Met
    50                  55                  60

Gln Lys Glu Ile Leu Asn Thr Pro Leu Leu Thr Val Gln Glu Gly Ala
65                  70                  75                  80

Val Glu Asp Leu Ile Leu Thr Glu Pro Glu Pro Glu His Thr Gly Lys
                85                  90                  95

Cys Arg Val Ser Gly Val Val Leu Val Asp Gly Ser Thr Val Tyr Ala
            100                 105                 110

Glu Ser Val Ile Leu Thr Thr Gly Thr Phe Leu Arg Gly Met Ile Val
        115                 120                 125

Ile Gly Leu Glu Thr His Pro Ala Gly Arg Leu Gly Asp Gln Pro Ser
130                 135                 140

Ile Gly Leu Ala Gln Thr Leu Glu Lys Leu Gly Phe Val Val Gly Arg
145                 150                 155                 160

Leu Lys Thr Gly Thr Pro Pro Arg Ile Ala Lys Glu Ser Ile Asn Phe
                165                 170                 175

Ser Ile Leu Asn Lys His Ile Pro Asp Asn Pro Ser Ile Pro Phe Ser
            180                 185                 190
```

-continued

```
Phe Thr Asn Glu Thr Val Trp Ile Lys Pro Glu Asp Gln Leu Pro Cys
        195                 200                 205

Tyr Leu Thr His Thr Asn Pro Arg Val Asp Glu Ile Val Leu Lys Asn
    210                 215                 220

Leu His Leu Asn Ser His Val Lys Glu Thr Thr Arg Gly Pro Arg Tyr
225                 230                 235                 240

Cys Pro Ser Ile Glu Ser Lys Val Leu Arg Phe Pro Asn Arg Leu His
                245                 250                 255

Gln Val Trp Leu Glu Pro Glu Gly Met Asp Ser Asp Leu Ile Tyr Pro
            260                 265                 270

Gln Gly Leu Ser Met Thr Leu Pro Ala Glu Leu Gln Glu Lys Met Ile
        275                 280                 285

Thr Cys Ile Arg Gly Leu Glu Lys Ala Lys Val Ile Gln Pro Asp Gly
    290                 295                 300

Val Leu Leu Leu Pro Arg Met Glu Cys Asn Gly Ala Ile Ser Ala
305                 310                 315                 320

His His Asn Leu Pro Leu Pro Gly Tyr Gly Val Gln Tyr Asp Tyr Leu
                325                 330                 335

Asp Pro Arg Gln Ile Thr Pro Ser Leu Glu Thr His Leu Val Gln Arg
            340                 345                 350

Leu Phe Phe Ala Gly Gln Ile Asn Gly Thr Thr Gly Tyr Glu Glu Ala
        355                 360                 365

Ala Ala Gln Gly Val Ile Ala Gly Ile Asn Ala Ser Leu Arg Val Ser
    370                 375                 380

Arg Lys Pro Pro Phe Val Val Ser Arg Thr Glu Gly Tyr Ile Gly Val
385                 390                 395                 400

Leu Ile Asp Asp Leu Thr Thr Leu Gly Thr Ser Glu Pro Tyr Arg Met
                405                 410                 415

Phe Thr Ser Arg Val Glu Phe Arg Leu Ser Leu Arg Pro Asp Asn Ala
            420                 425                 430

Asp Ser Arg Leu Thr Leu Arg Gly Tyr Lys Asp Ala Gly Cys Val Ser
        435                 440                 445

Gln Gln Arg Tyr Glu Arg Ala Cys Trp Met Lys Ser Ser Leu Glu Glu
    450                 455                 460

Gly Ile Ser Val Leu Lys Ser Ile Glu Phe Leu Ser Ser Lys Trp Lys
465                 470                 475                 480

Lys Leu Ile Pro Glu Ala Ser Ile Ser Thr Ser Arg Ser Leu Pro Val
                485                 490                 495

Arg Ala Leu Asp Val Leu Lys Tyr Glu Glu Val Asp Met Asp Ser Leu
            500                 505                 510

Ala Lys Ala Val Pro Glu Pro Leu Lys Lys Tyr Thr Lys Cys Arg Glu
        515                 520                 525

Leu Ala Glu Arg Leu Lys Ile Glu Ala Thr Tyr Glu Ser Val Leu Phe
    530                 535                 540

His Gln Leu Gln Glu Ile Lys Gly Val Gln Gln Asp Glu Ala Leu Gln
545                 550                 555                 560

Leu Pro Lys Asp Leu Asp Tyr Leu Thr Ile Arg Asp Val Ser Leu Ser
                565                 570                 575

His Glu Val Arg Glu Lys Leu His Phe Ser Arg Pro Gln Thr Ile Gly
            580                 585                 590

Ala Ala Ser Arg Ile Pro Gly Val Thr Pro Ala Ala Ile Ile Asn Leu
        595                 600                 605
```

```
Leu Arg Phe Val Lys Thr Thr Gln Arg Arg Gln Ser Ala Met Asn Glu
    610             615             620

Ser Ser Lys Thr Asp Gln Tyr Leu Cys Asp Ala Asp Arg Leu Gln Glu
625             630             635             640

Arg Glu Leu

<210> SEQ ID NO 44
<211> LENGTH: 123
<212> TYPE: PRT
<213> ORGANISM: Homo sapiens

<400> SEQUENCE: 44

Met Pro Phe Leu Tyr Asp Ile Ser Ser Cys Trp Thr Ser Phe Cys Phe
1               5                   10                  15

Leu Phe Phe Ser Pro Leu Asp Gly Val Leu Leu Cys Phe Pro Gly Trp
            20                  25                  30

Asn Ala Val Ala Arg Ser Gln Leu Thr Ala Thr Ser Ala Ser Gln Val
        35                  40                  45

Gln Ala Ile Leu Leu Val Ser Ala Ser Gly Val Ala Gly Ile Ile Gly
    50                  55                  60

Thr Cys His His Ala Gln Pro Ile Phe Val Phe Leu Val Glu Met Gly
65                  70                  75                  80

Phe His His Val Gly Gln Ala Cys Leu Lys Leu Leu Asn Ser Gly Asp
                85                  90                  95

Pro Pro Ala Ser Ala Ser Gln Ser Ala Gly Ile Thr Gly Met Ser His
            100                 105                 110

His Ala Arg Pro Phe Phe Phe Phe Ser Phe
        115                 120

<210> SEQ ID NO 45
<211> LENGTH: 133
<212> TYPE: PRT
<213> ORGANISM: Homo sapiens

<400> SEQUENCE: 45

Met Ser Glu Ala Glu Asn Glu Phe Ile Asn Trp Val Ala Thr Ala Ala
1               5                   10                  15

Ile Glu Ala Asn Cys Ser Gln Cys Trp Leu Cys Val Glu Leu Pro Glu
            20                  25                  30

Ala Ala Gly Asn Gly Leu Pro Trp Arg Ile Val Pro Ala Asn Ile Ser
        35                  40                  45

Glu Trp Ile Cys Gln Tyr Gln Trp Glu Trp Asp Asn Thr Trp Phe Cys
    50                  55                  60

Phe Asp Phe Leu Ser Gln Ser Val Ser Leu Ser Pro Arg Leu Glu Cys
65                  70                  75                  80

Ser Gly Thr Ile Leu Ala Gln Cys Asn Leu Cys Leu Leu Gly Ser Ser
                85                  90                  95

Asp Ser Pro Ala Ser Ala Ser Gln Val Ala Gly Ile Ile Gly Ala Cys
            100                 105                 110

Arg His Ala Trp Leu Ile Phe Cys Ile Phe Ser Arg Asp Gly Val Ser
        115                 120                 125

Pro Tyr Cys Pro Gly
    130

<210> SEQ ID NO 46
<211> LENGTH: 244
<212> TYPE: PRT
```

<213> ORGANISM: Homo sapiens

<400> SEQUENCE: 46

```
Met Ala Leu Phe Leu Asp Lys Met Gly Ser Leu Gln Lys Gly Asn Tyr
 1               5                  10                  15
Ser Ser Gln Ser Gly Met Ile Pro Gly Ser Trp Gln His Lys Met Lys
            20                  25                  30
Leu Gln Leu Ile Leu Lys Ser Lys Ala Tyr Tyr Val Leu Ser Asp
        35                  40                  45
Ala Ala Met Ser Leu Gln Lys Tyr Gly Arg Ala Leu Arg Tyr Ile Lys
    50                  55                  60
Leu Ala Leu Gln Ser His Asp Thr Tyr Cys Cys Leu Cys Thr Asn Met
65                  70                  75                  80
Leu Ser Glu Val Leu Leu Phe Leu Ser Gln Tyr Leu Thr Leu Cys Gly
                85                  90                  95
Asp Ile Gln Leu Met Leu Ala Gln Asn Ala Asn Asn Arg Ala Ala His
            100                 105                 110
Leu Glu Glu Phe His Tyr Gln Thr Lys Glu Asp Gln Glu Ile Leu His
        115                 120                 125
Ser Leu His Arg Glu Ser Ser Cys Gln Gly Val Pro Gln Ala Trp Thr
    130                 135                 140
Thr Trp Phe Thr Val Gly Leu Cys Ser Leu Ala His Ala Tyr Leu Ser
145                 150                 155                 160
Ile Gln Lys Arg Gly Arg Asn Ile Arg Val Leu Ile Phe Ala Leu Tyr
                165                 170                 175
Leu Phe Ile Tyr Phe Leu Arg Arg Ser Phe Ala Leu Val Ala Gln Ala
            180                 185                 190
Gly Val Gln Trp Cys Asn Leu Gly Ser Leu Lys Pro Pro Pro Pro Gly
        195                 200                 205
Phe Lys Gln Phe Ser Cys Leu Ser Leu Pro Ser Ser Trp Asn Tyr Arg
    210                 215                 220
His Ala Pro Pro Cys Pro Ala Ser Pro Pro Trp Pro Pro Lys Val Leu
225                 230                 235                 240
Gly Leu Gln Val
```

<210> SEQ ID NO 47
<211> LENGTH: 79
<212> TYPE: PRT
<213> ORGANISM: Homo sapiens

<400> SEQUENCE: 47

```
Arg Ser Leu Thr Leu Trp Pro Ser Leu Glu Tyr Ser Gly Thr Ile Ser
 1               5                  10                  15
Ala His Cys Asn Leu Arg Leu Pro Gly Ser Ser Asp Ser Arg Ala Ser
            20                  25                  30
Ala Ser Arg Ala Ala Gly Ile Thr Gly Val Ser His Cys Ala Arg Pro
        35                  40                  45
Cys Met Leu Phe Asp Pro Glu Phe Asp Leu Leu Ala Gly Val Gln Leu
    50                  55                  60
Leu Pro Phe Glu Pro Pro Thr Gly Lys Ala Leu Ser Arg Lys Asp
65                  70                  75
```

<210> SEQ ID NO 48
<211> LENGTH: 495
<212> TYPE: PRT
<213> ORGANISM: Homo sapiens

<400> SEQUENCE: 48

```
Met Glu Phe Arg Lys Leu Arg Gly Met Glu Thr Arg Pro Pro Ala Asn
1               5                   10                  15

Thr Ala Arg Leu Gln Pro Pro Arg Asp Leu Arg Ser Ser Ser Pro Arg
            20                  25                  30

Lys Gln Leu Ser Glu Ser Ser Asp Asp Tyr Asp Asp Val Asp Ile
        35                  40                  45

Pro Thr Pro Ala Glu Asp Thr Pro Pro Leu Pro Pro Lys Pro Lys
    50                  55                  60

Phe Arg Ser Pro Ser Asp Glu Gly Pro Gly Ser Met Gly Asp Asp Gly
65                  70                  75                  80

Gln Leu Ser Pro Gly Val Leu Val Arg Cys Ala Ser Gly Pro Pro
            85                  90                  95

Asn Ser Pro Arg Pro Gly Pro Pro Ser Thr Ser Ser Pro His Leu
            100                 105                 110

Thr Ala His Ser Glu Pro Ser Leu Trp Asn Pro Pro Ser Arg Glu Leu
            115                 120                 125

Asp Lys Pro Pro Leu Leu Pro Pro Lys Lys Glu Lys Met Lys Arg Lys
            130                 135                 140

Gly Cys Ala Leu Leu Val Lys Leu Phe Asn Gly Cys Pro Leu Arg Ile
145                 150                 155                 160

His Ser Thr Ala Ala Trp Thr His Pro Ser Thr Lys Asp Gln His Leu
                165                 170                 175

Leu Leu Gly Ala Glu Glu Gly Ile Phe Ile Leu Asn Arg Asn Asp Gln
            180                 185                 190

Glu Ala Thr Leu Glu Met Leu Phe Pro Ser Arg Thr Thr Trp Val Tyr
            195                 200                 205

Ser Ile Asn Asn Val Leu Met Ser Leu Ser Gly Lys Thr Pro His Leu
            210                 215                 220

Tyr Ser His Ser Ile Leu Gly Leu Leu Glu Arg Lys Glu Thr Arg Ala
225                 230                 235                 240

Gly Asn Pro Ile Ala His Ile Ser Pro His Arg Leu Leu Ala Arg Lys
            245                 250                 255

Asn Met Val Ser Thr Lys Ile Gln Asp Thr Lys Gly Cys Arg Ala Cys
            260                 265                 270

Cys Val Ala Glu Gly Ala Ser Ser Gly Gly Pro Phe Leu Cys Gly Ala
            275                 280                 285

Leu Glu Thr Ser Val Val Leu Leu Gln Trp Tyr Gln Pro Met Asn Lys
            290                 295                 300

Phe Leu Leu Val Arg Gln Val Leu Phe Pro Leu Pro Thr Pro Leu Ser
305                 310                 315                 320

Val Phe Ala Leu Leu Thr Gly Pro Gly Ser Glu Leu Pro Ala Val Cys
            325                 330                 335

Ile Gly Val Ser Pro Gly Arg Pro Gly Lys Ser Val Leu Phe His Thr
            340                 345                 350

Val Arg Phe Gly Ala Leu Ser Cys Trp Leu Gly Glu Met Ser Thr Glu
            355                 360                 365

His Arg Gly Pro Val Gln Val Thr Gln Val Glu Glu Asp Met Val Met
            370                 375                 380

Val Leu Met Asp Gly Ser Val Lys Leu Val Thr Pro Glu Gly Ser Pro
385                 390                 395                 400

Val Arg Gly Leu Arg Thr Pro Glu Ile Pro Met Thr Glu Ala Val Glu
```

```
                    405                 410                 415
Ala Val Ala Met Val Gly Gly Gln Leu Gln Ala Phe Trp Lys His Gly
                420                 425                 430

Val Gln Val Trp Ala Leu Gly Ser Asp Gln Leu Leu Gln Glu Leu Arg
            435                 440                 445

Asp Pro Thr Leu Thr Phe Arg Leu Leu Gly Ser Pro Arg Leu Glu Cys
        450                 455                 460

Ser Gly Thr Ile Ser Pro His Cys Asn Leu Leu Pro Gly Ser Ser
465                 470                 475                 480

Asn Ser Pro Ala Ser Ala Ser Arg Val Ala Gly Ile Thr Gly Leu
                485                 490                 495

<210> SEQ ID NO 49
<211> LENGTH: 102
<212> TYPE: PRT
<213> ORGANISM: Homo sapiens

<400> SEQUENCE: 49

Met Ser Met Val Leu Gly Gly Pro Phe Ser Lys Gly His Thr Ala Ser
  1               5                  10                  15

Asp Glu Tyr Phe Gln Ile Phe His Asn Ile Ser Phe Phe Glu Thr Glu
             20                  25                  30

Ser Cys Ser Val Ala Gln Ala Gly Val Gln Trp Cys Asn Leu Gly Ser
         35                  40                  45

Leu Gln Ala Leu Pro Pro Arg Phe Thr Pro Phe Ser Cys Leu Ser Leu
     50                  55                  60

Pro Ser Ser Trp Asp Tyr Arg His Pro Pro Cys Pro Asp Asn Val
 65                  70                  75                  80

Phe Val Phe Ser Val Glu Thr Gly Leu His Cys Val Ser Gln Asp Gly
                 85                  90                  95

Leu Asn Leu Leu Thr Leu
            100

<210> SEQ ID NO 50
<211> LENGTH: 257
<212> TYPE: PRT
<213> ORGANISM: Homo sapiens

<400> SEQUENCE: 50

Met Asp Cys Gly Ser Val Gly Gly Gln Arg Thr Gln Arg Leu Pro Gly
  1               5                  10                  15

Arg Gln Arg Leu Leu Phe Leu Pro Val Gly Leu Ser Gly Arg Pro Gly
             20                  25                  30

Gly Ser Glu Thr Ser Ala Arg Arg Cys Leu Ser Ala Leu Ser Asp Gly
         35                  40                  45

Leu Gly Ala Leu Arg Pro Arg Ala Pro Ala Ala Arg Gly Gly Val Ser
     50                  55                  60

Arg Ala Ser Pro Leu Leu Leu Leu Leu Val Pro Ser Pro Arg Leu
 65                  70                  75                  80

Ala Ala Ala Ala Pro Arg Arg Gln Leu Gly Asp Trp Glu Arg Ser Arg
                 85                  90                  95

Leu Gly Tyr Ala Ala Pro Pro Gly Arg Ser Ser Ala Trp Arg Cys
            100                 105                 110

Ser Pro Gly Val Ala Ala Ala Gly Ala Leu Pro Gln Tyr His Gly
            115                 120                 125

Pro Ala Pro Ala Leu Val Ser Cys Arg Arg Glu Leu Ser Leu Ser Ala
```

-continued

```
            130                 135                 140
Gly Ser Leu Gln Leu Glu Arg Lys Arg Arg Asp Phe Thr Ser Ser Gly
145                 150                 155                 160

Ser Arg Lys Leu Tyr Phe Asp Thr His Ala Leu Val Cys Leu Leu Glu
                165                 170                 175

Asp Asn Glu Ser His Ser Phe Ile Gln Ala Gly Val Gln Trp His Ser
            180                 185                 190

Leu Gly Leu Leu Gln Pro Pro Pro Gly Phe Lys Arg Ser Ser His
                195                 200                 205

Leu Ile Leu Leu Ser Ser Trp Asp Tyr Arg His Ala Pro Pro His Leu
210                 215                 220

Asp Asn Phe Ser Val Phe Leu Leu Glu Thr Gly Phe His His Val Gly
225                 230                 235                 240

Gln Ala Gly Leu Lys Leu Leu Thr Ser Ser Asp Pro Pro Thr Leu Ala
                245                 250                 255

Ser
```

<210> SEQ ID NO 51
<211> LENGTH: 92
<212> TYPE: PRT
<213> ORGANISM: Homo sapiens

<400> SEQUENCE: 51

```
Met Asn Phe Phe Lys Thr Glu Phe Leu Ser Val Thr Gln Ala Gly
  1               5                  10                  15

Met Gln Trp His Asn Phe Ser Ser Leu Gln Pro Leu Pro Pro Gly Phe
                20                  25                  30

Lys Gln Phe Ser Cys Leu Ser Leu Leu Ser Ser Trp Asp Tyr Arg His
            35                  40                  45

Thr Pro Pro Cys Pro Ala Asn Phe Cys Ile Phe Ser Arg Gly Gly Val
        50                  55                  60

Ser Pro Cys Trp Ser Gly Trp Ser Arg Thr Pro Asp Phe Met Ile His
65                  70                  75                  80

Pro Pro Arg Pro Pro Lys Val Leu Arg Leu Gln Lys
                85                  90
```

<210> SEQ ID NO 52
<211> LENGTH: 841
<212> TYPE: PRT
<213> ORGANISM: Homo sapiens

<400> SEQUENCE: 52

```
Met Pro Leu Ala Ala Tyr Cys Tyr Leu Arg Val Val Gly Lys Gly Ser
  1               5                  10                  15

Tyr Gly Glu Val Thr Leu Val Lys His Arg Arg Asp Gly Lys Gln Tyr
                20                  25                  30

Val Ile Lys Lys Leu Asn Leu Arg Asn Ala Ser Ser Arg Glu Arg Arg
            35                  40                  45

Ala Ala Glu Gln Glu Ala Gln Leu Leu Ser Gln Leu Lys His Pro Asn
        50                  55                  60

Ile Val Thr Tyr Lys Glu Ser Trp Glu Gly Gly Asp Gly Leu Leu Tyr
65                  70                  75                  80

Ile Val Met Gly Phe Cys Glu Gly Gly Asp Leu Tyr Arg Lys Leu Lys
                85                  90                  95

Glu Gln Lys Gly Gln Leu Leu Pro Glu Asn Gln Val Val Glu Trp Phe
            100                 105                 110
```

-continued

Val Gln Ile Ala Met Ala Leu Gln Tyr Leu His Glu Lys His Ile Leu
        115                 120                 125

His Arg Asp Leu Lys Thr Gln Asn Val Phe Leu Thr Arg Thr Asn Ile
    130                 135                 140

Ile Lys Val Gly Asp Leu Gly Ile Ala Arg Val Leu Glu Asn His Cys
145                 150                 155                 160

Asp Met Ala Ser Thr Leu Ile Gly Thr Pro Tyr Tyr Met Ser Pro Glu
                165                 170                 175

Leu Phe Ser Asn Lys Pro Tyr Asn Tyr Lys Ser Asp Val Trp Ala Leu
            180                 185                 190

Gly Cys Cys Val Tyr Glu Met Ala Thr Leu Lys His Ala Phe Asn Ala
        195                 200                 205

Lys Asp Met Asn Ser Leu Val Tyr Arg Ile Ile Glu Gly Lys Leu Pro
210                 215                 220

Pro Met Pro Arg Asp Tyr Ser Pro Glu Leu Ala Glu Leu Ile Arg Thr
225                 230                 235                 240

Met Leu Ser Lys Arg Pro Glu Arg Pro Ser Val Arg Ser Ile Leu
                245                 250                 255

Arg Gln Pro Tyr Ile Lys Arg Gln Ile Ser Phe Phe Leu Glu Ala Thr
                260                 265                 270

Lys Ile Lys Thr Ser Lys Asn Asn Ile Lys Asn Gly Asp Ser Gln Ser
            275                 280                 285

Lys Pro Phe Ala Thr Val Val Ser Gly Glu Ala Glu Ser Asn His Glu
        290                 295                 300

Val Ile His Pro Gln Pro Leu Ser Ser Glu Gly Ser Gln Thr Tyr Ile
305                 310                 315                 320

Met Gly Glu Gly Lys Cys Leu Ser Gln Glu Lys Pro Arg Ala Ser Gly
                325                 330                 335

Leu Leu Lys Ser Pro Ala Ser Leu Lys Ala His Thr Cys Lys Gln Asp
            340                 345                 350

Leu Ser Asn Thr Thr Glu Leu Ala Thr Ile Ser Ser Val Asn Ile Asp
        355                 360                 365

Ile Leu Pro Ala Lys Gly Arg Asp Ser Val Ser Asp Gly Phe Val Gln
370                 375                 380

Glu Asn Gln Pro Arg Tyr Leu Asp Ala Ser Asn Glu Leu Gly Gly Ile
385                 390                 395                 400

Cys Ser Ile Ser Gln Val Glu Glu Met Leu Gln Asp Asn Thr Lys
                405                 410                 415

Ser Ser Ala Gln Pro Glu Asn Leu Ile Pro Met Trp Ser Ser Asp Ile
            420                 425                 430

Val Thr Gly Glu Lys Asn Glu Pro Val Lys Pro Leu Gln Pro Leu Ile
        435                 440                 445

Lys Glu Gln Lys Pro Lys Asp Gln Ser Leu Ala Leu Ser Pro Lys Leu
450                 455                 460

Glu Cys Ser Gly Thr Ile Leu Ala His Ser Asn Leu Arg Leu Leu Gly
465                 470                 475                 480

Ser Ser Asp Ser Pro Ala Ser Ala Ser Arg Val Ala Gly Ile Thr Gly
                485                 490                 495

Val Cys His His Ala Gln Asp Gln Val Ala Gly Glu Cys Ile Ile Glu
            500                 505                 510

Lys Gln Gly Arg Ile His Pro Asp Leu Gln Pro His Asn Ser Gly Ser
        515                 520                 525

```
Glu Pro Ser Leu Ser Arg Gln Arg Arg Gln Lys Arg Arg Glu Gln Thr
    530                 535                 540
Glu His Arg Gly Glu Lys Arg Gln Val Arg Arg Asp Leu Phe Ala Phe
545                 550                 555                 560
Gln Glu Ser Pro Pro Arg Phe Leu Pro Ser His Pro Ile Val Gly Lys
                565                 570                 575
Val Asp Val Thr Ser Thr Gln Lys Glu Ala Glu Asn Gln Arg Arg Val
            580                 585                 590
Val Thr Gly Ser Val Ser Ser Arg Ser Ser Glu Met Ser Ser Ser
        595                 600                 605
Lys Asp Arg Pro Leu Ser Ala Arg Glu Arg Arg Leu Lys Gln Ser
    610                 615                 620
Gln Glu Glu Met Ser Ser Ser Gly Pro Ser Val Arg Lys Ala Ser Leu
625                 630                 635                 640
Ser Val Ala Gly Pro Gly Lys Pro Gln Glu Glu Asp Gln Pro Leu Pro
                645                 650                 655
Ala Arg Arg Leu Ser Ser Asp Cys Ser Val Thr Gln Glu Arg Lys Gln
            660                 665                 670
Ile His Cys Leu Ser Glu Asp Glu Leu Ser Ser Ser Thr Ser Ser Thr
        675                 680                 685
Asp Lys Ser Asp Gly Asp Tyr Gly Glu Gly Lys Gly Gln Thr Asn Glu
    690                 695                 700
Ile Asn Ala Leu Val Gln Leu Met Thr Gln Thr Leu Lys Leu Asp Ser
705                 710                 715                 720
Lys Glu Ser Cys Glu Asp Val Pro Val Ala Asn Pro Val Ser Glu Phe
                725                 730                 735
Lys Leu His Arg Lys Tyr Arg Asp Thr Leu Ile Leu His Gly Lys Val
            740                 745                 750
Ala Glu Glu Ala Glu Glu Ile His Phe Lys Glu Leu Pro Ser Ala Ile
        755                 760                 765
Met Pro Gly Ser Glu Lys Ile Arg Arg Leu Val Glu Val Leu Arg Thr
    770                 775                 780
Asp Val Ile Arg Gly Leu Gly Val Gln Leu Leu Glu Gln Val Tyr Asp
785                 790                 795                 800
Leu Leu Glu Glu Glu Asp Glu Phe Asp Arg Glu Val Arg Leu Arg Glu
                805                 810                 815
His Met Gly Glu Lys Tyr Thr Thr Tyr Ser Val Lys Ala Arg Gln Leu
            820                 825                 830
Lys Phe Phe Glu Glu Asn Met Asn Phe
        835                 840

<210> SEQ ID NO 53
<211> LENGTH: 85
<212> TYPE: PRT
<213> ORGANISM: Homo sapiens

<400> SEQUENCE: 53

Met Phe Ile Ser Phe Gly Arg Leu Ile Phe Ser Phe Phe Leu Thr Trp
1               5                   10                  15
Ser Leu Ser Leu Ser Pro Arg Leu Glu Cys Ser Gly Thr Ile Leu Ala
            20                  25                  30
His Cys Asn Pro Thr Ser Gln Val Gln Ala Ile Leu Pro Ala Ser Ala
        35                  40                  45
Ser Arg Val Ala Gly Ile Thr Gly Met His His Thr Cys Leu Ile
    50                  55                  60
```

```
Phe Val Leu Leu Val Lys Met Gly Phe Cys His Val Gly His Ala Gly
 65                  70                  75                  80

Leu Glu Leu Val Thr
                85

<210> SEQ ID NO 54
<211> LENGTH: 73
<212> TYPE: PRT
<213> ORGANISM: Homo sapiens

<400> SEQUENCE: 54

Met Glu Ser Gly Gln Pro Ser Leu Ser Phe Tyr Phe Leu Phe Ile Tyr
  1               5                  10                  15

Phe Phe Glu Ile Gly Ser His Phe Val Thr Gln Ala Gly Val Gln Trp
                 20                  25                  30

His Asn Leu Asp Ser Leu Gln Leu Ser Leu Ala Ser Ala Pro Gln Val
             35                  40                  45

Ala Gly Thr Thr Gly Ala Cys His His Ala Arg Leu Ile Phe Gly Val
         50                  55                  60

Phe Cys Arg Asp Trp Val Leu Pro Cys
 65                  70

<210> SEQ ID NO 55
<211> LENGTH: 181
<212> TYPE: PRT
<213> ORGANISM: Homo sapiens

<400> SEQUENCE: 55

Met Leu Leu Val Asp Ala Asp Gln Pro Glu Pro Met Arg Ser Gly Ala
  1               5                  10                  15

Arg Glu Leu Ala Leu Phe Leu Thr Pro Glu Pro Gly Ala Glu Ala Lys
                 20                  25                  30

Glu Val Glu Glu Thr Ile Glu Gly Met Leu Leu Arg Leu Glu Glu Phe
             35                  40                  45

Cys Ser Leu Ala Asp Leu Ile Arg Ser Asp Thr Ser Gln Ile Leu Glu
         50                  55                  60

Glu Asn Ile Pro Val Leu Lys Ala Lys Leu Thr Glu Met Arg Gly Ile
 65                  70                  75                  80

Tyr Ala Lys Val Asp Arg Leu Glu Ala Phe Val Lys Met Val Gly His
                 85                  90                  95

His Val Ala Phe Leu Glu Ala Asp Val Leu Gln Ala Glu Arg Asp His
            100                 105                 110

Gly Ala Phe Pro Gln Ala Leu Arg Arg Trp Leu Gly Ser Ala Gly Leu
        115                 120                 125

Pro Ser Phe Arg Asn Val Glu Cys Ser Gly Thr Ile Pro Ala Arg Cys
130                 135                 140

Asn Leu Arg Leu Pro Gly Ser Ser Asp Ser Pro Ala Ser Ala Ser Gln
145                 150                 155                 160

Val Ala Gly Ile Pro Glu Val Thr Cys Thr Gly Ala Arg Asp Val Arg
                165                 170                 175

Ala Ala His Thr Val
            180

<210> SEQ ID NO 56
<211> LENGTH: 876
<212> TYPE: PRT
<213> ORGANISM: Rattus norvegicus
```

<400> SEQUENCE: 56

```
Met Ser Arg Gly Asn Glu Asn Arg Leu Thr His Arg Arg Gln Thr Val
 1               5                  10                  15

Leu Arg Glu Lys Gly Arg Arg Leu Ala Asn Arg Gly Pro Ala Tyr Met
                20                  25                  30

Phe Asn Asp His Ser Thr Ser Leu Ser Ile Glu Glu Arg Phe Leu
                35                  40                  45

Asp Ala Ala Glu Tyr Gly Asn Ile Pro Val Val Arg Lys Met Leu Glu
        50                  55                  60

Glu Cys Leu Ser Leu Asn Val Asn Cys Val Asp Tyr Met Gly Gln Asn
 65                  70                  75                  80

Ala Leu Gln Leu Ala Val Ala Asn Glu His Leu Glu Ile Thr Glu Leu
                85                  90                  95

Leu Leu Lys Lys Glu Asn Leu Ser Arg Val Gly Asp Ala Leu Leu Leu
                100                 105                 110

Ala Ile Ser Lys Gly Tyr Val Arg Ile Val Glu Ala Ile Leu Asn His
                115                 120                 125

Pro Ala Phe Ala Glu Gly Lys Arg Leu Ala Thr Ser Pro Ser Gln Ser
        130                 135                 140

Glu Leu Gln Gln Asp Asp Phe Tyr Ala Tyr Asp Glu Asp Gly Thr Arg
145                 150                 155                 160

Phe Ser His Asp Val Thr Pro Ile Ile Leu Ala Ala His Cys Gln Glu
                165                 170                 175

Tyr Glu Ile Val His Thr Leu Leu Arg Lys Gly Ala Arg Ile Glu Arg
                180                 185                 190

Pro His Asp Tyr Phe Cys Lys Cys Thr Glu Cys Ser Gln Lys Gln Lys
                195                 200                 205

His Asp Ser Phe Ser His Ser Arg Ser Arg Ile Asn Ala Tyr Lys Gly
        210                 215                 220

Leu Ala Ser Pro Ala Tyr Leu Ser Leu Ser Ser Glu Asp Pro Val Met
225                 230                 235                 240

Thr Ala Leu Glu Leu Ser Asn Glu Leu Ala Val Leu Ala Asn Ile Glu
                245                 250                 255

Lys Glu Phe Lys Asn Asp Tyr Arg Lys Leu Ser Met Gln Cys Lys Asp
                260                 265                 270

Phe Val Val Gly Leu Leu Asp Leu Cys Arg Asn Thr Glu Glu Val Glu
                275                 280                 285

Ala Ile Leu Asn Gly Asp Ala Glu Thr Arg Gln Pro Gly Asp Leu Ala
                290                 295                 300

Arg Pro Asn Leu Ser Arg Leu Lys Leu Ala Ile Lys Tyr Glu Val Lys
305                 310                 315                 320

Lys Phe Val Ala His Pro Asn Cys Gln Gln Leu Leu Ser Ile Trp
                325                 330                 335

Tyr Glu Asn Leu Ser Gly Leu Arg Gln Gln Thr Met Ala Val Lys Phe
                340                 345                 350

Leu Val Val Leu Ala Val Ala Ile Gly Leu Pro Phe Leu Ala Leu Ile
                355                 360                 365

Tyr Trp Cys Ala Pro Cys Ser Lys Met Gly Lys Ile Leu Arg Gly Pro
        370                 375                 380

Phe Met Lys Phe Val Ala His Ala Ala Ser Phe Thr Ile Phe Leu Gly
385                 390                 395                 400

Leu Leu Val Met Asn Ala Ala Asp Arg Phe Glu Gly Thr Lys Leu Leu
```

```
                    405                 410                 415
Pro Asn Glu Thr Ser Thr Asp Asn Ala Arg Gln Leu Phe Arg Met Lys
                420                 425                 430
Thr Ser Cys Phe Ser Trp Met Glu Met Leu Ile Ile Ser Trp Val Ile
            435                 440                 445
Gly Met Ile Trp Ala Glu Cys Lys Glu Ile Trp Thr Gln Gly Pro Lys
        450                 455                 460
Glu Tyr Leu Phe Glu Leu Trp Asn Met Leu Asp Phe Gly Met Leu Ala
465                 470                 475                 480
Ile Phe Ala Ala Ser Phe Ile Ala Arg Phe Met Ala Phe Trp His Ala
                485                 490                 495
Ser Lys Ala Gln Ser Ile Ile Asp Ala Asn Asp Thr Leu Lys Asp Leu
                500                 505                 510
Thr Lys Val Thr Leu Gly Asp Asn Val Lys Tyr Tyr Asn Leu Ala Arg
            515                 520                 525
Ile Lys Trp Asp Pro Thr Asp Pro Gln Ile Ile Ser Glu Gly Leu Tyr
        530                 535                 540
Ala Ile Ala Val Val Leu Ser Phe Ser Arg Ile Ala Tyr Ile Leu Pro
545                 550                 555                 560
Ala Asn Glu Ser Phe Gly Pro Leu Gln Ile Ser Leu Gly Arg Thr Val
                565                 570                 575
Lys Asp Ile Phe Lys Phe Met Val Ile Phe Ile Met Val Phe Val Ala
            580                 585                 590
Phe Met Ile Gly Met Phe Asn Leu Tyr Ser Tyr Ile Gly Ala Lys
        595                 600                 605
Gln Asn Glu Ala Phe Thr Thr Val Glu Glu Ser Phe Lys Thr Leu Phe
610                 615                 620
Trp Ala Ile Phe Gly Leu Ser Glu Val Lys Ser Val Val Ile Asn Tyr
625                 630                 635                 640
Asn His Lys Phe Ile Glu Asn Ile Gly Tyr Val Leu Tyr Gly Val Tyr
                645                 650                 655
Asn Val Thr Met Val Ile Val Leu Leu Asn Met Leu Ile Ala Met Ile
                660                 665                 670
Asn Ser Ser Phe Gln Glu Ile Glu Asp Asp Ala Asp Val Glu Trp Lys
            675                 680                 685
Phe Ala Arg Ala Lys Leu Trp Phe Ser Tyr Phe Glu Glu Gly Arg Thr
        690                 695                 700
Leu Pro Val Pro Phe Asn Leu Val Pro Ser Pro Lys Ser Leu Leu Tyr
705                 710                 715                 720
Leu Leu Leu Lys Phe Lys Lys Trp Met Ser Glu Leu Ile Gln Gly His
                725                 730                 735
Lys Lys Gly Phe Gln Glu Asp Ala Glu Met Asn Lys Arg Asn Glu Glu
            740                 745                 750
Lys Lys Phe Gly Ile Leu Gly Ser His Glu Asp Leu Ser Lys Phe Ser
        755                 760                 765
Leu Asp Arg Asn Gln Leu Ala His Asn Lys Gln Ser Ser Thr Arg Ser
        770                 775                 780
Ser Glu Asp Phe His Leu Asn Ser Phe Ser Asn Pro Pro Arg Gln Tyr
785                 790                 795                 800
Gln Lys Ile Met Lys Arg Leu Ile Lys Arg Tyr Val Leu Gln Ala Gln
                805                 810                 815
Ile Asp Lys Glu Ser Asp Glu Val Asn Glu Gly Glu Leu Lys Glu Ile
            820                 825                 830
```

```
Lys Gln Asp Ile Ser Ser Leu Arg Tyr Glu Leu Leu Glu Glu Lys Ser
        835                 840                 845

Gln Asn Thr Glu Asp Leu Ala Glu Leu Ile Arg Lys Leu Gly Glu Arg
        850                 855                 860

Leu Ser Leu Glu Ser Lys Gln Glu Glu Ser Arg Arg
865                 870                 875

<210> SEQ ID NO 57
<211> LENGTH: 808
<212> TYPE: PRT
<213> ORGANISM: Rattus norvegicus

<400> SEQUENCE: 57

Met Ser Arg Gly Asn Glu Asn Arg Leu Thr His Arg Arg Gln Thr Val
  1               5                  10                  15

Leu Arg Glu Lys Gly Arg Arg Leu Ala Asn Arg Gly Pro Ala Tyr Met
                 20                  25                  30

Phe Asn Asp His Ser Thr Ser Leu Ser Ile Glu Glu Arg Phe Leu
         35                  40                  45

Asp Ala Ala Glu Tyr Gly Asn Ile Pro Val Val Arg Lys Met Leu Glu
     50                  55                  60

Glu Cys Leu Ser Leu Asn Val Asn Cys Val Asp Tyr Met Gly Gln Asn
 65                  70                  75                  80

Ala Leu Gln Leu Ala Val Ala Asn Glu His Leu Glu Ile Thr Glu Leu
                 85                  90                  95

Leu Leu Lys Lys Glu Asn Leu Ser Arg Val Gly Asp Ala Leu Leu Leu
                100                 105                 110

Ala Ile Ser Lys Gly Tyr Val Arg Ile Val Glu Ala Ile Leu Asn His
            115                 120                 125

Pro Ala Phe Ala Glu Gly Lys Arg Leu Ala Thr Ser Pro Ser Gln Ser
130                 135                 140

Glu Leu Gln Gln Asp Asp Phe Tyr Ala Tyr Asp Glu Asp Gly Thr Arg
145                 150                 155                 160

Phe Ser His Asp Val Thr Pro Ile Ile Leu Ala Ala His Cys Gln Glu
                165                 170                 175

Tyr Glu Ile Val His Thr Leu Leu Arg Lys Gly Ala Arg Ile Glu Arg
                180                 185                 190

Pro His Asp Tyr Phe Cys Lys Cys Thr Glu Cys Ser Gln Lys Gln Lys
            195                 200                 205

His Asp Ser Phe Ser His Ser Arg Ser Arg Ile Asn Ala Tyr Lys Gly
        210                 215                 220

Leu Ala Ser Pro Ala Tyr Leu Ser Leu Ser Ser Glu Asp Pro Val Met
225                 230                 235                 240

Thr Ala Leu Glu Leu Ser Asn Glu Leu Ala Val Leu Ala Asn Ile Glu
                245                 250                 255

Lys Glu Phe Lys Asn Asp Tyr Arg Lys Leu Ser Met Gln Cys Lys Asp
                260                 265                 270

Phe Val Val Gly Leu Leu Asp Leu Cys Arg Asn Thr Glu Glu Val Glu
            275                 280                 285

Ala Ile Leu Asn Gly Asp Ala Glu Thr Arg Gln Pro Gly Asp Leu Ala
        290                 295                 300

Arg Pro Asn Leu Ser Arg Leu Lys Leu Ala Ile Lys Tyr Glu Val Lys
305                 310                 315                 320

Lys Phe Val Ala His Pro Asn Cys Gln Gln Gln Leu Leu Ser Ile Trp
```

```
                325                 330                 335
Tyr Glu Asn Leu Ser Gly Leu Arg Gln Gln Thr Met Ala Val Lys Phe
                340                 345                 350

Leu Val Val Leu Ala Val Ala Ile Gly Leu Pro Phe Leu Ala Leu Ile
                355                 360                 365

Tyr Trp Cys Ala Pro Cys Ser Lys Met Gly Lys Ile Leu Arg Gly Pro
370                 375                 380

Phe Met Lys Phe Val Ala His Ala Ala Ser Phe Thr Ile Phe Leu Gly
385                 390                 395                 400

Leu Leu Val Met Asn Ala Ala Asp Arg Phe Glu Gly Thr Lys Leu Leu
                405                 410                 415

Pro Asn Glu Thr Ser Thr Asp Asn Ala Arg Gln Leu Phe Arg Met Lys
                420                 425                 430

Thr Ser Cys Phe Ser Trp Met Glu Met Leu Ile Ile Ser Trp Val Ile
                435                 440                 445

Gly Met Ile Trp Ala Glu Cys Lys Glu Ile Trp Thr Gln Gly Pro Lys
                450                 455                 460

Glu Tyr Leu Phe Glu Leu Trp Asn Met Leu Asp Phe Gly Met Leu Ala
465                 470                 475                 480

Ile Phe Ala Ala Ser Phe Ile Ala Arg Phe Met Ala Phe Trp His Ala
                485                 490                 495

Ser Lys Ala Gln Ser Ile Ile Asp Ala Asn Asp Thr Leu Lys Asp Leu
                500                 505                 510

Thr Lys Val Thr Leu Gly Asp Asn Val Lys Tyr Tyr Asn Leu Ala Arg
                515                 520                 525

Ile Lys Trp Asp Pro Thr Asp Pro Gln Ile Ile Ser Glu Gly Leu Tyr
                530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
                580                 585                 590

Phe Met Ile Gly Met Phe Asn Leu Tyr Ser Tyr Tyr Ile Gly Ala Lys
                595                 600                 605

Gln Asn Glu Ala Phe Thr Thr Val Glu Glu Ser Phe Lys Thr Leu Phe
                610                 615                 620

Trp Ala Ile Phe Gly Leu Ser Glu Val Arg Ser Val Val Ile Asn Tyr
625                 630                 635                 640

Asn His Lys Phe Ile Glu Asn Ile Gly Tyr Val Leu Tyr Gly Val Tyr
                645                 650                 655

Asn Val Thr Met Val Ile Val Leu Leu Asn Met Leu Ile Ala Met Ile
                660                 665                 670

Asn Ser Ser Phe Gln Glu Ile Glu Arg Asn Glu Lys Lys Phe Gly
                675                 680                 685

Ile Leu Gly Ser His Glu Asp Leu Ser Lys Phe Ser Leu Asp Arg Asn
                690                 695                 700

Gln Leu Ala His Asn Lys Gln Ser Ser Thr Arg Ser Ser Glu Asp Phe
705                 710                 715                 720

His Leu Asn Ser Phe Ser Asn Pro Pro Arg Gln Tyr Gln Lys Ile Met
                725                 730                 735

Lys Arg Leu Ile Lys Arg Tyr Val Leu Gln Ala Gln Ile Asp Lys Glu
                740                 745                 750
```

```
Ser Asp Glu Val Asn Glu Gly Leu Lys Glu Ile Lys Gln Asp Ile
        755                 760                 765
Ser Ser Leu Arg Tyr Glu Leu Leu Glu Lys Ser Gln Asn Thr Glu
        770                 775                 780
Asp Leu Ala Glu Leu Ile Arg Arg Leu Gly Glu Arg Leu Ser Leu Glu
785                 790                 795                 800
Ser Lys Gln Glu Glu Ser Arg Arg
                805

<210> SEQ ID NO 58
<211> LENGTH: 83
<212> TYPE: PRT
<213> ORGANISM: Homo sapiens

<400> SEQUENCE: 58

Met Glu Ser Arg Ser Val Ala Gln Ala Gly Val Gln Trp Pro Asp Leu
1               5                   10                  15
Gly Ser Leu Gln Pro Leu Pro Pro Arg Phe Lys Arg Phe Phe Cys Leu
                20                  25                  30
Ser Leu Gln Ser Ser Trp Asp Tyr Arg His Ala Pro Pro Arg Pro Ala
            35                  40                  45
Asn Phe Val Phe Leu Val Glu Thr Gly Phe Cys His Val Ser Gln Ala
        50                  55                  60
Gly Leu Glu Leu Leu Thr Ser Ser Asp Pro Pro Arg Pro Pro Lys
65                  70                  75                  80
Val Leu Arg

<210> SEQ ID NO 59
<211> LENGTH: 141
<212> TYPE: PRT
<213> ORGANISM: Homo sapiens

<400> SEQUENCE: 59

Met Ile Ser Val His Cys Asn Leu Cys Leu Pro Gly Ser Ser Asp Pro
1               5                   10                  15
Pro Ala Ser Ala Ser Gln Val Ala Gly Ile Thr Gly Val Arg His Cys
                20                  25                  30
Met Ala Ser Gly Ala Val Leu Asn Lys Val Arg Arg His Gln Cys Ser
            35                  40                  45
Gly Asp Leu Glu Val Arg Gly Ser His Gly Ser Leu Gly Glu Ala Pro
        50                  55                  60
Trp Gly Lys Ser Val Pro Gly Arg Gly Thr Ala Ser Arg Lys Gly Pro
65                  70                  75                  80
Gly Ala Gly Val Ile Gly Asn Ser Lys Glu Ala Ser Thr Gly Arg Ala
                85                  90                  95
Gln Trp Ser Ala Pro Val Ile Pro Ala Thr Gln Glu Ala Lys Ala Gly
                100                 105                 110
Gly Leu Leu Glu Pro Arg Ser Leu Ile Ser Ala Trp Ala Thr Tyr Gln
            115                 120                 125
Asp Leu Ile Ser Ile Asn Lys Leu Lys Glu Lys Arg Gly
        130                 135                 140

<210> SEQ ID NO 60
<211> LENGTH: 177
<212> TYPE: PRT
<213> ORGANISM: Homo sapiens
```

-continued

```
<400> SEQUENCE: 60

Met Thr Arg Ser Leu Phe Lys Gly Asn Phe Trp Ser Ala Asp Ile Leu
 1               5                  10                  15

Ser Thr Ile Gly Tyr Asp Asn Ile Ile Gln His Leu Asn Asn Gly Arg
             20                  25                  30

Lys Asn Cys Lys Glu Phe Glu Asp Phe Leu Lys Glu Arg Ala Ala Ile
         35                  40                  45

Glu Glu Arg Tyr Gly Lys Asp Leu Leu Asn Leu Ser Arg Lys Lys Pro
     50                  55                  60

Cys Gly Gln Ser Glu Ile Asn Thr Leu Lys Arg Ala Leu Glu Val Phe
 65                  70                  75                  80

Lys Gln Gln Val Asp Asn Val Ala Gln Cys His Ile Gln Leu Ala Gln
                 85                  90                  95

Ser Leu Arg Glu Glu Ala Arg Lys Met Glu Glu Phe Arg Glu Lys Gln
            100                 105                 110

Lys Leu Gln Arg Lys Lys Met Glu Ser His Ser Val Thr Gln Ala Gly
        115                 120                 125

Ala Gln Trp His Asp Leu Gly Ser Leu Gln Ala Leu Pro Pro Gly Phe
    130                 135                 140

Met Pro Phe Ser Cys Leu Ser Leu Pro Ser Ser Trp Asn Tyr Arg Leu
145                 150                 155                 160

Pro Pro Pro Pro Arg Leu Ala Glu Pro Arg Asn Gln Asp His Gly Val
                165                 170                 175

Ala

<210> SEQ ID NO 61
<211> LENGTH: 66
<212> TYPE: PRT
<213> ORGANISM: Homo sapiens

<400> SEQUENCE: 61

Met Glu Ser His Ser Val Thr Gln Ala Gly Val Gln Trp Arg Asp Leu
 1               5                  10                  15

Gly Ser Leu Gln Pro Leu Pro Pro Gly Phe Lys Gln Phe Ser His Leu
             20                  25                  30

Ser Leu Pro Ser Ser Trp Asp Tyr Arg Arg Val Pro Pro Tyr Leu Gly
         35                  40                  45

Asn Phe Cys Ile Phe Ser Gly Glu Gly Val Ser Pro Cys Trp Pro Gly
     50                  55                  60

Trp Ser
 65

<210> SEQ ID NO 62
<211> LENGTH: 392
<212> TYPE: PRT
<213> ORGANISM: Homo sapiens

<400> SEQUENCE: 62

Met Gly Ser Leu Ser Thr Ala Asn Val Glu Phe Cys Leu Asp Val Phe
 1               5                  10                  15

Lys Glu Leu Asn Ser Asn Asn Ile Gly Asp Asn Ile Phe Phe Ser Ser
             20                  25                  30

Leu Ser Leu Leu Tyr Ala Leu Ser Met Val Leu Leu Gly Ala Arg Gly
         35                  40                  45

Glu Thr Ala Glu Gln Leu Glu Lys Val Leu His Phe Ser His Thr Val
     50                  55                  60
```

```
Asp Ser Leu Lys Pro Gly Phe Lys Asp Ser Pro Lys Cys Ser Gln Ala
 65                  70                  75                  80

Gly Arg Ile His Ser Glu Phe Gly Val Glu Phe Ser Gln Ile Asn Gln
                 85                  90                  95

Pro Asp Ser Asn Cys Thr Leu Ser Ile Ala Asn Arg Leu Tyr Gly Thr
            100                 105                 110

Lys Thr Met Ala Phe His Gln Gln Tyr Leu Ser Cys Ser Glu Lys Trp
        115                 120                 125

Tyr Gln Ala Arg Leu Gln Thr Val Asp Phe Glu Gln Ser Thr Glu Glu
    130                 135                 140

Thr Arg Lys Thr Ile Asn Ala Trp Val Glu Asn Lys Thr Asn Gly Lys
145                 150                 155                 160

Val Ala Asn Leu Phe Gly Lys Ser Thr Ile Asp Pro Ser Ser Val Met
                165                 170                 175

Val Leu Val Asn Thr Ile Tyr Phe Lys Gly Gln Arg Gln Asn Lys Phe
            180                 185                 190

Gln Val Arg Glu Thr Val Lys Ser Pro Phe Gln Leu Ser Glu Gly Lys
        195                 200                 205

Asn Val Thr Val Glu Met Met Tyr Gln Ile Gly Thr Phe Lys Leu Ala
    210                 215                 220

Phe Val Lys Glu Pro Gln Met Gln Val Leu Glu Leu Pro Tyr Val Asn
225                 230                 235                 240

Asn Lys Leu Ser Met Ile Ile Leu Leu Pro Val Gly Ile Ala Asn Leu
                245                 250                 255

Lys Gln Ile Glu Lys Gln Leu Asn Ser Gly Thr Phe His Glu Trp Thr
            260                 265                 270

Ser Ser Ser Asn Met Met Glu Arg Glu Val Glu Val His Leu Pro Arg
        275                 280                 285

Phe Lys Leu Glu Ile Lys Tyr Glu Leu Asn Ser Leu Leu Lys Pro Leu
    290                 295                 300

Gly Val Thr Asp Leu Phe Asn Gln Val Lys Ala Asp Leu Ser Gly Met
305                 310                 315                 320

Ser Pro Thr Lys Gly Leu Tyr Leu Ser Lys Ala Ile His Lys Ser Tyr
                325                 330                 335

Leu Asp Val Ser Glu Glu Gly Thr Glu Ala Ala Ala Thr Gly Asp
            340                 345                 350

Ser Ile Ala Val Lys Ser Leu Pro Met Arg Ala Gln Phe Lys Ala Asn
        355                 360                 365

His Pro Phe Leu Phe Phe Ile Arg His Thr His Thr Asn Thr Ile Leu
    370                 375                 380

Phe Cys Gly Lys Leu Ala Ser Pro
385                 390

<210> SEQ ID NO 63
<211> LENGTH: 982
<212> TYPE: PRT
<213> ORGANISM: Homo sapiens

<400> SEQUENCE: 63

Met Ala Gln Phe Tyr Tyr Lys Arg Asn Val Asn Ala Pro Tyr Arg Asp
  1               5                  10                  15

Arg Ile Pro Leu Arg Ile Val Arg Ala Glu Ser Glu Leu Ser Pro Ser
                 20                  25                  30

Glu Lys Ala Tyr Leu Asn Ala Val Glu Lys Gly Asp Tyr Ala Ser Val
```

-continued

```
                35                  40                  45
Lys Lys Ser Leu Glu Glu Ala Glu Ile Tyr Phe Lys Ile Asn Ile Asn
 50                  55                  60

Cys Ile Asp Pro Leu Gly Arg Thr Ala Leu Leu Ile Ala Ile Glu Asn
 65                  70                  75                  80

Glu Asn Leu Glu Leu Ile Glu Leu Leu Ser Phe Asn Val Tyr Val
                 85                  90                  95

Gly Asp Ala Leu Leu His Ala Ile Arg Lys Glu Val Val Gly Ala Val
                100                 105                 110

Glu Leu Leu Leu Asn His Lys Lys Pro Ser Gly Glu Lys Gln Val Pro
                115                 120                 125

Pro Ile Leu Leu Asp Lys Gln Phe Ser Glu Phe Thr Pro Asp Ile Thr
                130                 135                 140

Pro Ile Ile Leu Ala Ala His Thr Asn Asn Tyr Glu Ile Ile Lys Leu
145                 150                 155                 160

Leu Val Gln Lys Gly Val Ser Val Pro Arg Pro His Glu Val Arg Cys
                165                 170                 175

Asn Cys Val Glu Cys Val Ser Ser Ser Asp Val Asp Ser Leu Arg His
                180                 185                 190

Ser Arg Ser Arg Leu Asn Ile Tyr Lys Ala Leu Ala Ser Pro Ser Leu
                195                 200                 205

Ile Ala Leu Ser Ser Glu Asp Pro Phe Leu Thr Ala Phe Gln Leu Ser
210                 215                 220

Trp Glu Leu Gln Glu Leu Ser Lys Val Glu Asn Glu Phe Lys Ser Glu
225                 230                 235                 240

Tyr Glu Glu Leu Ser Arg Gln Cys Lys Gln Phe Ala Lys Asp Leu Leu
                245                 250                 255

Asp Gln Thr Arg Ser Ser Arg Glu Leu Glu Ile Ile Leu Asn Tyr Arg
                260                 265                 270

Asp Asp Asn Ser Leu Ile Glu Glu Gln Ser Gly Asn Asp Leu Ala Arg
                275                 280                 285

Leu Lys Leu Ala Ile Lys Tyr Arg Gln Lys Glu Phe Val Ala Gln Pro
290                 295                 300

Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys
                340                 345                 350

Ser Pro Leu Gly Leu Phe Ile Arg Lys Pro Phe Ile Lys Phe Ile Cys
                355                 360                 365

His Thr Ala Ser Tyr Leu Thr Phe Leu Phe Leu Leu Leu Leu Ala Ser
                370                 375                 380

Gln His Ile Asp Arg Ser Asp Leu Asn Arg Gln Gly Pro Pro Thr
385                 390                 395                 400

Ile Val Glu Trp Met Ile Leu Pro Trp Val Leu Gly Phe Ile Trp Gly
                405                 410                 415

Glu Ile Lys Gln Met Trp Asp Gly Gly Leu Gln Asp Tyr Ile His Asp
                420                 425                 430

Trp Trp Asn Leu Met Asp Phe Val Met Asn Ser Leu Tyr Leu Ala Thr
                435                 440                 445

Ile Ser Leu Lys Ile Val Ala Phe Val Lys Tyr Ser Ala Leu Asn Pro
450                 455                 460
```

-continued

```
Arg Glu Ser Trp Asp Met Trp His Pro Thr Leu Val Ala Glu Ala Leu
465                 470                 475                 480

Phe Ala Ile Ala Asn Ile Phe Ser Ser Leu Arg Leu Ile Ser Leu Phe
            485                 490                 495

Thr Ala Asn Ser His Leu Gly Pro Leu Gln Ile Ser Leu Gly Arg Met
        500                 505                 510

Leu Leu Asp Ile Leu Lys Phe Leu Phe Ile Tyr Cys Leu Val Leu Leu
    515                 520                 525

Ala Phe Ala Asn Gly Leu Asn Gln Leu Tyr Phe Tyr Tyr Glu Glu Thr
530                 535                 540

Lys Gly Leu Thr Cys Lys Gly Ile Arg Cys Glu Lys Gln Asn Asn Ala
545                 550                 555                 560

Phe Ser Thr Leu Phe Glu Thr Leu Gln Ser Leu Phe Trp Ser Ile Phe
            565                 570                 575

Gly Leu Ile Asn Leu Tyr Val Thr Asn Val Lys Ala Gln His Glu Phe
        580                 585                 590

Thr Glu Phe Val Gly Ala Thr Met Phe Gly Thr Tyr Asn Val Ile Ser
    595                 600                 605

Leu Val Val Leu Leu Asn Met Leu Ile Ala Met Met Asn Asn Ser Tyr
610                 615                 620

Gln Leu Ile Ala Asp His Ala Asp Ile Glu Trp Lys Phe Ala Arg Thr
625                 630                 635                 640

Lys Leu Trp Met Ser Tyr Phe Glu Glu Gly Thr Leu Pro Thr Pro
            645                 650                 655

Phe Asn Val Ile Pro Ser Pro Lys Ser Leu Trp Tyr Leu Ile Lys Trp
        660                 665                 670

Ile Trp Thr His Leu Cys Lys Lys Lys Met Arg Arg Lys Pro Glu Ser
    675                 680                 685

Phe Gly Thr Ile Gly Val Arg Thr Gln His Arg Ala Ala Asp Asn
690                 695                 700

Leu Arg Arg His His Gln Tyr Gln Glu Val Met Arg Asn Leu Val Lys
705                 710                 715                 720

Arg Tyr Val Ala Ala Met Ile Arg Asp Ala Lys Thr Glu Glu Gly Leu
            725                 730                 735

Thr Glu Glu Asn Phe Lys Glu Leu Lys Gln Asp Ile Ser Ser Phe Arg
        740                 745                 750

Phe Glu Val Leu Gly Leu Leu Arg Gly Ser Lys Leu Ser Thr Ile Gln
    755                 760                 765

Ser Ala Asn Ala Ser Lys Glu Ser Ser Asn Ser Ala Asp Ser Asp Glu
770                 775                 780

Lys Ser Asp Ser Glu Gly Asn Ser Lys Asp Lys Lys Asn Phe Ser
785                 790                 795                 800

Leu Phe Asp Leu Thr Thr Leu Ile His Pro Arg Ser Ala Ala Ile Ala
            805                 810                 815

Ser Glu Arg His Asn Ile Ser Asn Gly Ser Ala Leu Val Val Gln Glu
        820                 825                 830

Pro Pro Arg Glu Lys Gln Arg Lys Val Asn Phe Val Thr Asp Ile Lys
    835                 840                 845

Asn Phe Gly Leu Phe His Arg Arg Ser Lys Gln Asn Ala Ala Glu Gln
850                 855                 860

Asn Ala Asn Gln Ile Phe Ser Val Ser Glu Glu Val Ala Arg Gln Gln
865                 870                 875                 880
```

-continued

```
Ala Ala Gly Pro Leu Glu Arg Asn Ile Gln Leu Glu Ser Arg Gly Leu
                885                 890                 895

Ala Ser Arg Gly Asp Leu Ser Ile Pro Gly Leu Ser Glu Gln Cys Val
            900                 905                 910

Leu Val Asp His Arg Glu Arg Asn Thr Asp Thr Leu Gly Leu Gln Val
            915                 920                 925

Gly Lys Arg Val Cys Pro Phe Lys Ser Glu Lys Val Val Glu Asp
    930                 935                 940

Thr Val Pro Ile Ile Pro Lys Glu Lys His Ala Lys Glu Asp Ser
945                 950                 955                 960

Ser Ile Asp Tyr Asp Leu Asn Leu Pro Asp Thr Val Thr His Glu Asp
                965                 970                 975

Tyr Val Thr Thr Arg Leu
            980

<210> SEQ ID NO 64
<211> LENGTH: 323
<212> TYPE: PRT
<213> ORGANISM: Homo sapiens

<400> SEQUENCE: 64

Met Ala Gln Phe Tyr Tyr Lys Arg Asn Val Asn Ala Pro Tyr Arg Asp
1               5                   10                  15

Arg Ile Pro Leu Arg Ile Val Arg Ala Glu Ser Glu Leu Ser Pro Ser
                20                  25                  30

Glu Lys Ala Tyr Leu Asn Ala Val Glu Lys Gly Asp Tyr Ala Ser Val
            35                  40                  45

Lys Lys Ser Leu Glu Glu Ala Glu Ile Tyr Phe Lys Ile Asn Ile Asn
        50                  55                  60

Cys Ile Asp Pro Leu Gly Arg Thr Ala Leu Leu Ile Ala Ile Glu Asn
65                  70                  75                  80

Glu Asn Leu Glu Leu Ile Glu Leu Leu Leu Ser Phe Asn Val Tyr Val
                85                  90                  95

Gly Asp Ala Leu Leu His Ala Ile Arg Lys Glu Val Val Gly Ala Val
                100                 105                 110

Glu Leu Leu Leu Asn His Lys Lys Pro Ser Gly Glu Lys Gln Val Pro
            115                 120                 125

Pro Ile Leu Leu Asp Lys Gln Phe Ser Glu Phe Thr Pro Asp Ile Thr
        130                 135                 140

Pro Ile Ile Leu Ala Ala His Thr Asn Asn Tyr Glu Ile Ile Lys Leu
145                 150                 155                 160

Leu Val Gln Lys Gly Val Ser Val Pro Arg Pro His Glu Val Arg Cys
                165                 170                 175

Asn Cys Val Glu Cys Val Ser Ser Asp Val Asp Ser Leu Arg His
            180                 185                 190

Ser Arg Ser Arg Leu Asn Ile Tyr Lys Ala Leu Ala Ser Pro Ser Leu
        195                 200                 205

Ile Ala Leu Ser Ser Glu Asp Pro Phe Leu Thr Ala Phe Gln Leu Ser
    210                 215                 220

Trp Glu Leu Gln Glu Leu Ser Lys Val Glu Asn Glu Phe Lys Ser Glu
225                 230                 235                 240

Tyr Glu Glu Leu Ser Arg Gln Cys Lys Gln Phe Ala Lys Asp Leu Leu
                245                 250                 255

Asp Gln Thr Arg Ser Ser Arg Glu Leu Glu Ile Ile Leu Asn Tyr Arg
            260                 265                 270
```

```
Asp Asp Asn Ser Leu Ile Glu Glu Gln Ser Gly Asn Asp Leu Ala Arg
        275                 280                 285

Leu Lys Leu Ala Ile Lys Tyr Arg Gln Lys Glu Ala Ser Tyr Gly Glu
    290                 295                 300

Lys Leu Asn Arg Cys Gly Met Ala Asp Phe Arg Thr Thr Ser Met Ile
305                 310                 315                 320

Gly Gly Ile

<210> SEQ ID NO 65
<211> LENGTH: 930
<212> TYPE: PRT
<213> ORGANISM: Rattus norvegicus

<400> SEQUENCE: 65

Met Ser Gln Ser Pro Gly Phe Val Thr Arg Arg Gly Gly Ser Pro Lys
  1               5                  10                  15

Ala Ala Pro Gly Ala Gly Ala Arg Arg Asn Glu Ser Gln Asp Tyr Leu
                 20                  25                  30

Leu Met Asp Glu Leu Gly Asp Asp Gly Tyr Pro Gln Leu Gln Gln Pro
             35                  40                  45

Pro Tyr Gly Tyr Tyr Pro Ser Phe Arg Gly Asn Glu Asn Arg Leu Thr
         50                  55                  60

His Arg Arg Gln Thr Val Leu Arg Glu Lys Gly Arg Arg Leu Ala Asn
 65                  70                  75                  80

Arg Gly Pro Ala Tyr Met Phe Asn Asp His Ser Thr Ser Leu Ser Ile
                 85                  90                  95

Glu Glu Glu Arg Phe Leu Asp Ala Ala Glu Tyr Gly Asn Ile Pro Val
            100                 105                 110

Val Arg Lys Met Leu Glu Glu Cys Leu Ser Leu Asn Val Asn Cys Val
            115                 120                 125

Asp Tyr Met Gly Gln Asn Ala Leu Gln Leu Ala Val Ala Asn Glu His
        130                 135                 140

Leu Glu Ile Thr Glu Leu Leu Leu Lys Lys Glu Asn Leu Ser Arg Val
145                 150                 155                 160

Gly Asp Ala Leu Leu Leu Ala Ile Ser Lys Gly Tyr Val Arg Ile Val
                165                 170                 175

Glu Ala Ile Leu Asn His Pro Ala Phe Ala Glu Gly Lys Arg Leu Ala
            180                 185                 190

Thr Ser Pro Ser Gln Ser Glu Leu Gln Gln Asp Asp Phe Tyr Ala Tyr
        195                 200                 205

Asp Glu Asp Gly Thr Arg Phe Ser His Asp Val Thr Pro Ile Ile Leu
    210                 215                 220

Ala Ala His Cys Gln Glu Tyr Glu Ile Val His Thr Leu Leu Arg Lys
225                 230                 235                 240

Gly Ala Arg Ile Glu Arg Pro His Asp Tyr Phe Cys Lys Cys Thr Glu
                245                 250                 255

Cys Ser Gln Lys Gln Lys His Asp Ser Phe Ser His Ser Arg Ser Arg
            260                 265                 270

Ile Asn Ala Tyr Lys Gly Leu Ala Ser Pro Ala Tyr Leu Ser Leu Ser
        275                 280                 285

Ser Glu Asp Pro Val Met Thr Ala Leu Glu Leu Ser Asn Glu Leu Ala
    290                 295                 300

Val Leu Ala Asn Ile Glu Lys Glu Phe Lys Asn Asp Tyr Arg Lys Leu
305                 310                 315                 320
```

-continued

```
Ser Met Gln Cys Lys Asp Phe Val Gly Leu Leu Asp Leu Cys Arg
            325                 330                 335

Asn Thr Glu Glu Val Glu Ala Ile Leu Asn Gly Asp Ala Glu Thr Arg
            340                 345                 350

Gln Pro Gly Asp Leu Ala Arg Pro Asn Leu Ser Arg Leu Lys Leu Ala
            355                 360                 365

Ile Lys Tyr Glu Val Lys Lys Phe Val Ala His Pro Asn Cys Gln Gln
370                 375                 380

Gln Leu Leu Ser Ile Trp Tyr Glu Asn Leu Ser Gly Leu Arg Gln Gln
385                 390                 395                 400

Thr Met Ala Val Lys Phe Leu Val Leu Ala Val Ala Ile Gly Leu
                405                 410                 415

Pro Phe Leu Ala Leu Ile Tyr Trp Cys Ala Pro Cys Ser Lys Met Gly
            420                 425                 430

Lys Ile Leu Arg Gly Pro Phe Met Lys Phe Val Ala His Ala Ala Ser
            435                 440                 445

Phe Thr Ile Phe Leu Gly Leu Leu Val Met Asn Ala Ala Asp Arg Phe
450                 455                 460

Glu Gly Thr Lys Leu Leu Pro Asn Glu Thr Ser Thr Asp Asn Ala Arg
465                 470                 475                 480

Gln Leu Phe Arg Met Lys Thr Ser Cys Phe Ser Trp Met Glu Met Leu
                485                 490                 495

Ile Ile Ser Trp Val Ile Gly Met Ile Trp Ala Glu Cys Lys Glu Ile
            500                 505                 510

Trp Thr Gln Gly Pro Lys Glu Tyr Leu Phe Glu Leu Trp Asn Met Leu
            515                 520                 525

Asp Phe Gly Met Leu Ala Ile Phe Ala Ala Ser Phe Ile Ala Arg Phe
            530                 535                 540

Met Ala Phe Trp His Ala Ser Lys Ala Gln Ser Ile Ile Asp Ala Asn
545                 550                 555                 560

Asp Thr Leu Lys Asp Leu Thr Lys Val Thr Leu Gly Asp Asn Val Lys
                565                 570                 575

Tyr Tyr Asn Leu Ala Arg Ile Lys Trp Asp Pro Thr Asp Pro Gln Ile
            580                 585                 590

Ile Ser Glu Gly Leu Tyr Ala Ile Ala Val Val Leu Ser Phe Ser Arg
            595                 600                 605

Ile Ala Tyr Ile Leu Pro Ala Asn Glu Ser Phe Gly Pro Leu Gln Ile
            610                 615                 620

Ser Leu Gly Arg Thr Val Lys Asp Ile Phe Lys Phe Met Val Ile Phe
625                 630                 635                 640

Ile Met Val Phe Val Ala Phe Met Ile Gly Met Phe Asn Leu Tyr Ser
                645                 650                 655

Tyr Tyr Ile Gly Ala Lys Gln Asn Glu Ala Phe Thr Thr Val Glu Glu
            660                 665                 670

Ser Phe Lys Thr Leu Phe Trp Ala Ile Phe Gly Leu Ser Glu Val Lys
            675                 680                 685

Ser Val Val Ile Asn Tyr Asn His Lys Phe Ile Glu Asn Ile Gly Tyr
            690                 695                 700

Val Leu Tyr Gly Val Tyr Asn Val Thr Met Val Ile Val Leu Leu Asn
705                 710                 715                 720

Met Leu Ile Ala Met Ile Asn Ser Ser Phe Gln Glu Ile Glu Asp Asp
                725                 730                 735
```

Ala Asp Val Glu Trp Lys Phe Ala Arg Ala Lys Leu Trp Phe Ser Tyr
         740                 745                 750

Phe Glu Glu Gly Arg Thr Leu Pro Val Pro Phe Asn Leu Val Pro Ser
         755                 760                 765

Pro Lys Ser Leu Leu Tyr Leu Leu Lys Phe Lys Lys Trp Met Ser
770                 775                 780

Glu Leu Ile Gln Gly His Lys Lys Gly Phe Gln Glu Asp Ala Glu Met
785                 790                 795                 800

Asn Lys Arg Asn Glu Glu Lys Lys Phe Gly Ile Leu Gly Ser His Glu
                805                 810                 815

Asp Leu Ser Lys Phe Ser Leu Asp Arg Asn Gln Leu Ala His Asn Lys
         820                 825                 830

Gln Ser Ser Thr Arg Ser Ser Glu Asp Phe His Leu Asn Ser Phe Ser
         835                 840                 845

Asn Pro Pro Arg Gln Tyr Gln Lys Ile Met Lys Arg Leu Ile Lys Arg
850                 855                 860

Tyr Val Leu Gln Ala Gln Ile Asp Lys Glu Ser Asp Glu Val Asn Glu
865                 870                 875                 880

Gly Glu Leu Lys Glu Ile Lys Gln Asp Ile Ser Ser Leu Arg Tyr Glu
                885                 890                 895

Leu Leu Glu Glu Lys Ser Gln Asn Thr Glu Asp Leu Ala Glu Leu Ile
         900                 905                 910

Arg Lys Leu Gly Glu Arg Leu Ser Leu Glu Ser Lys Gln Glu Glu Ser
         915                 920                 925

Arg Arg
    930

<210> SEQ ID NO 66
<211> LENGTH: 139
<212> TYPE: PRT
<213> ORGANISM: Homo sapiens

<400> SEQUENCE: 66

Met Gly His Pro Arg Ala Ile Gln Pro Ser Val Phe Phe Ser Pro Tyr
1               5                   10                  15

Asp Val His Phe Leu Leu Tyr Pro Ile Arg Cys Pro Tyr Leu Lys Ile
            20                  25                  30

Gly Arg Phe His Ile Lys Leu Lys Gly Leu His Phe Leu Phe Ser Phe
        35                  40                  45

Leu Phe Phe Phe Glu Thr Gln Ser His Ser Val Thr Arg Leu Glu
50                  55                  60

Cys Ser Gly Thr Ile Ser Ala His Cys Asn Leu Cys Leu Pro Gly Ser
65                  70                  75                  80

Ser Asn Ser Pro Ala Ser Ala Ser Arg Val Ala Gly Thr Ala Gly Thr
                85                  90                  95

Cys Arg Arg Ala Gln Leu Ile Phe Val Phe Leu Ala Glu Met Gly Phe
            100                 105                 110

His His Val Gly Arg Asp Gly Leu Asp Leu Asn Leu Val Ile His Pro
        115                 120                 125

Pro Arg Ser Pro Lys Ala Leu Gly Leu Gln Ala
    130                 135

<210> SEQ ID NO 67
<211> LENGTH: 392
<212> TYPE: PRT
<213> ORGANISM: Homo sapiens -continued

```
<400> SEQUENCE: 67

Met Gly Ser Leu Ser Thr Ala Asn Val Glu Phe Cys Leu Asp Val Phe
 1               5                  10                  15

Lys Glu Leu Asn Ser Asn Asn Ile Gly Asp Asn Ile Phe Phe Ser Ser
             20                  25                  30

Leu Ser Leu Leu Tyr Ala Leu Ser Met Val Leu Leu Gly Ala Arg Gly
         35                  40                  45

Glu Thr Ala Glu Gln Leu Glu Lys Val Leu His Phe Ser His Thr Val
     50                  55                  60

Asp Ser Leu Lys Pro Gly Phe Lys Asp Ser Pro Lys Cys Ser Gln Ala
 65                  70                  75                  80

Gly Arg Ile His Ser Glu Phe Gly Val Glu Phe Ser Gln Ile Asn Gln
                 85                  90                  95

Pro Asp Ser Asn Cys Thr Leu Ser Ile Ala Asn Arg Leu Tyr Gly Thr
            100                 105                 110

Lys Thr Met Ala Phe His Gln Gln Tyr Leu Ser Cys Ser Glu Lys Trp
        115                 120                 125

Tyr Gln Ala Arg Leu Gln Thr Val Asp Phe Glu Gln Ser Thr Glu Glu
    130                 135                 140

Thr Arg Lys Met Ile Asn Ala Trp Val Glu Asn Lys Thr Asn Gly Lys
145                 150                 155                 160

Val Ala Asn Leu Phe Gly Lys Ser Thr Ile Asp Pro Ser Ser Val Met
                165                 170                 175

Val Leu Val Asn Thr Ile Tyr Phe Lys Gly Gln Arg Gln Asn Lys Phe
            180                 185                 190

Gln Val Arg Glu Thr Val Lys Ser Pro Phe Gln Leu Ser Glu Gly Lys
        195                 200                 205

Asn Val Thr Val Glu Met Met Tyr Gln Ile Gly Thr Phe Lys Leu Ala
    210                 215                 220

Phe Val Lys Glu Pro Gln Met Gln Val Leu Glu Leu Pro Tyr Val Asn
225                 230                 235                 240

Asn Lys Leu Ser Met Ile Ile Leu Leu Pro Val Gly Ile Ala Asn Leu
                245                 250                 255

Lys Gln Ile Glu Lys Gln Leu Asn Ser Gly Thr Phe His Glu Trp Thr
            260                 265                 270

Ser Ser Ser Asn Met Met Glu Arg Glu Val Glu Val His Leu Pro Arg
        275                 280                 285

Phe Lys Leu Glu Ile Lys Tyr Glu Leu Asn Ser Leu Leu Lys Pro Leu
    290                 295                 300

Gly Val Thr Asp Leu Phe Asn Gln Val Lys Ala Asp Leu Ser Gly Met
305                 310                 315                 320

Ser Pro Thr Lys Gly Leu Tyr Leu Ser Lys Ala Ile His Lys Ser Tyr
                325                 330                 335

Leu Asp Val Ser Glu Glu Gly Thr Glu Ala Ala Ala Thr Gly Asp
            340                 345                 350

Ser Ile Ala Val Lys Ser Leu Pro Met Arg Ala Gln Phe Lys Ala Asn
        355                 360                 365

His Pro Phe Leu Phe Phe Ile Arg His Thr His Thr Asn Thr Ile Leu
    370                 375                 380

Phe Cys Gly Lys Leu Ala Ser Pro
385                 390
```

```
<210> SEQ ID NO 68
<211> LENGTH: 862
<212> TYPE: PRT
<213> ORGANISM: Homo sapiens

<400> SEQUENCE: 68
```

| | | | | | | | | | | | | | | |
|---|---|---|---|---|---|---|---|---|---|---|---|---|---|---|
| Met | Leu | Arg | Asn | Ser | Thr | Phe | Lys | Asn | Met | Gln | Arg | Arg | His | Thr Thr |
| 1 | | | | 5 | | | | | 10 | | | | | 15 |
| Leu | Arg | Glu | Lys | Gly | Arg | Arg | Gln | Ala | Ile | Arg | Gly | Pro | Ala | Tyr Met |
| | | | 20 | | | | | 25 | | | | | 30 | |
| Phe | Asn | Glu | Lys | Gly | Thr | Ser | Leu | Thr | Pro | Glu | Glu | Arg | Phe | Leu |
| | | 35 | | | | | 40 | | | | | 45 | | |
| Asp | Ser | Ala | Glu | Tyr | Gly | Asn | Ile | Pro | Val | Val | Arg | Lys | Met | Leu Glu |
| | 50 | | | | | 55 | | | | | 60 | | | |
| Glu | Ser | Lys | Thr | Leu | Asn | Phe | Asn | Cys | Val | Asp | Tyr | Met | Gly | Gln Asn |
| 65 | | | | | 70 | | | | | 75 | | | | | 80 |
| Ala | Leu | Gln | Leu | Ala | Val | Gly | Asn | Glu | His | Leu | Glu | Val | Thr | Glu Leu |
| | | | | 85 | | | | | 90 | | | | | 95 |
| Leu | Leu | Lys | Lys | Glu | Asn | Leu | Ala | Arg | Val | Gly | Asp | Ala | Leu | Pro Leu |
| | | | 100 | | | | | 105 | | | | | 110 | |
| Ala | Ile | Ser | Lys | Gly | Tyr | Val | Arg | Ile | Val | Glu | Ala | Ile | Leu | Asn His |
| | | 115 | | | | | 120 | | | | | 125 | | |
| Pro | Ala | Phe | Ala | Gln | Gly | Gln | Arg | Leu | Thr | Leu | Ser | Pro | Leu | Glu Gln |
| | 130 | | | | | 135 | | | | | 140 | | | |
| Glu | Leu | Arg | Asp | Asp | Phe | Tyr | Ala | Tyr | Asp | Glu | Asp | Gly | Thr | Arg |
| 145 | | | | | 150 | | | | | 155 | | | | | 160 |
| Phe | Ser | His | Asp | Ile | Thr | Pro | Ile | Ile | Leu | Ala | Ala | His | Cys | Gln Glu |
| | | | | 165 | | | | | 170 | | | | | 175 |
| Tyr | Glu | Ile | Val | His | Ile | Leu | Leu | Leu | Lys | Gly | Ala | Arg | Ile | Glu Arg |
| | | | 180 | | | | | 185 | | | | | 190 | |
| Pro | His | Asp | Tyr | Phe | Cys | Lys | Cys | Asn | Glu | Cys | Thr | Glu | Lys | Gln Arg |
| | | 195 | | | | | 200 | | | | | 205 | | |
| Lys | Asp | Ser | Phe | Ser | His | Ser | Arg | Ser | Arg | Met | Asn | Ala | Tyr | Lys Gly |
| | 210 | | | | | 215 | | | | | 220 | | | |
| Leu | Ala | Ser | Ala | Ala | Tyr | Leu | Ser | Leu | Ser | Ser | Glu | Asp | Pro | Val Leu |
| 225 | | | | | 230 | | | | | 235 | | | | | 240 |
| Thr | Ala | Leu | Glu | Leu | Ser | Asn | Glu | Leu | Ala | Arg | Leu | Ala | Asn | Ile Glu |
| | | | | 245 | | | | | 250 | | | | | 255 |
| Thr | Glu | Phe | Lys | Asn | Asp | Tyr | Arg | Lys | Leu | Ser | Met | Gln | Cys | Lys Asp |
| | | | 260 | | | | | 265 | | | | | 270 | |
| Phe | Val | Val | Gly | Val | Leu | Asp | Leu | Cys | Arg | Asp | Thr | Glu | Glu | Val Glu |
| | | 275 | | | | | 280 | | | | | 285 | | |
| Ala | Ile | Leu | Asn | Gly | Asp | Val | Asn | Phe | Gln | Val | Trp | Ser | Asp | His His |
| | 290 | | | | | 295 | | | | | 300 | | | |
| Arg | Pro | Ser | Leu | Ser | Arg | Ile | Lys | Leu | Ala | Ile | Lys | Tyr | Glu | Val Lys |
| 305 | | | | | 310 | | | | | 315 | | | | | 320 |
| Lys | Phe | Val | Ala | His | Pro | Asn | Cys | Gln | Gln | Gln | Leu | Leu | Thr | Met Trp |
| | | | | 325 | | | | | 330 | | | | | 335 |
| Tyr | Glu | Asn | Leu | Ser | Gly | Leu | Arg | Gln | Gln | Ser | Ile | Ala | Val | Lys Phe |
| | | | 340 | | | | | 345 | | | | | 350 | |
| Leu | Ala | Val | Phe | Gly | Val | Ser | Ile | Gly | Leu | Pro | Phe | Leu | Ala | Ile Ala |
| | | 355 | | | | | 360 | | | | | 365 | | |
| Tyr | Trp | Ile | Ala | Pro | Cys | Ser | Lys | Leu | Gly | Arg | Thr | Leu | Arg | Ser Pro |
| | 370 | | | | | 375 | | | | | 380 | | | |

```
Phe Met Lys Phe Val Ala His Ala Val Ser Phe Thr Ile Phe Leu Gly
385                 390                 395                 400

Leu Leu Val Val Asn Ala Ser Asp Arg Phe Glu Gly Val Lys Thr Leu
            405                 410                 415

Pro Asn Glu Thr Phe Thr Asp Tyr Pro Lys Gln Ile Phe Arg Val Lys
        420                 425                 430

Thr Thr Gln Phe Ser Trp Thr Glu Met Leu Ile Met Lys Trp Val Leu
        435                 440                 445

Gly Met Ile Trp Ser Glu Cys Lys Glu Ile Trp Glu Glu Gly Pro Arg
        450                 455                 460

Glu Tyr Val Leu His Leu Trp Asn Leu Leu Asp Phe Gly Met Leu Ser
465                 470                 475                 480

Ile Phe Val Ala Ser Phe Thr Ala Arg Phe Met Ala Phe Leu Lys Ala
            485                 490                 495

Thr Glu Ala Gln Leu Tyr Val Asp Gln His Val Gln Asp Asp Thr Leu
            500                 505                 510

His Asn Val Ser Leu Pro Pro Glu Val Ala Tyr Phe Thr Tyr Ala Arg
            515                 520                 525

Asp Lys Trp Trp Pro Ser Asp Pro Gln Ile Ile Ser Glu Gly Leu Tyr
        530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
            580                 585                 590

Phe Met Ile Gly Met Phe Asn Leu Tyr Ser Tyr Arg Gly Ala Lys
            595                 600                 605

Tyr Asn Pro Ala Phe Thr Thr Val Glu Glu Ser Phe Lys Thr Leu Phe
610                 615                 620

Trp Ser Ile Phe Gly Leu Ser Glu Val Ile Ser Val Val Leu Lys Tyr
625                 630                 635                 640

Asp His Lys Phe Ile Glu Asn Ile Gly Tyr Val Leu Tyr Gly Val Tyr
            645                 650                 655

Asn Val Thr Met Val Val Val Leu Leu Asn Met Leu Ile Ala Met Ile
            660                 665                 670

Asn Asn Ser Tyr Gln Glu Ile Glu Glu Asp Ala Asp Val Glu Trp Lys
            675                 680                 685

Phe Ala Arg Ala Lys Leu Trp Leu Ser Tyr Phe Asp Glu Gly Arg Thr
690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Lys Leu Cys Lys Ser Lys
            725                 730                 735

Ala Lys Ser Cys Glu Asn Asp Leu Glu Met Gly Met Leu Asn Ser Lys
            740                 745                 750

Phe Lys Lys Thr Arg Tyr Gln Ala Gly Met Arg Asn Ser Glu Asn Leu
        755                 760                 765

Thr Ala Asn Asn Thr Leu Ser Lys Pro Thr Arg Tyr Gln Lys Ile Met
770                 775                 780

Lys Arg Leu Ile Lys Arg Tyr Val Leu Lys Ala Gln Val Asp Arg Glu
785                 790                 795                 800

Asn Asp Glu Val Asn Glu Gly Glu Leu Lys Glu Ile Lys Gln Asp Ile
```

```
                805                 810                 815
Ser Ser Leu Arg Tyr Glu Leu Leu Glu Glu Lys Ser Gln Ala Thr Gly
        820                 825                 830

Glu Leu Ala Asp Leu Ile Gln Gln Leu Ser Glu Lys Phe Gly Lys Asn
        835                 840                 845

Leu Asn Lys Asp His Leu Arg Val Asn Lys Gly Lys Asp Ile
        850                 855                 860

<210> SEQ ID NO 69
<211> LENGTH: 1265
<212> TYPE: PRT
<213> ORGANISM: Homo sapiens

<400> SEQUENCE: 69

Met Lys Val Arg Leu Leu Arg Gln Leu Ser Ala Ala Lys Val Lys
  1               5                  10                  15

Ala Pro Ser Gly Leu Gln Gly Pro Pro Gln Ala His Gln Phe Ile Ser
        20                  25                  30

Leu Leu Leu Glu Glu Tyr Gly Ala Leu Cys Gln Ala Ala Arg Ser Ile
        35                  40                  45

Ser Thr Phe Leu Gly Thr Leu Glu Asn Glu His Leu Lys Lys Phe Gln
        50                  55                  60

Val Thr Trp Glu Leu His Asn Lys His Leu Phe Glu Asn Leu Val Phe
 65                  70                  75                  80

Ser Glu Pro Leu Leu Gln Ser Asn Leu Pro Ala Leu Val Ser Gln Ile
        85                  90                  95

Arg Leu Gly Thr Thr Thr His Asp Thr Cys Ser Glu Asp Thr Tyr Ser
        100                 105                 110

Thr Leu Leu Gln Arg Tyr Gln Arg Ser Glu Glu Glu Leu Arg Arg Val
        115                 120                 125

Ala Glu Glu Trp Leu Glu Cys Gln Lys Arg Ile Asp Ala Tyr Val Asp
        130                 135                 140

Glu Gln Met Thr Met Lys Thr Lys Gln Arg Met Leu Thr Glu Asp Trp
145                 150                 155                 160

Glu Leu Phe Lys Gln Arg Arg Phe Ile Glu Glu Gln Leu Thr Asn Lys
        165                 170                 175

Lys Ala Val Thr Gly Glu Asn Asn Phe Thr Asp Thr Met Arg His Val
        180                 185                 190

Leu Ser Ser Arg Leu Ser Met Pro Asp Cys Pro Asn Cys Asn Tyr Arg
        195                 200                 205

Arg Arg Cys Ala Cys Asp Asp Cys Ser Leu Ser His Ile Leu Thr Cys
        210                 215                 220

Gly Ile Met Asp Pro Pro Val Thr Asp Asp Ile His Ile His Gln Leu
225                 230                 235                 240

Pro Leu Gln Val Asp Pro Ala Pro Asp Tyr Leu Ala Glu Arg Ser Pro
        245                 250                 255

Pro Ser Val Ser Ser Ala Ser Ser Gly Ser Gly Ser Ser Ser Pro Ile
        260                 265                 270

Thr Ile Gln Gln His Pro Arg Leu Ile Leu Thr Asp Ser Gly Ser Ala
        275                 280                 285

Pro Thr Phe Cys Ser Asp Asp Glu Asp Val Ala Pro Leu Ser Ala Lys
        290                 295                 300

Phe Ala Asp Ile Tyr Pro Leu Ser Asn Tyr Asp Asp Thr Glu Val Val
305                 310                 315                 320
```

```
Ala Asn Met Asn Gly Ile His Ser Glu Leu Asn Gly Gly Glu Asn
                325                 330                 335

Met Ala Leu Lys Asp Glu Ser Pro Gln Ile Ser Ser Thr Ser Ser Ser
            340                 345                 350

Ser Ser Glu Ala Asp Asp Glu Glu Ala Asp Gly Glu Ser Ser Gly Glu
                355                 360                 365

Pro Pro Gly Ala Pro Lys Glu Asp Gly Val Leu Gly Ser Arg Ser Pro
        370                 375                 380

Arg Thr Glu Glu Ser Lys Ala Asp Ser Pro Pro Ser Tyr Pro Thr
385                 390                 395                 400

Gln Gln Ala Glu Gln Ala Pro Asn Thr Cys Glu Cys His Val Cys Lys
                    405                 410                 415

Gln Glu Ala Ser Gly Leu Thr Pro Ser Ala Met Thr Ala Gly Ala Leu
                420                 425                 430

Pro Pro Gly His Gln Phe Leu Ser Pro Glu Lys Pro Thr His Pro Ala
        435                 440                 445

Leu His Leu Tyr Pro His Ile His Gly His Val Pro Leu His Thr Val
    450                 455                 460

Pro His Leu Pro Arg Pro Leu Ile His Pro Thr Leu Tyr Ala Thr Pro
465                 470                 475                 480

Pro Phe Thr His Ser Lys Ala Leu Pro Pro Ala Pro Val Gln Asn His
                485                 490                 495

Thr Asn Lys His Gln Val Phe Asn Ala Ser Leu Gln Asp His Ile Tyr
                500                 505                 510

Pro Ser Cys Phe Gly Asn Thr Pro Glu Trp Asn Ser Ser Lys Phe Ile
            515                 520                 525

Ser Leu Trp Gly Ser Glu Val Met Asn Asp Lys Asn Trp Asn Pro Gly
    530                 535                 540

Thr Phe Leu Pro Asp Thr Ile Ser Gly Ser Glu Ile Leu Gly Pro Thr
545                 550                 555                 560

Leu Ser Glu Thr Arg Pro Glu Ala Leu Pro Pro Ser Ser Asn Glu
                565                 570                 575

Thr Pro Ala Val Ser Asp Ser Lys Glu Lys Asn Ala Ala Lys Lys
            580                 585                 590

Lys Cys Leu Tyr Asn Phe Gln Asp Ala Phe Met Glu Ala Asn Lys Val
    595                 600                 605

Val Met Ala Thr Ser Ser Ala Thr Ser Ser Val Ser Cys Thr Ala Thr
    610                 615                 620

Thr Val Gln Ser Ser Asn Ser Gln Phe Arg Val Ser Ser Lys Arg Pro
625                 630                 635                 640

Pro Ser Val Gly Asp Val Phe His Gly Ile Ser Lys Glu Asp His Arg
                645                 650                 655

His Ser Ala Pro Ala Ala Pro Arg Asn Ser Pro Thr Gly Leu Ala Pro
                660                 665                 670

Leu Pro Ala Leu Ser Pro Ala Ala Leu Ser Pro Ala Ala Leu Ser Pro
            675                 680                 685

Ala Ser Thr Pro His Leu Ala Asn Leu Ala Ala Pro Ser Phe Pro Lys
    690                 695                 700

Thr Ala Thr Thr Thr Pro Gly Phe Val Asp Thr Arg Lys Ser Phe Cys
705                 710                 715                 720

Pro Ala Pro Leu Pro Pro Ala Thr Asp Gly Ser Ile Ser Ala Pro Pro
                725                 730                 735

Ser Val Cys Ser Asp Pro Asp Cys Glu Gly His Arg Cys Glu Asn Gly
```

```
                    740             745             750
Val Tyr Asp Pro Gln Gln Asp Gly Asp Glu Ser Ala Asp Glu Asp
        755                 760             765

Ser Cys Ser Glu His Ser Ser Thr Ser Thr Ser Thr Asn Gln Lys
770                 775                 780

Glu Gly Lys Tyr Cys Asp Cys Cys Tyr Cys Glu Phe Phe Gly His Gly
785                 790             795                 800

Gly Pro Pro Ala Ala Pro Thr Ser Arg Asn Tyr Ala Glu Met Arg Glu
                805                 810              815

Lys Leu Arg Leu Arg Leu Thr Lys Arg Lys Glu Glu Gln Pro Lys Lys
            820             825                 830

Met Asp Gln Ile Ser Glu Arg Glu Ser Val Val Asp His Arg Arg Val
            835             840              845

Glu Asp Leu Leu Gln Phe Ile Asn Ser Ser Glu Thr Lys Pro Val Ser
        850             855             860

Ser Thr Arg Ala Ala Lys Arg Ala Arg His Lys Gln Arg Lys Leu Glu
865             870             875                 880

Glu Lys Ala Arg Leu Glu Ala Glu Ala Arg Glu His Leu His
            885             890             895

Leu Gln Glu Glu Gln Arg Arg Glu Glu Glu Asp Glu Glu Glu
            900             905             910

Glu Glu Asp Arg Phe Lys Glu Phe Gln Arg Leu Gln Glu Leu Gln
            915             920             925

Lys Leu Arg Ala Val Lys Lys Lys Lys Glu Arg Pro Ser Lys Asp
        930             935             940

Cys Pro Lys Leu Asp Met Leu Thr Arg Asn Phe Gln Ala Ala Thr Glu
945             950             955                 960

Ser Val Pro Asn Ser Gly Asn Ile His Asn Gly Ser Leu Glu Gln Thr
            965             970             975

Glu Glu Pro Glu Thr Ser Ser His Ser Pro Ser Arg His Met Asn His
            980             985             990

Ser Glu Pro Arg Pro Gly Leu Gly Ala Asp Gly Asp Ala Ala Asp Pro
        995             1000            1005

Val Asp Thr Arg Asp Ser Lys Phe Leu Leu Pro Lys Glu Val Asn Gly
    1010            1015            1020

Lys Gln His Glu Pro Leu Ser Phe Phe Asp Ile Met Gln His His
1025            1030            1035            1040

Lys Glu Gly Asn Gly Lys Gln Lys Leu Arg Gln Thr Ser Lys Ala Ser
            1045            1050            1055

Ser Glu Pro Ala Arg Arg Pro Thr Glu Pro Pro Lys Ala Thr Glu Gly
        1060            1065            1070

Gln Ser Lys Pro Arg Ala Gln Thr Glu Ser Lys Ala Lys Val Val Asp
        1075            1080            1085

Leu Met Ser Ile Thr Glu Gln Lys Arg Glu Glu Arg Lys Val Asn Ser
    1090            1095            1100

Asn Asn Asn Asn Lys Lys Gln Leu Asn His Ile Lys Asp Glu Lys Ser
1105            1110            1115            1120

Asn Pro Thr Pro Met Glu Pro Thr Ser Pro Gly Glu His Gln Gln Asn
            1125            1130            1135

Ser Lys Leu Val Leu Ala Glu Ser Pro Gln Pro Lys Gly Lys Asn Lys
        1140            1145            1150

Lys Asn Lys Lys Lys Lys Gly Asp Arg Val Asn Asn Ser Ile Asp Gly
        1155            1160            1165
```

```
Val Ser Leu Leu Pro Ser Leu Gly Tyr Asn Gly Ala Ile Leu Ala
    1170                1175                1180

His Cys Asn Leu Arg Leu Pro Gly Ser Ser Asp Cys Ala Ala Ser Ala
1185                1190                1195                1200

Ser Gln Val Val Gly Ile Thr Asp Asp Val Phe Leu Pro Lys Asp Ile
                1205                1210                1215

Asp Leu Asp Ser Val Asp Met Asp Glu Thr Glu Arg Glu Val Glu Tyr
                1220                1225                1230

Phe Lys Arg Phe Cys Leu Asp Ser Ala Arg Gln Thr Arg Gln Arg Leu
                1235                1240                1245

Ser Ile Asn Trp Ser Asn Phe Ser Leu Lys Lys Ala Thr Phe Ala Ala
    1250                1255                1260

His
1265

<210> SEQ ID NO 70
<211> LENGTH: 392
<212> TYPE: PRT
<213> ORGANISM: Homo sapiens

<400> SEQUENCE: 70

Met Gly Ser Leu Ser Thr Ala Asn Val Glu Phe Cys Leu Asp Val Phe
  1               5                  10                  15

Lys Glu Leu Asn Ser Asn Asn Ile Gly Asp Asn Ile Phe Phe Ser Ser
                 20                  25                  30

Leu Ser Leu Leu Tyr Ala Leu Ser Met Val Leu Leu Gly Ala Arg Gly
             35                  40                  45

Glu Thr Ala Glu Gln Leu Glu Lys Val Leu His Phe Ser His Thr Val
     50                  55                  60

Asp Ser Leu Lys Pro Gly Phe Lys Asp Ser Pro Lys Cys Ser Gln Ala
 65                  70                  75                  80

Gly Arg Ile His Ser Glu Phe Gly Val Glu Phe Ser Gln Ile Asn Gln
                 85                  90                  95

Pro Asp Ser Asn Cys Thr Leu Ser Ile Ala Asn Arg Leu Tyr Gly Thr
                100                 105                 110

Lys Thr Met Ala Phe His Gln Gln Tyr Leu Ser Cys Ser Glu Lys Trp
            115                 120                 125

Tyr Gln Ala Arg Leu Gln Thr Val Asp Phe Glu Gln Ser Thr Glu Glu
130                 135                 140

Thr Arg Lys Met Ile Asn Ala Trp Val Glu Asn Lys Thr Asn Gly Lys
145                 150                 155                 160

Val Ala Asn Leu Phe Gly Lys Ser Thr Ile Asp Pro Ser Ser Val Met
                165                 170                 175

Val Leu Val Asn Ile Ile Tyr Phe Lys Gly Gln Arg Gln Asn Lys Phe
            180                 185                 190

Gln Val Arg Glu Thr Val Lys Ser Pro Phe Gln Leu Ser Glu Gly Lys
        195                 200                 205

Asn Val Thr Val Glu Met Met Tyr Gln Ile Gly Thr Phe Lys Leu Ala
    210                 215                 220

Phe Val Lys Glu Pro Gln Met Gln Val Leu Glu Leu Pro Tyr Val Asn
225                 230                 235                 240

Asn Lys Leu Ser Met Ile Ile Leu Leu Pro Val Gly Ile Ala Asn Leu
                245                 250                 255

Lys Gln Ile Glu Lys Gln Leu Asn Ser Gly Thr Phe His Glu Trp Thr
```

```
                   260                 265                 270
Ser Ser Ser Asn Met Met Glu Arg Glu Val Glu Val His Leu Pro Arg
            275                 280                 285

Phe Lys Leu Glu Ile Lys Tyr Glu Leu Asn Ser Leu Leu Lys Pro Leu
            290                 295                 300

Gly Val Thr Asp Leu Phe Asn Gln Val Lys Ala Asp Leu Ser Gly Met
305                 310                 315                 320

Ser Pro Thr Lys Gly Leu Tyr Leu Ser Lys Ala Ile His Lys Ser Tyr
            325                 330                 335

Leu Asp Val Ser Glu Glu Gly Thr Glu Ala Ala Ala Thr Gly Asp
            340                 345                 350

Ser Ile Ala Val Lys Ser Leu Pro Met Arg Ala Gln Phe Lys Ala Asn
            355                 360                 365

His Pro Phe Leu Phe Phe Ile Arg His Thr His Thr Asn Thr Ile Leu
            370                 375                 380

Phe Cys Gly Lys Leu Ala Ser Pro
385                 390

<210> SEQ ID NO 71
<211> LENGTH: 793
<212> TYPE: PRT
<213> ORGANISM: Homo sapiens

<400> SEQUENCE: 71

Met Met Ala Ala Leu Tyr Pro Ser Thr Asp Leu Ser Gly Ala Ser Ser
  1               5                  10                  15

Ser Ser Leu Pro Ser Ser Pro Ser Ser Ser Pro Asn Glu Val Met
             20                  25                  30

Ala Leu Lys Asp Val Arg Glu Val Lys Glu Glu Asn Thr Leu Asn Glu
             35                  40                  45

Lys Leu Phe Leu Leu Ala Cys Asp Lys Gly Asp Tyr Tyr Met Val Lys
         50                  55                  60

Lys Ile Leu Glu Glu Asn Ser Ser Gly Asp Leu Asn Ile Asn Cys Val
 65                  70                  75                  80

Asp Val Leu Gly Arg Asn Ala Val Thr Ile Thr Ile Glu Asn Glu Asn
                 85                  90                  95

Leu Asp Ile Leu Gln Leu Leu Asp Tyr Gly Cys Gln Ser Ala Asp
             100                 105                 110

Ala Leu Leu Val Ala Ile Asp Ser Glu Val Val Gly Ala Val Asp Ile
         115                 120                 125

Leu Leu Asn His Arg Pro Lys Arg Ser Ser Arg Pro Thr Ile Val Lys
130                 135                 140

Leu Met Glu Arg Ile Gln Asn Pro Glu Tyr Ser Thr Thr Met Asp Val
145                 150                 155                 160

Ala Pro Val Ile Leu Ala Ala His Arg Asn Asn Tyr Glu Ile Leu Thr
                 165                 170                 175

Met Leu Leu Lys Gln Asp Val Ser Leu Pro Lys Pro His Ala Val Gly
             180                 185                 190

Cys Glu Cys Thr Leu Cys Ser Ala Lys Asn Lys Lys Asp Ser Leu Arg
         195                 200                 205

His Ser Arg Phe Arg Leu Asp Ile Tyr Arg Cys Leu Ala Ser Pro Ala
     210                 215                 220

Leu Ile Met Leu Thr Glu Glu Asp Pro Ile Leu Arg Ala Phe Glu Leu
225                 230                 235                 240
```

-continued

```
Ser Ala Asp Leu Lys Glu Leu Ser Leu Val Glu Val Glu Phe Arg Asn
            245                 250                 255

Asp Tyr Glu Glu Leu Ala Arg Gln Cys Lys Met Phe Ala Lys Asp Leu
        260                 265                 270

Leu Ala Gln Ala Arg Asn Ser Arg Glu Leu Glu Val Ile Leu Asn His
    275                 280                 285

Thr Ser Ser Asp Glu Pro Leu Asp Lys Arg Gly Leu Leu Glu Glu Arg
290                 295                 300

Met Asn Leu Ser Arg Leu Lys Leu Ala Ile Lys Tyr Asn Gln Lys Glu
305                 310                 315                 320

Phe Val Ser Gln Ser Asn Cys Gln Gln Phe Leu Asn Thr Val Trp Phe
                325                 330                 335

Gly Gln Met Ser Gly Tyr Arg Arg Lys Pro Thr Cys Lys Lys Ile Met
            340                 345                 350

Thr Val Leu Thr Val Gly Ile Phe Trp Pro Val Leu Ser Leu Cys Tyr
        355                 360                 365

Leu Ile Ala Pro Lys Ser Gln Phe Gly Arg Ile Ile His Thr Pro Phe
    370                 375                 380

Met Lys Phe Ile Ile His Gly Ala Ser Tyr Phe Thr Phe Leu Leu Leu
385                 390                 395                 400

Leu Asn Leu Tyr Ser Leu Val Tyr Asn Glu Asp Lys Lys Asn Thr Met
                405                 410                 415

Gly Pro Ala Leu Glu Arg Ile Asp Tyr Leu Leu Ile Leu Trp Ile Ile
            420                 425                 430

Gly Met Ile Trp Ser Asp Ile Lys Arg Leu Trp Tyr Glu Gly Leu Glu
        435                 440                 445

Asp Phe Leu Glu Glu Ser Arg Asn Gln Leu Ser Phe Val Met Asn Ser
450                 455                 460

Leu Tyr Leu Ala Thr Phe Ala Leu Lys Val Val Ala His Asn Lys Phe
465                 470                 475                 480

His Asp Phe Ala Asp Arg Lys Asp Trp Asp Ala Phe His Pro Thr Leu
                485                 490                 495

Val Ala Glu Gly Leu Phe Ala Phe Ala Asn Val Leu Ser Tyr Leu Arg
            500                 505                 510

Leu Phe Phe Met Tyr Thr Thr Ser Ser Ile Leu Gly Pro Leu Gln Ile
        515                 520                 525

Ser Met Gly Gln Met Leu Gln Asp Phe Gly Lys Phe Leu Gly Met Phe
530                 535                 540

Leu Leu Val Leu Phe Ser Phe Thr Ile Gly Leu Thr Gln Leu Tyr Asp
545                 550                 555                 560

Lys Gly Tyr Thr Ser Lys Glu Gln Lys Asp Cys Val Gly Ile Phe Cys
                565                 570                 575

Glu Gln Gln Ser Asn Asp Thr Phe His Ser Phe Ile Gly Thr Cys Phe
            580                 585                 590

Ala Leu Phe Trp Tyr Ile Phe Ser Leu Ala His Val Ala Ile Phe Val
        595                 600                 605

Thr Arg Phe Ser Tyr Gly Glu Glu Leu Gln Ser Phe Val Gly Ala Val
610                 615                 620

Ile Val Gly Thr Tyr Asn Val Val Val Ile Val Leu Thr Lys Leu
625                 630                 635                 640

Leu Val Ala Met Leu His Lys Ser Phe Gln Leu Ile Ala Asn His Glu
                645                 650                 655

Asp Lys Glu Trp Lys Phe Ala Arg Ala Lys Leu Trp Leu Ser Tyr Phe
```

```
                  660                 665                 670
Asp Asp Lys Cys Thr Leu Pro Pro Phe Asn Ile Ile Pro Ser Pro
        675                 680                 685

Lys Thr Ile Cys Tyr Met Ile Ser Ser Leu Ser Lys Trp Ile Cys Ser
    690                 695                 700

His Thr Ser Lys Gly Lys Val Lys Arg Gln Asn Ser Leu Lys Glu Trp
705                 710                 715                 720

Arg Asn Leu Lys Gln Lys Arg Asp Glu Asn Tyr Gln Lys Val Met Cys
                725                 730                 735

Cys Leu Val His Arg Tyr Leu Thr Ser Met Arg Gln Lys Met Gln Ser
            740                 745                 750

Thr Asp Gln Ala Thr Val Glu Asn Leu Asn Glu Leu Arg Gln Asp Leu
        755                 760                 765

Ser Lys Phe Arg Asn Glu Ile Arg Asp Leu Leu Gly Phe Arg Thr Ser
    770                 775                 780

Lys Tyr Ala Met Phe Tyr Pro Arg Asn
785                 790

<210> SEQ ID NO 72
<211> LENGTH: 982
<212> TYPE: PRT
<213> ORGANISM: Homo sapiens

<400> SEQUENCE: 72

Met Ala Gln Phe Tyr Tyr Lys Arg Asn Val Asn Ala Pro Tyr Arg Asp
1               5                   10                  15

Arg Ile Pro Leu Arg Ile Val Arg Ala Glu Ser Glu Leu Ser Pro Ser
                20                  25                  30

Glu Lys Ala Tyr Leu Asn Ala Val Glu Lys Gly Asp Tyr Ala Ser Val
            35                  40                  45

Lys Lys Ser Leu Glu Glu Ala Glu Ile Tyr Phe Lys Ile Asn Ile Asn
        50                  55                  60

Cys Ile Asp Pro Leu Gly Arg Thr Ala Leu Leu Ile Ala Ile Glu Asn
65                  70                  75                  80

Glu Asn Leu Glu Leu Ile Glu Leu Leu Leu Ser Phe Asn Val Tyr Val
                85                  90                  95

Gly Asp Ala Leu Leu His Ala Ile Arg Lys Glu Val Val Gly Ala Val
                100                 105                 110

Glu Leu Leu Leu Asn His Lys Lys Pro Ser Gly Glu Lys Gln Val Pro
            115                 120                 125

Pro Ile Leu Leu Asp Lys Gln Phe Ser Glu Phe Thr Pro Asp Ile Thr
        130                 135                 140

Pro Ile Ile Leu Ala Ala His Thr Asn Asn Tyr Glu Ile Ile Lys Leu
145                 150                 155                 160

Leu Val Gln Lys Gly Val Ser Val Pro Arg Pro His Glu Val Arg Cys
                165                 170                 175

Asn Cys Val Glu Cys Val Ser Ser Asp Val Asp Ser Leu Arg His
                180                 185                 190

Ser Arg Ser Arg Leu Asn Ile Tyr Lys Ala Leu Ala Ser Pro Ser Leu
        195                 200                 205

Ile Ala Leu Ser Ser Glu Asp Pro Phe Leu Thr Ala Phe Gln Leu Ser
        210                 215                 220

Trp Glu Leu Gln Glu Leu Ser Lys Val Glu Asn Glu Phe Lys Ser Glu
225                 230                 235                 240
```

-continued

```
Tyr Glu Glu Leu Ser Arg Gln Cys Lys Gln Phe Ala Lys Asp Leu Leu
                245                 250                 255

Asp Gln Thr Arg Ser Ser Arg Glu Leu Glu Ile Ile Leu Asn Tyr Arg
            260                 265                 270

Asp Asp Asn Ser Leu Ile Glu Glu Gln Ser Gly Asn Asp Leu Ala Arg
        275                 280                 285

Leu Lys Leu Ala Ile Lys Tyr Arg Gln Lys Glu Phe Val Ala Gln Pro
    290                 295                 300

Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys
                340                 345                 350

Ser Pro Leu Gly Leu Phe Ile Arg Lys Pro Phe Ile Lys Phe Ile Cys
                355                 360                 365

His Thr Ala Ser Tyr Leu Thr Phe Leu Phe Leu Leu Leu Leu Ala Ser
            370                 375                 380

Gln His Ile Asp Arg Ser Asp Leu Asn Arg Gln Gly Pro Pro Thr
385                 390                 395                 400

Ile Val Glu Trp Met Ile Leu Pro Trp Val Leu Gly Phe Ile Trp Gly
                405                 410                 415

Glu Ile Lys Gln Met Trp Asp Gly Gly Leu Gln Asp Tyr Ile His Asp
            420                 425                 430

Trp Trp Asn Leu Met Asp Phe Val Met Asn Ser Leu Tyr Leu Ala Thr
        435                 440                 445

Ile Ser Leu Lys Ile Val Ala Phe Val Lys Tyr Ser Ala Leu Asn Pro
    450                 455                 460

Arg Glu Ser Trp Asp Met Trp His Pro Thr Leu Val Ala Glu Ala Leu
465                 470                 475                 480

Phe Ala Ile Ala Asn Ile Phe Ser Ser Leu Arg Leu Ile Ser Leu Phe
                485                 490                 495

Thr Ala Asn Ser His Leu Gly Pro Leu Gln Ile Ser Leu Gly Arg Met
            500                 505                 510

Leu Leu Asp Ile Leu Lys Phe Leu Phe Ile Tyr Cys Leu Val Leu Leu
        515                 520                 525

Ala Phe Ala Asn Gly Leu Asn Gln Leu Tyr Phe Tyr Tyr Glu Glu Thr
    530                 535                 540

Lys Gly Leu Thr Cys Lys Gly Ile Arg Cys Glu Lys Gln Asn Asn Ala
545                 550                 555                 560

Phe Ser Thr Leu Phe Glu Thr Leu Gln Ser Leu Phe Trp Ser Ile Phe
                565                 570                 575

Gly Leu Ile Asn Leu Tyr Val Thr Asn Val Lys Ala Gln His Glu Phe
            580                 585                 590

Thr Glu Phe Val Gly Ala Thr Met Phe Gly Thr Tyr Asn Val Ile Ser
        595                 600                 605

Leu Val Val Leu Leu Asn Met Leu Ile Ala Met Met Asn Asn Ser Tyr
    610                 615                 620

Gln Leu Ile Ala Asp His Ala Asp Ile Glu Trp Lys Phe Ala Arg Thr
625                 630                 635                 640

Lys Leu Trp Met Ser Tyr Phe Glu Glu Gly Gly Thr Leu Pro Thr Pro
                645                 650                 655

Phe Asn Val Ile Pro Ser Pro Lys Ser Leu Trp Tyr Leu Ile Lys Trp
```

```
                        660                 665                 670
Ile Trp Thr His Leu Cys Lys Lys Met Arg Arg Lys Pro Glu Ser
            675                 680                 685
Phe Gly Thr Ile Gly Val Arg Thr Gln His Arg Arg Ala Ala Asp Asn
        690                 695                 700
Leu Arg Arg His His Gln Tyr Gln Val Ile Met Arg Asn Leu Val Lys
705                 710                 715                 720
Arg Tyr Val Ala Ala Met Ile Arg Asp Ala Lys Thr Glu Glu Gly Leu
                725                 730                 735
Thr Glu Glu Asn Phe Lys Glu Leu Lys Gln Asp Ile Ser Ser Phe Arg
            740                 745                 750
Phe Glu Val Leu Gly Leu Leu Arg Gly Ser Lys Leu Ser Thr Ile Gln
            755                 760                 765
Ser Ala Asn Ala Ser Lys Glu Ser Ser Asn Ser Ala Asp Ser Asp Glu
            770                 775                 780
Lys Ser Asp Ser Glu Gly Asn Ser Lys Asp Lys Lys Asn Phe Ser
785                 790                 795                 800
Leu Phe Asp Leu Thr Thr Leu Ile His Pro Arg Ser Ala Ala Ile Ala
                805                 810                 815
Ser Glu Arg His Asn Ile Ser Asn Gly Ser Ala Leu Val Val Gln Glu
                820                 825                 830
Pro Pro Arg Glu Lys Gln Arg Lys Val Asn Phe Val Thr Asp Ile Lys
            835                 840                 845
Asn Phe Gly Leu Phe His Arg Arg Ser Lys Gln Asn Ala Ala Glu Gln
        850                 855                 860
Asn Ala Asn Gln Ile Phe Ser Val Ser Glu Glu Val Ala Arg Gln Gln
865                 870                 875                 880
Ala Ala Gly Pro Leu Glu Arg Asn Ile Gln Leu Glu Ser Arg Gly Leu
                885                 890                 895
Ala Ser Arg Gly Asp Leu Ser Ile Pro Gly Leu Ser Glu Gln Cys Val
            900                 905                 910
Leu Val Asp His Arg Glu Arg Asn Thr Asp Thr Leu Gly Leu Gln Val
            915                 920                 925
Gly Lys Arg Val Cys Pro Phe Lys Ser Glu Lys Val Val Glu Asp
        930                 935                 940
Thr Val Pro Ile Ile Pro Lys Glu Lys His Ala Lys Glu Glu Asp Ser
945                 950                 955                 960
Ser Ile Asp Tyr Asp Leu Asn Leu Pro Asp Thr Val Thr His Glu Asp
                965                 970                 975
Tyr Val Thr Thr Arg Leu
            980

<210> SEQ ID NO 73
<211> LENGTH: 930
<212> TYPE: PRT
<213> ORGANISM: Mus musculus

<400> SEQUENCE: 73

Met Ser Gln Ser Pro Arg Phe Val Thr Arg Arg Gly Gly Ser Leu Lys
1               5                   10                  15
Ala Ala Pro Gly Ala Gly Thr Arg Arg Asn Glu Ser Gln Asp Tyr Leu
            20                  25                  30
Leu Met Asp Glu Leu Gly Asp Asp Gly Tyr Pro Gln Leu Pro Leu Pro
        35                  40                  45
```

-continued

```
Pro Tyr Gly Tyr Tyr Pro Ser Phe Arg Gly Asn Glu Asn Arg Leu Thr
    50                  55                  60

His Arg Arg Gln Thr Ile Leu Arg Glu Lys Gly Arg Arg Leu Ala Asn
 65                  70                  75                  80

Arg Gly Pro Ala Tyr Met Phe Asn Asp His Ser Thr Ser Leu Ser Ile
                 85                  90                  95

Glu Glu Glu Arg Phe Leu Asp Ala Ala Glu Tyr Gly Asn Ile Pro Val
            100                 105                 110

Val Arg Lys Met Leu Glu Glu Cys His Ser Leu Asn Val Asn Cys Val
        115                 120                 125

Asp Tyr Met Gly Gln Asn Ala Leu Gln Leu Ala Val Ala Asn Glu His
    130                 135                 140

Leu Glu Ile Thr Glu Leu Leu Leu Lys Lys Glu Asn Leu Ser Arg Val
145                 150                 155                 160

Gly Asp Ala Leu Leu Leu Ala Ile Ser Lys Gly Tyr Val Arg Ile Val
                165                 170                 175

Glu Ala Ile Leu Asn His Pro Ala Phe Ala Glu Gly Lys Arg Leu Ala
            180                 185                 190

Thr Ser Pro Ser Gln Ser Glu Leu Gln Gln Asp Phe Tyr Ala Tyr
        195                 200                 205

Asp Glu Asp Gly Thr Arg Phe Ser His Asp Val Thr Pro Ile Ile Leu
    210                 215                 220

Ala Ala His Cys Gln Glu Tyr Glu Ile Val His Thr Leu Leu Arg Lys
225                 230                 235                 240

Gly Ala Arg Ile Glu Arg Pro His Asp Tyr Phe Cys Lys Cys Thr Glu
                245                 250                 255

Cys Ser Gln Lys Gln Lys His Asp Ser Phe Ser His Ser Arg Ser Arg
            260                 265                 270

Ile Asn Ala Tyr Lys Gly Leu Ala Ser Pro Ala Tyr Leu Ser Leu Ser
        275                 280                 285

Ser Glu Asp Pro Val Met Thr Ala Leu Glu Leu Ser Asn Glu Leu Ala
    290                 295                 300

Val Leu Ala Asn Ile Glu Lys Glu Phe Lys Asn Asp Tyr Arg Lys Leu
305                 310                 315                 320

Ser Met Gln Cys Lys Asp Phe Val Val Gly Leu Leu Asp Leu Cys Arg
                325                 330                 335

Asn Thr Glu Glu Val Glu Ala Ile Leu Asn Gly Asp Ala Glu Thr Arg
            340                 345                 350

Gln Pro Gly Asp Phe Gly Arg Pro Asn Leu Ser Arg Leu Lys Leu Ala
        355                 360                 365

Ile Lys Tyr Glu Val Lys Lys Phe Val Ala His Pro Asn Cys Gln Gln
    370                 375                 380

Gln Leu Leu Ser Ile Trp Tyr Glu Asn Leu Ser Gly Leu Arg Gln Gln
385                 390                 395                 400

Thr Met Ala Val Lys Phe Leu Val Val Leu Ala Val Ala Ile Gly Leu
                405                 410                 415

Pro Phe Leu Ala Leu Ile Tyr Trp Cys Ala Pro Cys Ser Lys Met Gly
            420                 425                 430

Lys Ile Leu Arg Gly Pro Phe Met Lys Phe Val Ala His Ala Ala Ser
        435                 440                 445

Phe Thr Ile Phe Leu Gly Leu Leu Val Met Asn Ala Ala Asp Arg Phe
    450                 455                 460

Glu Gly Thr Lys Leu Leu Pro Asn Glu Thr Ser Thr Asp Asn Ala Arg
```

-continued

```
            465                 470                 475                 480
Gln Leu Phe Arg Met Lys Thr Ser Cys Phe Ser Trp Met Glu Met Leu
                    485                 490                 495
Ile Ile Ser Trp Val Ile Gly Met Ile Trp Ala Glu Cys Lys Glu Ile
                500                 505                 510
Trp Thr Gln Gly Pro Lys Glu Tyr Leu Phe Glu Leu Trp Asn Met Leu
                515                 520                 525
Asp Phe Gly Met Leu Ala Ile Phe Ala Ala Ser Phe Ile Ala Arg Phe
            530                 535                 540
Met Ala Phe Trp His Ala Ser Lys Ala Gln Ser Ile Ile Asp Ala Asn
545                 550                 555                 560
Asp Thr Leu Lys Asp Leu Thr Lys Val Thr Leu Gly Asp Asn Val Lys
                565                 570                 575
Tyr Tyr Asn Leu Ala Arg Ile Lys Trp Asp Pro Thr Asp Pro Gln Ile
                580                 585                 590
Ile Ser Glu Gly Leu Tyr Ala Ile Ala Val Val Leu Ser Phe Ser Arg
            595                 600                 605
Ile Ala Tyr Ile Leu Pro Ala Asn Glu Ser Phe Gly Pro Leu Gln Ile
            610                 615                 620
Ser Leu Gly Arg Thr Val Lys Asp Ile Phe Lys Phe Met Val Ile Phe
625                 630                 635                 640
Ile Met Val Phe Val Ala Phe Met Ile Gly Met Phe Asn Leu Tyr Ser
                645                 650                 655
Tyr Tyr Ile Gly Ala Lys Gln Asn Glu Ala Phe Thr Thr Val Glu Glu
                660                 665                 670
Ser Phe Lys Thr Leu Phe Trp Ala Ile Phe Gly Leu Ser Glu Val Lys
                675                 680                 685
Ser Val Val Ile Asn Tyr Asn His Lys Phe Ile Glu Asn Ile Gly Tyr
                690                 695                 700
Val Leu Tyr Gly Val Tyr Asn Val Thr Met Val Ile Val Leu Leu Asn
705                 710                 715                 720
Met Leu Ile Ala Met Ile Asn Ser Ser Phe Gln Glu Ile Glu Asp Asp
                725                 730                 735
Ala Asp Val Glu Trp Lys Phe Ala Arg Ala Lys Leu Trp Phe Ser Tyr
                740                 745                 750
Phe Glu Glu Gly Arg Thr Leu Pro Val Pro Phe Asn Leu Val Pro Ser
                755                 760                 765
Pro Lys Ser Leu Leu Tyr Leu Leu Leu Lys Phe Lys Trp Met Cys
                770                 775                 780
Glu Leu Ile Gln Gly Gln Lys Gln Gly Phe Gln Glu Asp Ala Glu Met
785                 790                 795                 800
Asn Lys Arg Asn Glu Glu Lys Lys Phe Gly Ile Ser Gly Ser His Glu
                805                 810                 815
Asp Leu Ser Lys Phe Ser Leu Asp Lys Asn Gln Leu Ala His Asn Lys
                820                 825                 830
Gln Ser Ser Thr Arg Ser Ser Glu Asp Tyr His Leu Asn Ser Phe Ser
                835                 840                 845
Asn Pro Pro Arg Gln Tyr Gln Lys Ile Met Lys Arg Leu Ile Lys Arg
            850                 855                 860
Tyr Val Leu Gln Ala Gln Ile Asp Lys Glu Ser Asp Glu Val Asn Glu
865                 870                 875                 880
Gly Glu Leu Lys Glu Ile Lys Gln Asp Ile Ser Ser Leu Arg Tyr Glu
                885                 890                 895
```

-continued

Leu Leu Glu Glu Lys Ser Gln Asn Thr Glu Asp Leu Ala Glu Leu Ile
                900                 905                 910

Arg Lys Leu Gly Glu Arg Leu Ser Leu Glu Pro Lys Leu Glu Glu Ser
            915                 920                 925

Arg Arg
    930

<210> SEQ ID NO 74
<211> LENGTH: 826
<212> TYPE: PRT
<213> ORGANISM: Homo sapiens

<400> SEQUENCE: 74

Pro Ser Gly Leu Pro Leu Leu Pro Val Leu Phe Ala Leu Gly Gly Leu
  1               5                  10                  15

Leu Leu Leu Ser Asn Ala Ser Cys Val Gly Val Leu Trp Gln Arg
                 20                  25                  30

Arg Leu Arg Arg Leu Ala Glu Ala Leu Asn Phe Pro Pro His Leu His
             35                  40                  45

Pro Gly Arg Ser Glu Glu Asp Arg Val Arg Asn Glu Tyr Glu Glu Ser
     50                   55                   60

Gln Trp Thr Gly Glu Arg Asp Thr Gln Ser Ser Thr Val Ser Thr Thr
 65                   70                   75                   80

Glu Ala Glu Pro Tyr Tyr Arg Ser Leu Arg Asp Phe Ser Pro Gln Leu
                 85                   90                   95

Pro Pro Thr Gln Glu Glu Val Ser Tyr Ser Arg Gly Phe Thr Gly Glu
                100                  105                  110

Asp Glu Asp Met Ala Phe Pro Gly His Leu Tyr Asp Glu Val Glu Arg
            115                  120                  125

Thr Tyr Pro Pro Ser Gly Ala Trp Gly Pro Leu Tyr Asp Glu Val Gln
    130                  135                  140

Met Gly Pro Trp Asp Leu His Trp Pro Glu Asp Thr Tyr Gln Asp Pro
145                  150                  155                  160

Arg Gly Ile Tyr Asp Gln Val Ala Gly Asp Leu Asp Thr Leu Glu Pro
                165                  170                  175

Asp Ser Leu Pro Phe Glu Leu Arg Gly His Leu Val Trp Gly Phe Asn
            180                  185                  190

His Val Ser Gln Ala Gly Leu Lys Leu Leu Ala Ser Asp Pro Pro
        195                  200                  205

Ala Ser Ala Ser Gln Ser Ala Glu Ile Thr Glu Ser His Ser Val Val
    210                  215                  220

Gln Val Gly Val Gln Trp Arg Tyr Phe Gly Ser Leu His Pro Leu Pro
225                  230                  235                  240

Pro Gly Ser Arg Asp Ser Leu Ala Ser Ala Ser Arg Ile Ala Gly Ile
                245                  250                  255

Thr Ala Pro Trp Glu Ala Glu Val Ser Arg Ser Pro Gln Gly Thr Gln
            260                  265                  270

Asp Ser Pro Val Thr Arg Ser Gly Pro Pro Ser Arg Gly Trp Gln Ser
        275                  280                  285

Leu Ser Phe Asp Gly Gly Ala Phe His Leu Lys Gly Thr Gly Glu Leu
    290                  295                  300

Thr Arg Ala Leu Leu Val Leu Arg Leu Cys Ala Trp Pro Pro Leu Val
305                  310                  315                  320

Thr His Gly Leu Leu Leu Gln Ala Trp Ser Arg Arg Leu Leu Gly Ser

-continued

```
                325                 330                 335
Arg Leu Ser Gly Ala Phe Leu Arg Ala Ser Val Tyr Gly Gln Phe Val
            340                 345                 350
Ala Gly Glu Thr Ala Glu Val Lys Gly Cys Val Gln Gln Leu Arg
            355                 360                 365
Thr Leu Ser Leu Arg Pro Leu Leu Ala Val Pro Thr Glu Glu Pro
370                 375                 380
Asp Ser Ala Ala Lys Arg Met Arg Leu His His Val Gly Gln Ala Gly
385                 390                 395                 400
Leu Glu Leu Leu Thr Pro Ala Ala Ser Gly Ser Val Ala Gln Ala Gly
                405                 410                 415
Val Gln Trp Arg Gln Ser Ser Asp Arg Gly Gly Asn Gln Ala Ala
            420                 425                 430
Ala Ser Arg Ser Ser Leu Leu Gln Glu Ala Ala Phe Ser Pro Pro Cys
            435                 440                 445
Gly Arg Leu Gln Leu Pro Ala Gln Pro Ala Ser Arg His Gly Ala Arg
            450                 455                 460
Gly Arg Gly Ser Met Lys Ala Lys Ser Leu Thr Ser Arg His Leu Leu
465                 470                 475                 480
Ala Ser Gln Gly Gln Glu Thr Ile Ile Lys Thr Lys Val Arg Ile Pro
                485                 490                 495
Ala Leu Trp Lys Ala Glu Pro Gly Gln His Ser Lys Thr Pro Ser Gln
            500                 505                 510
Gln Asn Lys Ser Gln Tyr Val Thr Thr Leu Trp Glu Ala Asp Val Gly
            515                 520                 525
Arg Ser Leu Glu Asn Leu Gln Val Ser Cys Leu Asn Ala Glu Gln Asn
            530                 535                 540
Gln His Leu Arg Ala Ser Leu Ser Arg Leu His Arg Val Thr Pro Pro
545                 550                 555                 560
Ala Gly Thr Ser Thr Ser Gly Pro Pro Ser Ala Ala Cys Ile Gly Trp
                565                 570                 575
His Ser Arg Leu His Arg Val Ala Gln Tyr Ala Arg Ala Gln His Val
            580                 585                 590
Arg Leu Leu Val Asp Ala Glu Tyr Thr Ser Leu Asn Pro Ala Leu Ser
            595                 600                 605
Leu Leu Val Ala Ala Leu Ala Val Arg Trp Asn Ser Pro Gly Glu Gly
            610                 615                 620
Gly Pro Trp Val Trp Asn Thr Tyr Gln Ala Cys Leu Lys Asp Thr Phe
625                 630                 635                 640
Glu Arg Leu Gly Arg Asp Ala Glu Ala His Arg Ala Gly Leu Ala
                645                 650                 655
Phe Gly Val Lys Leu Val Arg Gly Ala Tyr Leu Asp Lys Glu Arg Ala
            660                 665                 670
Val Ala Gln Leu His Gly Met Glu Asp Pro Thr Gln Pro Asp Tyr Glu
            675                 680                 685
Ala Thr Ser Glu Leu Asn Arg Ala Ser Pro Phe Ser Tyr Ser Arg Cys
            690                 695                 700
Leu Glu Leu Met Leu Thr His Val Ala Arg His Gly Pro Met Cys His
705                 710                 715                 720
Leu Met Val Ala Ser His Asn Glu Glu Ser Val Arg Gln Ala Thr Lys
                725                 730                 735
Arg Met Trp Glu Leu Gly Ile Pro Leu Asp Gly Thr Val Cys Phe Gly
            740                 745                 750
```

```
Gln Leu Leu Gly Met Cys Asp His Val Ser Leu Ala Leu Gly Gln Ala
            755                 760                 765

Gly Tyr Val Val Tyr Lys Ser Ile Pro Tyr Gly Ser Leu Glu Glu Val
            770                 775                 780

Ile Pro Tyr Leu Ile Arg Arg Ala Gln Glu Asn Arg Ser Val Leu Gln
785                 790                 795                 800

Gly Ala Arg Arg Glu Gln Glu Leu Leu Ser Gln Glu Leu Trp Arg Arg
                805                 810                 815

Leu Leu Pro Gly Cys Arg Arg Ile Pro His
            820                 825

<210> SEQ ID NO 75
<211> LENGTH: 39
<212> TYPE: PRT
<213> ORGANISM: Homo sapiens

<400> SEQUENCE: 75

Ser Cys Ser Val Thr Leu Ala Gly Val Gln Trp Arg Asp Leu Gly Leu
1               5                   10                  15

Leu Gln Pro Leu Pro Pro Lys Phe Lys Arg Phe Ser Cys Leu Ser Phe
            20                  25                  30

Pro Ser Ser Trp Asp Tyr Arg
        35

<210> SEQ ID NO 76
<211> LENGTH: 46
<212> TYPE: PRT
<213> ORGANISM: Homo sapiens

<400> SEQUENCE: 76

Glu Met Glu Phe Asn Cys Glu Ser Cys Ser Val Thr Leu Ala Gly Val
1               5                   10                  15

Gln Trp Arg Asp Leu Gly Leu Leu Gln Pro Leu Pro Pro Lys Phe Lys
            20                  25                  30

Arg Phe Ser Cys Leu Ser Phe Pro Ser Ser Trp Asp Tyr Arg
            35                  40                  45

<210> SEQ ID NO 77
<211> LENGTH: 810
<212> TYPE: PRT
<213> ORGANISM: Homo sapiens

<400> SEQUENCE: 77

Met Cys Pro Gly Ile Pro Gly Pro Arg Ala Glu Ala Val Gly Thr
1               5                   10                  15

Thr His Pro Phe Ser Ser Pro Gly Ala Trp Leu Gly Ser Gly Ser Gly
            20                  25                  30

Ser Gly Pro Val Gly Ala Pro Pro Ser Pro Gly Leu Pro Pro Ser
        35                  40                  45

Trp Ala Ala Met Met Ala Ala Leu Tyr Pro Ser Thr Asp Leu Ser Gly
    50                  55                  60

Ala Ser Ser Ser Ser Leu Pro Ser Ser Pro Ser Ser Ser Ser Pro Asn
65                  70                  75                  80

Glu Val Met Ala Leu Lys Asp Val Arg Glu Val Lys Glu Glu Asn Thr
                85                  90                  95

Leu Asn Glu Lys Leu Phe Leu Leu Ala Cys Asp Lys Gly Asp Tyr Tyr
            100                 105                 110
```

```
Met Val Lys Lys Ile Leu Glu Glu Asn Ser Ser Gly Asp Leu Asn Ile
        115                 120                 125

Asn Cys Val Asp Val Leu Gly Arg Asn Ala Val Thr Ile Thr Ile Glu
        130                 135                 140

Asn Glu Asn Leu Asp Ile Leu Gln Leu Leu Asp Tyr Gly Cys Gln
145                 150                 155                 160

Lys Leu Met Glu Arg Ile Gln Asn Pro Glu Tyr Ser Thr Thr Met Asp
                165                 170                 175

Val Ala Pro Val Ile Leu Ala Ala His Arg Asn Asn Tyr Glu Ile Leu
                180                 185                 190

Thr Met Leu Leu Lys Gln Asp Val Ser Leu Pro Lys Pro His Ala Val
            195                 200                 205

Gly Cys Glu Cys Thr Leu Cys Ser Ala Lys Asn Lys Lys Asp Ser Leu
        210                 215                 220

Arg His Ser Arg Phe Arg Leu Asp Ile Tyr Arg Cys Leu Ala Ser Pro
225                 230                 235                 240

Ala Leu Ile Met Leu Thr Glu Glu Asp Pro Ile Leu Arg Ala Phe Glu
                245                 250                 255

Leu Ser Ala Asp Leu Lys Glu Leu Ser Leu Val Glu Val Glu Phe Arg
            260                 265                 270

Asn Asp Tyr Glu Glu Leu Ala Arg Gln Cys Lys Met Phe Ala Lys Asp
        275                 280                 285

Leu Leu Ala Gln Ala Arg Asn Ser Arg Glu Leu Glu Val Ile Leu Asn
        290                 295                 300

His Thr Ser Ser Asp Glu Pro Leu Asp Lys Arg Gly Leu Leu Glu Glu
305                 310                 315                 320

Arg Met Asn Leu Ser Arg Leu Lys Leu Ala Ile Lys Tyr Asn Gln Lys
                325                 330                 335

Glu Phe Val Ser Gln Ser Asn Cys Gln Gln Phe Leu Asn Thr Val Trp
            340                 345                 350

Phe Gly Gln Met Ser Gly Tyr Arg Arg Lys Pro Thr Cys Lys Lys Ile
        355                 360                 365

Met Thr Val Leu Thr Val Gly Ile Phe Trp Pro Val Leu Ser Leu Cys
        370                 375                 380

Tyr Leu Ile Ala Pro Lys Ser Gln Phe Gly Arg Ile Ile His Thr Pro
385                 390                 395                 400

Phe Met Lys Phe Ile Ile His Gly Ala Ser Tyr Phe Thr Phe Leu Leu
                405                 410                 415

Leu Leu Asn Leu Tyr Ser Leu Val Tyr Asn Glu Asp Lys Lys Asn Thr
            420                 425                 430

Met Gly Pro Ala Leu Glu Arg Ile Asp Tyr Leu Leu Ile Leu Trp Ile
        435                 440                 445

Ile Gly Met Ile Trp Ser Asp Ile Lys Arg Leu Trp Tyr Glu Gly Leu
        450                 455                 460

Glu Asp Phe Leu Glu Glu Ser Arg Asn Gln Leu Ser Phe Val Met Asn
465                 470                 475                 480

Ser Leu Tyr Leu Ala Thr Phe Ala Leu Lys Val Val Ala His Asn Lys
                485                 490                 495

Phe His Asp Phe Ala Asp Arg Lys Asp Trp Asp Ala Phe His Pro Thr
            500                 505                 510

Leu Val Ala Glu Gly Leu Phe Ala Phe Ala Asn Val Leu Ser Tyr Leu
        515                 520                 525

Arg Leu Phe Phe Met Tyr Thr Thr Ser Ser Ile Leu Gly Pro Leu Gln
```

-continued

```
                530                 535                 540
Ile Ser Met Gly Gln Met Leu Gln Asp Phe Gly Lys Phe Leu Gly Met
545                 550                 555                 560

Phe Leu Leu Val Leu Phe Ser Phe Thr Ile Gly Leu Thr Gln Leu Tyr
                565                 570                 575

Asp Lys Gly Tyr Thr Ser Lys Glu Gln Lys Asp Cys Val Gly Ile Phe
            580                 585                 590

Cys Glu Gln Gln Ser Asn Asp Thr Phe His Ser Phe Ile Gly Thr Cys
                595                 600                 605

Phe Ala Leu Phe Trp Tyr Ile Phe Ser Leu Ala His Val Ala Ile Phe
            610                 615                 620

Val Thr Arg Phe Ser Tyr Gly Glu Glu Leu Gln Ser Phe Val Gly Ala
625                 630                 635                 640

Val Ile Val Gly Thr Tyr Asn Val Val Val Ile Val Leu Thr Lys
                            645                 650             655

Leu Leu Val Ala Met Leu His Lys Ser Phe Gln Leu Ile Ala Asn His
                660                 665                 670

Glu Asp Lys Glu Trp Lys Phe Ala Arg Ala Lys Leu Trp Leu Ser Tyr
            675                 680                 685

Phe Asp Asp Lys Cys Thr Leu Pro Pro Phe Asn Ile Ile Pro Ser
690                 695                 700

Pro Lys Thr Ile Cys Tyr Met Ile Ser Ser Leu Ser Lys Trp Ile Cys
705                 710                 715                 720

Ser His Thr Ser Lys Gly Lys Val Lys Arg Gln Asn Ser Leu Lys Glu
                725                 730                 735

Trp Arg Asn Leu Lys Gln Lys Arg Asp Glu Asn Tyr Gln Lys Val Met
                740                 745                 750

Cys Cys Leu Val His Arg Tyr Leu Thr Ser Met Arg Gln Lys Met Gln
                755                 760                 765

Ser Thr Asp Gln Ala Thr Val Glu Asn Leu Asn Glu Leu Arg Gln Asp
                770                 775                 780

Leu Ser Lys Phe Arg Asn Glu Ile Arg Asp Leu Leu Gly Phe Arg Thr
785                 790                 795                 800

Ser Lys Tyr Ala Met Phe Tyr Pro Arg Asn
                805                 810

<210> SEQ ID NO 78
<211> LENGTH: 876
<212> TYPE: PRT
<213> ORGANISM: Mus musculus

<400> SEQUENCE: 78

Met Ser Arg Gly Asn Glu Asn Arg Leu Thr His Arg Gln Thr Ile
1               5                   10                  15

Leu Arg Glu Lys Gly Arg Arg Leu Ala Asn Arg Gly Pro Ala Tyr Met
                20                  25                  30

Phe Asn Asp His Ser Thr Ser Leu Ser Ile Glu Glu Arg Phe Leu
                35                  40                  45

Asp Ala Ala Glu Tyr Gly Asn Ile Pro Val Val Arg Lys Met Leu Glu
            50                  55                  60

Glu Cys His Ser Leu Asn Val Asn Cys Val Asp Tyr Met Gly Gln Asp
65                  70                  75                  80

Ala Leu Gln Leu Ala Val Ala Asn Glu His Leu Glu Ile Thr Glu Leu
                85                  90                  95
```

```
Leu Leu Lys Lys Glu Asn Leu Ser Arg Val Gly Asp Ala Leu Leu Leu
             100                 105                 110

Ala Ile Ser Lys Gly Tyr Val Arg Ile Val Glu Ala Ile Leu Asn His
         115                 120                 125

Pro Ala Phe Ala Glu Gly Lys Arg Leu Ala Thr Ser Pro Ser Gln Ser
     130                 135                 140

Glu Leu Gln Gln Asp Asp Phe Tyr Ala Tyr Asp Glu Asp Gly Thr Arg
145                 150                 155                 160

Phe Ser His Asp Val Thr Pro Ile Ile Leu Ala Ala His Cys Gln Glu
                 165                 170                 175

Tyr Glu Ile Val His Thr Leu Leu Arg Lys Gly Ala Arg Ile Glu Arg
             180                 185                 190

Pro His Asp Tyr Phe Cys Lys Cys Thr Glu Cys Ser Gln Lys Gln Lys
         195                 200                 205

His Asp Ser Phe Ser His Ser Arg Ser Arg Ile Asn Ala Tyr Lys Gly
     210                 215                 220

Leu Ala Ser Pro Ala Tyr Leu Ser Leu Ser Ser Glu Asp Pro Val Met
225                 230                 235                 240

Thr Ala Leu Glu Leu Ser Asn Glu Leu Ala Val Leu Ala Asn Ile Glu
                 245                 250                 255

Lys Glu Phe Lys Asn Asp Tyr Arg Lys Leu Ser Met Gln Cys Lys Asp
             260                 265                 270

Phe Val Val Gly Leu Leu Asp Leu Cys Arg Asn Thr Glu Glu Val Glu
         275                 280                 285

Ala Ile Leu Asn Gly Asp Ala Glu Thr Arg Gln Pro Gly Asp Phe Gly
     290                 295                 300

Arg Pro Asn Leu Ser Arg Leu Lys Leu Ala Ile Lys Tyr Glu Val Lys
305                 310                 315                 320

Lys Phe Val Ala His Pro Asn Cys Gln Gln Gln Leu Leu Ser Ile Trp
                 325                 330                 335

Tyr Glu Asn Leu Ser Gly Leu Arg Gln Gln Thr Met Ala Val Lys Phe
             340                 345                 350

Leu Val Val Leu Ala Val Ala Ile Gly Leu Pro Phe Leu Ala Leu Ile
         355                 360                 365

Tyr Trp Cys Ala Pro Cys Ser Lys Met Gly Lys Ile Leu Arg Gly Pro
     370                 375                 380

Phe Met Lys Phe Val Ala His Ala Ala Ser Phe Thr Ile Phe Leu Gly
385                 390                 395                 400

Leu Leu Val Met Asn Ala Ala Asp Arg Phe Glu Gly Thr Lys Leu Leu
                 405                 410                 415

Pro Asn Glu Thr Ser Thr Asp Asn Ala Arg Gln Leu Phe Arg Met Lys
             420                 425                 430

Thr Ser Cys Phe Ser Trp Met Glu Met Leu Ile Ile Ser Trp Val Ile
         435                 440                 445

Gly Met Ile Trp Ala Glu Cys Lys Glu Ile Trp Thr Gln Gly Pro Lys
     450                 455                 460

Glu Tyr Leu Phe Glu Leu Trp Asn Met Leu Asp Phe Gly Met Leu Ala
465                 470                 475                 480

Ile Phe Ala Ala Ser Phe Ile Ala Arg Phe Met Ala Phe Trp His Ala
                 485                 490                 495

Ser Lys Ala Gln Ser Ile Ile Asp Ala Asn Asp Thr Leu Lys Asp Leu
             500                 505                 510

Thr Lys Val Thr Leu Gly Asp Asn Val Lys Tyr Tyr Asn Leu Ala Arg
```

```
                515                 520                 525
Ile Lys Trp Asp Pro Thr Asp Pro Gln Ile Ile Ser Glu Gly Leu Tyr
        530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
                580                 585                 590

Phe Met Ile Gly Met Phe Asn Leu Tyr Ser Tyr Tyr Ile Gly Ala Lys
        595                 600                 605

Gln Asn Glu Ala Phe Thr Thr Val Glu Glu Ser Phe Lys Thr Leu Phe
        610                 615                 620

Trp Ala Ile Phe Gly Leu Ser Glu Val Lys Ser Val Val Ile Asn Tyr
625                 630                 635                 640

Asn His Lys Phe Ile Glu Asn Ile Gly Tyr Val Leu Tyr Gly Val Tyr
                645                 650                 655

Asn Val Thr Met Val Ile Val Leu Leu Asn Met Leu Ile Ala Met Ile
                660                 665                 670

Asn Ser Ser Phe Gln Glu Ile Glu Asp Asp Ala Asp Val Glu Trp Lys
        675                 680                 685

Phe Ala Arg Ala Lys Leu Trp Phe Ser Tyr Phe Glu Glu Gly Arg Thr
        690                 695                 700

Leu Pro Val Pro Phe Asn Leu Val Pro Ser Pro Lys Ser Leu Leu Tyr
705                 710                 715                 720

Leu Leu Leu Lys Phe Lys Lys Trp Met Cys Glu Leu Ile Gln Gly Gln
                725                 730                 735

Lys Gln Gly Phe Gln Glu Asp Ala Glu Met Asn Lys Arg Asn Glu Glu
                740                 745                 750

Lys Lys Phe Gly Ile Ser Gly Ser His Glu Asp Leu Ser Lys Phe Ser
        755                 760                 765

Leu Asp Lys Asn Gln Leu Ala His Asn Lys Gln Ser Ser Thr Arg Ser
        770                 775                 780

Ser Glu Asp Tyr His Leu Asn Ser Phe Ser Asn Pro Pro Arg Gln Tyr
785                 790                 795                 800

Gln Lys Ile Met Lys Arg Leu Ile Lys Arg Tyr Val Leu Gln Ala Gln
                805                 810                 815

Ile Asp Lys Glu Ser Asp Glu Val Asn Glu Gly Glu Leu Lys Glu Ile
                820                 825                 830

Lys Gln Asp Ile Ser Ser Leu Arg Tyr Glu Leu Leu Glu Glu Lys Ser
        835                 840                 845

Gln Asn Thr Glu Asp Leu Ala Glu Leu Ile Arg Lys Leu Gly Glu Arg
        850                 855                 860

Leu Ser Leu Glu Pro Lys Leu Glu Glu Ser Arg Arg
865                 870                 875

<210> SEQ ID NO 79
<211> LENGTH: 368
<212> TYPE: PRT
<213> ORGANISM: Homo sapiens

<400> SEQUENCE: 79

Asp Arg Leu Ser Leu Leu Ser Pro Arg Leu Glu Cys Asn Gly Met Ile
1               5                   10                  15
```

-continued

```
Leu Ala His Cys Lys Leu Arg Leu Pro Gly Phe Lys Arg Phe Ser Cys
             20                  25                  30
Leu Ser Leu Pro Ser Ser Trp Asp Tyr Arg His Val Pro Pro Arg Gln
         35                  40                  45
Val His Phe Val Phe Ser Val Glu Thr Gly Phe His Arg Ala Gly Gln
     50                  55                  60
Ala Gly Leu Glu Leu Leu Thr Ser Ser Val Pro Pro Thr Ser Ala Phe
 65                  70                  75                  80
Pro Lys Cys Trp Asp Tyr Arg Arg Asp Asp Gln Ala Trp Pro Thr Leu
                 85                  90                  95
Ser Ser Phe Arg Gly Leu Asn Lys Phe Ala Phe Leu Pro Lys Phe Phe
            100                 105                 110
Ala His Pro Ile Ser Gln Phe Gln Arg Val Glu Cys Asn Val Gly Cys
        115                 120                 125
Pro Ile Leu Leu Ala Met Lys Tyr Leu Ala Tyr Ser Ser Leu Pro Gly
    130                 135                 140
Ala Asp Thr Met Leu Tyr Phe Tyr Phe Tyr Glu Gln Glu Ala Ser Leu
145                 150                 155                 160
Ala Val Cys Asn Ile Cys Arg Gln Lys Phe His Trp Val Leu Tyr Gln
                165                 170                 175
Ile Ser His Leu Tyr Arg Gly Val Ile Val Asp Asn Phe Leu Leu His
            180                 185                 190
Pro Asp Gly Arg Phe Thr Trp Thr Ile Phe Phe Leu Ser Trp Val Lys
        195                 200                 205
Gln Asn Ser Leu Val Asp Phe Phe Gly Thr Glu Ser Arg Ser Val
    210                 215                 220
Ala Leu Leu Pro Arg Leu Glu Cys Ser Gly Ala Met Ser Thr Leu His
225                 230                 235                 240
Thr Val Leu Arg Pro Ala Tyr Ser His Ile Tyr His Pro Asp Val Lys
                245                 250                 255
Glu Lys Thr His Phe Leu Gly Asn Val Phe Asn Lys Arg Lys Leu Gln
            260                 265                 270
Lys Lys Ile Leu Lys Thr Pro Asn Pro Leu Cys Ala Leu His Ser Ala
        275                 280                 285
Pro Ser Pro Ser Leu Pro Pro Phe Leu Arg Cys Thr Gly Arg Leu Pro
    290                 295                 300
Phe Tyr Leu Gly Leu Asp Asp Phe Leu Phe Val Ala Gly Ala Leu Met
305                 310                 315                 320
Phe Leu Pro Val Ser Phe Leu Asn Pro His Thr Leu Thr Trp Pro Pro
                325                 330                 335
Gln Cys Cys Thr Arg Ser Asp Cys Asn Pro Leu Arg Gly Gln Arg Glu
            340                 345                 350
Ile Ser Ala Leu Ser His Ser Leu Pro Thr Gly Leu Ser Met Pro Leu
        355                 360                 365
```

<210> SEQ ID NO 80
<211> LENGTH: 341
<212> TYPE: PRT
<213> ORGANISM: Homo sapiens

<400> SEQUENCE: 80

```
Met Ala Ala Leu Tyr Ala Cys Thr Lys Cys His Gln Arg Phe Pro Phe
 1               5                  10                  15
Glu Ala Leu Ser Gln Gly Gln Gln Leu Cys Lys Glu Cys Arg Ile Ala
             20                  25                  30
```

```
His Pro Val Val Lys Cys Thr Tyr Cys Arg Thr Glu Tyr Gln Gln Glu
            35                  40                  45

Arg Leu Glu Cys Asn Gly Thr Ile Ser Ala His Cys Asn Leu His Leu
     50                  55                  60

Pro Gly Ser Ser Asp Ser Pro Ala Ser Ser Arg Val Ala Gly Ile
 65                  70                  75                  80

Thr Gly Ile Lys Thr Asn Thr Ile Cys Lys Lys Cys Ala Gln Asn Val
                 85                  90                  95

Gln Leu Tyr Gly Thr Pro Lys Pro Cys Gln Tyr Cys Asn Ile Ile Ala
                100                 105                 110

Ala Phe Ile Gly Asn Lys Cys Gln Arg Cys Thr Asn Ser Glu Lys Lys
             115                 120                 125

Tyr Gly Pro Pro Tyr Ser Cys Glu Gln Cys Lys Gln Gln Cys Ala Phe
             130                 135                 140

Asp Arg Lys Asp Arg Lys Val Asp Gly Lys Leu Leu Cys Trp
145                 150                 155                 160

Leu Cys Thr Leu Ser Tyr Lys Arg Val Leu Gln Lys Thr Lys Glu Gln
                165                 170                 175

Arg Lys His Leu Ser Ser Ser Arg Ala Gly His Gln Glu Lys Glu
             180                 185                 190

Gln Tyr Ser Arg Leu Ser Gly Gly His Tyr Asn Ser Gln Lys Thr
             195                 200                 205

Leu Ser Thr Ser Ser Ile Gln Asn Glu Ile Pro Lys Lys Ser Lys
     210                 215                 220

Phe Glu Ser Ile Thr Thr Asn Gly Asp Ser Phe Ser Pro Asp Leu Ala
225                 230                 235                 240

Leu Asp Ser Pro Gly Thr Asp His Phe Val Ile Ala Gln Leu Lys
                245                 250                 255

Glu Glu Val Ala Thr Leu Lys Lys Met Leu His Gln Lys Asp Gln Met
             260                 265                 270

Ile Leu Glu Lys Glu Lys Lys Ile Thr Glu Leu Lys Ala Asp Phe Gln
     275                 280                 285

Tyr Gln Glu Ser Gln Met Arg Ala Lys Met Asn Gln Met Glu Lys Thr
 290                 295                 300

His Lys Glu Val Thr Glu Gln Leu Gln Ala Lys Asn Arg Glu Leu Leu
305                 310                 315                 320

Lys Gln Ala Ala Ala Leu Ser Lys Ser Lys Ser Glu Lys Ser Gly
                325                 330                 335

Ala Ile Thr Ser Pro
            340

<210> SEQ ID NO 81
<211> LENGTH: 312
<212> TYPE: PRT
<213> ORGANISM: Homo sapiens

<400> SEQUENCE: 81

Met Ala Ala Leu Tyr Ala Cys Thr Lys Cys His Gln Arg Phe Pro Phe
 1               5                  10                  15

Glu Ala Leu Ser Gln Gly Gln Gln Leu Cys Lys Glu Cys Arg Ile Ala
             20                  25                  30

His Pro Val Val Lys Cys Thr Tyr Cys Arg Thr Glu Tyr Gln Gln Glu
            35                  40                  45

Arg Leu Glu Cys Asn Gly Thr Ile Ser Ala His Cys Asn Leu His Leu
     50                  55                  60
```

```
            50                  55                  60
Pro Gly Ser Ser Asp Ser Pro Ala Ser Ser Arg Val Ala Gly Ile
 65                  70                  75                  80

Thr Gly Ile Lys Thr Asn Thr Ile Cys Lys Lys Cys Ala Gln Asn Val
                 85                  90                  95

Gln Leu Tyr Gly Thr Pro Lys Pro Cys Gln Tyr Cys Asn Ile Ile Ala
                100                 105                 110

Ala Phe Ile Gly Asn Lys Cys Gln Arg Cys Thr Asn Ser Glu Lys Lys
            115                 120                 125

Tyr Gly Pro Pro Tyr Ser Cys Glu Gln Cys Lys Gln Gln Cys Ala Phe
130                 135                 140

Asp Arg Lys Asp Asp Arg Lys Lys Val Asp Gly Lys Leu Leu Cys Trp
145                 150                 155                 160

Leu Cys Thr Leu Ser Tyr Lys Arg Val Leu Gln Lys Thr Lys Glu Gln
                165                 170                 175

Arg Lys His Leu Ser Ser Ser Arg Ala Gly His Gln Glu Lys Glu
            180                 185                 190

Gln Tyr Ser Arg Leu Ser Gly Gly His Tyr Asn Ser Phe Ser Pro
        195                 200                 205

Asp Leu Ala Leu Asp Ser Pro Gly Thr Asp His Phe Val Ile Ile Ala
        210                 215                 220

Gln Leu Lys Glu Glu Val Ala Thr Leu Lys Lys Met Leu His Gln Lys
225                 230                 235                 240

Asp Gln Met Ile Leu Glu Lys Glu Lys Lys Ile Thr Glu Leu Lys Ala
                245                 250                 255

Asp Phe Gln Tyr Gln Glu Ser Gln Met Arg Ala Lys Met Asn Gln Met
                260                 265                 270

Glu Lys Thr His Lys Glu Val Thr Glu Gln Leu Gln Ala Lys Asn Arg
                275                 280                 285

Glu Leu Leu Lys Gln Ala Ala Leu Ser Lys Ser Lys Lys Ser Glu
            290                 295                 300

Lys Ser Gly Ala Ile Thr Ser Pro
305                 310

<210> SEQ ID NO 82
<211> LENGTH: 100
<212> TYPE: PRT
<213> ORGANISM: Homo sapiens

<400> SEQUENCE: 82

Phe Phe Phe Phe Phe Phe Glu Thr Glu Ser Cys Ser Val Ala Glu Ala
  1               5                  10                  15

Gly Val Gln Trp Cys Asp Leu Gly Ser Leu Lys Ser Pro Pro Pro Gly
             20                  25                  30

Ser Ser Asp Ser Pro Ala Ser Ala Ser Arg Val Ala Gly Ile Thr Gly
         35                  40                  45

Met His His His Thr Gln Leu Ile Phe Val Phe Leu Val Glu Thr Gly
     50                  55                  60

Ser His Met Gln Leu Ser Asp Ser Thr Leu Val Ile Thr Thr Ala Gln
 65                  70                  75                  80

Asn Ala Lys Ile Thr Ala Arg Ala Pro Arg Asp Leu Phe Phe Phe Phe
             85                  90                  95

Phe Phe Phe Phe
            100
```

```
<210> SEQ ID NO 83
<211> LENGTH: 56
<212> TYPE: PRT
<213> ORGANISM: Homo sapiens

<400> SEQUENCE: 83

Leu Pro Leu Pro Arg Met Glu Cys Arg Gly Met Ile Ser Ala His
 1               5                  10                  15

Cys Asn Leu Cys Arg Ser Gly Ser Ser Asp Ser Pro Ala Ser Ala Ser
                20                  25                  30

Arg Val Ala Gly Ile Thr Gly Thr Cys His His Ala Gln Leu Ser Phe
            35                  40                  45

Pro Phe Phe Leu Phe Met Arg Trp
        50                  55

<210> SEQ ID NO 84
<211> LENGTH: 46
<212> TYPE: PRT
<213> ORGANISM: Homo sapiens

<400> SEQUENCE: 84

Leu Pro Leu Pro Arg Met Glu Cys Arg Gly Met Ile Ser Ala His
 1               5                  10                  15

Cys Asn Leu Cys Arg Ser Gly Ser Ser Asp Ser Pro Ala Ser Ala Ser
                20                  25                  30

Arg Val Ala Gly Ile Thr Gly Thr Cys His His Ala Gln Leu
            35                  40                  45

<210> SEQ ID NO 85
<211> LENGTH: 699
<212> TYPE: PRT
<213> ORGANISM: Homo sapiens
<220> FEATURE:
<221> NAME/KEY: MOD_RES
<222> LOCATION: (677)
<223> OTHER INFORMATION: Variable amino acid

<400> SEQUENCE: 85

Met Asp Ile Glu Asp Glu Glu Asn Met Ser Ser Ser Thr Asp Val
 1               5                  10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly Gly
            35                  40                  45

Pro Gly Arg Lys Arg Pro Leu Glu Glu Gly Ser Asn Gly His Ser Lys
        50                  55                  60

Tyr Arg Leu Lys Lys Arg Arg Lys Thr Pro Gly Pro Val Leu Pro Lys
 65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160
```

-continued

```
Val Asn Thr Asp Phe Thr Ser Asp Gln Ala Asp Phe Pro Asp Thr Leu
            165                 170                 175
Phe Asn Gly Phe Glu Thr Pro Asp Lys Ala Glu Pro Pro Phe Tyr Val
            180                 185                 190
Gly Ser Asn Gly Asp Asp Ser Phe Ser Ser Gly Asp Leu Ser Leu
            195                 200                 205
Ser Ala Ser Pro Val Pro Ala Ser Leu Ala Gln Pro Pro Leu Pro Val
    210                 215                 220
Leu Pro Pro Phe Pro Pro Ser Gly Lys Asn Pro Val Met Ile Leu
225                 230                 235                 240
Asn Glu Leu Arg Pro Gly Leu Lys Tyr Asp Phe Leu Ser Glu Ser Gly
                245                 250                 255
Glu Ser His Ala Lys Ser Phe Val Met Ser Val Val Asp Gly Gln
            260                 265                 270
Phe Phe Glu Gly Ser Gly Arg Asn Lys Lys Leu Ala Lys Ala Arg Ala
            275                 280                 285
Ala Gln Ser Ala Leu Ala Ala Ile Phe Asn Leu His Leu Asp Gln Thr
    290                 295                 300
Pro Ser Arg Gln Pro Ile Pro Ser Glu Gly Leu Gln Leu His Leu Pro
305                 310                 315                 320
Gln Val Leu Ala Asp Ala Val Ser Arg Leu Val Leu Gly Lys Phe Gly
                325                 330                 335
Asp Leu Thr Asp Asn Phe Ser Ser Pro His Ala Arg Arg Lys Val Leu
            340                 345                 350
Ala Gly Val Val Met Thr Thr Gly Thr Asp Val Lys Asp Ala Lys Val
            355                 360                 365
Ile Ser Val Ser Thr Gly Thr Lys Cys Ile Asn Gly Glu Tyr Met Ser
    370                 375                 380
Asp Arg Gly Leu Ala Leu Asn Asp Cys His Ala Glu Ile Ile Ser Arg
385                 390                 395                 400
Arg Ser Leu Leu Arg Phe Leu Tyr Thr Gln Leu Glu Leu Tyr Leu Asn
                405                 410                 415
Asn Lys Asp Asp Gln Lys Arg Ser Ile Phe Gln Lys Ser Glu Arg Gly
            420                 425                 430
Gly Phe Arg Leu Lys Glu Asn Val Gln Phe His Leu Tyr Ile Ser Thr
            435                 440                 445
Ser Pro Cys Gly Asp Ala Arg Ile Phe Ser Pro His Glu Pro Ile Leu
    450                 455                 460
Glu Gly Ser Arg Ser Tyr Thr Gln Ala Gly Val Gln Trp Cys Asn His
465                 470                 475                 480
Gly Ser Leu Gln Pro Arg Pro Gly Leu Leu Ser Asp Pro Ser Thr
                485                 490                 495
Ser Thr Phe Gln Gly Ala Gly Thr Thr Glu Pro Ala Asp Arg His Pro
            500                 505                 510
Asn Arg Lys Ala Arg Gly Gln Leu Arg Thr Lys Ile Glu Ser Gly Glu
            515                 520                 525
Gly Thr Ile Pro Val Arg Ser Asn Ala Ser Ile Gln Thr Trp Asp Gly
    530                 535                 540
Val Leu Gln Gly Glu Arg Leu Leu Thr Met Ser Cys Ser Asp Lys Ile
545                 550                 555                 560
Ala Arg Trp Asn Val Val Gly Ile Gln Gly Ser Leu Leu Ser Ile Phe
                565                 570                 575
Val Glu Pro Ile Tyr Phe Ser Ser Ile Ile Leu Gly Ser Leu Tyr His
```

```
            580                 585                 590
Gly Asp His Leu Ser Arg Ala Met Tyr Gln Arg Ile Ser Asn Ile Glu
            595                 600                 605

Asp Leu Pro Pro Leu Tyr Thr Leu Asn Lys Pro Leu Leu Ser Gly Ile
            610                 615                 620

Ser Asn Ala Glu Ala Arg Gln Pro Gly Lys Ala Pro Asn Phe Ser Val
625                 630                 635                 640

Asn Trp Thr Val Gly Asp Ser Ala Ile Glu Val Ile Asn Ala Thr Thr
                    645                 650                 655

Gly Lys Asp Glu Leu Gly Arg Ala Ser Arg Leu Cys Lys His Ala Leu
            660                 665                 670

Tyr Cys Arg Trp Xaa Ala Cys Ala Arg Gln Gly Ser Leu Pro Leu Thr
            675                 680                 685

Thr Leu Gln Asp Tyr Gln Ala Gln Arg Val Pro
690                 695

<210> SEQ ID NO 86
<211> LENGTH: 331
<212> TYPE: PRT
<213> ORGANISM: Homo sapiens

<400> SEQUENCE: 86

Met Leu Leu Ser Gln Asn Ala Phe Ile Val Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
            35                  40                  45

Arg Ser Ile Leu Ser Trp Glu Leu Lys Asn His Ser Ile Val Pro Thr
        50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
            115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
            195                 200                 205

Ser Val Tyr Leu Glu His Ser Asp Glu Gln Ala Val Ile Lys Ser Pro
        210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255
```

```
Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Thr Lys Gly Trp
            275                 280                 285

Asn Ala Val Ala Ile His Arg Cys Ser His Asn Ala Leu Gln Ser Glu
            290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
                325                 330

<210> SEQ ID NO 87
<211> LENGTH: 841
<212> TYPE: PRT
<213> ORGANISM: Homo sapiens

<400> SEQUENCE: 87

Met Pro Leu Ala Ala Tyr Cys Tyr Leu Arg Val Val Gly Lys Gly Ser
 1               5                  10                  15

Tyr Gly Glu Val Thr Leu Val Lys His Arg Arg Asp Gly Lys Gln Tyr
             20                  25                  30

Val Ile Lys Lys Leu Asn Leu Arg Asn Ala Ser Ser Arg Glu Arg Arg
         35                  40                  45

Ala Ala Glu Gln Glu Ala Gln Leu Leu Ser Gln Leu Lys His Pro Asn
     50                  55                  60

Ile Val Thr Tyr Lys Glu Ser Trp Glu Gly Gly Asp Gly Leu Leu Tyr
 65                  70                  75                  80

Ile Val Met Gly Phe Cys Glu Gly Gly Asp Leu Tyr Arg Lys Leu Lys
                 85                  90                  95

Glu Gln Lys Gly Gln Leu Leu Pro Glu Asn Gln Val Val Glu Trp Phe
            100                 105                 110

Val Gln Ile Ala Met Ala Leu Gln Tyr Leu His Glu Lys His Ile Leu
        115                 120                 125

His Arg Asp Leu Lys Thr Gln Asn Val Phe Leu Thr Arg Thr Asn Ile
    130                 135                 140

Ile Lys Val Gly Asp Leu Gly Ile Ala Arg Val Leu Glu Asn His Cys
145                 150                 155                 160

Asp Met Ala Ser Thr Leu Ile Gly Thr Pro Tyr Tyr Met Ser Pro Glu
                165                 170                 175

Leu Phe Ser Asn Lys Pro Tyr Asn Tyr Lys Ser Asp Val Trp Ala Leu
            180                 185                 190

Gly Cys Cys Val Tyr Glu Met Ala Thr Leu Lys His Ala Phe Asn Ala
        195                 200                 205

Lys Asp Met Asn Ser Leu Val Tyr Arg Ile Ile Glu Gly Lys Leu Pro
    210                 215                 220

Ala Met Pro Arg Asp Tyr Ser Pro Glu Leu Ala Glu Leu Ile Arg Thr
225                 230                 235                 240

Met Leu Ser Lys Arg Pro Glu Arg Pro Ser Val Arg Ser Ile Leu
                245                 250                 255

Arg Gln Pro Tyr Ile Lys Arg Gln Ile Ser Phe Phe Leu Glu Ala Thr
            260                 265                 270

Lys Ile Lys Thr Ser Lys Asn Asn Ile Lys Asn Gly Asp Ser Gln Ser
        275                 280                 285

Lys Pro Phe Ala Thr Val Val Ser Gly Glu Ala Glu Ser Asn His Glu
    290                 295                 300
```

-continued

```
Val Ile His Pro Gln Pro Leu Ser Ser Glu Gly Ser Gln Thr Tyr Ile
305                 310                 315                 320

Met Gly Glu Gly Lys Cys Leu Ser Gln Glu Lys Pro Arg Ala Ser Gly
            325                 330                 335

Leu Leu Lys Ser Pro Ala Ser Leu Lys Ala His Thr Cys Lys Gln Asp
                340                 345                 350

Leu Ser Asn Thr Thr Glu Leu Ala Thr Ile Ser Ser Val Asn Ile Asp
            355                 360                 365

Ile Leu Pro Ala Lys Gly Arg Asp Ser Val Ser Asp Gly Phe Val Gln
    370                 375                 380

Glu Asn Gln Pro Arg Tyr Leu Asp Ala Ser Asn Glu Leu Gly Gly Ile
385                 390                 395                 400

Cys Ser Ile Ser Gln Val Glu Glu Met Leu Gln Asp Asn Thr Lys
                405                 410                 415

Ser Ser Ala Gln Pro Glu Asn Leu Ile Pro Met Trp Ser Ser Asp Ile
                420                 425                 430

Val Thr Gly Glu Lys Asn Glu Pro Val Lys Pro Leu Gln Pro Leu Ile
            435                 440                 445

Lys Glu Gln Lys Pro Lys Asp Gln Ser Leu Ala Leu Ser Pro Lys Leu
450                 455                 460

Glu Cys Ser Gly Thr Ile Leu Ala His Ser Asn Leu Arg Leu Leu Gly
465                 470                 475                 480

Ser Ser Asp Ser Pro Ala Ser Ala Ser Arg Val Ala Gly Ile Thr Gly
                485                 490                 495

Val Cys His His Ala Gln Asp Gln Val Ala Gly Glu Cys Ile Ile Glu
            500                 505                 510

Lys Gln Gly Arg Ile His Pro Asp Leu Gln Pro His Asn Ser Gly Ser
            515                 520                 525

Glu Pro Ser Leu Ser Arg Gln Arg Arg Gln Lys Arg Glu Gln Thr
                530                 535                 540

Glu His Arg Gly Glu Lys Arg Gln Val Arg Arg Asp Leu Phe Ala Phe
545                 550                 555                 560

Gln Glu Ser Pro Pro Arg Phe Leu Pro Ser His Pro Ile Val Gly Lys
                565                 570                 575

Val Asp Val Thr Ser Thr Gln Lys Glu Ala Glu Asn Gln Arg Arg Val
            580                 585                 590

Val Thr Gly Ser Val Ser Ser Arg Ser Ser Glu Met Ser Ser Ser
            595                 600                 605

Lys Asp Arg Pro Leu Ser Ala Arg Glu Arg Arg Leu Lys Gln Ser
610                 615                 620

Gln Glu Glu Met Ser Ser Ser Gly Pro Ser Val Arg Lys Ala Ser Leu
625                 630                 635                 640

Ser Val Ala Gly Pro Gly Lys Pro Gln Glu Glu Asp Gln Pro Leu Pro
                645                 650                 655

Ala Arg Arg Leu Ser Ser Asp Cys Ser Val Thr Gln Glu Arg Lys Gln
                660                 665                 670

Ile His Cys Leu Ser Glu Asp Glu Leu Ser Ser Thr Ser Ser Thr
        675                 680                 685

Asp Lys Ser Asp Gly Asp Tyr Gly Glu Gly Lys Gly Gln Thr Asn Glu
        690                 695                 700

Ile Asn Ala Leu Val Gln Leu Met Thr Gln Thr Leu Lys Leu Asp Ser
705                 710                 715                 720
```

```
Lys Glu Ser Cys Glu Asp Val Pro Val Ala Asn Pro Val Ser Glu Phe
                725                 730                 735

Lys Leu His Arg Lys Tyr Arg Asp Thr Leu Ile Leu His Gly Lys Val
            740                 745                 750

Ala Glu Glu Ala Glu Ile His Phe Lys Glu Leu Pro Ser Ala Ile
        755                 760                 765

Met Pro Gly Ser Glu Lys Ile Arg Arg Leu Val Glu Val Leu Arg Thr
770                 775                 780

Asp Val Ile Arg Gly Leu Gly Val Gln Leu Leu Glu Gln Val Tyr Asp
785                 790                 795                 800

Leu Leu Glu Glu Glu Asp Glu Phe Asp Arg Glu Val Arg Leu Arg Glu
                805                 810                 815

His Met Gly Glu Lys Tyr Thr Thr Tyr Ser Val Lys Ala Arg Gln Leu
            820                 825                 830

Lys Phe Phe Glu Glu Asn Met Asn Phe
            835                 840

<210> SEQ ID NO 88
<211> LENGTH: 759
<212> TYPE: PRT
<213> ORGANISM: Homo sapiens

<400> SEQUENCE: 88

Met Met Ala Ala Leu Tyr Pro Ser Thr Asp Leu Ser Gly Ala Ser Ser
 1               5                  10                  15

Ser Ser Leu Pro Ser Ser Pro Ser Ser Ser Pro Asn Glu Val Met
            20                  25                  30

Ala Leu Lys Asp Val Arg Glu Val Lys Glu Glu Asn Thr Leu Asn Glu
        35                  40                  45

Lys Leu Phe Leu Leu Ala Cys Asp Lys Gly Asp Tyr Tyr Met Val Lys
    50                  55                  60

Lys Ile Leu Glu Glu Asn Ser Ser Gly Asp Leu Asn Ile Asn Cys Val
65                  70                  75                  80

Asp Val Leu Gly Arg Asn Ala Val Thr Ile Thr Ile Glu Asn Glu Asn
                85                  90                  95

Leu Asp Ile Leu Gln Leu Leu Asp Tyr Gly Cys Gln Lys Leu Met
            100                 105                 110

Glu Arg Ile Gln Asn Pro Glu Tyr Ser Thr Thr Met Asp Val Ala Pro
        115                 120                 125

Val Ile Leu Ala Ala His Arg Asn Asn Tyr Glu Ile Leu Thr Met Leu
    130                 135                 140

Leu Lys Gln Asp Val Ser Leu Pro Lys Pro His Ala Val Gly Cys Glu
145                 150                 155                 160

Cys Thr Leu Cys Ser Ala Lys Asn Lys Lys Asp Ser Leu Arg His Ser
                165                 170                 175

Arg Phe Arg Leu Asp Ile Tyr Arg Cys Leu Ala Ser Pro Ala Leu Ile
            180                 185                 190

Met Leu Thr Glu Glu Asp Pro Ile Leu Arg Ala Phe Glu Leu Ser Ala
        195                 200                 205

Asp Leu Lys Glu Leu Ser Leu Val Glu Val Glu Phe Arg Asn Asp Tyr
    210                 215                 220

Glu Glu Leu Ala Arg Gln Cys Lys Met Phe Ala Lys Asp Leu Leu Ala
225                 230                 235                 240

Gln Ala Arg Asn Ser Arg Glu Leu Glu Val Ile Leu Asn His Thr Ser
                245                 250                 255
```

```
Ser Asp Glu Pro Leu Asp Lys Arg Gly Leu Leu Glu Arg Met Asn
            260                 265                 270

Leu Ser Arg Leu Lys Leu Ala Ile Lys Tyr Asn Gln Lys Glu Phe Val
        275                 280                 285

Ser Gln Ser Asn Cys Gln Gln Phe Leu Asn Thr Val Trp Phe Gly Gln
        290                 295                 300

Met Ser Gly Tyr Arg Arg Lys Pro Thr Cys Lys Lys Ile Met Thr Val
305                 310                 315                 320

Leu Thr Val Gly Ile Phe Trp Pro Val Leu Ser Leu Cys Tyr Leu Ile
                325                 330                 335

Ala Pro Lys Ser Gln Phe Gly Arg Ile Ile His Thr Pro Phe Met Lys
            340                 345                 350

Phe Ile Ile His Gly Ala Ser Tyr Phe Thr Phe Leu Leu Leu Leu Asn
            355                 360                 365

Leu Tyr Ser Leu Val Tyr Asn Glu Asp Lys Lys Asn Thr Met Gly Pro
        370                 375                 380

Ala Leu Glu Arg Ile Asp Tyr Leu Leu Ile Leu Trp Ile Ile Gly Met
385                 390                 395                 400

Ile Trp Ser Asp Ile Lys Arg Leu Trp Tyr Glu Gly Leu Glu Asp Phe
                405                 410                 415

Leu Glu Glu Ser Arg Asn Gln Leu Ser Phe Val Met Asn Ser Leu Tyr
            420                 425                 430

Leu Ala Thr Phe Ala Leu Lys Val Val Ala His Asn Lys Phe His Asp
            435                 440                 445

Phe Ala Asp Arg Lys Asp Trp Asp Ala Phe His Pro Thr Leu Val Ala
450                 455                 460

Glu Gly Leu Phe Ala Phe Ala Asn Val Leu Ser Tyr Leu Arg Leu Phe
465                 470                 475                 480

Phe Met Tyr Thr Thr Ser Ser Ile Leu Gly Pro Leu Gln Ile Ser Met
                485                 490                 495

Gly Gln Met Leu Gln Asp Phe Gly Lys Phe Leu Gly Met Phe Leu Leu
            500                 505                 510

Val Leu Phe Ser Phe Thr Ile Gly Leu Thr Gln Leu Tyr Asp Lys Gly
            515                 520                 525

Tyr Thr Ser Lys Glu Gln Lys Asp Cys Val Gly Ile Phe Cys Glu Gln
        530                 535                 540

Gln Ser Asn Asp Thr Phe His Ser Phe Ile Gly Thr Cys Phe Ala Leu
545                 550                 555                 560

Phe Trp Tyr Ile Phe Ser Leu Ala His Val Ala Ile Phe Val Thr Arg
                565                 570                 575

Phe Ser Tyr Gly Glu Leu Gln Ser Phe Val Gly Ala Val Ile Val
            580                 585                 590

Gly Thr Tyr Asn Val Val Val Ile Val Leu Thr Lys Leu Leu Val
        595                 600                 605

Ala Met Leu His Lys Ser Phe Gln Leu Ile Ala Asn His Glu Asp Lys
        610                 615                 620

Glu Trp Lys Phe Ala Arg Ala Lys Leu Trp Leu Ser Tyr Phe Asp Asp
625                 630                 635                 640

Lys Cys Thr Leu Pro Pro Pro Phe Asn Ile Ile Pro Ser Pro Lys Thr
                645                 650                 655

Ile Cys Tyr Met Ile Ser Ser Leu Ser Lys Trp Ile Cys Ser His Thr
                660                 665                 670
```

```
Ser Lys Gly Lys Val Lys Arg Gln Asn Ser Leu Lys Glu Trp Arg Asn
        675                 680                 685

Leu Lys Gln Lys Arg Asp Glu Asn Tyr Gln Lys Val Met Cys Cys Leu
        690                 695                 700

Val His Arg Tyr Leu Thr Ser Met Arg Gln Lys Met Gln Ser Thr Asp
705                 710                 715                 720

Gln Ala Thr Val Glu Asn Leu Asn Glu Leu Arg Gln Asp Leu Ser Lys
                725                 730                 735

Phe Arg Asn Glu Ile Arg Asp Leu Leu Gly Phe Arg Thr Ser Lys Tyr
                740                 745                 750

Ala Met Phe Tyr Pro Arg Asn
        755

<210> SEQ ID NO 89
<211> LENGTH: 848
<212> TYPE: PRT
<213> ORGANISM: Homo sapiens

<400> SEQUENCE: 89

Met Glu Gly Ser Pro Ser Leu Arg Arg Met Thr Val Met Arg Glu Lys
 1               5                  10                  15

Gly Arg Arg Gln Ala Val Arg Gly Pro Ala Phe Met Phe Asn Asp Arg
                20                  25                  30

Gly Thr Ser Leu Thr Ala Glu Glu Arg Phe Leu Asp Ala Ala Glu
            35                  40                  45

Tyr Gly Asn Ile Pro Val Val Arg Lys Met Leu Glu Glu Ser Lys Thr
        50                  55                  60

Leu Asn Val Asn Cys Val Asp Tyr Met Gly Gln Asn Ala Leu Gln Leu
65                  70                  75                  80

Ala Val Gly Asn Glu His Leu Glu Val Thr Glu Leu Leu Leu Lys Lys
                85                  90                  95

Glu Asn Leu Ala Arg Ile Gly Asp Ala Leu Leu Leu Ala Ile Ser Lys
                100                 105                 110

Gly Tyr Val Arg Ile Val Glu Ala Ile Leu Asn His Pro Gly Phe Ala
            115                 120                 125

Ala Ser Lys Arg Leu Thr Leu Ser Pro Cys Glu Gln Glu Leu Gln Asp
        130                 135                 140

Asp Asp Phe Tyr Ala Tyr Asp Glu Asp Gly Thr Arg Phe Ser Pro Asp
145                 150                 155                 160

Ile Thr Pro Ile Ile Leu Ala Ala His Cys Gln Lys Tyr Glu Val Val
                165                 170                 175

His Met Leu Leu Met Lys Gly Ala Arg Ile Glu Arg Pro His Asp Tyr
                180                 185                 190

Phe Cys Lys Cys Gly Asp Cys Met Glu Lys Gln Arg His Asp Ser Phe
            195                 200                 205

Ser His Ser Arg Ser Arg Ile Asn Ala Tyr Lys Gly Leu Ala Ser Pro
        210                 215                 220

Ala Tyr Leu Ser Leu Ser Ser Glu Asp Pro Val Leu Thr Ala Leu Glu
225                 230                 235                 240

Leu Ser Asn Glu Leu Ala Lys Leu Ala Asn Ile Glu Lys Glu Phe Lys
                245                 250                 255

Asn Asp Tyr Arg Lys Leu Ser Met Gln Cys Lys Asp Phe Val Val Gly
                260                 265                 270

Val Leu Asp Leu Cys Arg Asp Ser Glu Glu Val Glu Ala Ile Leu Asn
            275                 280                 285
```

-continued

Gly Asp Leu Glu Ser Ala Glu Pro Leu Glu Val His Arg His Lys Ala
    290                 295                 300

Ser Leu Ser Arg Val Lys Leu Ala Ile Lys Tyr Glu Val Lys Lys Phe
305                 310                 315                 320

Val Ala His Pro Asn Cys Gln Gln Leu Thr Ile Trp Tyr Glu
                325                 330                 335

Asn Leu Ser Gly Leu Arg Glu Gln Thr Ile Ala Ile Lys Cys Leu Val
            340                 345                 350

Val Leu Val Val Ala Leu Gly Leu Pro Phe Leu Ala Ile Gly Tyr Trp
        355                 360                 365

Ile Ala Pro Cys Ser Arg Leu Gly Lys Ile Leu Arg Ser Pro Phe Met
    370                 375                 380

Lys Phe Val Ala His Ala Ala Ser Phe Ile Ile Phe Leu Gly Leu Leu
385                 390                 395                 400

Val Phe Asn Ala Ser Asp Arg Phe Glu Gly Ile Thr Thr Leu Pro Asn
                405                 410                 415

Ile Thr Val Thr Asp Tyr Pro Lys Gln Ile Phe Arg Val Lys Thr Thr
            420                 425                 430

Gln Phe Thr Trp Thr Glu Met Leu Ile Met Val Trp Val Leu Gly Met
        435                 440                 445

Met Trp Ser Glu Cys Lys Glu Leu Trp Leu Gly Pro Arg Glu Tyr
    450                 455                 460

Ile Leu Gln Leu Trp Asn Val Leu Asp Phe Gly Met Leu Ser Ile Phe
465                 470                 475                 480

Ile Ala Ala Phe Thr Ala Arg Phe Leu Ala Phe Leu Gln Ala Thr Lys
                485                 490                 495

Ala Gln Gln Tyr Val Asp Ser Tyr Val Gln Glu Ser Asp Leu Ser Glu
            500                 505                 510

Val Thr Leu Pro Pro Glu Ile Gln Tyr Phe Thr Tyr Ala Arg Asp Lys
        515                 520                 525

Trp Leu Pro Ser Asp Pro Gln Ile Ile Ser Glu Gly Leu Tyr Ala Ile
    530                 535                 540

Ala Val Val Leu Ser Phe Ser Arg Ile Ala Tyr Ile Leu Pro Ala Asn
545                 550                 555                 560

Glu Ser Phe Gly Pro Leu Gln Ile Ser Leu Gly Arg Thr Val Lys Asp
                565                 570                 575

Ile Phe Lys Phe Met Val Leu Phe Ile Met Val Phe Phe Ala Phe Met
            580                 585                 590

Ile Gly Met Phe Ile Leu Tyr Ser Tyr Tyr Leu Gly Ala Lys Val Asn
        595                 600                 605

Ala Ala Phe Thr Thr Val Glu Glu Ser Phe Lys Thr Leu Phe Trp Ser
    610                 615                 620

Ile Phe Gly Leu Ser Glu Val Thr Ser Val Val Leu Lys Tyr Asp His
625                 630                 635                 640

Lys Phe Ile Glu Asn Ile Gly Tyr Val Leu Tyr Gly Ile Tyr Asn Val
                645                 650                 655

Thr Met Val Val Val Leu Leu Asn Met Leu Ile Ala Met Ile Asn Ser
            660                 665                 670

Ser Tyr Gln Glu Ile Glu Asp Asp Ser Asp Val Glu Trp Lys Phe Ala
        675                 680                 685

Arg Ser Lys Leu Trp Leu Ser Tyr Phe Asp Asp Gly Lys Thr Leu Pro
    690                 695                 700

-continued

```
Pro Pro Phe Ser Leu Val Pro Ser Pro Lys Ser Phe Val Tyr Phe Ile
705                 710                 715                 720

Met Arg Ile Val Asn Phe Pro Lys Cys Arg Arg Arg Leu Gln Lys
            725                 730                 735

Asp Ile Glu Met Gly Met Gly Asn Ser Lys Ser Arg Leu Asn Leu Phe
            740                 745                 750

Thr Gln Ser Asn Ser Arg Val Phe Glu Ser His Ser Phe Asn Ser Ile
            755                 760                 765

Leu Asn Gln Pro Thr Arg Tyr Gln Gln Ile Met Lys Arg Leu Ile Lys
770                 775                 780

Arg Tyr Val Leu Lys Ala Gln Val Asp Lys Glu Asn Asp Glu Val Asn
785                 790                 795                 800

Glu Gly Glu Leu Lys Glu Ile Lys Gln Asp Ile Ser Ser Leu Arg Tyr
                805                 810                 815

Glu Leu Leu Glu Asp Lys Ser Gln Ala Thr Glu Glu Leu Ala Ile Leu
                820                 825                 830

Ile His Lys Leu Ser Glu Lys Leu Asn Pro Ser Met Leu Arg Cys Glu
835                 840                 845
```

<210> SEQ ID NO 90
<211> LENGTH: 215
<212> TYPE: PRT
<213> ORGANISM: Homo sapiens

<400> SEQUENCE: 90

```
Met Ser Glu Thr Val Pro Pro Ala Pro Ala Ala Ser Ala Ala Pro Glu
1               5                   10                  15

Lys Pro Leu Ala Gly Lys Lys Ala Lys Lys Pro Ala Lys Ala Ala Ala
            20                  25                  30

Ala Ser Lys Lys Lys Pro Ala Gly Pro Ser Val Ser Glu Leu Ile Val
            35                  40                  45

Gln Ala Ala Ser Ser Ser Lys Glu Arg Gly Gly Val Ser Leu Ala Ala
        50                  55                  60

Leu Lys Lys Ala Leu Ala Ala Ala Gly Tyr Asp Val Glu Lys Asn Asn
65                  70                  75                  80

Ser Arg Ile Lys Leu Gly Ile Lys Ser Leu Val Ser Lys Gly Thr Leu
                85                  90                  95

Val Gln Thr Lys Gly Thr Gly Ala Ser Gly Ser Phe Lys Leu Asn Lys
            100                 105                 110

Lys Ala Ser Ser Val Glu Thr Lys Pro Gly Ala Ser Lys Val Ala Thr
            115                 120                 125

Lys Thr Lys Ala Thr Gly Ala Ser Lys Lys Leu Lys Lys Ala Thr Gly
            130                 135                 140

Ala Ser Lys Lys Ser Val Lys Thr Pro Lys Lys Ala Lys Lys Pro Ala
145                 150                 155                 160

Ala Thr Arg Lys Ser Ser Lys Asn Pro Lys Lys Pro Lys Thr Val Lys
                165                 170                 175

Pro Lys Lys Val Ala Lys Ser Pro Ala Lys Ala Lys Ala Val Lys Pro
            180                 185                 190

Lys Ala Ala Lys Ala Arg Val Thr Lys Pro Lys Thr Ala Lys Pro Lys
            195                 200                 205

Lys Ala Ala Pro Lys Lys Lys
            210                 215
```

<210> SEQ ID NO 91

<211> LENGTH: 931
<212> TYPE: PRT
<213> ORGANISM: Homo sapiens

<400> SEQUENCE: 91

```
Met Ser Gln Ser Pro Ala Phe Gly Pro Arg Arg Gly Ser Pro Arg
 1               5                  10                  15

Gly Ala Ala Gly Ala Ala Ala Arg Arg Asn Glu Ser Gln Asp Tyr Leu
                20                  25                  30

Leu Met Asp Ser Glu Leu Gly Glu Asp Gly Cys Pro Gln Ala Pro Leu
            35                  40                  45

Pro Cys Tyr Gly Tyr Tyr Pro Cys Phe Arg Gly Ser Asp Asn Arg Leu
    50                  55                  60

Ala His Arg Arg Gln Thr Val Leu Arg Glu Lys Gly Arg Arg Leu Ala
65                  70                  75                  80

Asn Arg Gly Pro Ala Tyr Met Phe Ser Asp Arg Ser Thr Ser Leu Ser
                85                  90                  95

Ile Glu Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
    115                 120                 125

Val Asp Tyr Met Gly Gln Asn Ala Leu Gln Leu Ala Val Ala Asn Glu
130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
    195                 200                 205

Tyr Asp Glu Asp Gly Thr Arg Phe Ser His Asp Val Thr Pro Ile Ile
210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
    275                 280                 285

Ser Ser Glu Asp Pro Val Met Thr Ala Leu Glu Leu Ser Asn Glu Leu
290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Cys
                325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
    355                 360                 365

Ala Ile Lys Tyr Glu Val Lys Lys Phe Val Ala His Pro Asn Cys Gln
370                 375                 380

Gln Gln Leu Leu Ser Ile Trp Tyr Glu Asn Leu Ser Gly Leu Arg Gln
```

```
             385                 390                 395                 400
Gln Thr Met Ala Val Lys Phe Leu Val Val Leu Ala Val Ala Ile Gly
                405                 410                 415
Leu Pro Phe Leu Ala Leu Ile Tyr Trp Phe Ala Pro Cys Ser Lys Met
            420                 425                 430
Gly Lys Ile Met Arg Gly Pro Phe Met Lys Phe Val Ala His Ala Ala
                435                 440                 445
Ser Phe Thr Ile Phe Leu Gly Leu Leu Val Met Asn Ala Ala Asp Arg
            450                 455                 460
Phe Glu Gly Thr Lys Leu Leu Pro Asn Glu Thr Ser Thr Asp Asn Ala
465                 470                 475                 480
Lys Gln Leu Phe Arg Met Lys Thr Ser Cys Phe Ser Trp Met Glu Met
                485                 490                 495
Leu Ile Ile Ser Trp Val Ile Gly Met Ile Trp Ala Glu Cys Lys Glu
                500                 505                 510
Ile Trp Thr Gln Gly Pro Lys Glu Tyr Leu Phe Glu Leu Trp Asn Met
            515                 520                 525
Leu Asp Phe Gly Met Leu Ala Ile Phe Ala Ala Ser Phe Ile Ala Arg
            530                 535                 540
Phe Met Ala Phe Trp His Ala Ser Lys Ala Gln Ser Ile Ile Asp Ala
545                 550                 555                 560
Asn Asp Thr Leu Lys Asp Leu Thr Lys Val Thr Leu Gly Asp Asn Val
                565                 570                 575
Lys Tyr Tyr Asn Leu Ala Arg Ile Lys Trp Asp Pro Ser Asp Pro Gln
            580                 585                 590
Ile Ile Ser Glu Gly Leu Tyr Ala Ile Ala Val Val Leu Ser Phe Ser
            595                 600                 605
Arg Ile Ala Tyr Ile Leu Pro Ala Asn Glu Ser Phe Gly Pro Leu Gln
            610                 615                 620
Ile Ser Leu Gly Arg Thr Val Lys Asp Ile Phe Lys Phe Met Val Ile
625                 630                 635                 640
Phe Ile Met Val Phe Val Ala Phe Met Ile Gly Met Phe Asn Leu Tyr
                645                 650                 655
Ser Tyr Tyr Ile Gly Ala Lys Gln Asn Glu Ala Phe Thr Thr Val Glu
                660                 665                 670
Glu Ser Phe Lys Thr Leu Phe Trp Ala Ile Phe Gly Leu Ser Glu Val
            675                 680                 685
Lys Ser Val Val Ile Asn Tyr Asn His Lys Phe Ile Glu Asn Ile Gly
            690                 695                 700
Tyr Val Leu Tyr Gly Val Tyr Asn Val Thr Met Val Ile Val Leu Leu
705                 710                 715                 720
Asn Met Leu Ile Ala Met Ile Asn Ser Ser Phe Gln Glu Ile Glu Asp
                725                 730                 735
Asp Ala Asp Val Glu Trp Lys Phe Ala Arg Ala Lys Leu Trp Phe Ser
            740                 745                 750
Tyr Phe Glu Glu Gly Arg Thr Leu Pro Val Pro Phe Asn Leu Val Pro
            755                 760                 765
Ser Pro Lys Ser Leu Phe Tyr Leu Leu Leu Lys Leu Lys Lys Trp Ile
            770                 775                 780
Ser Glu Leu Phe Gln Gly His Lys Lys Gly Phe Gln Glu Asp Ala Glu
785                 790                 795                 800
Met Asn Lys Ile Asn Glu Glu Lys Lys Leu Gly Ile Leu Gly Ser His
                805                 810                 815
```

```
Glu Asp Leu Ser Lys Leu Ser Leu Asp Lys Lys Gln Val Gly His Asn
            820                 825                 830

Lys Gln Pro Ser Ile Arg Ser Glu Asp Phe His Leu Asn Ser Phe
            835                 840                 845

Asn Asn Pro Pro Arg Gln Tyr Gln Lys Ile Met Lys Arg Leu Ile Lys
    850                 855                 860

Arg Tyr Val Leu Gln Ala Gln Ile Asp Lys Glu Ser Asp Glu Val Asn
865                 870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Glu Lys Leu Ser Met Glu Pro Asn Gln Glu Glu
            915                 920                 925

Thr Asn Arg
    930

<210> SEQ ID NO 92

<400> SEQUENCE: 92

000

<210> SEQ ID NO 93
<211> LENGTH: 15
<212> TYPE: PRT
<213> ORGANISM: Homo sapiens

<400> SEQUENCE: 93

Ser Arg Asp Pro Pro Ala Ser Ala Ser Gln Val Thr Gly Ile Arg
1               5                   10                  15

<210> SEQ ID NO 94
<211> LENGTH: 396
<212> TYPE: PRT
<213> ORGANISM: Homo sapiens

<400> SEQUENCE: 94

Met Ala Ser Leu Ser Arg Ala Leu Arg Val Ala Ala Ala His Pro Arg
1               5                   10                  15

Gln Ser Pro Thr Arg Gly Met Gly Pro Cys Asn Leu Ser Ser Ala Ala
            20                  25                  30

Gly Pro Thr Ala Glu Lys Ser Val Pro Tyr Gln Arg Thr Leu Lys Glu
        35                  40                  45

Gly Gln Gly Thr Ser Val Val Ala Gln Gly Pro Ser Arg Pro Leu Pro
    50                  55                  60

Ser Thr Ala Asn Val Val Val Ile Gly Gly Ser Leu Gly Cys Gln
65                  70                  75                  80

Thr Leu Tyr His Leu Ala Lys Leu Gly Met Ser Gly Ala Val Leu Leu
                85                  90                  95

Glu Arg Glu Arg Leu Thr Ser Gly Thr Thr Trp His Thr Ala Gly Leu
            100                 105                 110

Leu Trp Gln Leu Arg Pro Ser Asp Val Glu Val Glu Leu Leu Ala His
            115                 120                 125

Thr Arg Arg Val Val Ser Arg Glu Leu Glu Glu Thr Gly Leu His
    130                 135                 140

Thr Gly Trp Ile Gln Asn Gly Gly Leu Phe Ile Ala Ser Asn Arg Gln
```

-continued

```
                145                 150                 155                 160
Arg Leu Asp Glu Tyr Lys Arg Leu Met Ser Leu Gly Lys Ala Tyr Gly
                    165                 170                 175
Val Glu Ser His Val Leu Ser Pro Ala Glu Thr Lys Thr Leu Tyr Pro
                180                 185                 190
Leu Met Asn Val Asp Asp Leu Tyr Gly Thr Leu Tyr Val Pro His Asp
            195                 200                 205
Gly Thr Met Asp Pro Ala Gly Thr Cys Thr Thr Leu Ala Arg Ala Ala
        210                 215                 220
Ser Ala Arg Gly Ala Gln Val Ile Glu Asn Cys Pro Val Thr Gly Ile
225                 230                 235                 240
Arg Val Trp Thr Asp Asp Phe Gly Val Arg Arg Val Ala Gly Val Glu
                    245                 250                 255
Thr Gln His Gly Ser Ile Gln Thr Pro Cys Val Val Asn Cys Ala Gly
                260                 265                 270
Val Trp Ala Ser Ala Val Gly Arg Met Ala Gly Val Lys Val Pro Leu
            275                 280                 285
Val Ala Met His His Ala Tyr Val Val Thr Glu Arg Ile Glu Gly Ile
        290                 295                 300
Gln Ser Phe Thr Leu Leu Pro Thr Leu Glu Tyr Ser Gly Thr Val Ser
305                 310                 315                 320
Ala His Cys Asn Leu Arg Leu Pro Gly Ser Ser Asn Ser Arg Ala Ser
                    325                 330                 335
Ala Ser His Val Ala Gly Ile Lys Cys Ala Arg His His Thr Arg Leu
                340                 345                 350
Ile Phe Phe Cys Ile Leu Val Glu Thr Glu Phe His His Val Ala Lys
            355                 360                 365
Ala Gly Leu Glu Leu Leu Ser Ser Gly Asn Pro Pro Ile Ser Asp Phe
        370                 375                 380
Gln Ser Ala Arg Ile Thr Gly Val Ser His His Ala
385                 390                 395
```

<210> SEQ ID NO 95
<211> LENGTH: 72
<212> TYPE: PRT
<213> ORGANISM: Homo sapiens

<400> SEQUENCE: 95

```
Leu Leu Trp Val Leu Leu Trp Ala Thr Val Leu Gly Leu Leu Cys Gln
  1               5                  10                  15
Arg Leu Ala Ala Arg Leu Gly Val Val Thr Gly Lys Asp Leu Gly Glu
                20                  25                  30
Val Cys His Leu Tyr Tyr Pro Lys Ser Glu Ser Arg Ser Val Ala Gln
            35                  40                  45
Ser Gly Val Gln Trp Cys Asp Val Ser Ser Leu Gln Pro Leu Pro Pro
        50                  55                  60
Arg Cys Pro Ala Pro Ser Ser Gly
65                  70
```

<210> SEQ ID NO 96
<211> LENGTH: 84
<212> TYPE: PRT
<213> ORGANISM: Homo sapiens

<400> SEQUENCE: 96

```
Met Glu Thr Glu Ser Gly Ser Val Ala Gln Ala Gly Val Gln Trp His
```

-continued

```
                 1               5              10              15
Asn Leu Gly Ser Leu Gln Pro Pro Ser Arg Leu Lys Gln Leu Ser
                20              25              30

Tyr Leu Ser Leu Pro Ser Ser Trp Asp Tyr Arg Cys Thr Pro His
                35              40              45

Pro Ala Asn Phe Leu Tyr Phe Asn Arg Asp Gly Ile Ser Pro Cys Cys
                50              55              60

Pro Gly Trp Ser Pro Thr Pro Lys Leu Thr Gln Ser Thr His Leu Gly
 65                 70              75                      80

Leu Ser Lys Cys
```

<210> SEQ ID NO 97
<211> LENGTH: 836
<212> TYPE: PRT
<213> ORGANISM: Homo sapiens

<400> SEQUENCE: 97

```
                 1               5              10              15
Met Ala Gln Phe Tyr Tyr Lys Arg Asn Val Asn Ala Pro Tyr Arg Asp
 1                  5              10                      15

Arg Ile Pro Leu Arg Ile Val Arg Ala Glu Ser Glu Leu Ser Pro Ser
                20              25              30

Glu Lys Ala Tyr Leu Asn Ala Val Glu Lys Gly Asp Tyr Ala Ser Val
                35              40              45

Lys Lys Ser Leu Glu Glu Ala Glu Ile Tyr Phe Lys Ile Asn Ile Asn
                50              55              60

Cys Ile Asp Pro Leu Gly Arg Thr Ala Leu Leu Ile Ala Ile Glu Asn
 65                 70              75                      80

Glu Asn Leu Glu Leu Ile Glu Leu Leu Leu Ser Phe Asn Val Tyr Val
                85              90              95

Gly Asp Ala Leu Leu His Ala Ile Arg Lys Glu Val Val Gly Ala Val
                100             105             110

Glu Leu Leu Leu Asn His Lys Lys Pro Ser Gly Glu Lys Gln Val Pro
                115             120             125

Pro Ile Leu Leu Asp Lys Gln Phe Ser Glu Phe Thr Pro Asp Ile Thr
                130             135             140

Pro Ile Ile Leu Ala Ala His Thr Asn Asn Tyr Glu Ile Ile Lys Leu
145                 150             155                     160

Leu Val Gln Lys Gly Val Ser Val Pro Arg Pro His Glu Val Arg Cys
                165             170             175

Asn Cys Val Glu Cys Val Ser Ser Asp Val Asp Ser Leu Arg His
                180             185             190

Ser Arg Ser Arg Leu Asn Ile Tyr Lys Ala Leu Ala Ser Pro Ser Leu
                195             200             205

Ile Ala Leu Ser Ser Glu Asp Pro Phe Leu Thr Ala Phe Gln Leu Ser
                210             215             220

Trp Glu Leu Gln Glu Leu Ser Lys Val Glu Asn Glu Phe Lys Ser Glu
225                 230             235                     240

Tyr Glu Glu Leu Ser Arg Gln Cys Lys Gln Phe Ala Lys Asp Leu Leu
                245             250             255

Asp Gln Thr Arg Ser Ser Arg Glu Leu Glu Ile Ile Leu Asn Tyr Arg
                260             265             270

Asp Asp Asn Ser Leu Ile Glu Glu Gln Ser Gly Asn Asp Leu Ala Arg
                275             280             285

Leu Lys Leu Ala Ile Lys Tyr Arg Gln Lys Glu Phe Val Ala Gln Pro
```

```
        290                 295                 300
Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys
                340                 345                 350

Ser Pro Leu Gly Leu Phe Ile Arg Lys Pro Phe Ile Lys Phe Ile Cys
                355                 360                 365

His Thr Ala Ser Tyr Leu Thr Phe Leu Phe Leu Leu Leu Leu Ala Ser
        370                 375                 380

Gln His Ile Asp Arg Ser Asp Leu Asn Arg Gln Gly Pro Pro Pro Thr
385                 390                 395                 400

Ile Val Glu Trp Met Ile Leu Pro Trp Val Leu Gly Phe Ile Trp Gly
                405                 410                 415

Glu Ile Lys Gln Met Trp Asp Gly Gly Leu Gln Asp Tyr Ile His Asp
                420                 425                 430

Trp Trp Asn Leu Met Asp Phe Val Met Asn Ser Leu Tyr Leu Ala Thr
            435                 440                 445

Ile Ser Leu Lys Ile Val Ala Phe Val Lys Tyr Ser Ala Leu Asn Pro
        450                 455                 460

Arg Glu Ser Trp Asp Met Trp His Pro Thr Leu Val Ala Glu Ala Leu
465                 470                 475                 480

Phe Ala Ile Ala Asn Ile Phe Ser Ser Leu Arg Leu Ile Ser Leu Phe
                485                 490                 495

Thr Ala Asn Ser His Leu Gly Pro Leu Gln Ile Ser Leu Gly Arg Met
                500                 505                 510

Leu Leu Asp Ile Leu Lys Phe Leu Phe Ile Tyr Cys Leu Val Leu Leu
            515                 520                 525

Ala Phe Ala Asn Gly Leu Asn Gln Leu Tyr Phe Tyr Tyr Glu Glu Thr
        530                 535                 540

Lys Gly Leu Thr Cys Lys Gly Ile Arg Cys Glu Lys Gln Asn Asn Ala
545                 550                 555                 560

Phe Ser Thr Leu Phe Glu Thr Leu Gln Ser Leu Phe Trp Ser Ile Phe
                565                 570                 575

Gly Leu Ile Asn Leu Tyr Val Thr Asn Val Lys Ala Gln His Glu Phe
                580                 585                 590

Thr Glu Phe Val Gly Ala Thr Met Phe Gly Thr Tyr Asn Val Ile Ser
            595                 600                 605

Leu Val Val Leu Leu Asn Met Leu Ile Ala Met Met Asn Asn Ser Tyr
        610                 615                 620

Gln Leu Ile Ala Asp His Ala Asp Ile Glu Trp Lys Phe Ala Arg Thr
625                 630                 635                 640

Lys Leu Trp Met Ser Tyr Phe Glu Glu Gly Thr Leu Pro Thr Pro
                645                 650                 655

Phe Asn Val Ile Pro Ser Pro Lys Ser Leu Trp Tyr Leu Ile Lys Trp
                660                 665                 670

Ile Trp Thr His Leu Cys Lys Lys Met Arg Arg Lys Pro Glu Ser
            675                 680                 685

Phe Gly Thr Ile Gly Arg Arg Ala Ala Asp Asn Leu Arg Arg His His
            690                 695                 700

Gln Tyr Gln Glu Val Met Arg Asn Leu Val Lys Arg Tyr Val Ala Ala
705                 710                 715                 720
```

```
Met Ile Arg Asp Ala Lys Thr Glu Glu Val Ala Arg Gln Gln Ala Ala
                725                 730                 735

Gly Pro Leu Glu Arg Asn Ile Gln Leu Glu Ser Arg Gly Leu Ala Ser
            740                 745                 750

Arg Gly Asp Leu Ser Ile Pro Gly Leu Ser Glu Gln Cys Val Leu Val
            755                 760                 765

Asp His Arg Glu Arg Asn Thr Asp Thr Leu Gly Leu Gln Val Gly Lys
            770                 775                 780

Arg Val Cys Pro Phe Lys Ser Glu Lys Val Val Glu Asp Thr Val
785                 790                 795                 800

Pro Ile Ile Pro Lys Glu Lys His Ala Lys Glu Glu Asp Ser Ser Ile
                805                 810                 815

Asp Tyr Asp Leu Asn Leu Pro Asp Thr Val Thr His Glu Asp Tyr Val
            820                 825                 830

Thr Thr Arg Leu
            835

<210> SEQ ID NO 98
<211> LENGTH: 828
<212> TYPE: PRT
<213> ORGANISM: Homo sapiens

<400> SEQUENCE: 98

Met Ala Gln Phe Tyr Tyr Lys Arg Asn Val Asn Ala Pro Tyr Arg Asp
1               5                   10                  15

Arg Ile Pro Leu Arg Ile Val Arg Ala Glu Ser Glu Leu Ser Pro Ser
            20                  25                  30

Glu Lys Ala Tyr Leu Asn Ala Val Glu Lys Gly Asp Tyr Ala Ser Val
        35                  40                  45

Lys Lys Ser Leu Glu Glu Ala Glu Ile Tyr Phe Lys Ile Asn Ile Asn
    50                  55                  60

Cys Ile Asp Pro Leu Gly Arg Thr Ala Leu Leu Ile Ala Ile Glu Asn
65                  70                  75                  80

Glu Asn Leu Glu Leu Ile Glu Leu Leu Leu Ser Phe Asn Val Tyr Val
                85                  90                  95

Gly Asp Ala Leu Leu His Ala Ile Arg Lys Glu Val Val Gly Ala Val
            100                 105                 110

Glu Leu Leu Leu Asn His Lys Lys Pro Ser Gly Glu Lys Gln Val Pro
        115                 120                 125

Pro Ile Leu Leu Asp Lys Gln Phe Ser Glu Phe Thr Pro Asp Ile Thr
    130                 135                 140

Pro Ile Ile Leu Ala Ala His Thr Asn Asn Tyr Glu Ile Ile Lys Leu
145                 150                 155                 160

Leu Val Gln Lys Gly Val Ser Val Pro Arg Pro His Glu Val Arg Cys
                165                 170                 175

Asn Cys Val Glu Cys Val Ser Ser Asp Val Asp Ser Leu Arg His
            180                 185                 190

Ser Arg Ser Arg Leu Asn Ile Tyr Lys Ala Leu Ala Ser Pro Ser Leu
        195                 200                 205

Ile Ala Leu Ser Ser Glu Asp Pro Phe Leu Thr Ala Phe Gln Leu Ser
    210                 215                 220

Trp Glu Leu Gln Glu Leu Ser Lys Val Glu Asn Glu Phe Lys Ser Glu
225                 230                 235                 240

Tyr Glu Glu Leu Ser Arg Gln Cys Lys Gln Phe Ala Lys Asp Leu Leu
```

-continued

```
                245                 250                 255
Asp Gln Thr Arg Ser Ser Arg Glu Leu Glu Ile Ile Leu Asn Tyr Arg
                260                 265                 270

Asp Asp Asn Ser Leu Ile Glu Glu Gln Ser Gly Asn Asp Leu Ala Arg
                275                 280                 285

Leu Lys Leu Ala Ile Lys Tyr Arg Gln Lys Glu Phe Val Ala Gln Pro
                290                 295                 300

Asn Cys Gln Gln Leu Leu Ala Ser Arg Trp Tyr Asp Glu Phe Pro Gly
305                 310                 315                 320

Trp Arg Arg Arg His Trp Ala Val Lys Met Val Thr Cys Phe Ile Ile
                325                 330                 335

Gly Leu Leu Phe Pro Val Phe Ser Val Cys Tyr Leu Ile Ala Pro Lys
                340                 345                 350

Ser Pro Leu Gly Leu Phe Ile Arg Lys Pro Phe Ile Lys Phe Ile Cys
                355                 360                 365

His Thr Ala Ser Tyr Leu Thr Phe Leu Phe Leu Leu Leu Leu Ala Ser
                370                 375                 380

Gln His Ile Asp Arg Ser Asp Leu Asn Arg Gln Gly Pro Pro Pro Thr
385                 390                 395                 400

Ile Val Glu Trp Met Ile Leu Pro Trp Val Leu Gly Phe Ile Trp Gly
                405                 410                 415

Glu Ile Lys Gln Met Trp Asp Gly Gly Leu Gln Asp Tyr Ile His Asp
                420                 425                 430

Trp Trp Asn Leu Met Asp Phe Val Met Asn Ser Leu Tyr Leu Ala Thr
                435                 440                 445

Ile Ser Leu Lys Ile Val Ala Phe Val Lys Tyr Ser Ala Leu Asn Pro
450                 455                 460

Arg Glu Ser Trp Asp Met Trp His Pro Thr Leu Val Ala Glu Ala Leu
465                 470                 475                 480

Phe Ala Ile Ala Asn Ile Phe Ser Ser Leu Arg Leu Ile Ser Leu Phe
                485                 490                 495

Thr Ala Asn Ser His Leu Gly Pro Leu Gln Ile Ser Leu Gly Arg Met
                500                 505                 510

Leu Leu Asp Ile Leu Lys Phe Leu Phe Ile Tyr Cys Leu Val Leu Leu
                515                 520                 525

Ala Phe Ala Asn Gly Leu Asn Gln Leu Tyr Phe Tyr Glu Glu Thr
                530                 535                 540

Lys Gly Leu Thr Cys Lys Gly Ile Arg Cys Glu Lys Gln Asn Asn Ala
545                 550                 555                 560

Phe Ser Thr Leu Phe Glu Thr Leu Gln Ser Leu Phe Trp Ser Ile Phe
                565                 570                 575

Gly Leu Ile Asn Leu Tyr Val Thr Asn Val Lys Ala Gln His Glu Phe
                580                 585                 590

Thr Glu Phe Val Gly Ala Thr Met Phe Gly Thr Tyr Asn Val Ile Ser
                595                 600                 605

Leu Val Val Leu Leu Asn Met Leu Ile Ala Met Met Asn Asn Ser Tyr
                610                 615                 620

Gln Leu Ile Ala Arg Arg Ala Ala Asp Asn Leu Arg Arg His His Gln
625                 630                 635                 640

Tyr Gln Glu Val Met Arg Asn Leu Val Lys Arg Tyr Val Ala Ala Met
                645                 650                 655

Ile Arg Asp Ala Lys Thr Glu Glu Gly Leu Thr Glu Glu Asn Phe Lys
                660                 665                 670
```

-continued

```
Glu Leu Lys Gln Asp Ile Ser Ser Phe Arg Phe Glu Val Leu Gly Leu
            675                 680                 685
Leu Arg Gly Ser Lys Leu Ser Thr Ile Gln Ser Ala Asn Ala Ser Lys
        690                 695                 700
Glu Ser Ser Asn Ser Ala Asp Ser Asp Glu Lys Ser Asp Ser Glu Glu
705                 710                 715                 720
Glu Val Ala Arg Gln Gln Ala Ala Gly Pro Leu Glu Arg Asn Ile Gln
                725                 730                 735
Leu Glu Ser Arg Gly Leu Ala Ser Arg Gly Asp Leu Ser Ile Pro Gly
            740                 745                 750
Leu Ser Glu Gln Cys Val Leu Val Asp His Arg Glu Arg Asn Thr Asp
        755                 760                 765
Thr Leu Gly Leu Gln Val Gly Lys Arg Val Cys Pro Phe Lys Ser Glu
    770                 775                 780
Lys Val Val Glu Asp Thr Val Pro Ile Ile Pro Lys Glu Lys His
785                 790                 795                 800
Ala Lys Glu Glu Asp Ser Ser Ile Asp Tyr Asp Leu Asn Leu Pro Asp
                805                 810                 815
Thr Val Thr His Glu Asp Tyr Val Thr Thr Arg Leu
            820                 825
```

<210> SEQ ID NO 99
<211> LENGTH: 73
<212> TYPE: PRT
<213> ORGANISM: Homo sapiens
<220> FEATURE:
<221> NAME/KEY: MOD_RES
<222> LOCATION: (18)
<223> OTHER INFORMATION: Variable amino acid

<400> SEQUENCE: 99

```
Met Arg Thr Lys Ser Glu Arg Glu Ile His Leu Cys Val Leu Gly Phe
1               5                   10                  15
Phe Xaa Phe Phe Phe Glu Thr Gly Ser Arg Ser Val Ala Gln Ala Gly
            20                  25                  30
Val Gln Arg His Ser His Gly Ser Leu Gln Pro Arg Pro Pro Gly Leu
        35                  40                  45
Ile Gln Phe Ser His Leu Ser Leu Pro Ser Ser Trp Asp Tyr Arg His
    50                  55                  60
Ala Pro Pro His Leu Val Asn Phe Leu
65                  70
```

<210> SEQ ID NO 100
<211> LENGTH: 61
<212> TYPE: PRT
<213> ORGANISM: Homo sapiens

<400> SEQUENCE: 100

```
Arg Phe Phe Phe Phe Phe Phe Phe Glu Glu Ser Arg Ser Phe Ala Gln
1               5                   10                  15
Ala Gly Val Gln Trp Arg Tyr Leu Gly Ser Leu Gln Pro Pro Pro Pro
            20                  25                  30
Gly Phe Thr Arg Phe Ser Cys Leu Ser Leu Ser Ser Trp Asp Tyr
        35                  40                  45
Arg Arg Pro Pro Pro Arg Pro Ala Asn Phe Leu Tyr Phe
    50                  55                  60
```

-continued

<210> SEQ ID NO 101
<211> LENGTH: 1258
<212> TYPE: PRT
<213> ORGANISM: Homo sapiens

<400> SEQUENCE: 101

```
Glu Leu Ser Phe Pro Leu Leu Ser Leu Asp Phe Gly Ala His Gln Gly
  1               5                  10                  15

Leu Gly Ser Ala Asp Met Gly Asp Met Lys Thr Pro Asp Phe Asp Asp
             20                  25                  30

Leu Leu Ala Ala Phe Asp Ile Pro Asp Ile Asp Ala Asn Glu Ala Ile
         35                  40                  45

His Ser Gly Pro Glu Glu Asn Glu Gly Pro Gly Pro Gly Lys Pro
     50                  55                  60

Glu Pro Gly Val Gly Ser Glu Ser Glu Asp Thr Ala Ala Ser Ala
 65                  70                  75                  80

Gly Asp Gly Pro Gly Val Pro Ala Gln Ala Ser Asp His Gly Leu Pro
                 85                  90                  95

Pro Pro Asp Ile Ser Val Val Ser Val Ile Val Lys Asn Thr Val Cys
            100                 105                 110

Pro Glu Gln Ser Glu Ala Leu Ala Gly Gly Ser Ala Gly Asp Gly Ala
        115                 120                 125

Gln Ala Ala Gly Val Thr Lys Glu Gly Pro Val Gly Pro His Arg Met
130                 135                 140

Gln Asn Gly Phe Gly Ser Pro Glu Pro Ser Leu Pro Gly Thr Pro His
145                 150                 155                 160

Ser Pro Ala Pro Pro Ser Gly Gly Thr Trp Lys Glu Lys Gly Met Glu
                165                 170                 175

Gly Lys Thr Pro Leu Asp Leu Phe Ala His Phe Gly Pro Glu Pro Gly
            180                 185                 190

Asp His Ser Asp Pro Leu Pro Pro Ser Ala Pro Ser Pro Thr Arg Glu
        195                 200                 205

Gly Ala Leu Thr Pro Pro Phe Pro Ser Ser Phe Glu Leu Ala Gln
    210                 215                 220

Glu Asn Gly Pro Gly Met Gln Pro Pro Val Ser Ser Pro Leu Gly
225                 230                 235                 240

Ala Leu Lys Gln Glu Ser Cys Ser Pro His His Pro Gln Val Leu Ala
                245                 250                 255

Gln Gln Gly Ser Gly Ser Ser Pro Lys Ala Thr Asp Ile Pro Ala Ser
            260                 265                 270

Ala Ser Pro Pro Val Ala Gly Val Pro Phe Phe Lys Gln Ser Pro
        275                 280                 285

Gly His Gln Ser Pro Leu Ala Ser Pro Lys Val Pro Val Cys Gln Pro
    290                 295                 300

Leu Lys Glu Glu Asp Asp Glu Gly Pro Val Asp Lys Ser Ser Pro
305                 310                 315                 320

Gly Ser Pro Gln Ser Pro Ser Ser Gly Ala Glu Ala Ala Asp Glu Asp
                325                 330                 335

Ser Asn Asp Ser Pro Ala Ser Ser Ser Arg Pro Leu Lys Val Arg
            340                 345                 350

Ile Lys Thr Ile Lys Thr Ser Cys Gly Asn Ile Thr Arg Thr Val Thr
        355                 360                 365

Gln Val Pro Ser Asp Pro Asp Pro Ala Pro Leu Ala Glu Gly Ala
    370                 375                 380
```

-continued

```
Phe Leu Ala Glu Ala Ser Leu Leu Lys Leu Ser Pro Ala Thr Pro Thr
385                 390                 395                 400

Ser Glu Gly Pro Lys Val Val Ser Val Gln Leu Gly Asp Gly Thr Arg
                405                 410                 415

Leu Lys Gly Thr Val Leu Pro Val Ala Thr Ile Gln Asn Ala Ser Thr
            420                 425                 430

Ala Met Leu Met Ala Ala Ser Val Ala Arg Lys Ala Val Val Leu Pro
        435                 440                 445

Gly Gly Thr Ala Thr Ser Pro Lys Met Ile Ala Lys Asn Val Leu Gly
450                 455                 460

Leu Val Pro Gln Ala Leu Pro Lys Ala Asp Gly Arg Ala Gly Leu Gly
465                 470                 475                 480

Thr Gly Gly Gln Lys Val Asn Gly Ala Ser Val Val Met Val Gln Pro
                485                 490                 495

Ser Lys Thr Ala Thr Gly Pro Ser Thr Gly Gly Thr Val Ile Ser
            500                 505                 510

Arg Thr Gln Ser Ser Leu Val Glu Ala Phe Asn Lys Ile Leu Asn Ser
        515                 520                 525

Lys Asn Leu Leu Pro Ala Tyr Arg Pro Asn Leu Ser Pro Pro Ala Glu
530                 535                 540

Ala Gly Leu Ala Leu Pro Pro Thr Gly Tyr Arg Cys Leu Glu Cys Gly
545                 550                 555                 560

Asp Ala Phe Ser Leu Glu Lys Ser Leu Ala Arg His Tyr Asp Arg Arg
                565                 570                 575

Ser Met Arg Ile Glu Val Thr Cys Asn His Cys Ala Arg Arg Leu Val
            580                 585                 590

Phe Phe Asn Lys Cys Ser Leu Leu His Ala Arg Glu His Lys Asp
        595                 600                 605

Lys Gly Leu Val Met Gln Cys Ser His Leu Val Met Arg Pro Val Ala
610                 615                 620

Leu Asp Gln Met Val Gly Gln Pro Asp Ile Thr Pro Leu Leu Pro Val
625                 630                 635                 640

Ala Val Pro Pro Val Ser Gly Pro Leu Ala Leu Pro Ala Leu Gly Lys
                645                 650                 655

Gly Glu Gly Ala Ile Thr Ser Ser Ala Ile Thr Thr Val Ala Ala Glu
            660                 665                 670

Ala Pro Val Leu Pro Leu Ser Thr Glu Pro Pro Ala Ala Pro Ala Thr
        675                 680                 685

Ser Ala Tyr Thr Cys Phe Arg Cys Leu Glu Cys Lys Glu Gln Cys Arg
690                 695                 700

Asp Lys Ala Gly Met Ala Ala His Phe Gln Gln Leu Gly Pro Pro Ala
705                 710                 715                 720

Pro Gly Ala Thr Ser Asn Val Cys Pro Thr Cys Pro Met Met Leu Pro
                725                 730                 735

Asn Arg Cys Ser Phe Ser Ala His Gln Arg Met His Lys Asn Arg Pro
            740                 745                 750

Pro His Val Cys Pro Glu Cys Gly Gly Asn Phe Leu Gln Ala Asn Phe
        755                 760                 765

Gln Thr His Leu Arg Glu Ala Cys Leu His Val Ser Arg Arg Val Gly
770                 775                 780

Tyr Arg Cys Pro Ser Cys Ser Val Val Phe Gly Gly Val Asn Ser Ile
785                 790                 795                 800

Lys Ser His Ile Gln Thr Ser His Cys Glu Val Phe His Lys Cys Pro
```

-continued

```
                805                 810                 815
Ile Cys Pro Met Ala Phe Lys Ser Gly Pro Ser Ala His Ala His Leu
            820                 825                 830
Tyr Ser Gln His Pro Ser Phe Gln Thr Gln Ala Lys Leu Ile Tyr
            835                 840                 845
Lys Cys Ala Met Cys Asp Thr Val Phe Thr His Lys Pro Leu Leu Ser
            850                 855                 860
Ser His Phe Asp Gln His Leu Leu Pro Gln Arg Val Ser Val Phe Lys
865                 870                 875                 880
Cys Pro Ser Cys Pro Leu Leu Phe Ala Gln Lys Arg Thr Met Leu Glu
            885                 890                 895
His Leu Lys Asn Thr His Gln Ser Gly Arg Leu Glu Glu Thr Ala Gly
            900                 905                 910
Lys Gly Ala Gly Gly Ala Leu Leu Thr Pro Lys Thr Glu Pro Glu Glu
            915                 920                 925
Leu Ala Val Ser Gln Gly Gly Ala Ala Pro Ala Thr Glu Glu Ser Ser
            930                 935                 940
Ser Ser Ser Glu Glu Glu Glu Val Pro Ser Ser Pro Glu Pro Pro Arg
945                 950                 955                 960
Pro Ala Lys Arg Pro Arg Arg Glu Leu Gly Ser Lys Gly Leu Lys Gly
            965                 970                 975
Gly Gly Gly Gly Pro Gly Gly Trp Thr Cys Gly Leu Cys His Ser Trp
            980                 985                 990
Phe Pro Glu Arg Asp Glu Tyr Val Ala His Met Lys Lys Glu His Gly
            995                 1000                1005
Lys Ser Val Lys Lys Phe Pro Cys Arg Leu Cys Glu Arg Ser Phe Cys
            1010                1015                1020
Ser Ala Pro Ser Leu Arg Arg His Val Arg Val Asn His Glu Gly Ile
1025                1030                1035                1040
Lys Arg Val Tyr Pro Cys Arg Tyr Cys Thr Glu Gly Lys Arg Thr Phe
            1045                1050                1055
Ser Ser Arg Leu Ile Leu Glu Lys His Val Gln Val Arg His Gly Leu
            1060                1065                1070
Gln Leu Gly Ala Gln Ser Pro Gly Arg Gly Thr Thr Leu Ala Arg Gly
            1075                1080                1085
Ser Ser Ala Arg Ala Gln Gly Pro Gly Arg Lys Arg Arg Gln Ser Ser
            1090                1095                1100
Asp Ser Cys Ser Glu Glu Pro Asp Ser Thr Thr Pro Ala Lys Ser
1105                1110                1115                1120
Pro Arg Gly Gly Pro Gly Ser Gly Gly His Gly Pro Leu Arg Tyr Arg
            1125                1130                1135
Ser Ser Ser Ser Thr Glu Gln Ser Leu Met Met Gly Leu Arg Val Glu
            1140                1145                1150
Asp Gly Ala Gln Gln Cys Leu Asp Cys Gly Leu Cys Phe Ala Ser Pro
            1155                1160                1165
Gly Ser Leu Ser Arg His Arg Phe Ile Ser His Lys Lys Arg Arg Gly
            1170                1175                1180
Val Gly Lys Ala Ser Ala Leu Gly Leu Gly Asp Gly Glu Glu Glu Ala
1185                1190                1195                1200
Pro Pro Ser Arg Ser Asp Pro Asp Gly Gly Asp Ser Pro Leu Pro Ala
            1205                1210                1215
Ser Gly Gly Pro Leu Thr Cys Lys Val Cys Gly Lys Ser Cys Asp Ser
            1220                1225                1230
```

-continued

Pro Leu Asn Leu Lys Thr His Phe Arg Thr His Gly Met Ala Phe Ile
    1235                1240                1245

Arg Ala Arg Gln Gly Ala Val Gly Asp Asn
    1250                1255

<210> SEQ ID NO 102
<211> LENGTH: 930
<212> TYPE: PRT
<213> ORGANISM: Mus musculus

<400> SEQUENCE: 102

Met Ser Gln Ser Pro Arg Phe Val Thr Arg Gly Gly Ser Leu Lys
1               5                   10                  15

Ala Ala Pro Gly Ala Gly Thr Arg Arg Asn Glu Ser Gln Asp Tyr Leu
            20                  25                  30

Leu Met Asp Glu Leu Gly Asp Asp Gly Tyr Pro Gln Leu Pro Leu Pro
        35                  40                  45

Pro Tyr Gly Tyr Tyr Pro Ser Phe Arg Gly Asn Glu Asn Arg Leu Thr
    50                  55                  60

His Arg Arg Gln Thr Ile Leu Arg Glu Lys Gly Arg Arg Leu Ala Asn
65                  70                  75                  80

Arg Gly Pro Ala Tyr Met Phe Asn Asp His Ser Thr Ser Leu Ser Ile
                85                  90                  95

Glu Glu Glu Arg Phe Leu Asp Ala Val Glu Tyr Gly Asn Ile Pro Val
            100                 105                 110

Val Trp Lys Met Leu Glu Glu Cys His Ser Leu Asn Val Asn Cys Val
        115                 120                 125

Asp Tyr Met Gly Gln Asn Ala Leu Gln Leu Ala Val Ala Asn Glu His
    130                 135                 140

Leu Glu Ile Thr Glu Leu Leu Leu Lys Lys Glu Asn Leu Ser Arg Val
145                 150                 155                 160

Gly Asp Ala Leu Leu Leu Ala Ile Ser Lys Gly Tyr Val Arg Ile Val
                165                 170                 175

Glu Ala Ile Leu Asn His Pro Ser Phe Ala Glu Gly Lys Arg Leu Ala
            180                 185                 190

Thr Ser Pro Ser Gln Ser Glu Leu Gln Gln Asp Asp Phe Tyr Ala Tyr
        195                 200                 205

Asp Glu Asp Gly Thr Arg Phe Ser His Asp Val Thr Pro Ile Ile Leu
    210                 215                 220

Ala Ala His Cys Gln Glu Tyr Glu Ile Val His Thr Leu Leu Arg Lys
225                 230                 235                 240

Gly Ala Arg Ile Glu Arg Pro His Asp Tyr Phe Cys Lys Cys Thr Glu
                245                 250                 255

Cys Ser Gln Lys Gln Lys His Asp Ser Phe Ser His Ser Arg Ser Arg
            260                 265                 270

Ile Asn Ala Tyr Lys Gly Leu Ala Ser Pro Ala Tyr Leu Ser Leu Ser
        275                 280                 285

Ser Glu Asp Pro Val Met Thr Ala Leu Glu Leu Ser Asn Glu Leu Ala
    290                 295                 300

Val Leu Ala Asn Ile Glu Lys Glu Phe Lys Asn Asp Tyr Arg Lys Leu
305                 310                 315                 320

Ser Met Gln Cys Lys Asp Phe Val Val Gly Leu Leu Asp Leu Cys Arg
                325                 330                 335

Asn Thr Glu Glu Val Glu Ala Ile Leu Asn Gly Asp Ala Glu Thr Arg

-continued

```
                    340                 345                 350
Gln Pro Gly Asp Phe Gly Arg Pro Asn Leu Ser Arg Leu Lys Leu Ala
                355                 360                 365
Ile Lys Asp Glu Val Lys Lys Phe Val Ala His Pro Asn Cys Gln Gln
370                 375                 380
Gln Leu Leu Ser Ile Trp Tyr Glu Asn Leu Ser Gly Leu Arg Gln Gln
385                 390                 395                 400
Thr Met Ala Val Lys Phe Leu Val Val Leu Ala Val Ala Ile Gly Leu
                    405                 410                 415
Pro Phe Leu Ala Leu Ile Tyr Trp Cys Ala Pro Cys Ser Lys Met Gly
                420                 425                 430
Lys Ile Leu Pro Arg Pro Phe Met Lys Phe Val Ala His Ala Ala Ser
                435                 440                 445
Phe Thr Ile Phe Leu Gly Leu Leu Val Met Asn Ala Ala Asp Arg Phe
                450                 455                 460
Glu Gly Thr Lys Leu Leu Pro Asn Glu Thr Thr Asp Asn Ala Arg
465                 470                 475                 480
Gln Leu Phe Arg Met Lys Thr Ser Cys Phe Ser Trp Met Glu Met Leu
                    485                 490                 495
Ile Ile Ser Trp Val Ile Gly Met Ile Trp Ala Glu Cys Lys Glu Ile
                500                 505                 510
Trp Thr Gln Gly Pro Lys Glu Tyr Leu Phe Glu Leu Trp Asn Met Leu
                515                 520                 525
Asp Phe Gly Met Leu Ala Ile Phe Ala Ala Ser Phe Ile Ala Arg Phe
                530                 535                 540
Met Ala Phe Trp His Ala Ser Lys Ala Gln Ser Ile Ile Asp Ala Asn
545                 550                 555                 560
Asp Thr Leu Lys Asp Leu Thr Lys Val Thr Leu Gly Asp Asn Val Lys
                    565                 570                 575
Tyr Tyr Asn Leu Ala Arg Ile Lys Trp Asp Pro Thr Asp Pro Gln Ile
                580                 585                 590
Ile Ser Glu Gly Leu Tyr Ala Ile Ala Val Val Leu Ser Phe Ser Arg
                595                 600                 605
Ile Ala Tyr Ile Leu Pro Ala Asn Glu Ser Phe Gly Pro Leu Gln Ile
                610                 615                 620
Ser Leu Gly Arg Thr Val Lys Asp Ile Phe Lys Phe Met Val Ile Phe
625                 630                 635                 640
Ile Met Val Phe Val Ala Phe Met Ile Gly Met Phe Asn Leu Tyr Ser
                    645                 650                 655
Tyr Tyr Ile Gly Ala Lys Gln Asn Glu Ala Phe Thr Thr Val Glu Glu
                660                 665                 670
Ser Phe Lys Thr Leu Phe Trp Ala Ile Phe Gly Leu Ser Glu Val Lys
                675                 680                 685
Ser Val Val Ile Asn Tyr Asn His Lys Phe Ile Glu Asn Ile Gly Tyr
                690                 695                 700
Val Leu Tyr Gly Val Tyr Asn Val Thr Met Val Ile Val Leu Leu Asn
705                 710                 715                 720
Met Leu Ile Ala Met Ile Asn Ser Ser Phe Gln Glu Ile Glu Asp Asp
                    725                 730                 735
Ala Asp Val Glu Trp Lys Phe Ala Arg Ala Lys Leu Trp Phe Ser Tyr
                740                 745                 750
Phe Glu Glu Gly Arg Thr Leu Pro Val Pro Phe Asn Leu Val Pro Ser
                755                 760                 765
```

-continued

```
Pro Lys Ser Leu Leu Tyr Leu Leu Lys Phe Lys Lys Trp Met Cys
    770                 775                 780

Glu Leu Ile Gln Gly Gln Lys Gln Gly Phe Gln Glu Asp Ala Glu Met
785                 790                 795                 800

Asn Lys Arg Asn Glu Glu Lys Lys Phe Gly Ile Ser Gly Ser His Glu
            805                 810                 815

Asp Leu Ser Lys Phe Ser Leu Asp Lys Asn Gln Leu Ala His Asn Lys
        820                 825                 830

Gln Ser Ser Thr Arg Ser Ser Glu Asp Tyr His Leu Asn Ser Phe Ser
    835                 840                 845

Asn Pro Pro Arg Gln Tyr Gln Lys Ile Met Lys Arg Leu Ile Lys Arg
850                 855                 860

Tyr Val Leu Gln Ala Gln Ile Asp Lys Glu Ser Asp Glu Val Asn Glu
865                 870                 875                 880

Gly Glu Leu Lys Glu Ile Lys Gln Asp Ile Ser Ser Leu Arg Tyr Glu
            885                 890                 895

Leu Leu Glu Glu Lys Ser Gln Asn Ser Glu Asp Leu Ala Glu Leu Ile
        900                 905                 910

Arg Lys Leu Gly Glu Arg Leu Ser Leu Glu Pro Lys Leu Glu Glu Ser
    915                 920                 925

Arg Arg
    930

<210> SEQ ID NO 103
<211> LENGTH: 522
<212> TYPE: PRT
<213> ORGANISM: Homo sapiens

<400> SEQUENCE: 103

Gly Phe Leu Pro Ala Thr Lys Asn Leu Leu Asn Glu Lys Asn His Gly
1               5                   10                  15

Val Leu His Thr Ser Val Val Leu Leu Thr Glu Met Cys Glu Arg Ser
            20                  25                  30

Pro Asp Met Leu Ala His Phe Arg Glu Asn Glu Lys Leu Val Pro Gln
        35                  40                  45

Leu Val Arg Ile Leu Lys Asn Leu Ile Met Ser Gly Tyr Ser Pro Gly
    50                  55                  60

His Asp Val Ser Gly Ile Ser Asp Pro Phe Leu Gln Val Arg Ile Leu
65                  70                  75                  80

Arg Leu Leu Arg Ile Leu Gly Arg Asn Asp Asp Ser Ser Glu Ala
            85                  90                  95

Met Asn Asp Ile Leu Ala Gln Val Ala Thr Asn Thr Glu Thr Ser Lys
        100                 105                 110

Asn Val Gly Asn Ala Ile Leu Tyr Glu Thr Val Leu Thr Ile Met Asp
    115                 120                 125

Ile Lys Ser Glu Ser Gly Leu Arg Val Leu Ala Ile Asn Ile Leu Gly
130                 135                 140

Arg Phe Leu Leu Asn Asn Asp Lys Asn Ile Arg Tyr Val Ala Leu Thr
145                 150                 155                 160

Ser Leu Leu Lys Thr Val Gln Thr Asp His Asn Ala Val Gln Arg His
            165                 170                 175

Arg Ser Thr Ile Val Asp Cys Leu Lys Asp Leu Asp Val Ser Ile Lys
        180                 185                 190

Arg Arg Ala Met Glu Leu Ser Phe Ala Leu Val Asn Gly Asn Asn Ile
```

```
                    195                 200                 205
Arg Gly Met Met Lys Glu Leu Leu Tyr Phe Leu Asp Ser Cys Glu Pro
    210                 215                 220

Glu Phe Lys Ala Asp Cys Ala Ser Gly Ile Phe Leu Ala Ala Glu Lys
225                 230                 235                 240

Tyr Ala Pro Ser Lys Arg Trp His Ile Asp Thr Ile Met Arg Val Leu
                245                 250                 255

Thr Thr Ala Gly Ser Tyr Val Arg Asp Asp Ala Val Pro Asn Leu Ile
            260                 265                 270

Gln Leu Ile Thr Asn Ser Val Glu Met His Ala Tyr Thr Val Gln Arg
        275                 280                 285

Leu Tyr Lys Ala Ile Leu Gly Asp Tyr Ser Gln Gln Pro Leu Val Gln
    290                 295                 300

Val Ala Ala Trp Cys Ile Gly Glu Tyr Gly Asp Leu Leu Val Ser Gly
305                 310                 315                 320

Gln Cys Glu Glu Glu Pro Ile Gln Val Thr Glu Asp Glu Val Leu
                325                 330                 335

Asp Ile Leu Glu Ser Val Leu Ile Ser Asn Met Ser Thr Ser Val Thr
            340                 345                 350

Arg Gly Tyr Ala Leu Thr Ala Ile Met Lys Leu Ser Thr Arg Phe Thr
        355                 360                 365

Cys Thr Val Asn Arg Ile Lys Lys Val Val Ser Ile Tyr Gly Ser Ser
    370                 375                 380

Ile Asp Val Glu Leu Gln Arg Arg Ala Val Glu Tyr Asn Ala Leu Phe
385                 390                 395                 400

Lys Lys Tyr Asp His Met Arg Ser Ala Leu Leu Glu Arg Met Pro Val
                405                 410                 415

Met Glu Lys Val Thr Thr Asn Gly Pro Thr Glu Ile Val Gln Thr Asn
            420                 425                 430

Gly Glu Thr Glu Pro Ala Pro Leu Glu Thr Lys Pro Pro Ser Gly
        435                 440                 445

Pro Gln Pro Thr Ser Gln Ala Asn Asp Leu Leu Asp Leu Leu Gly Gly
    450                 455                 460

Asn Asp Ile Thr Pro Val Ile Pro Thr Ala Pro Thr Ser Lys Pro Ser
465                 470                 475                 480

Ser Ala Gly Gly Glu Leu Leu Asp Leu Leu Gly Asp Ile Asn Leu Thr
                485                 490                 495

Gly Ser His Ser Val Ser Gln Ala Gly Val Gln Trp Asp Tyr Leu Gly
            500                 505                 510

Ser Leu Gln Pro Leu Pro Pro Ala Phe Arg
        515                 520

<210> SEQ ID NO 104
<211> LENGTH: 407
<212> TYPE: PRT
<213> ORGANISM: Homo sapiens

<400> SEQUENCE: 104

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45
```

```
Leu Ala Gly Ala Arg Gln Gly Gly Ser His Thr Arg Ser Ser Phe Leu
 50                  55                  60

Thr Phe Leu Cys Gly Leu Val Leu Thr Asp Phe Leu Gly Leu Leu Val
 65                  70                  75                  80

Thr Gly Thr Ile Val Val Ser Gln His Ala Ala Leu Phe Glu Trp His
                 85                  90                  95

Ala Val Asp Pro Gly Cys Arg Leu Cys Arg Phe Met Gly Val Val Met
            100                 105                 110

Ile Phe Phe Gly Leu Ser Pro Leu Leu Gly Ala Ala Met Ala Ser
        115                 120                 125

Glu Arg Tyr Leu Gly Ile Thr Arg Pro Phe Ser Arg Pro Ala Val Ala
    130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
        195                 200                 205

Gly Leu Ser Phe Leu Leu Asn Thr Val Ser Val Ala Thr Leu Cys His
    210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
        275                 280                 285

Glu Leu Leu Ile Tyr Leu Arg Val Ala Thr Trp Asn Gln Ile Leu Asp
    290                 295                 300

Pro Trp Val Tyr Ile Leu Phe Arg Arg Ala Val Leu Arg Arg Leu Gln
305                 310                 315                 320

Pro Arg Leu Ser Thr Arg Pro Arg Arg Ser Leu Thr Leu Trp Pro Ser
                325                 330                 335

Leu Glu Tyr Ser Gly Thr Ile Ser Ala His Cys Asn Leu Arg Leu Pro
            340                 345                 350

Gly Ser Ser Asp Ser Arg Ala Ser Ala Ser Arg Ala Ala Gly Ile Thr
        355                 360                 365

Gly Val Ser His Cys Ala Arg Pro Cys Met Leu Phe Asp Pro Glu Phe
    370                 375                 380

Asp Leu Leu Ala Gly Val Gln Leu Leu Pro Phe Glu Pro Pro Thr Gly
385                 390                 395                 400

Lys Ala Leu Ser Arg Lys Asp
                405

<210> SEQ ID NO 105
<211> LENGTH: 741
<212> TYPE: PRT
<213> ORGANISM: Homo sapiens

<400> SEQUENCE: 105

Met Asp Ile Glu Asp Glu Glu Asn Met Ser Ser Ser Thr Asp Val
 1               5                  10                  15
```

-continued

```
Lys Glu Asn Arg Asn Leu Asp Asn Val Ser Pro Lys Asp Gly Ser Thr
                 20                  25                  30

Pro Gly Pro Gly Glu Gly Ser Gln Leu Ser Asn Gly Gly Gly Gly Gly
         35                  40                  45

Pro Gly Arg Lys Arg Pro Leu Glu Glu Gly Ser Asn Gly His Ser Lys
     50                  55                  60

Tyr Arg Leu Lys Lys Arg Arg Lys Thr Pro Gly Pro Val Leu Pro Lys
 65                  70                  75                  80

Asn Ala Leu Met Gln Leu Asn Glu Ile Lys Pro Gly Leu Gln Tyr Thr
                 85                  90                  95

Leu Leu Ser Gln Thr Gly Pro Val His Ala Pro Leu Phe Val Met Ser
             100                 105                 110

Val Glu Val Asn Gly Gln Val Phe Glu Gly Ser Gly Pro Thr Lys Lys
         115                 120                 125

Lys Ala Lys Leu His Ala Ala Glu Lys Ala Leu Arg Ser Phe Val Gln
     130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                 165                 170                 175

Phe Asn Gly Phe Glu Thr Pro Asp Lys Ala Glu Pro Pro Phe Tyr Val
             180                 185                 190

Gly Ser Asn Gly Asp Asp Ser Phe Ser Ser Ser Gly Asp Leu Ser Leu
         195                 200                 205

Ser Ala Ser Pro Val Pro Ala Ser Leu Ala Gln Pro Pro Leu Pro Val
     210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                 245                 250                 255

Glu Ser His Ala Lys Ser Phe Val Met Ser Val Val Asp Gly Gln
             260                 265                 270

Phe Phe Glu Gly Ser Gly Arg Asn Lys Lys Leu Ala Lys Ala Arg Ala
     275                 280                 285

Ala Gln Ser Ala Leu Ala Ala Ile Phe Asn Leu His Leu Asp Gln Thr
     290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                 325                 330                 335

Asp Leu Thr Asp Asn Phe Ser Ser Pro His Ala Arg Arg Lys Val Leu
             340                 345                 350

Ala Gly Val Val Met Thr Thr Gly Thr Asp Val Lys Asp Ala Lys Val
         355                 360                 365

Ile Ser Val Ser Thr Gly Thr Lys Cys Ile Asn Gly Glu Tyr Met Ser
 370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                 405                 410                 415

Asn Lys Asp Asp Gln Lys Arg Ser Ile Phe Gln Lys Ser Glu Arg Gly
             420                 425                 430
```

```
Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Gly Ser Arg Ser Tyr Thr Gln Ala Gly Val Gln Trp Cys Asn His
465                 470                 475                 480

Gly Ser Leu Gln Pro Arg Pro Gly Leu Leu Ser Asp Pro Ser Thr
            485                 490                 495

Ser Thr Phe Gln Gly Ala Gly Thr Thr Glu Pro Ala Asp Arg His Pro
            500                 505                 510

Asn Arg Lys Ala Arg Gly Gln Leu Arg Thr Lys Ile Glu Ser Gly Glu
        515                 520                 525

Gly Thr Ile Pro Val Arg Ser Asn Ala Ser Ile Gln Thr Trp Asp Gly
    530                 535                 540

Val Leu Gln Gly Glu Arg Leu Leu Thr Met Ser Cys Ser Asp Lys Ile
545                 550                 555                 560

Ala Arg Trp Asn Val Val Gly Ile Gln Gly Ser Leu Leu Ser Ile Phe
            565                 570                 575

Val Glu Pro Ile Tyr Phe Ser Ser Ile Ile Leu Gly Ser Leu Tyr His
            580                 585                 590

Gly Asp His Leu Ser Arg Ala Met Tyr Gln Arg Ile Ser Asn Ile Glu
        595                 600                 605

Asp Leu Pro Pro Leu Tyr Thr Leu Asn Lys Pro Leu Leu Ser Gly Ile
    610                 615                 620

Ser Asn Ala Glu Ala Arg Gln Pro Gly Lys Ala Pro Asn Phe Ser Val
625                 630                 635                 640

Asn Trp Thr Val Gly Asp Ser Ala Ile Glu Val Ile Asn Ala Thr Thr
            645                 650                 655

Gly Lys Asp Glu Leu Gly Arg Ala Ser Arg Leu Cys Lys His Ala Leu
        660                 665                 670

Tyr Cys Arg Trp Met Arg Val His Gly Lys Val Pro Ser His Leu Leu
    675                 680                 685

Arg Ser Lys Ile Thr Lys Pro Asn Val Tyr His Glu Ser Lys Leu Ala
690                 695                 700

Ala Lys Glu Tyr Gln Ala Ala Lys Ala Arg Leu Phe Thr Ala Phe Ile
705                 710                 715                 720

Lys Ala Gly Leu Gly Ala Trp Val Glu Lys Pro Thr Glu Gln Asp Gln
            725                 730                 735

Phe Ser Leu Thr Pro
            740

<210> SEQ ID NO 106
<211> LENGTH: 714
<212> TYPE: PRT
<213> ORGANISM: Homo sapiens

<400> SEQUENCE: 106

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60
```

```
Tyr Arg Leu Lys Lys Arg Arg Lys Thr Pro Gly Pro Val Leu Pro Lys
 65                  70                  75                  80

Asn Ala Leu Met Gln Leu Asn Glu Ile Lys Pro Gly Leu Gln Tyr Thr
                 85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
450                 455                 460

Glu Gly Ser Arg Ser Tyr Thr Gln Ala Gly Val Gln Trp Cys Asn His
465                 470                 475                 480
```

```
Gly Ser Leu Gln Pro Arg Pro Pro Gly Leu Leu Ser Asp Pro Ser Thr
                485                 490                 495

Ser Thr Phe Gln Gly Ala Gly Thr Thr Glu Pro Ala Asp Arg His Pro
            500                 505                 510

Asn Arg Lys Ala Arg Gly Gln Leu Arg Thr Lys Ile Glu Ser Gly Glu
        515                 520                 525

Gly Thr Ile Pro Val Arg Ser Asn Ala Ser Ile Gln Thr Trp Asp Gly
    530                 535                 540

Val Leu Gln Gly Glu Arg Leu Leu Thr Met Ser Cys Ser Asp Lys Ile
545                 550                 555                 560

Ala Arg Trp Asn Val Gly Ile Gln Gly Ser Leu Leu Ser Ile Phe
                565                 570                 575

Val Glu Pro Ile Tyr Phe Ser Ser Ile Ile Leu Gly Ser Leu Tyr His
            580                 585                 590

Gly Asp His Leu Ser Arg Ala Met Tyr Gln Arg Ile Ser Asn Ile Glu
        595                 600                 605

Asp Leu Pro Pro Leu Tyr Thr Leu Asn Lys Pro Leu Leu Ser Gly Ile
    610                 615                 620

Ser Asn Ala Glu Ala Arg Gln Pro Gly Lys Ala Pro Asn Phe Ser Val
625                 630                 635                 640

Asn Trp Thr Val Gly Asp Ser Ala Ile Glu Val Ile Asn Ala Thr Thr
                645                 650                 655

Gly Lys Asp Glu Leu Gly Arg Ala Ser Arg Leu Cys Lys His Ala Leu
            660                 665                 670

Tyr Cys Arg Trp Met Arg Val His Gly Lys Val Pro Ser His Leu Leu
        675                 680                 685

Arg Ser Lys Ile Thr Lys Pro Asn Val Tyr His Glu Ser Lys Leu Ala
    690                 695                 700

Ala Lys Glu Tyr Gln Ala Ala Lys Val His
705                 710

<210> SEQ ID NO 107
<211> LENGTH: 76
<212> TYPE: PRT
<213> ORGANISM: Homo sapiens

<400> SEQUENCE: 107

Met Glu Val Leu Leu Phe Leu Phe Ile Phe Glu Thr Glu Ser Cys Ser
1               5                   10                  15

Val Ile Arg Leu Glu Cys Ser Gly Ser Leu Gln Pro Pro Pro Arg
            20                  25                  30

Phe Lys Gln Phe Ser Cys Leu Ser Leu Pro Ser Ser Trp Asp Tyr Arg
        35                  40                  45

Cys Pro Pro Cys Pro Ile Asn Phe Cys Ile Phe Gly Thr Asp Arg
    50                  55                  60

Val Ser Pro Cys Trp Pro Gly Trp Ser Arg Ser Arg
65                  70                  75

<210> SEQ ID NO 108
<211> LENGTH: 977
<212> TYPE: PRT
<213> ORGANISM: Homo sapiens

<400> SEQUENCE: 108

Met Ala Gln Phe Tyr Tyr Lys Arg Asn Val Asn Ala Pro Tyr Arg Asp
1               5                   10                  15
```

```
Arg Ile Pro Leu Arg Ile Val Arg Ala Glu Ser Glu Leu Ser Pro Ser
         20                  25                  30
Glu Lys Ala Tyr Leu Asn Ala Val Glu Lys Gly Asp Tyr Ala Ser Val
         35                  40                  45
Lys Lys Ser Leu Glu Glu Ala Glu Ile Tyr Phe Lys Ile Asn Ile Asn
         50                  55                  60
Cys Ile Asp Pro Leu Gly Arg Thr Ala Leu Leu Ile Ala Ile Glu Asn
 65              70                  75                  80
Glu Asn Leu Glu Leu Ile Glu Leu Leu Leu Ser Phe Asn Val Tyr Val
                 85                  90                  95
Gly Asp Ala Leu Leu His Ala Ile Arg Lys Glu Val Val Gly Ala Val
             100                 105                 110
Glu Leu Leu Leu Asn His Lys Lys Pro Ser Gly Glu Lys Gln Val Pro
             115                 120                 125
Pro Ile Leu Leu Asp Lys Gln Phe Ser Glu Phe Thr Pro Asp Ile Thr
         130                 135                 140
Pro Ile Ile Leu Ala Ala His Thr Asn Asn Tyr Glu Ile Ile Lys Leu
145             150                 155                 160
Leu Val Gln Lys Gly Val Ser Val Pro Arg Pro His Glu Val Arg Cys
                 165                 170                 175
Asn Cys Val Glu Cys Val Ser Ser Ser Asp Val Asp Ser Leu Arg His
             180                 185                 190
Ser Arg Ser Arg Leu Asn Ile Tyr Lys Ala Leu Ala Ser Pro Ser Leu
         195                 200                 205
Ile Ala Leu Ser Ser Glu Asp Pro Phe Leu Thr Ala Phe Gln Leu Ser
210             215                 220
Trp Glu Leu Gln Glu Leu Ser Lys Val Glu Asn Glu Phe Lys Ser Glu
225                 230                 235                 240
Tyr Glu Glu Leu Ser Arg Gln Cys Lys Gln Phe Ala Lys Asp Leu Leu
                 245                 250                 255
Asp Gln Thr Arg Ser Ser Arg Glu Leu Glu Ile Ile Leu Asn Tyr Arg
             260                 265                 270
Asp Asp Asn Ser Leu Ile Glu Glu Gln Ser Gly Asn Asp Leu Ala Arg
         275                 280                 285
Leu Lys Leu Ala Ile Lys Tyr Arg Gln Lys Glu Phe Val Ala Gln Pro
290             295                 300
Asn Cys Gln Gln Leu Leu Ala Ser Arg Trp Tyr Asp Glu Phe Pro Gly
305                 310                 315                 320
Trp Arg Arg Arg His Trp Ala Val Lys Met Val Thr Cys Phe Ile Ile
                 325                 330                 335
Gly Leu Leu Phe Pro Val Phe Ser Val Cys Tyr Leu Ile Ala Pro Lys
             340                 345                 350
Ser Pro Leu Gly Leu Phe Ile Arg Lys Pro Phe Ile Lys Phe Ile Cys
         355                 360                 365
His Thr Ala Ser Tyr Leu Thr Phe Leu Phe Leu Leu Leu Leu Ala Ser
         370                 375                 380
Gln His Ile Asp Arg Ser Asp Leu Asn Arg Gln Gly Pro Pro Pro Thr
385                 390                 395                 400
Ile Val Glu Trp Met Ile Leu Pro Trp Val Leu Gly Phe Ile Trp Gly
                 405                 410                 415
Glu Ile Lys Gln Met Trp Asp Gly Gly Leu Gln Asp Tyr Ile His Asp
             420                 425                 430
Trp Trp Asn Leu Met Asp Phe Val Met Asn Ser Leu Tyr Leu Ala Thr
```

-continued

```
              435                 440                 445
Ile Ser Leu Lys Ile Val Ala Phe Val Lys Tyr Ser Ala Leu Asn Pro
450                 455                 460
Arg Glu Ser Trp Asp Met Trp His Pro Thr Leu Val Ala Glu Ala Leu
465                 470                 475                 480
Phe Ala Ile Ala Asn Ile Phe Ser Ser Leu Arg Leu Ile Ser Leu Phe
                    485                 490                 495
Thr Ala Asn Ser His Leu Gly Pro Leu Gln Ile Ser Leu Gly Arg Met
                500                 505                 510
Leu Leu Asp Ile Leu Lys Phe Leu Phe Ile Tyr Cys Leu Val Leu Leu
        515                 520                 525
Ala Phe Ala Asn Gly Leu Asn Gln Leu Tyr Phe Tyr Tyr Glu Glu Thr
530                 535                 540
Lys Gly Leu Thr Cys Lys Gly Ile Arg Cys Glu Lys Gln Asn Asn Ala
545                 550                 555                 560
Phe Ser Thr Leu Phe Glu Thr Leu Gln Ser Leu Phe Trp Ser Ile Phe
                    565                 570                 575
Gly Leu Ile Asn Leu Tyr Val Thr Asn Val Lys Ala Gln His Glu Phe
                580                 585                 590
Thr Glu Phe Val Gly Ala Thr Met Phe Gly Thr Tyr Asn Val Ile Ser
            595                 600                 605
Leu Val Val Leu Leu Asn Met Leu Ile Ala Met Met Asn Asn Ser Tyr
        610                 615                 620
Gln Leu Ile Ala Asp His Ala Asp Ile Glu Trp Lys Phe Ala Arg Thr
625                 630                 635                 640
Lys Leu Trp Met Ser Tyr Phe Glu Glu Gly Thr Leu Pro Thr Pro
                    645                 650                 655
Phe Asn Val Ile Pro Ser Pro Lys Ser Leu Trp Tyr Leu Ile Lys Trp
                660                 665                 670
Ile Trp Thr His Leu Cys Lys Lys Lys Met Arg Arg Lys Pro Glu Ser
            675                 680                 685
Phe Gly Thr Ile Gly Arg Arg Ala Ala Asp Asn Leu Arg Arg His His
        690                 695                 700
Gln Tyr Gln Glu Val Met Arg Asn Leu Val Lys Arg Tyr Val Ala Ala
705                 710                 715                 720
Met Ile Arg Asp Ala Lys Thr Glu Glu Gly Leu Thr Glu Glu Asn Phe
                    725                 730                 735
Lys Glu Leu Lys Gln Asp Ile Ser Ser Phe Arg Phe Glu Val Leu Gly
                740                 745                 750
Leu Leu Arg Gly Ser Lys Leu Ser Thr Ile Gln Ser Ala Asn Ala Ser
            755                 760                 765
Lys Glu Ser Ser Asn Ser Ala Asp Ser Asp Glu Lys Ser Asp Ser Glu
        770                 775                 780
Gly Asn Ser Lys Asp Lys Lys Asn Phe Ser Leu Phe Asp Leu Thr
785                 790                 795                 800
Thr Leu Ile His Pro Arg Ser Ala Ala Ile Ala Ser Glu Arg His Asn
                    805                 810                 815
Ile Ser Asn Gly Ser Ala Leu Val Val Gln Glu Pro Pro Arg Glu Lys
                820                 825                 830
Gln Arg Lys Val Asn Phe Val Thr Asp Ile Lys Asn Phe Gly Leu Phe
            835                 840                 845
His Arg Arg Ser Lys Gln Asn Ala Ala Glu Gln Asn Ala Asn Gln Ile
        850                 855                 860
```

```
Phe Ser Val Ser Glu Glu Val Ala Arg Gln Gln Ala Ala Gly Pro Leu
865                 870                 875                 880

Glu Arg Asn Ile Gln Leu Glu Ser Arg Gly Leu Ala Ser Arg Gly Asp
                885                 890                 895

Leu Ser Ile Pro Gly Leu Ser Glu Gln Cys Val Leu Val Asp His Arg
                900                 905                 910

Glu Arg Asn Thr Asp Thr Leu Gly Leu Gln Val Gly Lys Arg Val Cys
                915                 920                 925

Pro Phe Lys Ser Glu Lys Val Val Glu Asp Thr Val Pro Ile Ile
930                 935                 940

Pro Lys Glu Lys His Ala Lys Glu Glu Asp Ser Ser Ile Asp Tyr Asp
945                 950                 955                 960

Leu Asn Leu Pro Asp Thr Val Thr His Glu Asp Tyr Val Thr Thr Arg
                965                 970                 975

Leu
```

<210> SEQ ID NO 109
<211> LENGTH: 275
<212> TYPE: PRT
<213> ORGANISM: Homo sapiens

<400> SEQUENCE: 109

```
Met Glu Ser Tyr Ser Val Thr Gln Ala Gly Val Gln Trp His Glu Leu
1               5                   10                  15

Cys Ser Leu Gln Pro Ser Pro Arg Phe Arg Glu Met Cys Ile Glu
            20                  25                  30

Gln Asp Gly Arg Val His Leu Thr Val Val Tyr Phe Gly Lys Glu Glu
            35                  40                  45

Ile Asn Glu Val Lys Gly Val Leu Glu Asn Thr Ser Lys Ala Ala Asn
50                  55                  60

Phe Arg Asn Phe Thr Phe Ile Gln Leu Asn Gly Glu Phe Ser Arg Gly
65                  70                  75                  80

Lys Gly Leu Asp Val Gly Ala Arg Phe Trp Lys Gly Ser Asn Val Leu
                85                  90                  95

Leu Phe Phe Cys Asp Val Asp Ile Tyr Phe Thr Ser Glu Phe Leu Asn
                100                 105                 110

Thr Cys Arg Leu Asn Thr Gln Pro Gly Lys Lys Val Phe Tyr Pro Val
            115                 120                 125

Leu Phe Ser Gln Tyr Asn Pro Gly Ile Ile Tyr Gly His His Asp Ala
130                 135                 140

Val Pro Pro Leu Glu Gln Gln Leu Val Ile Lys Lys Glu Thr Gly Phe
145                 150                 155                 160

Trp Arg Asp Phe Gly Phe Gly Met Thr Cys Gln Tyr Arg Ser Asp Phe
                165                 170                 175

Ile Asn Ile Gly Gly Phe Asp Leu Asp Ile Lys Gly Trp Gly Gly Glu
                180                 185                 190

Asp Val His Leu Tyr Arg Lys Tyr Leu His Ser Asn Leu Ile Val Val
            195                 200                 205

Arg Thr Pro Val Arg Gly Leu Phe His Leu Trp His Glu Lys Arg Cys
210                 215                 220

Met Asp Glu Leu Thr Pro Glu Gln Tyr Lys Met Cys Met Gln Ser Lys
225                 230                 235                 240

Ala Met Asn Glu Ala Ser His Gly Gln Leu Gly Met Leu Val Phe Arg
                245                 250                 255
```

His Glu Ile Glu Ala His Leu Arg Lys Gln Lys Gln Lys Thr Ser Ser
                260                 265                 270

Lys Lys Thr
        275

<210> SEQ ID NO 110
<211> LENGTH: 1084
<212> TYPE: PRT
<213> ORGANISM: Homo sapiens

<400> SEQUENCE: 110

Met Asp Ile Thr Leu Val Arg Lys Glu Leu Gln Glu Leu Gln Asn Leu
 1               5                  10                  15

Tyr Lys Gln Asn Ser Thr His Thr Ala Gln Gln Ala Glu Leu Ile Gln
                20                  25                  30

Gln Leu Gln Val Leu Asn Met Asp Thr Gln Lys Val Leu Arg Asn Gln
            35                  40                  45

Glu Asp Val His Thr Ala Glu Ser Ile Ser Tyr Gln Lys Leu Tyr Asn
        50                  55                  60

Glu Leu His Ile Cys Phe Glu Thr Thr Lys Ser Asn Glu Ala Met Leu
65                  70                  75                  80

Arg Gln Ser Val Thr Asn Leu Gln Asp Gln Leu Leu Gln Lys Glu Gln
                85                  90                  95

Glu Asn Ala Lys Leu Lys Glu Lys Leu Gln Glu Ser Gln Gly Ala Pro
            100                 105                 110

Leu Pro Leu Pro Gln Glu Ser Asp Pro Asp Tyr Ser Ala Gln Val Pro
        115                 120                 125

His Arg Pro Ser Leu Ser Ser Leu Glu Thr Leu Met Val Ser Gln Lys
    130                 135                 140

Ser Glu Ile Glu Tyr Leu Gln Glu Lys Leu Lys Ile Ala Asn Glu Lys
145                 150                 155                 160

Leu Ser Glu Asn Ile Ser Ala Asn Lys Gly Phe Ser Arg Lys Ser Ile
                165                 170                 175

Met Thr Ser Ala Glu Gly Lys His Lys Glu Pro Pro Val Lys Arg Ser
            180                 185                 190

Arg Ser Leu Ser Pro Lys Ser Ser Phe Thr Asp Ser Glu Glu Leu Gln
        195                 200                 205

Lys Leu Arg Lys Ala Glu Arg Lys Ile Glu Asn Leu Glu Lys Ala Leu
    210                 215                 220

Gln Leu Lys Ser Gln Glu Asn Asp Glu Leu Arg Asp Ala His Glu Lys
225                 230                 235                 240

Arg Lys Glu Arg Leu Gln Met Leu Gln Thr Asn Tyr Arg Ala Val Lys
                245                 250                 255

Glu Gln Leu Lys Gln Trp Glu Glu Gly Ser Gly Met Thr Glu Ile Arg
            260                 265                 270

Lys Ile Lys Arg Ala Asp Pro Gln Gln Leu Arg Gln Glu Asp Ser Asp
        275                 280                 285

Ala Val Trp Asn Glu Leu Ala Tyr Phe Lys Arg Glu Asn Gln Glu Leu
    290                 295                 300

Met Ile Gln Lys Met Asn Leu Glu Glu Leu Asp Glu Leu Lys Val
305                 310                 315                 320

His Ile Ser Ile Asp Lys Ala Ala Ile Gln Glu Leu Asn Arg Cys Val
                325                 330                 335

Ala Glu Arg Arg Glu Glu Gln Leu Phe Arg Ser Gly Glu Asp Asp Glu

-continued

```
                340                 345                 350
Val Lys Arg Ser Thr Pro Glu Lys Asn Gly Lys Glu Met Leu Glu Gln
            355                 360                 365

Thr Leu Gln Lys Val Ile Glu Leu Glu Asn Arg Leu Lys Ser Phe Glu
        370                 375                 380

Lys Arg Ser Arg Lys Leu Lys Glu Gly Asn Lys Lys Leu Met Lys Glu
385                 390                 395                 400

Asn Asp Phe Leu Lys Ser Leu Leu Lys Gln Gln Glu Asp Thr Glu
                    405                 410                 415

Thr Arg Glu Lys Glu Leu Glu Gln Ile Ile Lys Gly Ser Lys Asp Val
                420                 425                 430

Glu Lys Glu Asn Thr Glu Leu Gln Val Lys Ile Ser Glu Leu Glu Thr
            435                 440                 445

Glu Val Thr Ser Leu Arg Arg Gln Val Ala Glu Ala Asn Ala Leu Arg
        450                 455                 460

Asn Glu Asn Glu Glu Leu Ile Asn Pro Met Glu Lys Ser His Gln Ser
465                 470                 475                 480

Ala Asp Arg Ala Lys Ser Glu Met Ala Thr Met Lys Val Arg Ser Gly
                    485                 490                 495

Arg Tyr Asp Cys Lys Thr Thr Met Thr Lys Val Lys Phe Lys Ala Ala
                500                 505                 510

Lys Lys Asn Cys Ser Val Gly Arg His His Thr Val Leu Asn His Ser
            515                 520                 525

Ile Lys Val Met Ser Asn Val Phe Glu Asn Leu Ser Lys Asp Gly Trp
        530                 535                 540

Glu Asp Val Ser Glu Ser Ser Asp Ser Glu Ala Gln Thr Ser Gln
545                 550                 555                 560

Thr Leu Gly Thr Ile Ile Val Glu Thr Ser Gln Lys Ile Ser Pro Thr
                    565                 570                 575

Glu Asp Gly Lys Asp Gln Lys Glu Ser Asp Pro Thr Glu Asp Ser Gln
                580                 585                 590

Thr Gln Gly Lys Glu Ile Val Gln Thr Tyr Leu Asn Ile Asp Gly Lys
            595                 600                 605

Thr Pro Lys Asp Tyr Phe His Asp Lys Asn Ala Lys Lys Pro Thr Phe
        610                 615                 620

Gln Lys Lys Asn Cys Lys Met Gln Lys Ser Ser His Thr Ala Val Pro
625                 630                 635                 640

Thr Arg Val Asn Arg Glu Lys Tyr Lys Asn Ile Thr Ala Gln Lys Ser
                    645                 650                 655

Ser Ser Asn Ile Ile Leu Leu Arg Glu Arg Ile Ile Ser Leu Gln Gln
                660                 665                 670

Gln Asn Ser Val Leu Gln Asn Ala Lys Lys Thr Ala Glu Leu Ser Val
            675                 680                 685

Lys Glu Tyr Lys Glu Val Asn Glu Lys Leu Leu His Gln Gln Gln Val
        690                 695                 700

Ser Asp Gln Arg Phe Gln Thr Ser Arg Gln Thr Ile Lys Lys Leu Asn
705                 710                 715                 720

Leu Asp Leu Ala Gly Leu Arg Lys Glu Lys Glu Asp Leu Leu Lys Lys
                    725                 730                 735

Leu Glu Ser Ser Ser Glu Ile Thr Ser Leu Ala Glu Glu Asn Ser Gln
                740                 745                 750

Val Thr Phe Pro Arg Ile Gln Val Thr Ser Leu Ser Pro Ser Arg Ser
            755                 760                 765
```

-continued

```
Met Asp Leu Glu Met Lys Gln Leu Gln Tyr Lys Leu Lys Asn Ala Thr
    770                 775                 780

Asn Glu Leu Thr Lys Gln Ser Ser Asn Val Lys Thr Leu Lys Phe Glu
785                 790                 795                 800

Leu Leu Ala Lys Glu Glu His Ile Lys Glu Met His Glu Lys Ile Ser
                805                 810                 815

Arg Met Glu Arg Asp Ile Thr Met Lys Arg His Leu Ile Glu Asp Leu
            820                 825                 830

Lys Phe Arg Gln Lys Val Asn Leu Glu Ser Asn Lys Ser Phe Ser Glu
        835                 840                 845

Met Leu Gln Asn Leu Asp Lys Lys Val Lys Thr Leu Thr Glu Glu Cys
    850                 855                 860

Ser Asn Lys Lys Val Ser Ile Asp Ser Leu Lys Gln Arg Leu Asn Val
865                 870                 875                 880

Ala Val Lys Glu Lys Ser Gln Tyr Glu Gln Met Tyr Gln Lys Ser Lys
                885                 890                 895

Glu Glu Leu Glu Lys Lys Asp Leu Lys Leu Thr Leu Leu Val Ser Arg
            900                 905                 910

Ile Ser Glu Thr Glu Ser Ala Met Ala Glu Ile Glu Thr Ala Ala Ser
        915                 920                 925

Lys Gln Leu Gln Glu Leu Ala Leu Gln Ser Gln Val Leu Glu Gly
    930                 935                 940

Ala Gln Lys Thr Leu Leu Leu Ala Asn Glu Lys Val Glu Glu Phe Thr
945                 950                 955                 960

Thr Phe Val Lys Ala Leu Ala Lys Glu Leu Gln Asn Asp Val His Val
                965                 970                 975

Val Arg Arg Gln Ile Arg Glu Leu Lys Lys Met Lys Lys Asn Arg Asp
            980                 985                 990

Ala Cys Lys Thr Ser Thr His Lys Ala Gln Thr Leu Ala Ala Ser Ile
        995                 1000                1005

Leu Asn Ile Ser Arg Ser Asp Leu Glu Glu Ile Leu Asp Thr Glu Asp
    1010                1015                1020

Gln Val Glu Ile Glu Lys Thr Lys Ile Asp Ala Glu Asn Asp Lys Glu
1025                1030                1035                1040

Trp Met Leu Tyr Ile Gln Lys Leu Leu Glu Gly Gln Ser Leu Thr Leu
                1045                1050                1055

Ser Pro Arg Leu Lys Cys Asn Gly Ala Ile Met Ala His Gln Asn Leu
            1060                1065                1070

Arg Leu Pro Asp Ser Ser Ser Ala Ser Ala Ser
        1075                1080

<210> SEQ ID NO 111
<211> LENGTH: 687
<212> TYPE: PRT
<213> ORGANISM: Homo sapiens

<400> SEQUENCE: 111

Met Lys Val Val Pro Glu Lys Asn Ala Val Arg Ile Leu Trp Gly Arg
  1               5                  10                  15

Glu Arg Gly Ala Arg Ala Met Gly Ala Gln Arg Leu Leu Gln Glu Leu
             20                  25                  30

Val Glu Asp Lys Thr Arg Trp Met Lys Trp Glu Gly Lys Arg Val Glu
         35                  40                  45

Leu Pro Asp Ser Pro Arg Ser Thr Phe Leu Leu Ala Phe Ser Pro Asp
```

-continued

```
             50                  55                  60
Arg Thr Leu Leu Ala Ser Thr His Val Asn His Asn Ile Tyr Ile Thr
 65                  70                  75                  80

Glu Val Lys Thr Gly Lys Cys Val His Ser Leu Ile Gly His Arg Arg
                 85                  90                  95

Thr Pro Trp Cys Val Thr Phe His Pro Thr Ile Ser Gly Leu Ile Ala
            100                 105                 110

Ser Gly Cys Leu Asp Gly Glu Val Arg Ile Trp Asp Leu His Gly Gly
        115                 120                 125

Ser Glu Ser Trp Phe Thr Asp Ser Asn Asn Ala Ile Ala Ser Leu Ala
130                 135                 140

Phe His Pro Thr Ala Gln Leu Leu Ile Ala Thr Ala Asn Glu Ile
145                 150                 155                 160

His Phe Trp Asp Arg Ser Arg Arg Glu Pro Phe Ala Val Val Lys Thr
                165                 170                 175

Ala Ser Glu Met Glu Arg Val Arg Leu Val Arg Phe Asp Pro Leu Gly
            180                 185                 190

His Tyr Leu Leu Thr Ala Ile Val Asn Pro Ser Asn Gln Gln Gly Asp
        195                 200                 205

Asp Glu Pro Glu Ile Pro Ile Asp Gly Thr Glu Leu Ser His Tyr Arg
210                 215                 220

Gln Arg Ala Leu Leu Gln Ser Gln Pro Val Arg Arg Thr Pro Leu Leu
225                 230                 235                 240

His Asn Phe Leu His Met Leu Ser Ser Arg Ser Ser Gly Ile Gln Thr
                245                 250                 255

Glu Pro Phe His Pro Pro Glu Gln Ala Ser Ser Thr Gln Gln Asp Gln
            260                 265                 270

Gly Leu Leu Asn Arg Pro Ser Ala Phe Ser Thr Val Gln Ser Ser Thr
        275                 280                 285

Ala Gly Asn Thr Leu Arg Asn Leu Ser Leu Gly Pro Thr Arg Arg Ser
290                 295                 300

Leu Gly Gly Pro Leu Ser Ser His Pro Ser Arg Tyr His Arg Glu Ile
305                 310                 315                 320

Ala Pro Gly Leu Thr Gly Ser Glu Trp Thr Arg Thr Val Leu Ser Leu
                325                 330                 335

Asn Ser Arg Ser Glu Ala Glu Ser Met Pro Pro Arg Thr Ser Ala
            340                 345                 350

Ser Ser Val Ser Leu Leu Ser Val Leu Arg Gln Gln Glu Gly Gly Ser
        355                 360                 365

Gln Ala Ser Val Tyr Thr Ser Ala Thr Glu Gly Arg Gly Phe Pro Ala
370                 375                 380

Ser Gly Leu Ala Thr Glu Ser Asp Gly Gly Asn Gly Ser Ser Gln Asn
385                 390                 395                 400

Asn Ser Gly Ser Ile Arg His Glu Leu Gln Cys Asp Leu Arg Arg Phe
                405                 410                 415

Phe Leu Glu Tyr Asp Arg Leu Gln Glu Leu Asp Gln Ser Leu Ser Gly
            420                 425                 430

Glu Ala Pro Gln Thr Gln Gln Ala Gln Glu Met Leu Asn Asn Asn Ile
        435                 440                 445

Glu Ser Glu Arg Pro Gly Pro Ser His Gln Pro Thr Pro His Ser Ser
450                 455                 460

Glu Asn Asn Ser Asn Leu Ser Arg Gly His Leu Asn Arg Cys Arg Ala
465                 470                 475                 480
```

-continued

```
Cys His Asn Leu Leu Thr Phe Asn Asn Asp Thr Leu Arg Trp Glu Arg
                485                 490                 495

Thr Thr Pro Asn Tyr Ser Ser Gly Glu Ala Ser Ser Ser Trp Gln Val
            500                 505                 510

Pro Ser Ser Phe Glu Ser Val Pro Ser Ser Gly Ser Gln Leu Pro Pro
        515                 520                 525

Leu Glu Arg Thr Glu Gly Gln Thr Pro Ser Ser Arg Leu Glu Leu
    530                 535                 540

Ser Ser Ser Ala Ser Pro Gln Glu Glu Arg Thr Val Gly Val Ala Phe
545                 550                 555                 560

Asn Gln Glu Thr Gly His Trp Glu Arg Ile Tyr Thr Gln Ser Ser Arg
                565                 570                 575

Ser Gly Thr Val Ser Gln Glu Ala Leu His Gln Asp Met Pro Glu Glu
            580                 585                 590

Ser Ser Glu Glu Asp Ser Leu Arg Arg Ser Leu Ala Leu Ser Pro
        595                 600                 605

Arg Leu Glu Tyr Ser Gly Ala Ile Leu Ala His Cys Lys Leu Arg Leu
    610                 615                 620

Pro Gly Ser Cys His Ser Pro Ala Ser Ala Ser Gln Val Ala Gly Thr
625                 630                 635                 640

Thr Gly Ala His His His Ala Arg Leu Ile Phe Ala Phe Leu Val Glu
                645                 650                 655

Met Glu Phe His His Val Ser Gln Ala Gly Leu Glu Leu Leu Thr Ser
                660                 665                 670

Gly Asp Leu Pro Thr Ser Ala Ser Gln Val Leu Gly Leu Gln Ala
            675                 680                 685

<210> SEQ ID NO 112
<211> LENGTH: 152
<212> TYPE: PRT
<213> ORGANISM: Homo sapiens

<400> SEQUENCE: 112

Met Val His Ser Pro Arg Ser Leu Val Ala Asn Pro Ser Gln Val Leu
  1               5                  10                  15

Phe Phe Leu Ser Phe Leu Phe Phe Phe Leu Arg Gln Ser Phe Ala
                 20                  25                  30

Leu Val Ala Gln Ala Gly Val Gln Trp Arg Asn Leu Gly Ser Leu Gln
             35                  40                  45

Pro Pro Pro Gly Phe Lys Gln Phe Ser Cys Leu Ser Leu Leu Ser
     50                  55                  60

Ser Trp Asp Tyr Arg His Ala Pro Pro Cys Pro Ala Tyr Phe Val Phe
 65                  70                  75                  80

Leu Val Asp Met Gly Phe Pro His Val Gly Gln Thr Gly Leu Glu Leu
                 85                  90                  95

Leu Thr Ser Gly Asp Pro Pro Ala Ser Ala Ser Gln Ser Ala Gly Ile
            100                 105                 110

Thr Gly Gly Ser His Arg Ala Gln Pro Thr Ser Ser Asn Pro Tyr Gly
            115                 120                 125

Ile Val Phe Phe Phe Leu Pro Val Lys Thr Phe Ser Gly Met Ser Gln
        130                 135                 140

Glu Ala Gly Asp Cys Arg Glu Thr
145                 150
```

<210> SEQ ID NO 113
<211> LENGTH: 239
<212> TYPE: PRT
<213> ORGANISM: Homo sapiens

<400> SEQUENCE: 113

Met Pro Thr Ala Thr Gly Leu Thr Leu Leu Thr Ser Ala Ser Ser Ala
1               5                   10                  15

Ile Ser Asp Pro Gly Gly Glu Val Ser Ala Pro Trp Gly Gly Leu Arg
            20                  25                  30

Thr Trp Thr Gln Pro Leu Arg Cys Trp Glu Arg Leu Leu Pro Pro Pro
        35                  40                  45

Gly Asp Pro Arg Thr Val Ala Glu Asn Thr Gln Gln Asp Glu Cys Gly
    50                  55                  60

Leu Pro Gly Ser Cys Pro Ala Arg Pro Leu Ser Arg Lys Pro Glu Cys
65                  70                  75                  80

Gly Arg Glu Gly Ile Leu Pro Cys Cys Ser Ser Ala Trp Pro Glu
                85                  90                  95

Gly Ser Phe Arg Pro Phe Gln Met Asn Leu Phe Ser Phe Leu Ser Phe
            100                 105                 110

Phe Phe Leu Phe Phe Phe Leu Arg Trp Ser Leu Thr Leu Ser Pro
        115                 120                 125

Arg Leu Glu Cys Ser Ser Ala Ile Ser Ala His Cys Asn Leu Arg Leu
    130                 135                 140

Pro Gly Ser Ser Asn Ser Pro Ala Leu Ala Ser Gln Val Ala Gly Ile
145                 150                 155                 160

Thr Gly Ile Cys His His Ala Arg Gln Ile Phe Val Phe Leu Val Glu
                165                 170                 175

Thr Gly Phe Cys His Val Gly Gln Ala Gly Leu Glu Leu Leu Ile Ser
            180                 185                 190

Gly Asp Ser Pro Ala Ser Ala Phe Gln Ser Ala Gly Ile Ile Gly Val
        195                 200                 205

Ser His Arg Ala Arg Pro Gly Ser Val Phe Leu Ala Arg Ser Glu Glu
    210                 215                 220

Ser Leu Tyr Leu Arg Pro Gly Gln Gln Ser Gln Glu Val Lys Val
225                 230                 235

<210> SEQ ID NO 114
<211> LENGTH: 181
<212> TYPE: PRT
<213> ORGANISM: Homo sapiens

<400> SEQUENCE: 114

Met Leu Leu Val Asp Ala Asp Gln Pro Glu Pro Met Arg Ser Gly Ala
1               5                   10                  15

Arg Glu Leu Ala Leu Phe Leu Thr Pro Glu Pro Gly Ala Glu Ala Lys
            20                  25                  30

Glu Val Glu Glu Thr Ile Glu Gly Met Leu Leu Arg Leu Glu Glu Phe
        35                  40                  45

Cys Ser Leu Ala Asp Leu Ile Arg Ser Asp Thr Ser Gln Ile Leu Glu
    50                  55                  60

Glu Asn Ile Pro Val Leu Lys Ala Lys Leu Thr Glu Met Arg Gly Ile
65                  70                  75                  80

Tyr Ala Lys Val Asp Arg Leu Glu Ala Phe Val Lys Met Val Gly His
                85                  90                  95

His Val Ala Phe Leu Glu Ala Asp Val Leu Gln Ala Glu Arg Asp His

-continued

```
            100                 105                 110
Gly Ala Phe Pro Gln Ala Leu Arg Arg Trp Leu Gly Ser Ala Gly Leu
        115                 120                 125

Pro Ser Phe Arg Asn Val Glu Cys Ser Gly Thr Ile Pro Ala Arg Cys
130                 135                 140

Asn Leu Arg Leu Pro Gly Ser Ser Asp Ser Pro Ala Ser Ala Ser Gln
145                 150                 155                 160

Val Ala Gly Ile Thr Glu Val Thr Cys Thr Gly Ala Arg Asp Val Arg
                165                 170                 175

Ala Ala His Thr Val
            180

<210> SEQ ID NO 115
<211> LENGTH: 208
<212> TYPE: PRT
<213> ORGANISM: Homo sapiens

<400> SEQUENCE: 115

Met Ser Val Tyr Ser Gly Lys Val Leu Leu Gln Thr Thr Pro Pro His
1               5                   10                  15

Val Ile Gly Gln Leu Asp Lys Leu Ile Arg Glu Val Ser Thr Leu Asp
            20                  25                  30

Gly Val Leu Glu Val Arg Asn Glu His Phe Trp Thr Leu Gly Phe Gly
        35                  40                  45

Ser Leu Ala Gly Ser Val His Val Arg Ile Arg Arg Asp Ala Asn Glu
    50                  55                  60

Gln Met Val Leu Ala His Val Thr Asn Arg Leu Tyr Thr Leu Val Ser
65                  70                  75                  80

Thr Leu Thr Val Gln Ile Phe Lys Asp Asp Trp Ile Arg Pro Ala Leu
                85                  90                  95

Leu Ser Gly Pro Val Ala Ala Asn Val Leu Asn Phe Ser Asp His His
            100                 105                 110

Val Ile Pro Met Pro Leu Leu Lys Gly Thr Asp Gly Leu Asn Pro Tyr
        115                 120                 125

Val His Phe Leu Trp Lys Ile Asn Phe Phe Leu Phe Phe Asp Met Glu
    130                 135                 140

Ser Leu Ser Val Ala Gln Ala Gly Val Gln Trp His Asp Leu Gly Ser
145                 150                 155                 160

Leu Gln Pro His Leu Pro Gly Ser Ser Asn Ser Ala Cys Leu Ser Leu
                165                 170                 175

Pro Ser Ser Trp Asp Tyr Arg His Ala Pro Pro His Leu Pro Asn Phe
            180                 185                 190

Cys Ile Ile Ser Lys Asp Gly Val Leu Pro Cys Trp Pro Cys Trp Ser
        195                 200                 205

<210> SEQ ID NO 116
<211> LENGTH: 118
<212> TYPE: PRT
<213> ORGANISM: Homo sapiens

<400> SEQUENCE: 116

Met Glu Ser Arg Ser Val Ala Gln Thr Gly Val His Trp His Asn Leu
1               5                   10                  15

Ser Ser Leu Gln Pro Leu Pro Pro Arg Phe Lys Gln Phe Ser Cys Leu
            20                  25                  30

Ser Leu Arg Ser Ser Trp Asp Tyr Thr His Leu Pro Pro Cys Leu Ala
```

```
                35                  40                  45
Asn Phe Phe Val Phe Leu Val Glu Thr Ala Phe Arg His Val Gly Gln
 50                  55                  60
Ala Gly Leu Lys Leu Leu Thr Ser Gly Asp Gln Pro Thr Ser Ala Ser
 65                  70                  75                  80
Gln Ser Ala Gly Ile Thr Gly Ile Ser His Arg Thr Gln Pro Val Gly
                 85                  90                  95
Arg Phe Leu Ile Thr Asp Ser Ile Phe Leu Phe Val Thr Asp Leu Leu
                100                 105                 110
Lys Phe Ser Ile Ser Ser
            115

<210> SEQ ID NO 117
<211> LENGTH: 102
<212> TYPE: PRT
<213> ORGANISM: Homo sapiens

<400> SEQUENCE: 117

Met Ser Lys Val Leu Gly Gly Pro Phe Ser Lys Gly His Thr Ala Ser
  1               5                  10                  15
Asp Lys Tyr Phe Gln Ile Phe His Asn Ile Ser Phe Phe Glu Thr Glu
                 20                  25                  30
Ser Cys Ser Val Ala Gln Ala Gly Val Gln Trp Cys Asn Leu Gly Ser
             35                  40                  45
Leu Gln Ala Leu Pro Pro Arg Phe Thr Pro Phe Ser Cys Leu Ser Leu
 50                  55                  60
Pro Ser Ser Trp Asp Tyr Arg His Pro Pro Cys Pro Asp Asn Val
 65                  70                  75                  80
Phe Val Phe Ser Val Glu Thr Gly Phe His Cys Val Ser Gln Asp Gly
                 85                  90                  95
Leu Asn Leu Leu Thr Leu
            100

<210> SEQ ID NO 118
<211> LENGTH: 214
<212> TYPE: PRT
<213> ORGANISM: Homo sapiens

<400> SEQUENCE: 118

Met Ala Gln Gly Thr Leu Ile Arg Val Thr Pro Glu Gln Pro Thr His
  1               5                  10                  15
Ala Val Cys Val Leu Gly Thr Leu Thr Gln Leu Asp Ile Cys Ser Ser
                 20                  25                  30
Ala Pro Glu Asp Cys Thr Ser Phe Ser Ile Asn Ala Ser Pro Gly Val
             35                  40                  45
Val Val Asp Ile Ala His Ser Pro Pro Ala Lys Lys Ser Thr Gly
 50                  55                  60
Ser Ser Thr Trp Pro Leu Asp Pro Gly Val Glu Val Thr Leu Thr Met
 65                  70                  75                  80
Lys Ala Ala Ser Gly Ser Thr Gly Asp Gln Lys Val Gln Ile Ser Tyr
                 85                  90                  95
Tyr Gly Pro Lys Thr Pro Pro Val Lys Ala Leu Leu Tyr Leu Thr Ala
                100                 105                 110
Val Asp Gly Val Ser Pro Cys His Pro Gly Trp Ser Ala Met His Asp
            115                 120                 125
Leu Ala His Cys Asn Leu Arg Leu Gln Val Gln Ala Ile Leu Cys Phe
```

```
              130                 135                 140
Ser Val Pro Ser Ser Trp Thr Thr Gly Ala Cys His His Ala Trp Leu
145                 150                 155                 160

Ile Phe Val Phe Leu Val Glu Met Glu Phe His His Val Gly Gln Ala
                165                 170                 175

Gly Leu Glu Leu Leu Thr Ser Gly Asp Leu Pro Ala Ser Gly Ser Gln
                180                 185                 190

Ser Ala Arg Ile Thr Gly Met Asn His Cys Ala Arg Pro Ser Ile Phe
                195                 200                 205

Leu Ile Leu Lys Tyr Leu
    210

<210> SEQ ID NO 119
<211> LENGTH: 876
<212> TYPE: PRT
<213> ORGANISM: Homo sapiens

<400> SEQUENCE: 119

Met Ser Gln Ser Pro Ala Phe Gly Pro Arg Gly Ser Ser Pro Arg
1               5                   10                  15

Gly Ala Ala Gly Ala Ala Arg Arg Asn Glu Ser Gln Asp Tyr Leu
                20                  25                  30

Leu Met Asp Ser Glu Leu Gly Glu Asp Gly Cys Pro Gln Ala Pro Leu
            35                  40                  45

Pro Cys Tyr Gly Tyr Tyr Pro Cys Phe Arg Gly Ser Asp Asn Arg Leu
        50                  55                  60

Ala His Arg Arg Gln Thr Val Leu Arg Glu Lys Gly Arg Arg Leu Ala
65                  70                  75                  80

Asn Arg Gly Pro Ala Tyr Met Phe Ser Asp Arg Ser Thr Ser Leu Ser
                85                  90                  95

Ile Glu Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
        115                 120                 125

Val Asp Tyr Met Gly Gln Asn Ala Leu Gln Leu Ala Val Ala Asn Glu
130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
        195                 200                 205

Tyr Asp Glu Asp Gly Thr Arg Phe Ser His Asp Val Thr Pro Ile Ile
    210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
        275                 280                 285
```

```
Ser Ser Glu Asp Pro Val Met Thr Ala Leu Glu Leu Ser Asn Glu Leu
290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Arg
                325                 330                 335

Arg Asn Thr Glu Glu Val Glu Ala Ile Leu Asn Gly Asp Val Glu Thr
                340                 345                 350

Leu Gln Ser Gly Asp His Gly Arg Pro Asn Leu Ser Arg Leu Lys Leu
                355                 360                 365

Ala Ile Lys Tyr Glu Val Lys Lys Met Gly Lys Ile Met Arg Gly Pro
370                 375                 380

Phe Met Lys Phe Val Ala His Ala Ala Ser Phe Thr Ile Phe Leu Gly
385                 390                 395                 400

Leu Leu Val Met Asn Ala Ala Asp Arg Phe Glu Gly Thr Lys Leu Leu
                405                 410                 415

Pro Asn Glu Thr Ser Thr Asp Asn Ala Lys Gln Leu Phe Arg Met Lys
                420                 425                 430

Thr Ser Cys Phe Ser Trp Met Glu Met Leu Ile Ile Ser Trp Val Ile
                435                 440                 445

Gly Met Ile Trp Ala Glu Cys Lys Glu Ile Trp Thr Gln Gly Pro Lys
450                 455                 460

Glu Tyr Leu Phe Glu Leu Trp Asn Met Leu Asp Phe Gly Met Leu Ala
465                 470                 475                 480

Ile Phe Ala Ala Ser Phe Ile Ala Arg Phe Met Ala Phe Trp His Ala
                485                 490                 495

Ser Lys Ala Gln Ser Ile Ile Asp Ala Asn Asp Thr Leu Lys Asp Leu
                500                 505                 510

Thr Lys Val Thr Leu Gly Asp Asn Val Lys Tyr Tyr Asn Leu Ala Arg
                515                 520                 525

Ile Lys Trp Asp Pro Ser Asp Pro Gln Ile Ile Ser Glu Gly Leu Tyr
                530                 535                 540

Ala Ile Ala Val Val Leu Ser Phe Ser Arg Ile Ala Tyr Thr Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
                580                 585                 590

Phe Met Ile Gly Met Phe Asn Leu Tyr Ser Tyr Tyr Ile Gly Ala Lys
                595                 600                 605

Gln Asn Glu Ala Phe Thr Thr Val Glu Glu Ser Phe Lys Thr Leu Phe
                610                 615                 620

Trp Ala Ile Phe Gly Leu Ser Glu Val Lys Ser Val Val Ile Asn Tyr
625                 630                 635                 640

Asn His Lys Phe Ile Glu Asn Ile Gly Tyr Val Leu Tyr Gly Val Tyr
                645                 650                 655

Asn Val Thr Met Val Ile Val Leu Leu Asn Met Leu Ile Ala Met Ile
                660                 665                 670

Asn Ser Ser Phe Gln Glu Ile Glu Asp Asp Ala Asp Val Glu Trp Lys
                675                 680                 685

Phe Ala Arg Ala Lys Leu Trp Phe Ser Tyr Phe Glu Glu Gly Arg Thr
690                 695                 700

Leu Pro Val Pro Phe Asn Leu Val Pro Ser Pro Lys Ser Leu Phe Tyr
```

```
                705                 710                 715                 720
Leu Leu Leu Lys Leu Lys Lys Trp Ile Ser Glu Leu Phe Gln Gly His
                725                 730                 735

Lys Lys Gly Phe Gln Glu Asp Ala Glu Met Asn Lys Ile Asn Glu Glu
                740                 745                 750

Lys Lys Leu Gly Ile Leu Gly Ser His Glu Asp Leu Ser Lys Leu Ser
                755                 760                 765

Leu Asp Lys Lys Gln Val Gly His Asn Lys Gln Pro Ser Ile Arg Ser
        770                 775                 780

Ser Glu Asp Phe His Leu Asn Ser Phe Asn Asn Pro Pro Arg Gln Tyr
785                 790                 795                 800

Gln Lys Ile Met Lys Arg Leu Ile Lys Arg Tyr Val Leu Gln Ala Gln
                805                 810                 815

Ile Asp Lys Glu Ser Asp Glu Val Asn Glu Gly Glu Leu Lys Glu Ile
                820                 825                 830

Lys Gln Asp Ile Ser Ser Leu Arg Tyr Glu Leu Leu Glu Glu Lys Ser
                835                 840                 845

Gln Asn Thr Glu Asp Leu Ala Glu Leu Ile Arg Glu Leu Gly Glu Lys
                850                 855                 860

Leu Ser Met Glu Pro Asn Gln Glu Thr Asn Arg
865                 870                 875

<210> SEQ ID NO 120
<211> LENGTH: 862
<212> TYPE: PRT
<213> ORGANISM: Homo sapiens

<400> SEQUENCE: 120

Met Leu Arg Asn Ser Thr Phe Lys Asn Met Gln Arg Arg His Thr Thr
  1               5                  10                  15

Leu Arg Glu Lys Gly Arg Arg Gln Ala Ile Arg Gly Pro Ala Tyr Met
                 20                  25                  30

Phe Asn Glu Lys Gly Thr Ser Leu Thr Pro Glu Glu Glu Arg Phe Leu
             35                  40                  45

Asp Ser Ala Glu Tyr Gly Asn Ile Pro Val Val Arg Lys Met Leu Glu
     50                  55                  60

Glu Ser Lys Thr Leu Asn Phe Asn Cys Val Asp Tyr Met Gly Gln Asn
 65                  70                  75                  80

Ala Leu Gln Leu Ala Val Gly Asn Glu His Leu Glu Val Thr Glu Leu
                 85                  90                  95

Leu Leu Lys Lys Glu Asn Leu Ala Arg Val Gly Asp Ala Leu Leu Leu
                100                 105                 110

Ala Ile Ser Lys Gly Tyr Val Arg Ile Val Glu Ala Ile Leu Asn His
            115                 120                 125

Pro Ala Phe Ala Gln Gly Gln Arg Leu Thr Leu Ser Pro Leu Glu Gln
    130                 135                 140

Glu Leu Arg Asp Asp Asp Phe Tyr Ala Tyr Asp Glu Asp Gly Thr Arg
145                 150                 155                 160

Phe Ser His Asp Ile Thr Pro Ile Ile Leu Ala Ala His Cys Gln Glu
                165                 170                 175

Tyr Glu Ile Val His Ile Leu Leu Leu Lys Gly Ala Arg Ile Glu Arg
                180                 185                 190

Pro His Asp Tyr Phe Cys Lys Cys Asn Glu Cys Thr Glu Lys Gln Arg
            195                 200                 205
```

```
Lys Asp Ser Phe Ser His Ser Arg Ser Arg Met Asn Ala Tyr Lys Gly
210                 215                 220

Leu Ala Ser Ala Ala Tyr Leu Ser Leu Ser Ser Glu Asp Pro Val Leu
225                 230                 235                 240

Thr Ala Leu Glu Leu Ser Asn Glu Leu Ala Arg Leu Ala Asn Ile Glu
                245                 250                 255

Thr Glu Phe Lys Asn Asp Tyr Arg Lys Leu Ser Met Gln Cys Lys Asp
            260                 265                 270

Phe Val Val Gly Val Leu Asp Leu Cys Arg Asp Thr Glu Glu Val Glu
            275                 280                 285

Ala Ile Leu Asn Gly Asp Val Asn Phe Gln Val Trp Ser Asp His His
290                 295                 300

Arg Pro Ser Leu Ser Arg Ile Lys Leu Ala Ile Lys Tyr Glu Val Lys
305                 310                 315                 320

Lys Phe Val Ala His Pro Asn Cys Gln Gln Gln Leu Leu Thr Met Trp
                325                 330                 335

Tyr Glu Asn Leu Ser Gly Leu Arg Gln Gln Ser Ile Ala Val Lys Phe
            340                 345                 350

Leu Ala Val Phe Gly Val Ser Ile Gly Leu Pro Phe Leu Ala Ile Ala
            355                 360                 365

Tyr Trp Ile Ala Pro Cys Ser Lys Leu Gly Arg Thr Leu Arg Ser Pro
370                 375                 380

Phe Met Lys Phe Val Ala His Ala Val Ser Phe Thr Ile Phe Leu Gly
385                 390                 395                 400

Leu Leu Val Val Asn Ala Ser Asp Arg Phe Glu Gly Val Lys Thr Leu
                405                 410                 415

Pro Asn Glu Thr Phe Thr Asp Tyr Pro Lys Gln Ile Phe Arg Val Lys
            420                 425                 430

Thr Thr Gln Phe Ser Trp Thr Glu Met Leu Ile Met Lys Trp Val Leu
            435                 440                 445

Gly Met Ile Trp Ser Glu Cys Lys Glu Ile Trp Glu Glu Gly Pro Arg
450                 455                 460

Glu Tyr Val Leu His Leu Trp Asn Leu Leu Asp Phe Gly Met Leu Ser
465                 470                 475                 480

Ile Phe Val Ala Ser Phe Thr Ala Arg Phe Met Ala Phe Leu Lys Ala
                485                 490                 495

Thr Glu Ala Gln Leu Tyr Val Asp Gln His Val Gln Asp Asp Thr Leu
            500                 505                 510

His Asn Val Ser Leu Pro Pro Glu Val Ala Tyr Phe Thr Tyr Ala Arg
            515                 520                 525

Asp Lys Trp Trp Pro Ser Asp Pro Gln Ile Ile Ser Glu Gly Leu Tyr
530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Phe Ile Met Val Phe Val Val Ala
            580                 585                 590

Phe Met Ile Gly Met Phe Asn Leu Tyr Ser Tyr Arg Gly Ala Lys
            595                 600                 605

Tyr Asn Pro Ala Phe Thr Thr Val Glu Glu Ser Phe Lys Thr Leu Phe
610                 615                 620

Trp Ser Ile Phe Gly Leu Ser Glu Val Ile Ser Val Val Leu Lys Tyr
```

```
                625                 630                 635                 640
Asp His Lys Phe Ile Glu Asn Ile Gly Tyr Val Leu Tyr Gly Val Tyr
                        645                 650                 655

Asn Val Thr Met Val Val Leu Leu Asn Met Leu Ile Ala Met Ile
                660                 665                 670

Asn Asn Ser Tyr Gln Glu Ile Glu Glu Asp Ala Asp Val Glu Trp Lys
                        675                 680                 685

Phe Ala Arg Ala Lys Leu Trp Leu Ser Tyr Phe Asp Glu Gly Arg Thr
                690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Lys Leu Cys Lys Ser Lys
                        725                 730                 735

Ala Lys Ser Cys Glu Asn Asp Leu Glu Met Gly Met Leu Asn Ser Lys
                740                 745                 750

Phe Lys Lys Thr Arg Tyr Gln Ala Gly Met Arg Asn Ser Glu Asn Leu
                        755                 760                 765

Thr Ala Asn Asn Thr Leu Ser Lys Pro Thr Arg Tyr Gln Lys Ile Met
770                 775                 780

Lys Arg Leu Ile Lys Arg Tyr Val Leu Lys Ala Gln Val Asp Arg Glu
785                 790                 795                 800

Asn Asp Glu Val Asn Glu Gly Glu Leu Lys Glu Ile Lys Gln Asp Ile
                        805                 810                 815

Ser Ser Leu Arg Tyr Glu Leu Leu Glu Glu Lys Ser Gln Ala Thr Gly
                820                 825                 830

Glu Leu Ala Asp Leu Ile Gln Gln Leu Ser Glu Lys Phe Gly Lys Asn
                        835                 840                 845

Leu Asn Lys Asp His Leu Arg Val Asn Lys Gly Lys Asp Ile
850                 855                 860

<210> SEQ ID NO 121
<211> LENGTH: 893
<212> TYPE: PRT
<213> ORGANISM: Cavia porcellus

<400> SEQUENCE: 121

Met Asp Asp Gly Cys Pro Gln Leu Pro Leu Pro Pro His Gly Tyr Tyr
1               5                   10                  15

Pro Ser Leu Arg Gly Thr Asp Asn Arg Leu Thr His Arg Arg Gln Thr
                20                  25                  30

Val Leu Arg Glu Lys Gly Arg Arg Leu Ala Asn Arg Gly Pro Ala Tyr
            35                  40                  45

Met Phe Asn Asp His Ser Thr Thr Leu Ser Ile Glu Glu Glu Arg Phe
        50                  55                  60

Leu Asp Ala Ala Glu Tyr Gly Asn Ile Pro Val Val Arg Lys Met Leu
65                  70                  75                  80

Glu Glu Cys Leu Ser Leu Asn Val Asn Cys Val Asp Tyr Met Gly Gln
                85                  90                  95

Asn Ala Leu Gln Leu Ala Val Ala Asn Glu His Leu Glu Ile Thr Glu
                100                 105                 110

Leu Leu Leu Lys Lys Glu Asn Leu Ser Arg Val Gly Asp Ala Leu Leu
            115                 120                 125

Leu Ala Ile Ser Lys Gly Tyr Val Arg Ile Val Glu Ala Ile Leu Ser
        130                 135                 140
```

-continued

```
His Pro Ala Phe Ala Glu Gly Lys Arg Leu Ala Thr Ser Pro Ser Gln
145                 150                 155                 160

Ser Glu Leu Gln Gln Asp Asp Phe Tyr Ala Tyr Asp Glu Asp Gly Thr
                165                 170                 175

Arg Phe Ser His Asp Val Thr Pro Ile Ile Leu Ala Ala His Cys Gln
            180                 185                 190

Glu Tyr Glu Ile Val His Thr Leu Leu Arg Lys Gly Ala Arg Ile Glu
        195                 200                 205

Arg Pro His Asp Tyr Phe Cys Lys Cys Ser Glu Cys Asn Gln Lys Gln
    210                 215                 220

Lys His Asp Ser Phe Ser His Ser Arg Ser Arg Ile Asn Ala Tyr Lys
225                 230                 235                 240

Gly Leu Ala Ser Pro Ala Tyr Leu Ser Leu Ser Ser Glu Asp Pro Val
                245                 250                 255

Met Thr Ala Leu Glu Leu Ser Asn Glu Leu Ala Val Leu Ala Asn Ile
            260                 265                 270

Glu Lys Glu Phe Lys Asn Asp Tyr Lys Lys Leu Ser Met Gln Cys Lys
        275                 280                 285

Asp Phe Val Val Gly Leu Leu Asp Leu Cys Arg Asn Thr Glu Glu Val
    290                 295                 300

Glu Ala Ile Leu Asn Gly Asp Val Glu Thr Cys Gln Ser Gly Asp Gln
305                 310                 315                 320

Gly Arg Pro Asn Leu Ser Arg Leu Lys Leu Ala Ile Lys Tyr Glu Val
                325                 330                 335

Lys Lys Phe Val Ala His Pro Asn Cys Gln Gln Leu Leu Ser Ile
            340                 345                 350

Trp Tyr Glu Asn Leu Ser Gly Leu Arg Gln Gln Thr Met Ala Val Lys
        355                 360                 365

Phe Leu Val Val Leu Gly Val Ala Ile Gly Leu Pro Phe Leu Ala Leu
    370                 375                 380

Ile Tyr Trp Cys Ala Pro Cys Ser Lys Met Gly Lys Ile Met Arg Gly
385                 390                 395                 400

Pro Phe Met Lys Phe Val Ala His Ala Ala Ser Phe Thr Ile Phe Leu
                405                 410                 415

Gly Leu Leu Val Met Asn Ala Ala Asp Arg Phe Glu Gly Thr Lys Leu
            420                 425                 430

Arg Pro Asn Glu Thr Ser Thr Asp Asn Ala Lys Gln Leu Phe Arg Met
        435                 440                 445

Lys Thr Ser Cys Phe Ser Trp Met Glu Met Leu Ile Ile Ser Trp Val
450                 455                 460

Ile Gly Met Ile Trp Ala Glu Cys Lys Glu Ile Trp Ala Gln Gly Pro
465                 470                 475                 480

Lys Glu Tyr Leu Phe Glu Leu Trp Asn Met Leu Asp Phe Gly Met Leu
                485                 490                 495

Ala Ile Phe Ala Ala Ser Phe Ile Ala Arg Phe Met Ala Phe Trp His
            500                 505                 510

Ala Ser Lys Ala Gln Ser Ile Ile Asp Ala Asn Asp Thr Leu Lys Asp
        515                 520                 525

Leu Thr Lys Val Thr Leu Gly Glu Asp Val Lys Tyr Tyr Asn Leu Ala
    530                 535                 540

Arg Ile Lys Trp Asp Pro Ser Asp Pro Gln Ile Ile Ser Glu Gly Leu
545                 550                 555                 560

Tyr Ala Ile Ala Val Val Leu Ser Phe Ser Arg Ile Ala Tyr Ile Leu
```

```
                  565                 570                 575
Pro Ala Asn Glu Ser Phe Gly Pro Leu Gln Ile Ser Leu Gly Arg Thr
                580                 585                 590
Val Lys Asp Ile Phe Lys Phe Met Val Ile Phe Ile Met Val Phe Val
            595                 600                 605
Ala Phe Met Ile Gly Met Phe Asn Leu Tyr Ser Tyr Tyr Ile Gly Ala
        610                 615                 620
Lys Gln Asn Glu Ala Phe Thr Thr Val Glu Glu Ser Phe Lys Thr Leu
625                 630                 635                 640
Phe Trp Ala Ile Phe Gly Leu Ser Glu Val Lys Ser Val Val Ile Asn
                645                 650                 655
Tyr Asn His Lys Phe Ile Glu Asn Ile Gly Tyr Val Leu Tyr Gly Val
                660                 665                 670
Tyr Asn Val Thr Met Val Ile Val Leu Leu Asn Met Leu Ile Ala Met
                675                 680                 685
Ile Asn Ser Ser Phe Gln Glu Ile Glu Asp Asp Ala Asp Val Glu Trp
690                 695                 700
Lys Phe Ala Arg Ala Lys Leu Trp Phe Ser Tyr Phe Glu Glu Gly Arg
705                 710                 715                 720
Thr Leu Pro Val Pro Phe Asn Leu Val Pro Ser Pro Lys Ser Leu Leu
                725                 730                 735
Tyr Leu Leu Lys Phe Lys Lys Trp Gly Phe Glu Leu Phe Gln Gly
                740                 745                 750
His Lys Lys Ala Phe Gln Glu Asp Ala Glu Met Asn Lys Arg Asn Glu
            755                 760                 765
Glu Lys Lys Phe Gly Ile Leu Gly Ser His Glu Asp Leu Ser Lys Leu
770                 775                 780
Ser Val Asp Lys Lys Gln Leu Gly Gln Asn Lys Gln Ser Ser Ile Arg
785                 790                 795                 800
Ser Ser Glu Asp Phe His Leu Asn Ser Phe Asn Asn Pro Pro Arg Gln
                805                 810                 815
Tyr Gln Lys Ile Met Lys Arg Leu Ile Lys Arg Tyr Val Leu Gln Ala
            820                 825                 830
Gln Ile Asp Lys Glu Ser Asp Glu Val Asn Glu Gly Glu Leu Lys Glu
        835                 840                 845
Ile Lys Gln Asp Ile Ser Ser Leu Arg Tyr Glu Leu Leu Glu Glu Lys
        850                 855                 860
Ser Gln Asn Thr Glu Asp Leu Ala Glu Leu Ile Arg Lys Leu Gly Glu
865                 870                 875                 880
Lys Leu Ser Ser Glu Pro Lys Gln Glu Glu Ile Asn Arg
                885                 890

<210> SEQ ID NO 122
<211> LENGTH: 597
<212> TYPE: PRT
<213> ORGANISM: Cavia porcellus

<400> SEQUENCE: 122

Met Phe Asn Asp His Ser Thr Thr Leu Ser Ile Glu Glu Glu Arg Phe
1               5                   10                  15
Leu Asp Ala Ala Glu Tyr Gly Asn Ile Pro Val Val Arg Lys Met Leu
            20                  25                  30
Glu Glu Cys Leu Ser Leu Asn Val Asn Cys Val Asp Tyr Met Gly Gln
        35                  40                  45
```

```
Asn Ala Leu Gln Leu Ala Val Ala Asn Glu His Leu Glu Ile Thr Glu
 50                  55                  60

Leu Leu Leu Lys Lys Glu Asn Leu Ser Arg Val Gly Asp Ala Leu Leu
 65                  70                  75                  80

Leu Ala Ile Ser Lys Gly Tyr Val Arg Ile Val Glu Ala Ile Leu Ser
                 85                  90                  95

His Pro Ala Phe Ala Glu Gly Lys Arg Leu Ala Thr Ser Leu Ser Gln
            100                 105                 110

Ser Glu Leu Gln Gln Asp Asp Phe Tyr Ala Tyr Asp Glu Asp Gly Thr
        115                 120                 125

Arg Phe Ser His Asp Val Thr Pro Ile Ile Leu Ala Ala His Cys Gln
130                 135                 140

Glu Tyr Glu Ile Val His Thr Leu Leu Arg Lys Gly Ala Arg Ile Glu
145                 150                 155                 160

Arg Pro His Asp Tyr Phe Cys Lys Cys Ser Glu Cys Asn Gln Lys Gln
                165                 170                 175

Lys His Asp Ser Phe Ser His Ser Arg Ser Arg Ile Asn Ala Tyr Lys
            180                 185                 190

Gly Leu Ala Ser Pro Ala Tyr Leu Ser Leu Ser Ser Glu Asp Pro Val
        195                 200                 205

Met Thr Ala Leu Glu Leu Ser Asn Glu Leu Ala Val Leu Ala Asn Ile
210                 215                 220

Glu Lys Glu Phe Lys Asn Asp Tyr Lys Lys Leu Ser Met Gln Cys Lys
225                 230                 235                 240

Asp Phe Val Val Gly Leu Leu Asp Leu Cys Arg Asn Thr Glu Glu Val
                245                 250                 255

Glu Ala Ile Leu Asn Gly Asp Ile Glu Thr Cys Gln Pro Gly Asp Gln
            260                 265                 270

Gly Arg Pro Asn Leu Ser Arg Leu Lys Leu Ala Ile Lys Tyr Glu Val
        275                 280                 285

Lys Lys Phe Val Ala His Pro Asn Cys Gln Gln Leu Leu Ser Ile
290                 295                 300

Trp Tyr Glu Asn Leu Ser Gly Leu Arg Gln Gln Thr Met Ala Val Lys
305                 310                 315                 320

Phe Leu Val Val Leu Gly Val Ala Ile Gly Leu Pro Phe Leu Ala Leu
                325                 330                 335

Ile Tyr Trp Cys Ala Pro Cys Ser Lys Met Gly Lys Ile Met Arg Gly
            340                 345                 350

Pro Phe Met Lys Phe Val Ala His Ala Ala Ser Phe Thr Ile Phe Leu
        355                 360                 365

Gly Leu Leu Val Met Asn Ala Ala Asp Arg Phe Glu Gly Thr Lys Leu
370                 375                 380

Arg Pro Asn Glu Thr Ser Thr Asp Asn Ala Lys Gln Leu Phe Arg Met
385                 390                 395                 400

Lys Thr Ser Cys Phe Ser Trp Met Glu Met Leu Ile Ile Ser Trp Val
                405                 410                 415

Ile Gly Met Val Trp Ala Glu Cys Lys Glu Ile Trp Ala Gln Gly Pro
            420                 425                 430

Lys Glu Tyr Leu Phe Glu Leu Trp Asn Met Leu Asp Phe Gly Met Leu
        435                 440                 445

Ala Ile Phe Ala Ala Ser Phe Ile Ala Arg Phe Met Ala Phe Trp His
450                 455                 460

Ala Ser Lys Ala Gln Ser Ile Ile Asp Ala Asn Asp Thr Leu Lys Asp
```

```
                465                 470                 475                 480
Leu Thr Lys Val Thr Leu Gly Glu Asp Val Lys Tyr Tyr Asn Leu Ala
                        485                 490                 495
Arg Ile Lys Trp Asp Pro Ser Asp Pro Gln Ile Ile Ser Glu Gly Leu
                500                 505                 510
Tyr Ala Ile Ala Val Val Leu Ser Phe Ser Arg Ile Ala Tyr Ile Leu
                515                 520                 525
Pro Ala Asn Glu Ser Phe Gly Pro Leu Gln Ile Ser Leu Gly Arg Thr
                530                 535                 540
Val Lys Asp Ile Phe Lys Phe Met Val Ile Phe Ile Met Val Phe Val
545                 550                 555                 560
Ala Phe Met Ile Gly Met Phe Asn Leu Tyr Ser His Tyr Ile Gly Ala
                565                 570                 575
Lys Gln Asn Glu Ala Phe Thr Thr Tyr Val Ile Ser Asp Val Leu Thr
                580                 585                 590
Met Glu Ile Ala Asp
                595
```

<210> SEQ ID NO 123
<211> LENGTH: 815
<212> TYPE: PRT
<213> ORGANISM: Cavia porcellus

<400> SEQUENCE: 123

```
Met Asp Asp Gly Cys Pro Gln Leu Pro Leu Pro Pro His Gly Tyr Tyr
1               5                   10                  15
Pro Ser Leu Arg Gly Thr Asp Asn Arg Leu Thr His Arg Arg Gln Thr
                20                  25                  30
Val Leu Arg Glu Lys Gly Arg Arg Leu Ala Asn Arg Gly Pro Ala Tyr
            35                  40                  45
Met Phe Asn Asp His Ser Thr Thr Leu Ser Ile Glu Glu Glu Arg Phe
        50                  55                  60
Leu Asp Ala Ala Glu Tyr Gly Asn Ile Pro Val Val Arg Lys Met Leu
65                  70                  75                  80
Glu Glu Cys Leu Ser Leu Asn Val Asn Cys Val Asp Tyr Met Gly Gln
                85                  90                  95
Asn Ala Leu Gln Leu Ala Val Ala Asn Glu His Leu Glu Ile Thr Glu
                100                 105                 110
Leu Leu Leu Lys Lys Glu Asn Leu Ser Arg Val Gly Asp Ala Leu Leu
            115                 120                 125
Leu Ala Ile Ser Lys Gly Tyr Val Arg Ile Val Glu Ala Ile Leu Ser
        130                 135                 140
His Pro Ala Phe Ala Glu Gly Lys Arg Leu Ala Thr Ser Pro Ser Gln
145                 150                 155                 160
Ser Glu Leu Gln Gln Asp Asp Phe Tyr Ala Tyr Asp Glu Asp Gly Thr
                165                 170                 175
Arg Phe Ser His Asp Val Thr Pro Ile Ile Leu Ala Ala His Cys Gln
                180                 185                 190
Glu Tyr Glu Ile Val His Thr Leu Leu Arg Lys Gly Ala Arg Ile Glu
            195                 200                 205
Arg Pro His Asp Tyr Phe Cys Glu Cys Ser Glu Cys Asn Gln Lys Gln
        210                 215                 220
Lys His Asp Ser Phe Ser His Ser Arg Ser Arg Ile Asn Ala Tyr Lys
225                 230                 235                 240
```

```
-continued

Gly Leu Ala Ser Pro Ala Tyr Leu Ser Leu Ser Ser Glu Asp Pro Val
            245                 250                 255

Met Thr Ala Leu Glu Leu Ser Asn Glu Leu Ala Val Leu Ala Asn Ile
            260                 265                 270

Glu Lys Glu Phe Lys Asn Asp Tyr Lys Lys Leu Ser Met Gln Cys Lys
            275                 280                 285

Asp Phe Val Val Gly Leu Leu Asp Leu Cys Arg Asn Thr Glu Glu Val
290                 295                 300

Glu Ala Ile Leu Asn Gly Asp Val Glu Thr Cys Gln Pro Gly Asp Gln
305                 310                 315                 320

Gly Arg Pro Asn Leu Ser Arg Leu Lys Leu Ala Ile Lys Tyr Glu Val
            325                 330                 335

Lys Lys Phe Val Ala His Pro Asn Cys Gln Gln Gln Leu Leu Ser Ile
            340                 345                 350

Trp Tyr Glu Asn Leu Ser Gly Leu Arg Gln Gln Thr Met Ala Val Lys
            355                 360                 365

Phe Leu Val Val Leu Gly Val Ala Ile Gly Leu Pro Phe Leu Ala Leu
            370                 375                 380

Ile Tyr Trp Cys Ala Pro Cys Ser Lys Met Gly Lys Ile Met Arg Gly
385                 390                 395                 400

Pro Phe Met Lys Phe Val Ala His Ala Ala Ser Phe Thr Ile Phe Leu
            405                 410                 415

Gly Leu Leu Val Met Asn Ala Ala Asp Arg Phe Glu Gly Thr Lys Leu
            420                 425                 430

Arg Pro Asn Glu Thr Ser Thr Asp Asn Ala Lys Gln Leu Phe Arg Met
            435                 440                 445

Lys Thr Ser Cys Phe Ser Trp Met Glu Met Leu Ile Ile Ser Trp Val
            450                 455                 460

Ile Ala Arg Ile Lys Trp Asp Pro Ser Asp Pro Gln Ile Ile Ser Glu
465                 470                 475                 480

Gly Leu Tyr Ala Ile Ala Val Val Leu Ser Phe Ser Arg Ile Ala Tyr
            485                 490                 495

Ile Leu Pro Ala Asn Glu Ser Phe Gly Pro Leu Gln Ile Ser Leu Gly
            500                 505                 510

Arg Thr Val Lys Asp Ile Phe Lys Phe Met Val Ile Phe Ile Met Val
            515                 520                 525

Phe Val Ala Phe Met Ile Gly Met Phe His Leu Tyr Ser Tyr Tyr Ile
            530                 535                 540

Gly Ala Lys Gln Asn Glu Ala Phe Thr Thr Val Glu Glu Ser Phe Lys
545                 550                 555                 560

Thr Leu Phe Trp Ala Ile Phe Gly Leu Ser Glu Val Lys Ser Val Val
            565                 570                 575

Ile Asn Tyr Asn His Lys Phe Ile Glu Asn Ile Gly Tyr Val Leu Tyr
            580                 585                 590

Gly Val Tyr Asn Val Thr Met Val Ile Val Leu Leu Asn Met Leu Ile
            595                 600                 605

Ala Met Ile Asn Ser Ser Phe Gln Glu Ile Glu Asp Asp Ala Asp Val
            610                 615                 620

Glu Trp Lys Phe Ala Arg Ala Lys Leu Trp Phe Ser Tyr Phe Glu Glu
625                 630                 635                 640

Gly Arg Thr Leu Pro Val Pro Phe Asn Leu Val Pro Ser Pro Lys Ser
            645                 650                 655

Leu Leu Tyr Leu Leu Leu Lys Phe Lys Lys Trp Gly Phe Glu Leu Phe
```

-continued

```
                660                 665                 670
Gln Gly His Lys Lys Ala Phe Gln Glu Asp Ala Glu Met Asn Lys Arg
            675                 680                 685
Asn Glu Glu Lys Lys Phe Gly Ile Leu Gly Ser His Glu Asp Leu Ser
            690                 695                 700
Lys Leu Ser Val Asp Lys Lys Gln Leu Gly Gln Asn Lys Gln Ser Ser
705                 710                 715                 720
Ile Arg Ser Ser Glu Asp Phe His Leu Asn Ser Phe Asn Asn Pro Pro
                725                 730                 735
Arg Gln Tyr Gln Lys Ile Met Lys Arg Leu Ile Lys Arg Tyr Val Leu
            740                 745                 750
Gln Ala Gln Ile Asp Lys Glu Ser Asp Glu Val Asn Glu Gly Glu Leu
            755                 760                 765
Lys Glu Ile Lys Gln Asp Ile Ser Ser Leu Arg Tyr Glu Leu Leu Glu
            770                 775                 780
Glu Lys Ser Gln Asn Thr Glu Asp Leu Ala Glu Leu Ile Arg Lys Leu
785                 790                 795                 800
Gly Glu Lys Leu Ser Ser Glu Pro Lys Gln Glu Glu Ile Asn Arg
                805                 810                 815

<210> SEQ ID NO 124
<211> LENGTH: 876
<212> TYPE: PRT
<213> ORGANISM: Homo sapiens

<400> SEQUENCE: 124

Met Ser Gln Ser Pro Ala Phe Gly Pro Arg Arg Gly Ser Ser Pro Arg
1               5                   10                  15
Gly Ala Ala Gly Ala Ala Ala Arg Arg Asn Glu Ser Gln Asp Tyr Leu
                20                  25                  30
Leu Met Asp Ser Glu Leu Gly Glu Asp Gly Cys Pro Gln Ala Pro Leu
            35                  40                  45
Pro Cys Tyr Gly Tyr Tyr Pro Cys Phe Arg Gly Ser Asp Asn Arg Leu
        50                  55                  60
Ala His Arg Arg Gln Thr Val Leu Arg Glu Lys Gly Arg Arg Leu Ala
65                  70                  75                  80
Asn Arg Gly Pro Ala Tyr Met Phe Ser Asp Arg Ser Thr Ser Leu Ser
                85                  90                  95
Ile Glu Glu Glu Arg Phe Leu Asp Ala Ala Glu Tyr Gly Asn Ile Pro
            100                 105                 110
Val Val Arg Lys Met Leu Glu Glu Cys His Ser Leu Asn Val Asn Cys
        115                 120                 125
Val Asp Tyr Met Gly Gln Asn Ala Leu Gln Leu Ala Val Ala Asn Glu
    130                 135                 140
His Leu Glu Ile Thr Glu Leu Leu Leu Lys Lys Glu Asn Leu Ser Arg
145                 150                 155                 160
Val Gly Asp Ala Leu Leu Leu Ala Ile Ser Lys Gly Tyr Val Arg Ile
                165                 170                 175
Val Glu Ala Ile Leu Ser His Pro Ala Phe Ala Glu Gly Lys Arg Leu
            180                 185                 190
Ala Thr Ser Pro Ser Gln Ser Glu Leu Gln Gln Asp Asp Phe Tyr Ala
        195                 200                 205
Tyr Asp Glu Asp Gly Thr Arg Phe Ser His Asp Val Thr Pro Ile Ile
    210                 215                 220
```

-continued

```
Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
            245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
        275                 280                 285

Ser Ser Glu Asp Pro Val Met Thr Ala Leu Glu Leu Ser Asn Glu Leu
    290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Arg
                325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
        355                 360                 365

Ala Ile Lys Tyr Glu Val Lys Lys Met Gly Lys Ile Met Arg Gly Pro
370                 375                 380

Phe Met Lys Phe Val Ala His Ala Ala Ser Phe Thr Ile Phe Leu Gly
385                 390                 395                 400

Leu Leu Val Met Asn Ala Ala Asp Arg Phe Glu Gly Thr Lys Leu Leu
                405                 410                 415

Pro Asn Glu Thr Ser Thr Asp Asn Ala Lys Gln Leu Phe Arg Met Lys
            420                 425                 430

Thr Ser Cys Phe Ser Trp Met Glu Met Leu Ile Ile Ser Trp Val Ile
        435                 440                 445

Gly Met Ile Trp Ala Glu Cys Lys Glu Ile Trp Thr Gln Gly Pro Lys
    450                 455                 460

Glu Tyr Leu Phe Glu Leu Trp Asn Met Leu Asp Phe Gly Met Leu Ala
465                 470                 475                 480

Ile Phe Ala Ala Ser Phe Ile Ala Arg Phe Met Ala Phe Trp His Ala
                485                 490                 495

Ser Lys Ala Gln Ser Ile Ile Asp Ala Asn Asp Thr Leu Lys Asp Leu
            500                 505                 510

Thr Lys Val Thr Leu Gly Asp Asn Val Lys Tyr Tyr Asn Leu Ala Arg
        515                 520                 525

Ile Lys Trp Asp Pro Ser Asp Pro Gln Ile Ile Ser Glu Gly Leu Tyr
    530                 535                 540

Ala Ile Ala Val Val Leu Ser Phe Ser Arg Ile Ala Tyr Thr Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Met Val Phe Val Ala
            580                 585                 590

Phe Met Ile Gly Met Phe Asn Leu Tyr Ser Tyr Tyr Ile Gly Ala Lys
        595                 600                 605

Gln Asn Glu Ala Phe Thr Thr Val Glu Glu Ser Phe Lys Thr Leu Phe
    610                 615                 620

Trp Ala Ile Phe Gly Leu Ser Glu Val Lys Ser Val Val Ile Asn Tyr
625                 630                 635                 640

Asn His Lys Phe Ile Glu Asn Ile Gly Tyr Val Leu Tyr Gly Val Tyr
```

```
                        645                 650                 655
Asn Val Thr Met Val Ile Val Leu Leu Asn Met Leu Ile Ala Met Ile
                660                 665                 670
Asn Ser Ser Phe Gln Glu Ile Glu Asp Asp Ala Asp Val Glu Trp Lys
            675                 680                 685
Phe Ala Arg Ala Lys Leu Trp Phe Ser Tyr Phe Glu Glu Gly Arg Thr
        690                 695                 700
Leu Pro Val Pro Phe Asn Leu Val Pro Ser Pro Lys Ser Leu Phe Tyr
705                 710                 715                 720
Leu Leu Leu Lys Leu Lys Lys Trp Ile Ser Glu Leu Phe Gln Gly His
                725                 730                 735
Lys Lys Gly Phe Gln Glu Asp Ala Glu Met Asn Lys Ile Asn Glu Glu
                740                 745                 750
Lys Lys Leu Gly Ile Leu Gly Ser His Glu Asp Leu Ser Lys Leu Ser
            755                 760                 765
Leu Asp Lys Lys Gln Val Gly His Asn Lys Gln Pro Ser Ile Arg Ser
        770                 775                 780
Ser Glu Asp Phe His Leu Asn Ser Phe Asn Asn Pro Arg Gln Tyr
785                 790                 795                 800
Gln Lys Ile Met Lys Arg Leu Ile Lys Arg Tyr Val Leu Gln Ala Gln
                805                 810                 815
Ile Asp Lys Glu Ser Asp Glu Val Asn Glu Gly Leu Lys Glu Ile
                820                 825                 830
Lys Gln Asp Ile Ser Ser Leu Arg Tyr Glu Leu Leu Glu Glu Lys Ser
            835                 840                 845
Gln Asn Thr Glu Asp Leu Ala Glu Leu Ile Arg Glu Leu Gly Glu Lys
        850                 855                 860
Leu Ser Met Glu Pro Asn Gln Glu Glu Thr Asn Arg
865                 870                 875

<210> SEQ ID NO 125
<211> LENGTH: 1442
<212> TYPE: DNA
<213> ORGANISM: Homo sapiens
<220> FEATURE:
<221> NAME/KEY: CDS
<222> LOCATION: (15)..(1139)

<400> SEQUENCE: 125
tttttttttt tgag atg gag ttt tcg ctc ttg ttg ccc agg ctg gag tgc      50
              Met Glu Phe Ser Leu Leu Leu Pro Arg Leu Glu Cys
                1               5                   10 aat ggc gca atc tca gct cac cgc aac ctc cgc ctc ccg ggt tca agc      98
Asn Gly Ala Ile Ser Ala His Arg Asn Leu Arg Leu Pro Gly Ser Ser
        15                  20                  25 gat tct cct gcc tca gcc tcc cca gta gct ggg att aca ggc atg tgc     146
Asp Ser Pro Ala Ser Ala Ser Pro Val Ala Gly Ile Thr Gly Met Cys
    30                  35                  40 acc cac gct cgg cta att tgt att ttt tta gta gag atg gag ttt         194
Thr His Ala Arg Leu Ile Leu Tyr Phe Phe Leu Val Glu Met Glu Phe
45                  50                  55                  60 ctc cat gtt ggt cag gct ggt ctc gaa ctc ccg acc tca gat gat ccc     242
Leu His Val Gly Gln Ala Gly Leu Glu Leu Pro Thr Ser Asp Asp Pro
                65                  70                  75 tcc gtc tcg gcc tcc caa agt gct aga tac agg act ggc cac cat gcc    290
Ser Val Ser Ala Ser Gln Ser Ala Arg Tyr Arg Thr Gly His His Ala
            80                  85                  90
```

-continued

| | |
|---|---|
| cgg ctc tgc ctg gct aat ttt tgt ggt aga aac agg gtt tca ctg atg<br>Arg Leu Cys Leu Ala Asn Phe Cys Gly Arg Asn Arg Val Ser Leu Met<br>        95                    100                    105 | 338 |
| tgc cca agc tgg tct cct gag ctc aag cag tcc acc tgc ctc agc ctc<br>Cys Pro Ser Trp Ser Pro Glu Leu Lys Gln Ser Thr Cys Leu Ser Leu<br>110                    115                    120 | 386 |
| cca aag tgc tgg gat tac agg cgt gca gcc gtg cct ggc ctt ttt att<br>Pro Lys Cys Trp Asp Tyr Arg Arg Ala Ala Val Pro Gly Leu Phe Ile<br>125                    130                    135                  140 | 434 |
| tta ttt ttt tta aga cac agg tgt ccc act ctt acc cag gat gaa gtg<br>Leu Phe Phe Leu Arg His Arg Cys Pro Thr Leu Thr Gln Asp Glu Val<br>                  145                    150                    155 | 482 |
| cag tgg tgt gat cac agc tca ctg cag cct tca act cct gag atc aag<br>Gln Trp Cys Asp His Ser Ser Leu Gln Pro Ser Thr Pro Glu Ile Lys<br>                    160                    165                    170 | 530 |
| cat cct cct gcc tca gcc tcc caa gta gct ggg acc aaa gac atg cac<br>His Pro Pro Ala Ser Ala Ser Gln Val Ala Gly Thr Lys Asp Met His<br>175                    180                    185 | 578 |
| cac tac acc tgg cta att ttt att ttt att ttt aat ttt ttg aga cag<br>His Tyr Thr Trp Leu Ile Phe Ile Phe Ile Phe Asn Phe Leu Arg Gln<br>                  190                    195                    200 | 626 |
| agt ctc aac tct gtc acc cag gct gga gtg cag tgg cgc aat ctt ggc<br>Ser Leu Asn Ser Val Thr Gln Ala Gly Val Gln Trp Arg Asn Leu Gly<br>205                    210                    215                  220 | 674 |
| tca ctg caa cct ctg cct ccc ggg ttc aag tta ttc tcc tgc ccc agc<br>Ser Leu Gln Pro Leu Pro Pro Gly Phe Lys Leu Phe Ser Cys Pro Ser<br>                  225                    230                    235 | 722 |
| ctc ctg agt agc tgg gac tac agg cgc cca cca cgc cta gct aat ttt<br>Leu Leu Ser Ser Trp Asp Tyr Arg Arg Pro Pro Arg Leu Ala Asn Phe<br>                  240                    245                    250 | 770 |
| ttt gta ttt tta gta gag atg ggg ttc acc atg ttc gcc agg ttg atc<br>Phe Val Phe Leu Val Glu Met Gly Phe Thr Met Phe Ala Arg Leu Ile<br>                  255                    260                    265 | 818 |
| ttg atc tct gga cct tgt gat ctg cct gcc tcg gcc tcc caa agt gct<br>Leu Ile Ser Gly Pro Cys Asp Leu Pro Ala Ser Ala Ser Gln Ser Ala<br>270                    275                    280 | 866 |
| ggg att aca ggc gtg agc cac cac gcc cgg ctt att ttt aat ttt tgt<br>Gly Ile Thr Gly Val Ser His His Ala Arg Leu Ile Phe Asn Phe Cys<br>285                    290                    295                    300 | 914 |
| ttg ttt gaa atg gaa tct cac tct gtt acc cag gct gga gtg caa tgg<br>Leu Phe Glu Met Glu Ser His Ser Val Thr Gln Ala Gly Val Gln Trp<br>                  305                    310                    315 | 962 |
| cca aat ctc ggc tca ctg caa cct ctg cct ccc ggg ctc aag cga ttc<br>Pro Asn Leu Gly Ser Leu Gln Pro Leu Pro Pro Gly Leu Lys Arg Phe<br>                  320                    325                    330 | 1010 |
| tcc tgt ctc agc ctc cca agc agc tgg gat tac ggg cac ctg cca cca<br>Ser Cys Leu Ser Leu Pro Ser Ser Trp Asp Tyr Gly His Leu Pro Pro<br>335                    340                    345 | 1058 |
| cac ccc gct aat ttt tgt att ttc att aga ggc ggg gtt tca cca tat<br>His Pro Ala Asn Phe Cys Ile Phe Ile Arg Gly Gly Val Ser Pro Tyr<br>350                    355                    360 | 1106 |
| ttg tca ggc tgg tct caa act cct gac ctc agg tgacccacct gcctcagcct<br>Leu Ser Gly Trp Ser Gln Thr Pro Asp Leu Arg<br>365                    370                    375 | 1159 |
| tccaaagtgc tgggattaca ggcgtgagcc acctcaccca gccggctaat ttagataaaa | 1219 |
| aaatatgtag caatgggggg tcttgctatg ttgcccaggc tggtctcaaa cttctggctt | 1279 |

| | |
|---|---|
| catgcaatcc ttccaaatga gccacaacac ccagccagtc acattttta aacagttaca | 1339 |
| tctttatttt agtatactag aaagtaatac aataaacatg tcaaacctgc aaattcagta | 1399 |
| gtaacagagt tcttttataa cttttaaaca aagctttaga gca | 1442 |